United States Patent
Kalas et al.

(10) Patent No.: US 11,773,127 B2
(45) Date of Patent: Oct. 3, 2023

(54) COMPOUNDS AND METHODS FOR TREATING BACTERIAL INFECTIONS

(71) Applicant: Washington University, St. Louis, MO (US)

(72) Inventors: Vasilios Kalas, St. Louis, MO (US); James W. Janetka, St. Louis, MO (US); Scott Hultgren, St. Louis, MO (US); Jerry Pinkner, St. Louis, MO (US); Amarendar Maddirala, St. Louis, MO (US); Vishnu Damalanka, St. Louis, MO (US)

(73) Assignee: Washington University, St. Louis, MO (US)

( * ) Notice: Subject to any disclaimer, the term of this patent is extended or adjusted under 35 U.S.C. 154(b) by 3 days.

(21) Appl. No.: 16/762,724

(22) PCT Filed: Nov. 8, 2018

(86) PCT No.: PCT/US2018/059877
§ 371 (c)(1),
(2) Date: May 8, 2020

(87) PCT Pub. No.: WO2019/094631
PCT Pub. Date: May 16, 2019

(65) Prior Publication Data
US 2021/0171563 A1    Jun. 10, 2021

Related U.S. Application Data

(60) Provisional application No. 62/726,303, filed on Sep. 2, 2018, provisional application No. 62/583,357, filed on Nov. 8, 2017.

(51) Int. Cl.
| | |
|---|---|
| *C07H 15/203* | (2006.01) |
| *A61K 31/7034* | (2006.01) |
| *A61K 31/7048* | (2006.01) |
| *A61K 31/7056* | (2006.01) |
| *A61K 31/706* | (2006.01) |
| *A61K 45/06* | (2006.01) |
| *C07H 15/20* | (2006.01) |
| *C07H 15/26* | (2006.01) |
| *C07H 17/02* | (2006.01) |
| *C07H 17/04* | (2006.01) |

(52) U.S. Cl.
CPC ......... *C07H 15/203* (2013.01); *A61K 31/706* (2013.01); *A61K 31/7034* (2013.01); *A61K 31/7048* (2013.01); *A61K 31/7056* (2013.01); *A61K 45/06* (2013.01); *C07H 15/20* (2013.01); *C07H 15/26* (2013.01); *C07H 17/02* (2013.01); *C07H 17/04* (2013.01)

(58) Field of Classification Search
CPC ...... C07H 15/203; C07H 15/20; C07H 15/26; C07H 17/02; C07H 17/04
See application file for complete search history.

(56) References Cited

U.S. PATENT DOCUMENTS

| | | | |
|---|---|---|---|
| 4,464,531 A * | 8/1984 | Atsumi | C07H 17/02 536/17.3 |
| 5,444,050 A | 8/1995 | Kogan et al. | |
| 8,937,167 B2 | 1/2015 | Janetka et al. | |
| 9,567,362 B2 | 2/2017 | Janetka et al. | |
| 2007/0025939 A1 | 2/2007 | Fares et al. | |
| 2009/0263339 A1 | 10/2009 | Kyono et al. | |
| 2017/0247401 A1 | 8/2017 | Janetka et al. | |

OTHER PUBLICATIONS

Cumpstey et al., Org. Biomol. Chem., 2005, 3, p. 1922-1932. (Year: 2005).*
Moonens et al., Current Opinion in Structural Biology, 2017, 44, p. 48-58, Available online Dec. 30, 2016. (Year: 2016).*
Sinnott et al., Biochem. J., 1973, 133, p. 89-98. (Year: 1973).*
Capicciotti et al., ACS Omega, 2016, 1, p. 656-662 and Supporting Information. (Year: 2016).*
Khodair et al., Nucleosides, Nucleotides & Nucleic Acids, 2003, 22(11), p. 2061-2076. (Year: 2003).*
Andre et al., New J. Chem., 2010, 34, p. 2229-2240. (Year: 2010).*
Ghosh et al., Beilstein J. Org. Chem., 2013, 9, p. 974-982. (Year: 2013).*
Adams, P.D., et al., "PHENIX: a Comprehensive Python-based System for Macromolecular Structure Solution," 2010, Acta Crystallogr D Biol Crystallogr, 66(Pt2):213-221, 9 pages.
Aypak, C., et al., "Empiric Antibiotic Therapy in Acute UncomplicateUrinary Tract Infections and Fluoroquinolone Resistance: A Prospective Observational Study," 2009, Ann Clin Microbiol Antimicrob, 8:27, 7 pages.
Battye, T.G., et al., "iMOSFLM: a New Graphical Interface for Diffraction-image Processing with MOSFLM," 2011, Acta Crystallogr D Biol Crystallogr, 67(Pt4):271-281, 11 pages.
Berge, et al., "Pharmaceutical Salts," 1977, J Pharm Sci, 66/1:1-19, 19 pages.
Bouckaert, J., et al., "The affinity of the FimH fimbrial adhesin is receptor-driven and quasi-independent of *Escherichia coli* pathotypes," 2006, Mol Microbiol, 61/6:1556-1568, 13 pages.
Burger's Medicinal Chemistry and Drug Discovery, 5th Edition, 1995, Manfred E. Wolff, Ed., pp. 168-180 and 902-947, 13 pages.
Chang, Q., et al., "Antibiotics in agriculture and the risk to human health: How worried should we be?" 2015, Evol Appl, 8(3):240-247, 8 pages.
Conover, M.S., et al., "Inflammation-Induced Adhesin-Receptor Interaction Provides a Fitness Advantage to Uropathogenic *E. coli* during Chronic Infection," 2016, Cell Host Microbe, 2016. 20(4):482-492.
Efstathiou, S.P., et al., "Acute pyelonephritis in adults: Prediction of mortality and failure of treatment," 2003, Arch Intern Med, 2003. 163(10):1206-1212, 7 pages.

(Continued)

*Primary Examiner* — Jonathan S Lau
(74) *Attorney, Agent, or Firm* — Stinson LLP

(57) ABSTRACT

The present invention is directed to various compounds, compositions, and methods for treating bacterial infections such as urinary tract infections.

15 Claims, 17 Drawing Sheets

(56) References Cited

OTHER PUBLICATIONS

Ernst, B., et al., "From carbohydrate leads to glycomimetic drugs," 2009, Rev Drug Discov, 8(8):661-677, 17 pages.
Foxman, B., "The epidemiology of urinary tract infection," 2010, Nat Rev Urol, 7(12):653-660.
Foxman, B., "Epidemiology of urinary tract infections: incidence, morbidity, and economic costs," 2003. Dis Mon,49(2):53-70, 8 pages.
Griebling, T.L., "Urologic diseases in America project: Trends in resource use for urinary tract infections in women," 2005, J Urol, 173(4):1281-1287, 7 pages.
Guneysel, O., et al., "Trimethoprim/sulfamethoxazole resistance in urinary tract infections," 2009, J Emerg Med, 36(4):338-341.
Gupta, K., et al., "Patient-initiated treatment of uncomplicated recurrent urinary tract infections in young women," 2001, Ann Intern Med, 135(1): 9-16, 8 pages.
Han, Z., et al., "Structure-based drug design and optimization of mannoside bacterial FimH antagonists," 2010, J Med Chem, 53(12):4779-4792, 35 pages.
Hannan, T.J., et al., "Early severe inflammatory responses to uropathogenic *E. coli* predispose to chronic and recurrent urinary tract infection," 2010, PLoS Pathog, 6(8):e1001042, 19 pages.
Hsu, C.H., et al., "The Dependence of Carbohydrate-Aromatic Interaction Strengths on the Structure of the Carbohydrate," 2016, J Am Chem Soc, 138(24):7636-7648, 29 pages.
Hudson, K.L., et al., "Carbohydrate-Aromatic Interactions in Proteins," 2015, J Am Chem Soc, 137(48):15152-15160, 9 pages.
Hung, C.S., et al., "Structural basis of tropism of *Escherichia coli* to the bladder during urinary tract infection," 2002, Mol Microbiol, 44(4):903-915, 13 pages.
Irwin, J.J., et al., "Zinc: a free tool to discover chemistry for biology," 2012, J Chem Inf Model, 52(7): 1757-1768, 12 pages.
Jarvis, C., et al., "Antivirulence Isoquinolone Mannosides: Optimization of the Biaryl Aglycone for FimH Lectin Binding Affinity and Efficacy in the Treatment of Chronic UTI," 2016, ChemMedChem, 11(4):367-373, 17 pages.
Jones, C.H., et al., "FimH adhesin of type 1 pili is assembled into a fibrillar tip structure in the Enterobacteriaceae," 1995, Proc Natl Acad Sci USA, 92(6):2081-2085.
Kabsch, W., "XDS," 2010, Acta Crystallogr D Biol Crystallogr, 66(Pt 2):125-132, 8 pages.
Kalas, V., et al., "Evolutionary fine-tuning of conformational ensembles in FimH during host-pathogen interactions," 2017, Sci Adv, 3(2):e1601944, 15 pages.
Kalien, A.J., et al., "Current antibiotic therapy for isolated urinary tract infections in women," 2006, Arch Intern Med, 166(6):635-639, 5 pages.
Kardas, P., et al., "A systematic review and meta-analysis of misuse of antibiotic therapies in the community," 2005, Int J Antimicrob Agents, 26(2):106-113, 5 pages.
Karlowsky, J.A., et al., "Fluoroquinolone-resistant urinary isolates of *Escherichia coli* from outpatients are frequently multidrug resistant: Results from the North American Urinary Tract Infection Collaborative Alliance-Quinolone Resistance study," 2006, Antimicrob Agents Chemother, 50(6):2251-2254, 4 pages.
Llor, C., et al., "Antimicrobial resistance: risk associated with antibiotic overuse and initiatives to reduce the problem," 2014, Ther Adv Drug Saf, . 5(6): p. 229-241, 4 pages.
McGann, P., et al., "*Escherichia coli* Harboring mcr-1 and blaCTX-M on a Novel IncF Plasmid: First Report of mcr-1 in the United States," 2016, Antimicrob Agents Chemother, 60(7): 4420-4421 and 5107, 3 pages.
Mulvey, M.A., et al., "Induction and evasion of host defenses by type 1 -piliated uropathogenic *Escherichia coli*," 1998, Science, 282(5393)1494-1497, 5 pages.
Mydock-Mcgrane, L., et al., "Antivirulence C-Mannosides as Antibiotic-Sparing, Oral Therapeutics for Urinary Tract Infections." 2016, J Med Chem, 59(20):9390-9408, 19 pages.
O'Boyle, N.M., et al., "Open Babel: An open chemical toolbox," 2011, J Cheminform, 3:33, 14 pages.
Pertel, P.E., et al., "Risk factors for a poor outcome after therapy for acute pyelonephritis," 2006, BJU Int, 98(1):141-147, 7 pages.
Ramakrishnan, K., et al., "Diagnosis and management of acute pyelonephritis in adults," 2005, Am Fam Physician, 71(5):933-942, 10 pages.
Rasko, D.A., et al., "Anti-virulence strategies to combat bacteria-mediated disease," 2010, Nat Rev Drug Discov, 9(2):117-128, 12 pages.
Raz, R., et al., "Empiric use of trimethoprim-sulfamethoxazole (TMP-SMX) in the treatment of women with uncomplicated urinary tract infections, in a geographical area with a high prevalence of TMP-SMX-resistant uropathogens," 2002, Clin Infect Dis, 34(9):1165-1169, 5 pages.
Roberts, F.J., et al., "A three-year study of positive blood cultures, with emphasis on prognosis," 1991, Rev Infect Dis, 13(1)34-46, 14 pages.
Ronald, A., "The etiology of urinary tract infection: traditional and emerging pathogens," 2003, Dis Mon, 49(2):71-82, 12 pages.
Ronald, A.R., et al., "Urinary tract infection in adults: research priorities and strategies," 2001, Int J Antimicrob Agents, 17(4): p. 343-348, 6 pages.
Subashchandrabose, S., et al., "Host-specific induction of *Escherichia coli* fitness genes during human urinary tract infection," 2014, Proc Natl Acad Sci U S A, 111(51):18327-18332, 6 pages.
Ter Kuile, B.H., et al., "The risk of low concentrations of antibiotics in agriculture for resistance in human health care," 2016, FEMS Microbiol Lett, 363(19), 7 pages.
Trott, O., et al., "AutoDock Vina: improving the speed and accuracy of docking with a new scoring function, efficient optimization, and multithreading," 2010, J Comput Chem, 31(2): 455-461, 18.
Waksman, G., et al., "Structural biology of the chaperone-usher pathway of pilus biogenesis," 2009, Nat Rev Microbiol, 7(11):765-774, 10 pages.
Winn, M.D., et al., "Overview of the CCP4 suite and current developments," 2011, Acta Crystallogr D Biol Crystallogr, 67(Pt 4):235-242, 8 pages.
Wurpel, D.J., et al., "Chaperone-usher fimbriae of *Escherichia coli*," 2013, PLoS One, 8(1):e52835, 11 pages.
Antimicrobial Resistance: Global Report on Surveillance, 2014, World Health Organization, 256 pages.

\* cited by examiner

A

B

29β-NAc; IC$_{50}$ = 0.64 μM

A.

B.

A.

B.

COMPOUNDS AND METHODS FOR TREATING BACTERIAL INFECTIONS

CROSS-REFERENCE TO RELATED APPLICATIONS

This application is the 371 National Stage Application of International Application Serial No. PCT/US2018/059877, filed Nov. 8, 2018, and claims priority of U.S. provisional application Ser. No. 62/583,357, filed on Nov. 8, 2017, and U.S. provisional application Ser. No. 62/726,303, filed on Sep. 2, 2018, the entire disclosures of which are incorporated herein by reference.

STATEMENT REGARDING FEDERALLY SPONSORED RESEARCH OR DEVELOPMENT

This invention was made with government support under DK108840 awarded by the National Institutes of Health. The government has certain rights in the invention.

FIELD OF THE INVENTION

The present invention is directed to various compounds, compositions, and methods for treating bacterial infections such as urinary tract infections.

BACKGROUND OF THE INVENTION

Urinary tract infections (UTIs) are one of the most prevalent infections, afflicting 15 million women per year in the United States alone with annual healthcare costs exceeding $2-3 billion [1-3]. Nearly 50% of women will experience at least one UTI in their lifetime. Despite appropriate and often successful clearance of bacteriuria by antibiotic treatment, 20-30% of women will experience a recurrence within six months of the initial acute UTI [1,4]. Kidney infection, or pyelonephritis, represents a severe manifestation of UTI, with approximately 250,000 cases and 100,000 hospitalizations per year in the US [5]. Acute pyelonephritis requires hospital admission and intravenous antibiotics to thwart the long-term sequelae of kidney failure and renal scarring, and together with bacteremia, results in a mortality rate of 10-20% [6-8]. With the global dissemination and increase of antibiotic resistance, treatment of UTI is becoming a serious clinical challenge [9]. Antibiotic susceptibility tests indicate that many uropathogens are resistant to traditional first-line antibiotics like trimethoprim-sulfamethoxazole (TMP-SMZ) and even to last-line antibiotics such as ciprofloxacin and colistin [10-15]. The diminishing efficacy of antibiotic therapies toward UTIs and other infectious diseases necessitates alternative approaches to combatting bacterial pathogens. Recent efforts aim to target the virulence mechanisms that cause bacterial infection to provide much-needed therapeutic alternatives while simultaneously reducing the burden of antibiotic resistance and minimizing disruption of gastrointestinal microbial communities that are beneficial to human health [16].

Uropathogenic *E. coli* (UPEC) are the main etiological agent of UTIs, accounting for greater than 80% of community-acquired UTIs [17, 18]. Comparative genomic studies have revealed that UPEC are remarkably diverse such that only 60% of the genome is shared amongst all strains {Schreiber, 2017 #4724}. As a consequence, UTI risk and outcome are determined by complex interactions between host susceptibility and diverse bacterial urovirulence potentials, which can be driven by differences in the expression and regulation of conserved functions. The ability of UPEC to colonize various habitats such as gut, kidney and bladder, depends in large part on the repertoire of adhesins encoded in their genome. The most common mechanism for adhesion utilized by UPEC is mediated through the chaperone-usher pathway (CUP), which generates extracellular fibers termed pili that can confer bacterial adhesion to host and environmental surfaces, facilitate invasion into host tissues, and promote interaction with other bacteria to form biofilms [19]. Phylogenetic analysis of *Escherichia* genomes and plasmids predicts at least 38 distinct CUP pilus types, with single organisms capable of maintaining as many as 16 distinct CUP operons [20]. Many of these CUP pilus operons contain two-domain, tip-localized adhesins, each of which likely recognize specific ligands or receptors to mediate colonization of a host and/or environmental niche. For example, the type 1 pilus adhesin FimH binds mannosylated glycoproteins on the surface of the bladder epithelium, which is crucial for the establishment of cystitis [21, 22]. The structural basis of mannose recognition by the N-terminal receptor binding domain, or lectin domain (LD), of FimH has been leveraged to rationally develop high-affinity aryl mannosides [23-26]. In mouse models of UTI, it has been previously demonstrated that orally bioavailable mannosides that tightly bind FimH can prevent acute UTI, treat chronic UTI, and potentiate the efficacy of existing antibiotic treatments like TMP-SMZ, even against antibiotic-resistant *E. coli* strains [26]. Thus, use of mannosides that target the adhesin FimH represents the first successful application of an anti-virulence strategy in the treatment of UTI.

A homolog of the type 1 pilus, the F9 pilus is one of the most common CUP pili in the *E. coli* pan genome and an important urovirulence factor employed by UPEC for the maintenance of UTI {Wurpel, 2013 #4695; Wurpel, 2014 #4664}. It has been demonstrated that UPEC up-regulate the expression of F9 pili in response to bladder inflammation and epithelial remodeling induced upon UPEC infection [27]. These pili display the FimH-like adhesin FmlH, which is capable of binding terminal galactose (Gal), N-acetylgalactosamine (GalNAc), or Thomsen-Friedenreich (TF) antigen (Gal-β1-3-GalNAc-α). FmlH was shown to bind TF antigen within naive or infected kidneys and GalNAc or Tn antigen receptors within the inflamed bladder epithelium during chronic, unresolved UTI. Deletion of FmlH in the urosepsis isolate CFT073 resulted in a competitive defect in the ability of this strain to maintain murine UTI in C3H/HeN female mice. Furthermore, vaccination with the lectin domain of FmlH (FmlH$_{LD}$) as the challenge antigen significantly protected mice from developing UTI. Thus, FmlH has been shown to serve a key role in the UPEC pathogenesis cascade and represents a promising new target for novel anti-virulence therapies for UTI in both the bladder and kidney habitats.

BRIEF SUMMARY OF THE INVENTION

Generally, the present invention relates to various compounds, compositions, and methods that are useful for treating bacterial infections, including urinary tract infections. In various aspects, the present invention is directed to compounds of Formula (I) or salts or prodrugs thereof:

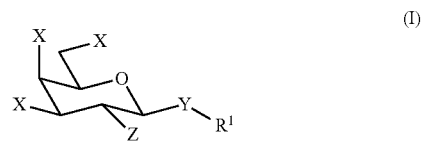

wherein:

each X is independently hydrogen, fluoro, or $OR^2$;

each $R^2$ is independently hydrogen or substituted or unsubstituted hydrocarbyl;

Y is O, S, substituted or unsubstituted hydrocarbylene, substituted or unsubstituted amino, substituted or unsubstituted amido, substituted or unsubstituted thio, $C(R^3)_2$, $(CH_2)_m$, $N(R^3)$, $N(H)R^3$, $CO_2$, $COOR^3$, $SO_2$, $SO_2R^3$, $(CH_2)_mO$, $O(CH_2)_m$, $(CH_2)_mS$, $S(CH_2)_m$, $C(O)$, $C(O)N(R^3)$, $N(R^3)C(O)$, $R^3N(R^3)C(O)$, $C(O)N(R^3)R^3$, $SO_2N(R^3)$, or $N(R_3)SO_2$, each $R^3$ is independently hydrogen or substituted or unsubstituted hydrocarbyl;

Z is hydrogen, $OR^4$, $SR^4$, or $NHR^4$;

each $R^4$ is independently hydrogen or substituted or unsubstituted hydrocarbyl;

each m is independently an integer from 0 to 10; and $R^1$ is a substituent of Formula (II), (III), (IV), (V), (VI), (VII), (VIII), (IX), (IXa), (X), (XI), (XII), (XIII), (XIV), or (XV):

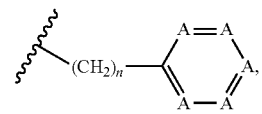
(II)

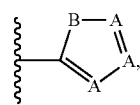
(III)

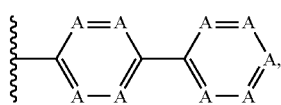
(IV)

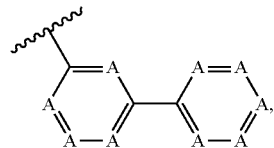
(V)

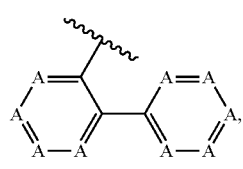
(VI)

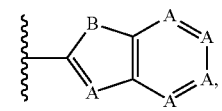
(VII)

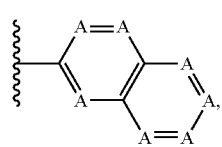
(VIII)

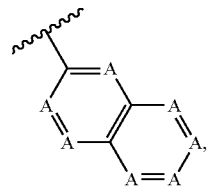
(IX)

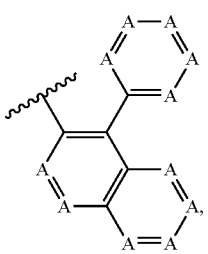
(IXa)

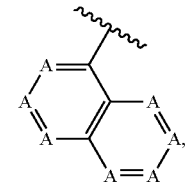
(X)

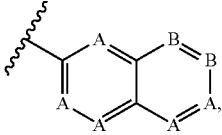
(XI)

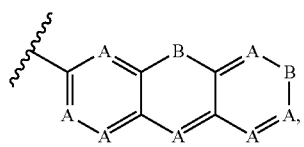
(XII)

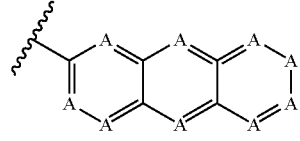
(XV)

wherein:

each A is independently $CR^5$ or N;

each B is independently O, S, C(O), $C(R^5)_2$, or $NR^6$;

each $R^5$ is independently hydrogen, oxygen, halo, substituted or unsubstituted amino, substituted or unsubstituted amido, substituted or unsubstituted haloalkyl, substituted or unsubstituted hydrocarbyl, substituted or unsubstituted aryl, $(CH_2)_pNO_2$, $(CH_2)_pCN$, $(CH_2)_pOR^7$, $(CH_2)_pC(R^7)_2OR^7$, $(CH_2)_pC(O)(R^7)_2$, $(CH_2)_pCO_2R^7$, $(CH_2)_pN(R^7)_2$, $(CH_2)_pSO_2R^7$, $(CH_2)_pN(SO_2R^7)_2$, $(CH_2)_pNR^7C(O)R^7$, $(CH_2)_pNR^7C(R^7)_2OR^7$, $(CH_2)_pNR^7CO_2R^7$, $(CH_2)_pNR^7C(O)N(R^7)_2$, $(CH_2)_pNR^7SO_2R^7$, $(CH_2)_pCON(R^7)_2$, $(CH_2)_pSO_2N(R^7)_2$, $(CH_2)_pN(R^7)SO_2N(R^7)_2$, or $(CH_2)_pOSO_2R^7$;

each $R^6$ is independently hydrogen, substituted or unsubstituted haloalkyl, substituted or unsubstituted hydrocarbyl, substituted or unsubstituted aryl, $(CH_2)_qNO_2$, $(CH_2)_qCN$, $(CH_2)_pOR^7$, $(CH_2)_pC(R^7)_2OR^7$, $(CH_2)_pC(O)(R^7)_2$, $(CH_2)_pCO_2R^7$, $(CH_2)_pN(R^7)_2$, $(CH_2)_pN(SO_2R^7)_2$, $(CH_2)_pSO_2R^7$, $(CH_2)_qNR^7C(O)R^7$, $(CH_2)_qNR^7C(R^7)_2OR^7$, $(CH_2)_qNR^7CO_2R^7$, $(CH_2)_qNR^7C(O)$ N(R⁷)₂, (CH₂)_qNR⁷SO₂R⁷, (CH₂)_pCON(R⁷)₂, (CH₂)_p SO₂N(R⁷)₂, (CH₂)_qN(R⁷) SO₂N(R⁷)₂, or (CH₂)_p OSO₂R⁷;

each $R^7$ is independently hydrogen or substituted or unsubstituted hydrocarbyl;

each n is independently an integer from 0 to 10;

each p is independently an integer from 0 to 10; and each q is independently an integer from 1 to 10, with the proviso that:

(a) when (i) each X is OH, (ii) Y is O, (iii) Z is OR⁴, (iv) $R^4$ is hydrogen, (v) $R^1$ is a substituent of Formula (II), and (vi) n is 0, then $R^1$ is not unsubstituted phenyl and each $R^5$ is not nitro or amino;

(b) when (i) each X is OH, (ii) Y is O, (iii) Z is OR⁴, (iv) $R^4$ is hydrogen, (v) $R^1$ is a substituent of Formula (VII), and (v) B is N, then $R^1$ is not unsubstituted indolyl and each $R^5$ is not chlorine;

c) when (i) each X is OH, (ii) Y is O, (iii) Z is OR⁴, (iv) $R^4$ is hydrogen, and (v) $R^1$ is a substituent of Formula (IX), then $R^1$ is not unsubstituted biphenyl;

(d) when (i) each X is OH, (ii) Y is O, (iii) Z is OR⁴, (iv) $R^4$ is hydrogen, and (v) $R^1$ is a substituent of Formula (X), then $R^1$ is not

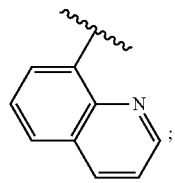 [SMILES: *c1cccc2cccnc12]

(e) when (i) each X is OH, (ii) Y is O, (iii) Z is OR⁴, (iv) $R^4$ is hydrogen, and (v) $R^1$ is a substituent of Formula (XI) or (XII), then each B is not C(O);

(f) when (i) each X is OH, (ii) Y is S, (iii) Z is OR⁴, (iv) $R^4$ is hydrogen, and (v) $R^1$ is a substituent of Formula (II), and (vi) n is 2, then $R^1$ is not unsubstituted phenyl; and (g) when (i) each X is OH, (ii) Y is O, (iii) Z is NHC(O)CH₃, (iv) $R^1$ is a substituent of Formula (II), and (v) n is 0, then $R^1$ is not unsubstituted phenyl and each $R^5$ is not nitro.

The present invention further relates to pharmaceutical compositions comprising a therapeutically effective amount of at least one compound described by Formula (I) or salt or prodrug thereof:

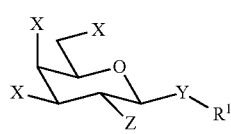

wherein:

each X is independently hydrogen, fluoro, or OR²;

each $R^2$ is independently hydrogen or substituted or unsubstituted hydrocarbyl;

Y is O, S, substituted or unsubstituted hydrocarbylene, substituted or unsubstituted amino, substituted or unsubstituted amido, substituted or unsubstituted thio, C(R³)₂, (CH₂)_m, N(R³), N(H)R³, CO₂, COOR³, SO₂, SO₂R³, (CH₂)_mO, O(CH₂)_m, (CH₂)_mS, S(CH₂)_m, C(O), C(O)N(R³), N(R³)C(O), R³N(R³)C(O), C(O)N(R³)R³, SO₂N(R³), or N(R³)SO₂, each $R^3$ is independently hydrogen or substituted or unsubstituted hydrocarbyl;

Z is hydrogen, OR⁴, SR⁴, or NHR⁴;

each $R^4$ is independently hydrogen or substituted or unsubstituted hydrocarbyl;

each m is independently an integer from 0 to 10; and $R^1$ is a substituent of Formula (II), (III), (IV), (V), (VI), (VII), (VIII), (IX), (IXa), (X), (XI), (XII), (XIII), (XIV), or (XV):

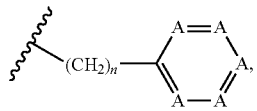

(II)

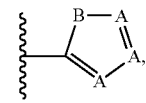

(III)

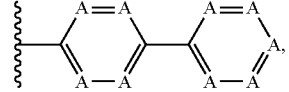

(IV)

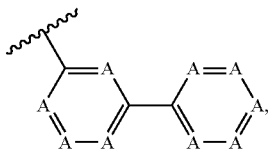

(V)

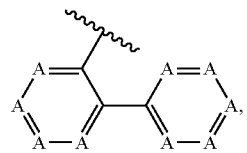

(VI)

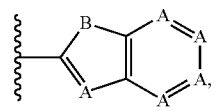

(VII)

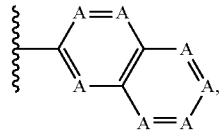

(VIII)

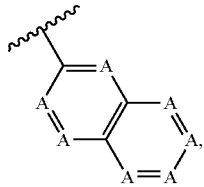

(IX)

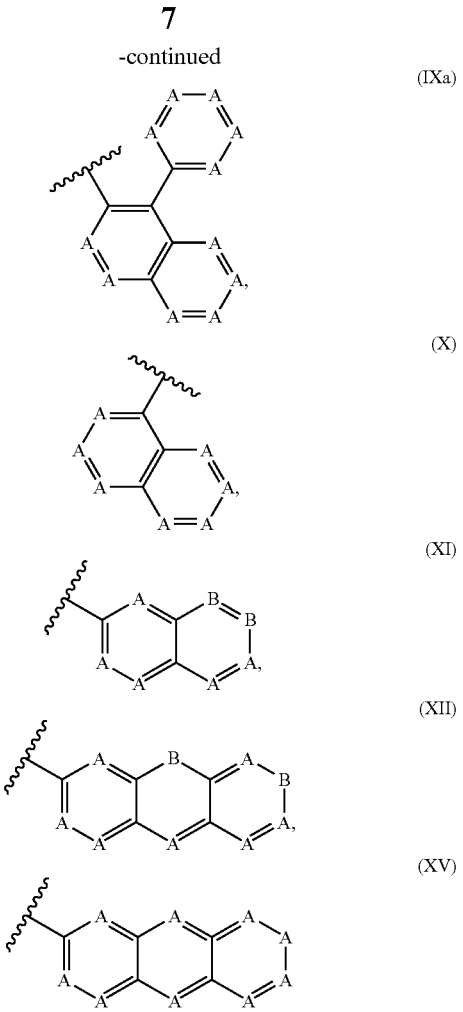

wherein:
each A is independently $CR^5$ or N;
each B is independently O, S, C(O), $C(R^5)_2$, or $NR^6$;
each $R^5$ is independently hydrogen, oxygen, halo, substituted or unsubstituted amino, substituted or unsubstituted amido, substituted or unsubstituted haloalkyl, substituted or unsubstituted hydrocarbyl, substituted or unsubstituted aryl, $(CH_2)_pNO_2$, $(CH_2)_pCN$, $(CH_2)_pOR^7$, $(CH_2)_pC(R^7)_2OR^7$, $(CH_2)_pC(O)(R^7)_2$, $(CH_2)_pCO_2R^7$, $(CH_2)_pN(R^7)_2$, $(CH_2)_pSO_2R^7$, $(CH_2)_pN(SO_2R^7)_2$, $(CH_2)_pNR^7C(O)R^7$, $(CH_2)_pNR^7C(R^7)_2OR^7$, $(CH_2)_pNR^7CO_2R^7$, $(CH_2)_pNR^7C(O)N(R^7)_2$, $(CH_2)_pNR^7SO_2R^7$, $(CH_2)_pCON(R^7)_2$, $(CH_2)_pSO_2N(R^7)_2$, $(CH_2)_pN(R^7)SO_2N(R^7)_2$, or $(CH_2)_pOSO_2R^7$;
each $R^6$ is independently hydrogen, substituted or unsubstituted haloalkyl, substituted or unsubstituted hydrocarbyl, substituted or unsubstituted aryl, $(CH_2)_pNO_2$, $(CH_2)_pCN$, $(CH_2)_pOR^7$, $(CH_2)_pC(R^7)_2OR^7$, $(CH_2)_pC(O)(R^7)_2$, $(CH_2)_pCO_2R'$, $(CH_2)_qN(R^7)_2$, $(CH_2)_pN(SO_2R^7)_2$, $(CH_2)_pSO_2R^7$, $(CH_2)_qNR^7C(O)R^7$, $(CH_2)_qNR^7C(R^7)_2OR^7$, $(CH_2)_qNR^7CO_2R^7$, $(CH_2)_qNR^7C(O)N(R^7)_2$, $(CH_2)_qNR^7SO_2R^7$, $(CH_2)_pCON(R^7)_2$, $(CH_2)_pSO_2N(R^7)_2$, $(CH_2)_qN(R^7)SO_2N(R^7)_2$, or $(CH_2)_pOSO_2R^7$;
each $R^7$ is independently hydrogen or substituted or unsubstituted hydrocarbyl;
each n is independently an integer from 0 to 10;
each p is independently an integer from 0 to 10; and
each q is independently an integer from 1 to 10.

The present invention also relates to methods of use including a method of treating a bacterial infection comprising administering to a subject in need thereof a pharmaceutical composition comprising a therapeutically effective amount of at least one compound as described herein.

Other objects and features will be in part apparent and in part pointed out hereinafter.

Panel shows a synthetic scheme for rationally designed compound 29β-NAc, with the carboxylic acid designed to interact with R142, the phenyl ring designed to interact with Y46, and the N-Acetyl group designed to interact with K132.

Figure 6:
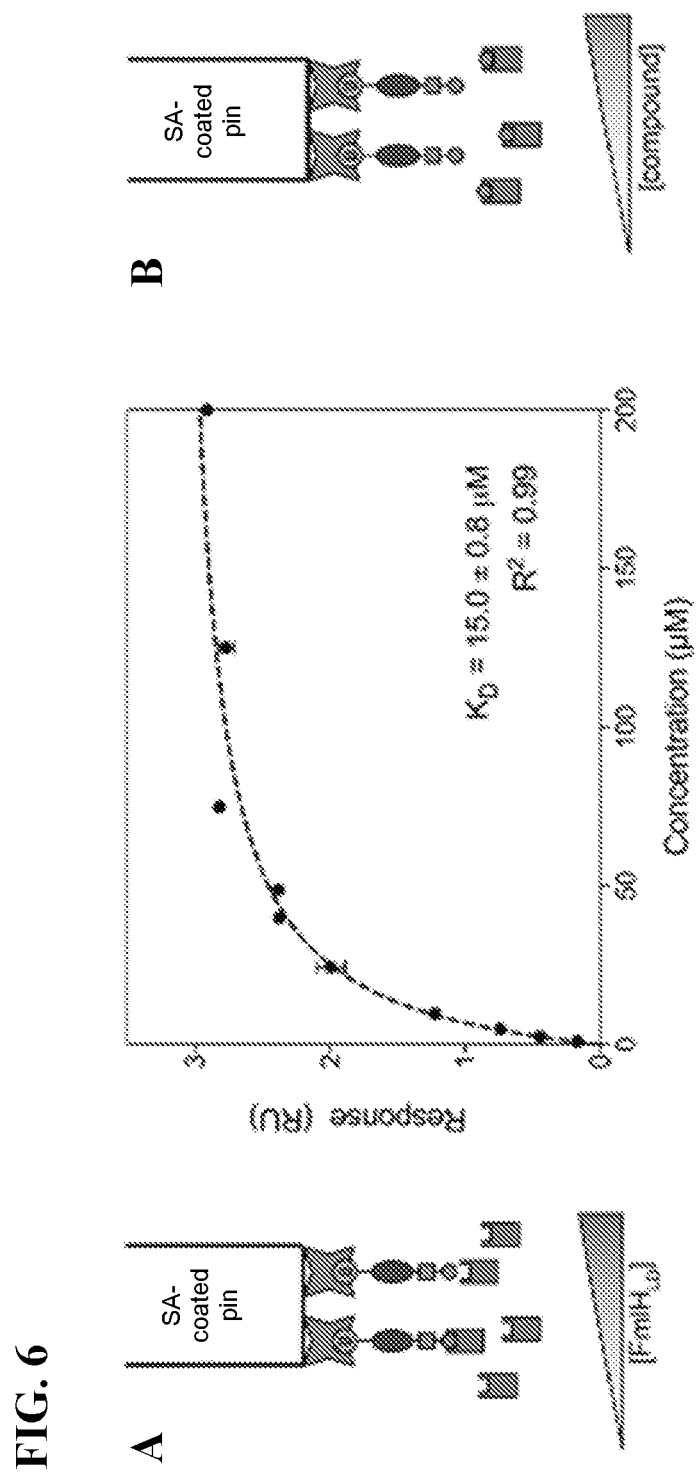

FIG. 6 shows a schematic of a binding assay and the binding curve of $FmlH_{LD}$ to biotinylated serine-TF with calculated $K_d$ and a schematic of the same binding assay in the presence of inhibiting compounds which was used to determine the inhibitory K; for each compound tested.

Figure 7:
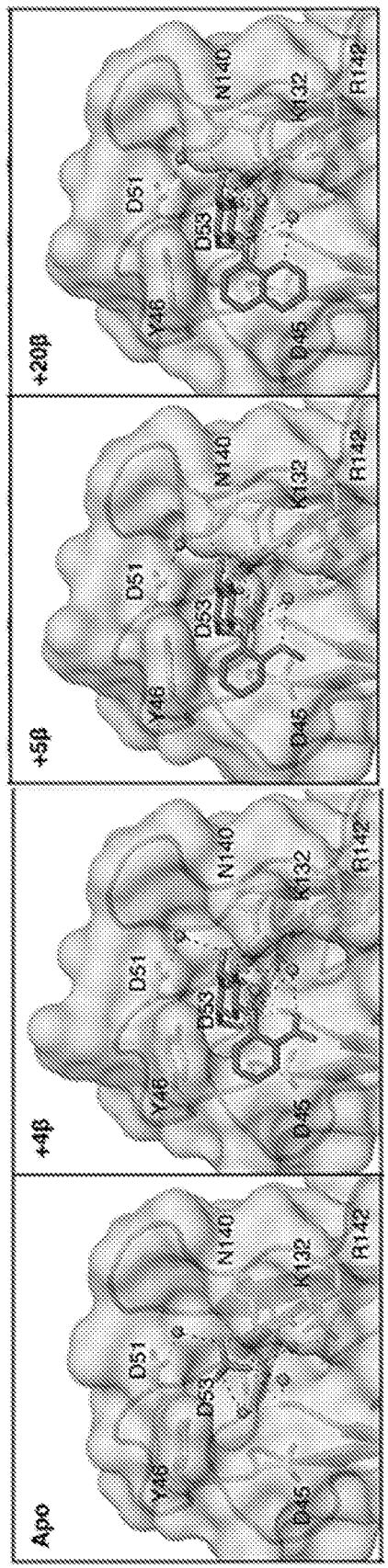
Figure 7:
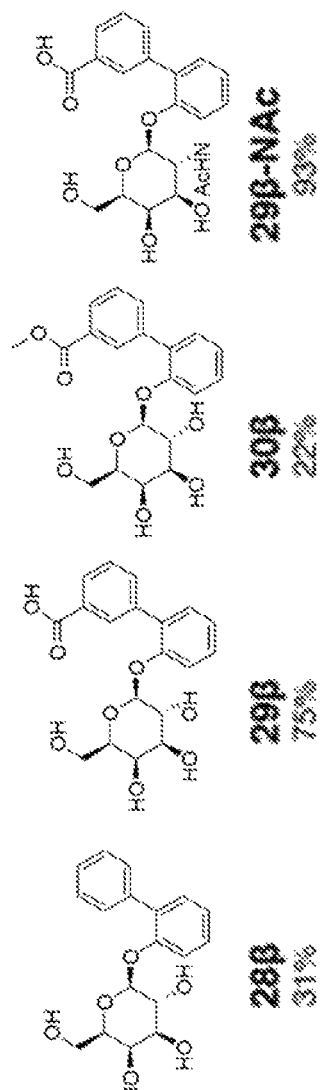
Figure 7:
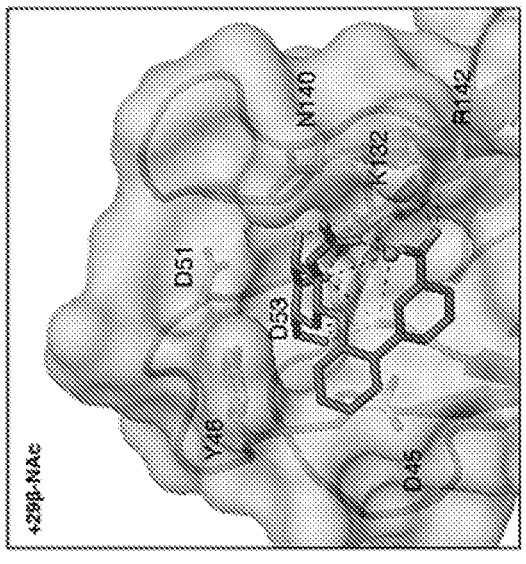

FIG. 7 shows crystal structures of sulfate ions or galactosides bound to the $FmlH_{LD}$ binding pocket with H-bonding (black dashed lines) indicated between sulfate ions or ligands (dark grey sticks), water molecules (spheres), or side chains (pale grey sticks). Panel A shows the apo $FmlH_{LD}$ crystal structure (PDB ID 6AOW), a $FmlH_{LD}$-4β co-crystal structure (PDB ID 6ARM), a $FmlH_{LD}$-5β co-crystal structure (PDB ID 6ARN), and a $FmlH_{LD}$-20β co-crystal structure (PDB ID 6ARO). Panel B shows the co-crystal structure of 29β-NAc bound to $FmlH_{LD}$ (PDB ID 6AS8). Panel C shows the structure of each compound with its corresponding % inhibition of $FmlH_{LD}$ binding in an ELISA-based competition assay.

Figure 8:
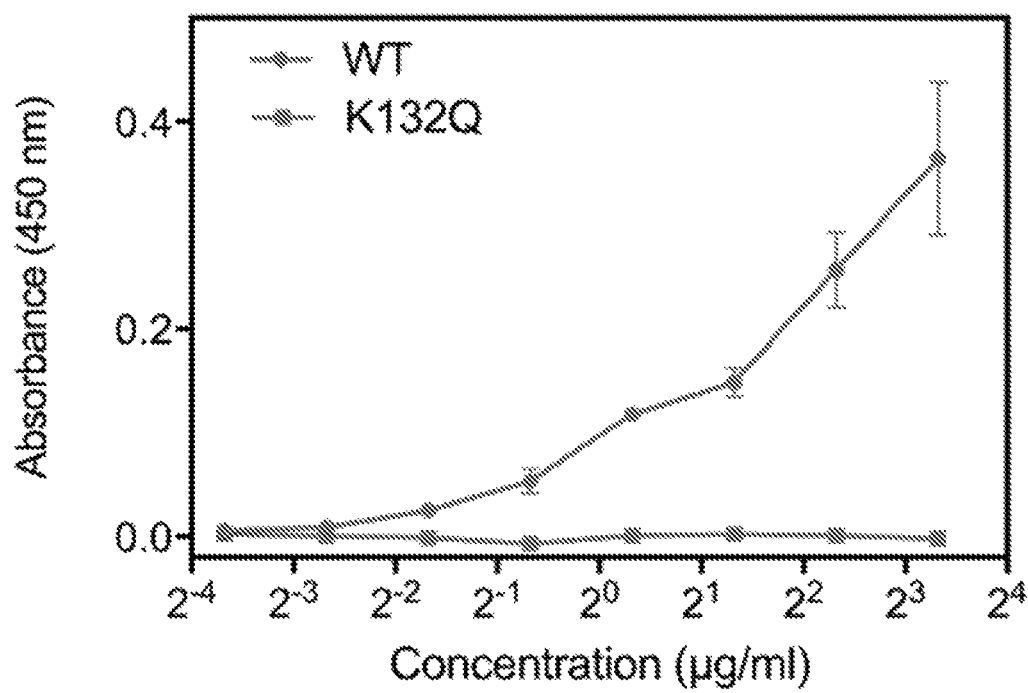

FIG. 8 is a line and scatter plot showing the absorbance (450 nm) measured for increasing concentrations of WT $FmlH_{LD}$ (blue) or K132Q $FmlH_{LD}$ (red) in an ELISA-based $FmlH_{LD}$-ds-BSM binding assay.

Figure 9:
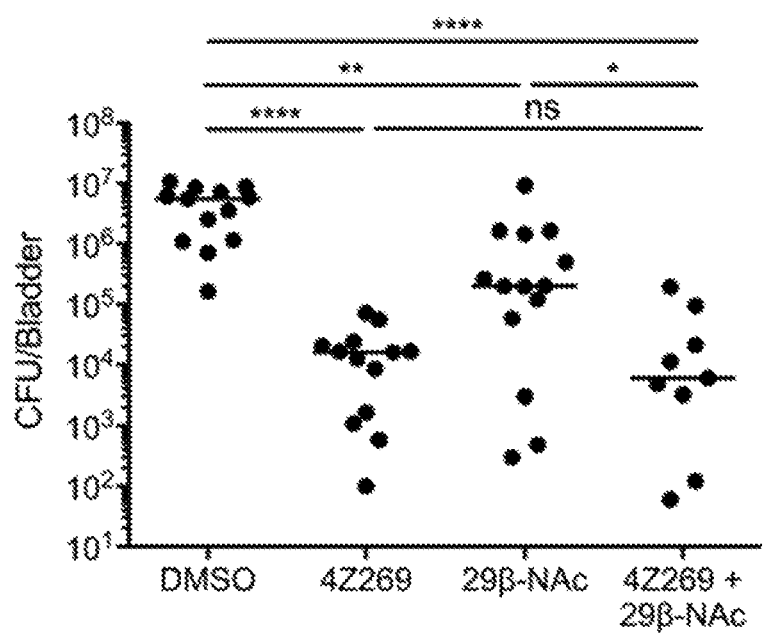
Figure 9:
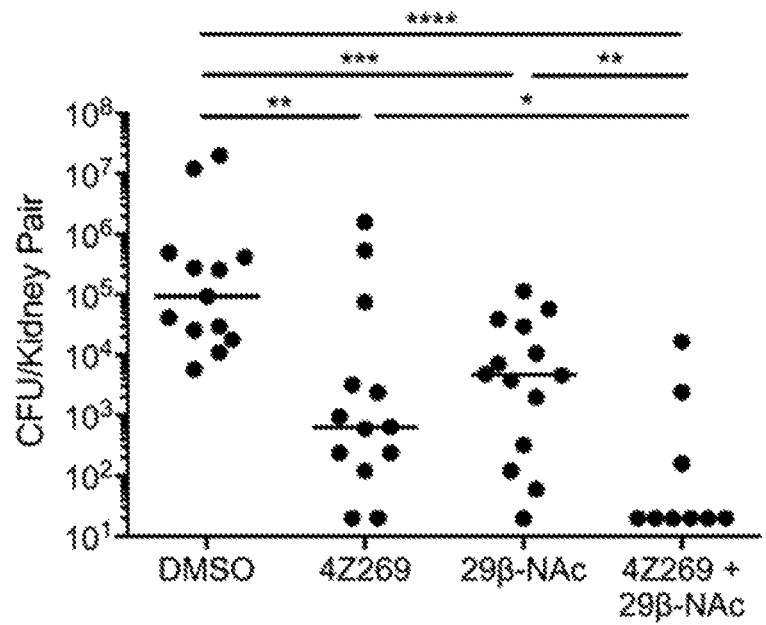

FIG. 9 shows two scatter plots showing bacterial titers (CFU) in the bladder, panel A, or kidney, panel B, of C3H/HeN mice experiencing chronic cystitis treated with transurethral inoculation of 50 mg/kg compound or vehicle controls.

Figure 10:
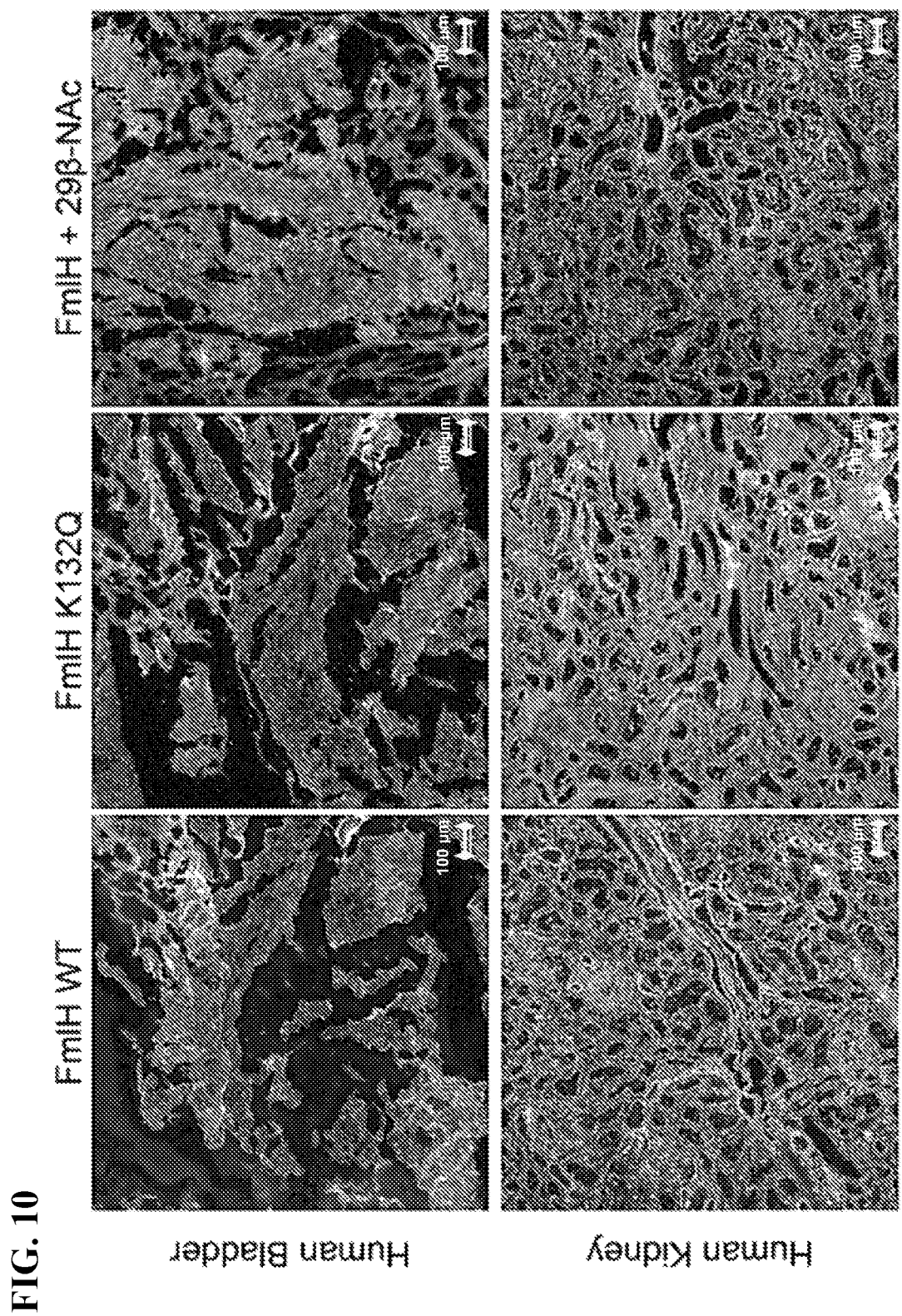

FIG. 10 shows immunofluorescence analysis of FmlH$_{LD}$ WT, FmlH$_{LD}$ K132Q, or FmlH$_{LD}$ WT in the presence of 29β-NAc binding to human bladder or human kidney tissue. White corresponds to FmlH.

Figure 11:
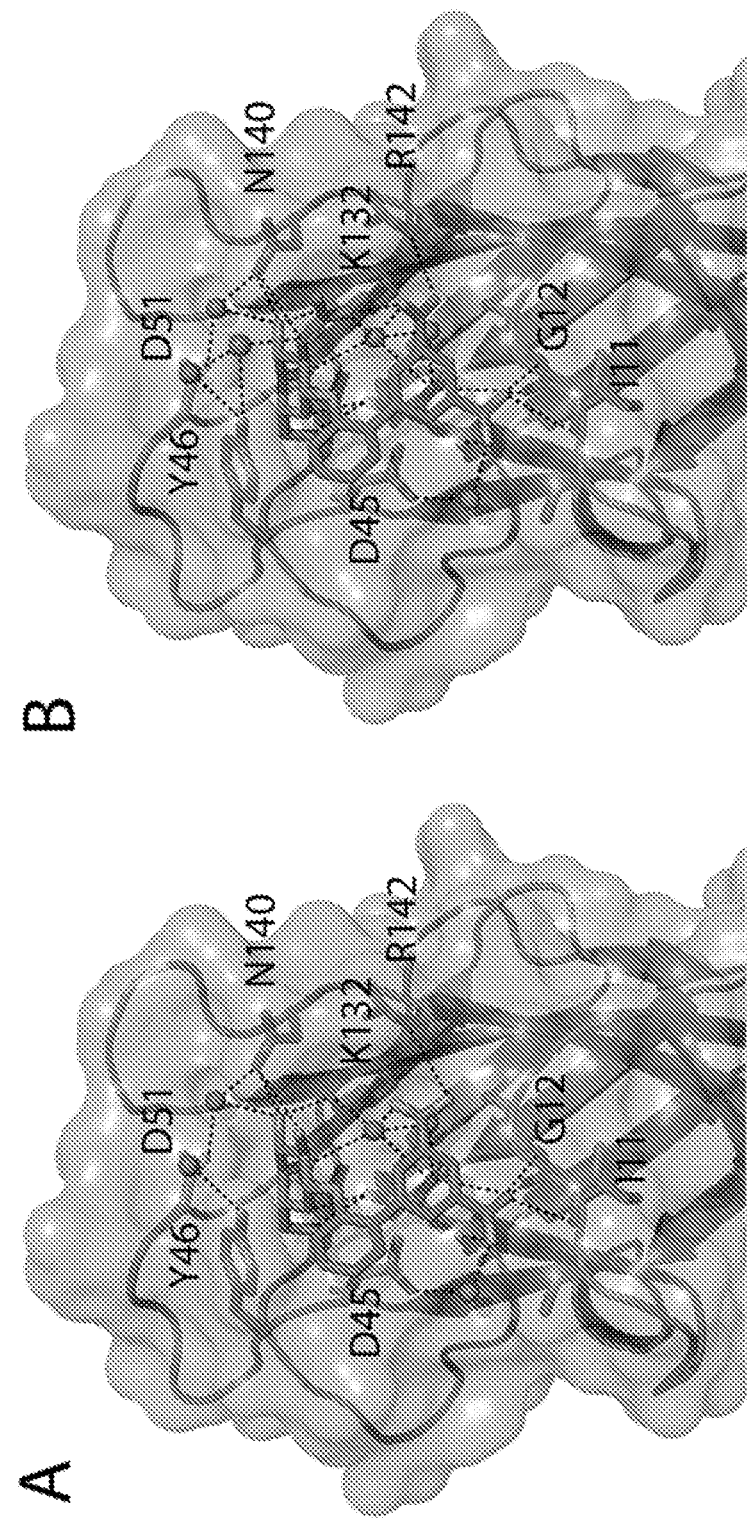

FIG. 11 shows the X-Ray crystal structure of FmlH$^{LD}$ in complex with Gal 2050 (Panel A) and GalNAc 3029 (Panel B) (PDB ID 6MAP). Direct and water-mediated interactions between the N-acetyl group on the galactose ring and the nitro group on the second phenyl ring result in decreased relative potency.

Figure 12:
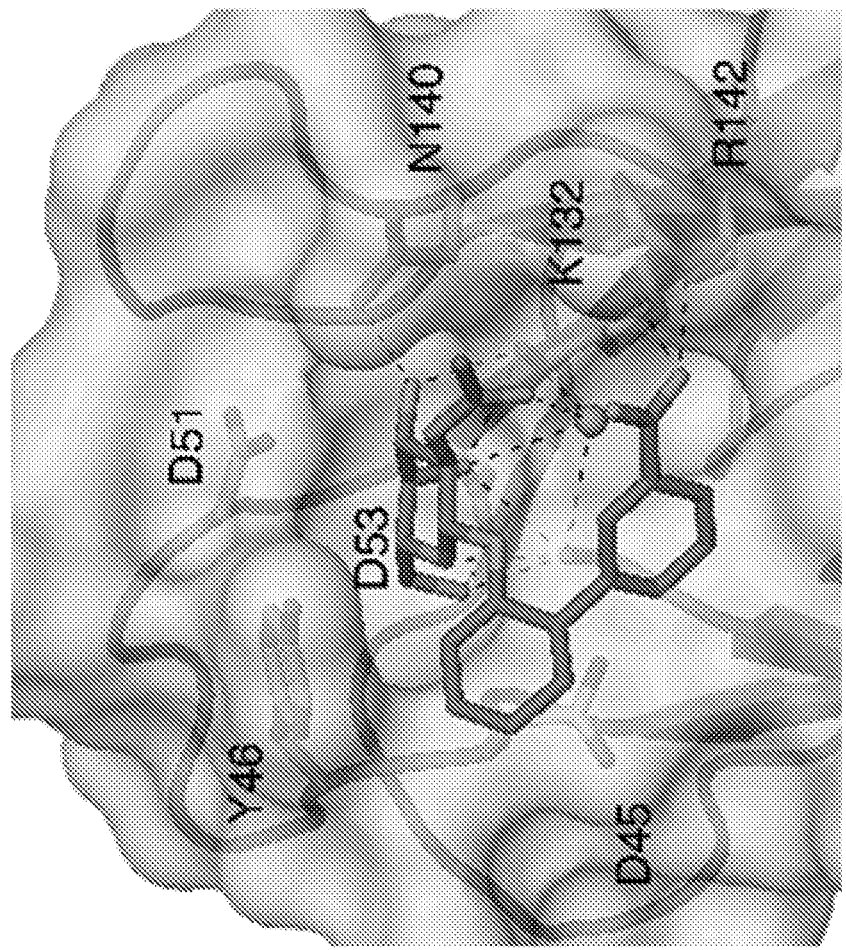
Figure 12:
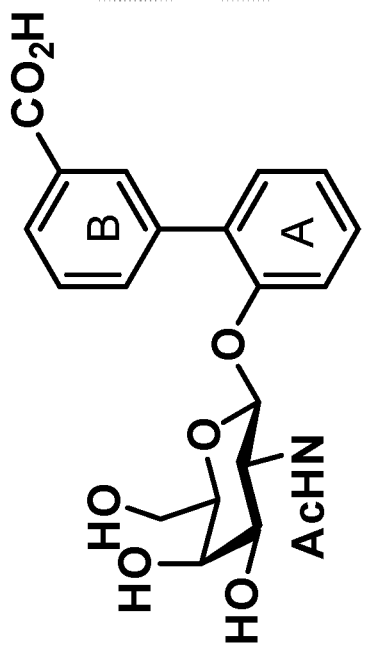

FIG. 12 shows the structure of 29β-NAc and it in complex with FmlH (PDB ID 6AS8). The COOH group on ring B engaged in charge-charge interactions with guadinium side chain of R142, while a series of direct and water-mediated H-bonds between the acetamide moiety and residue K132. Additionally, phenyl ring A forms edge-to-face π-stacking interactions with Y46.

Figure 13:
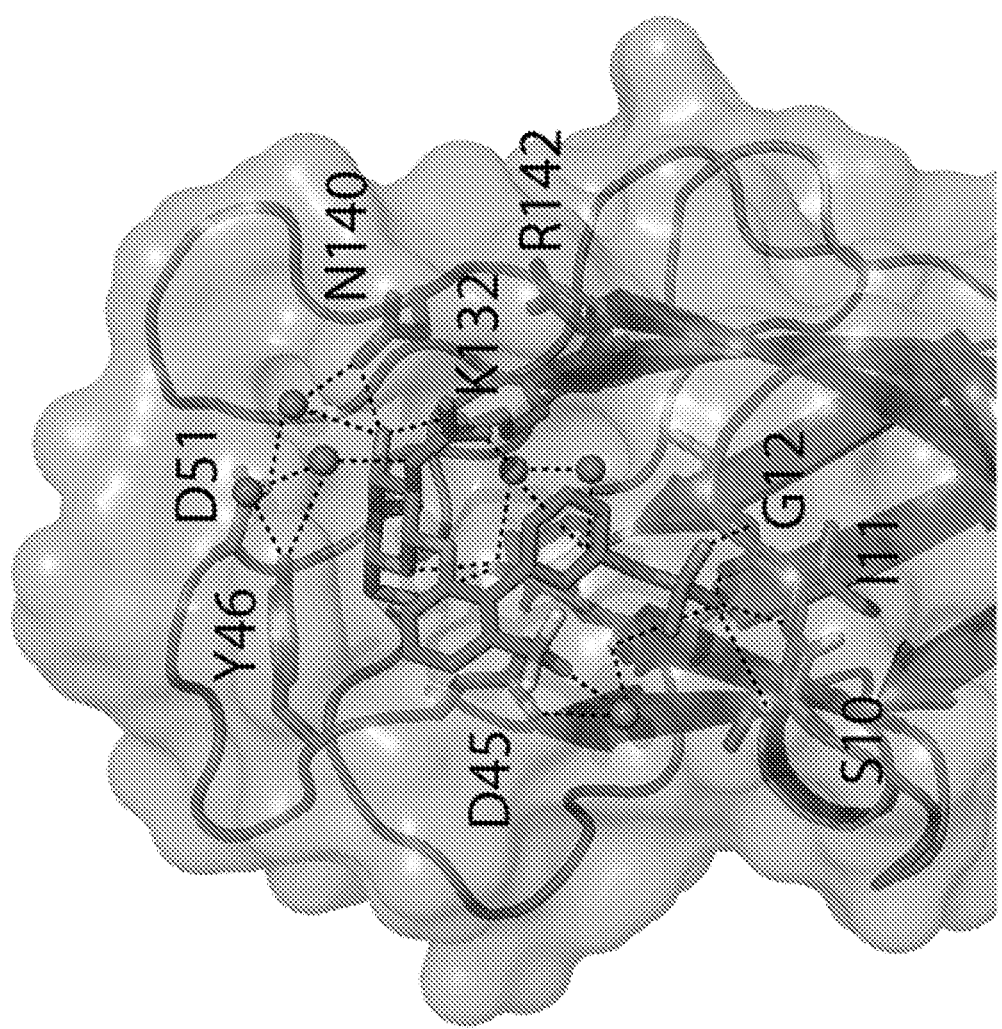

FIG. 13 shows the X-Ray crystal structure of FmlH$^{LD}$ in complex with 3090 (PDB ID 6MAW). The sulfonyl oxygens form novel contacts with the backbone of S10 and I11 in loop 1 and the backbone of S2 in the N-terminus of the mature protein. Additionally, one fluorine in the trifluoromethyl group interacts with D45.

Figure 14:
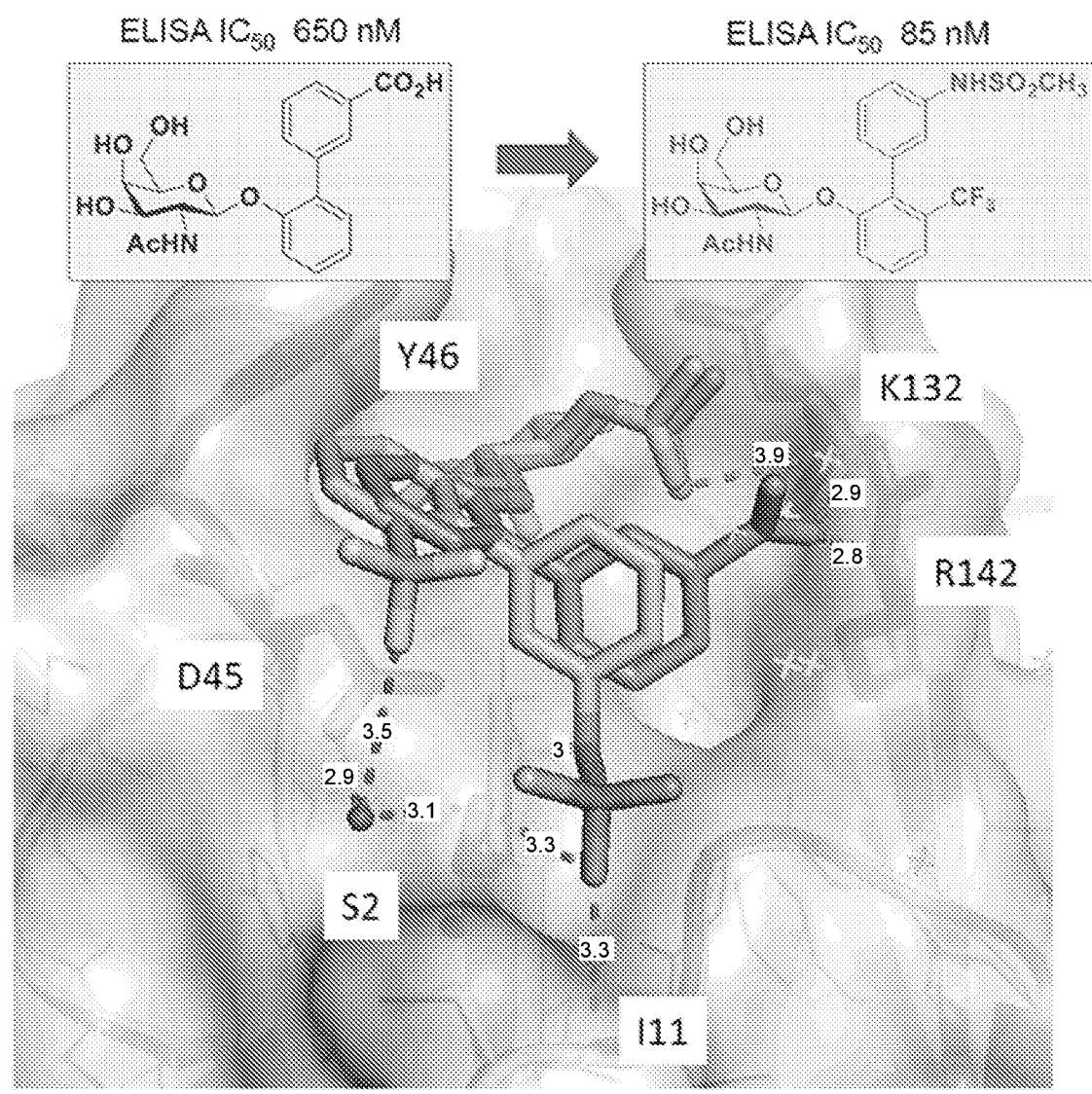

FIG. 14 is an overlay of the X-ray crystal structure of FmlH$^{LD}$ in complex with 3090 (dark grey structure) and 29β-NAc (light grey structure). Also shown are comparative structures of 29β-NAc (left) and 3090 (right) with their corresponding IC$_{50}$ values.

Figure 15:
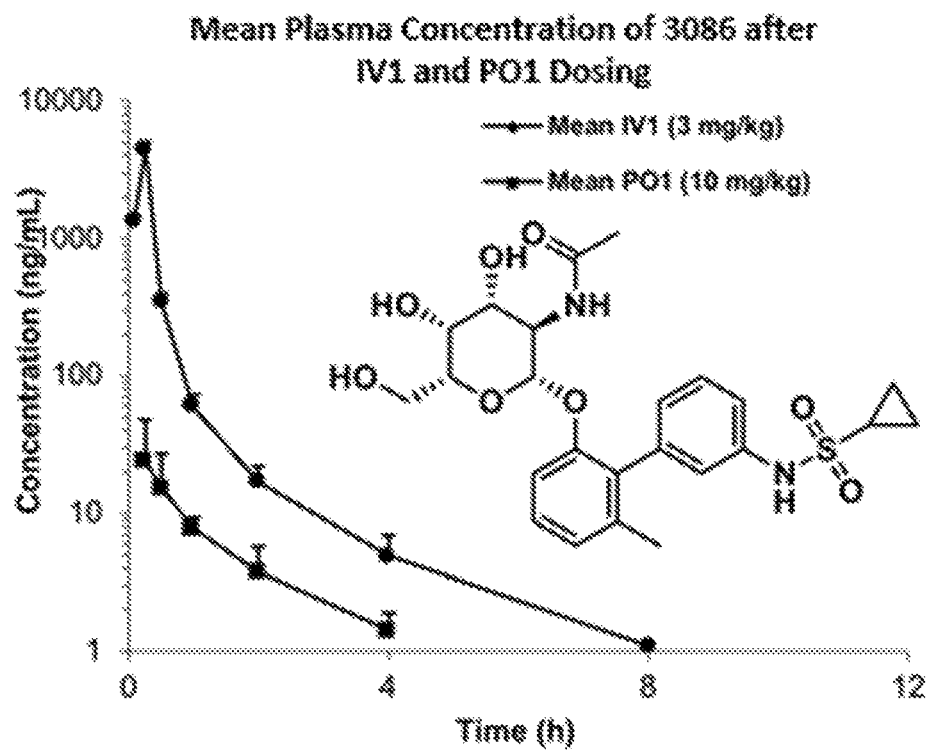
Figure 15:
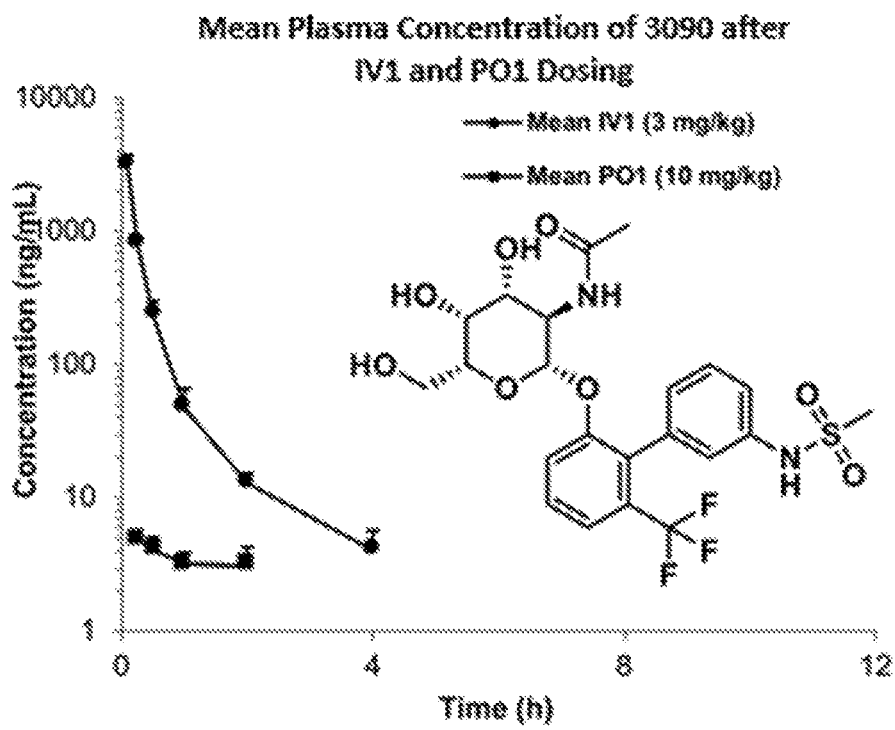

FIG. 15 shows line graphs depicting the mean plasma concentration over time of compound 3086 (panel A) or 3090 (panel B) in mice after IV and PO1 dosing.

Figure 16:
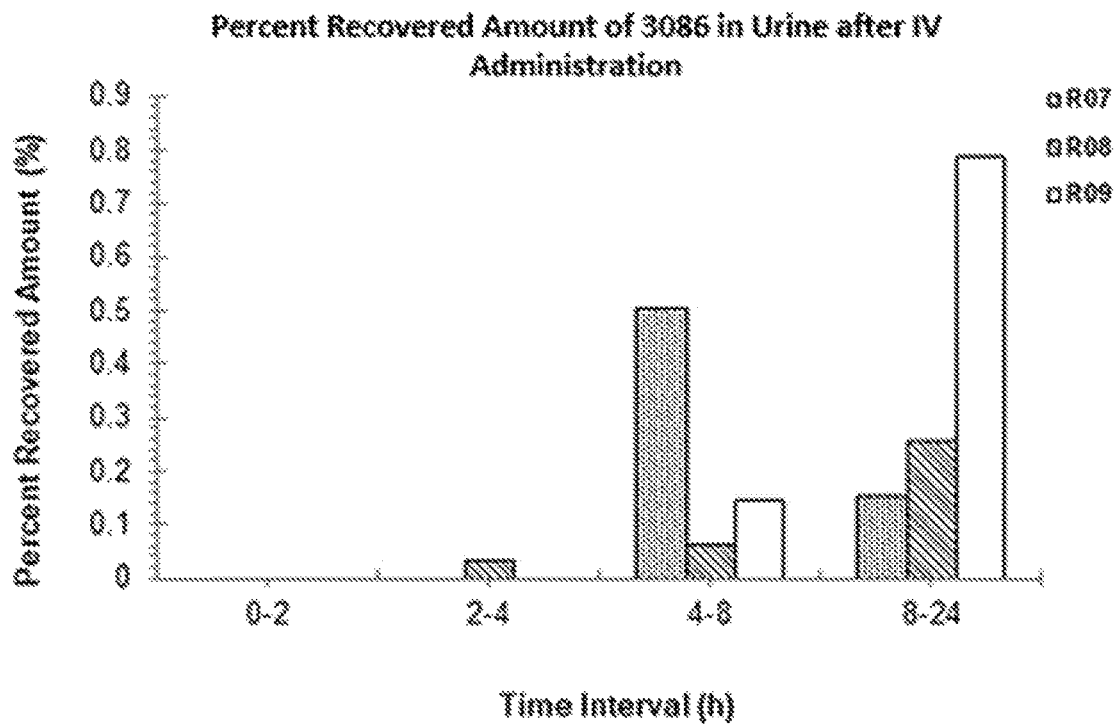
Figure 16:
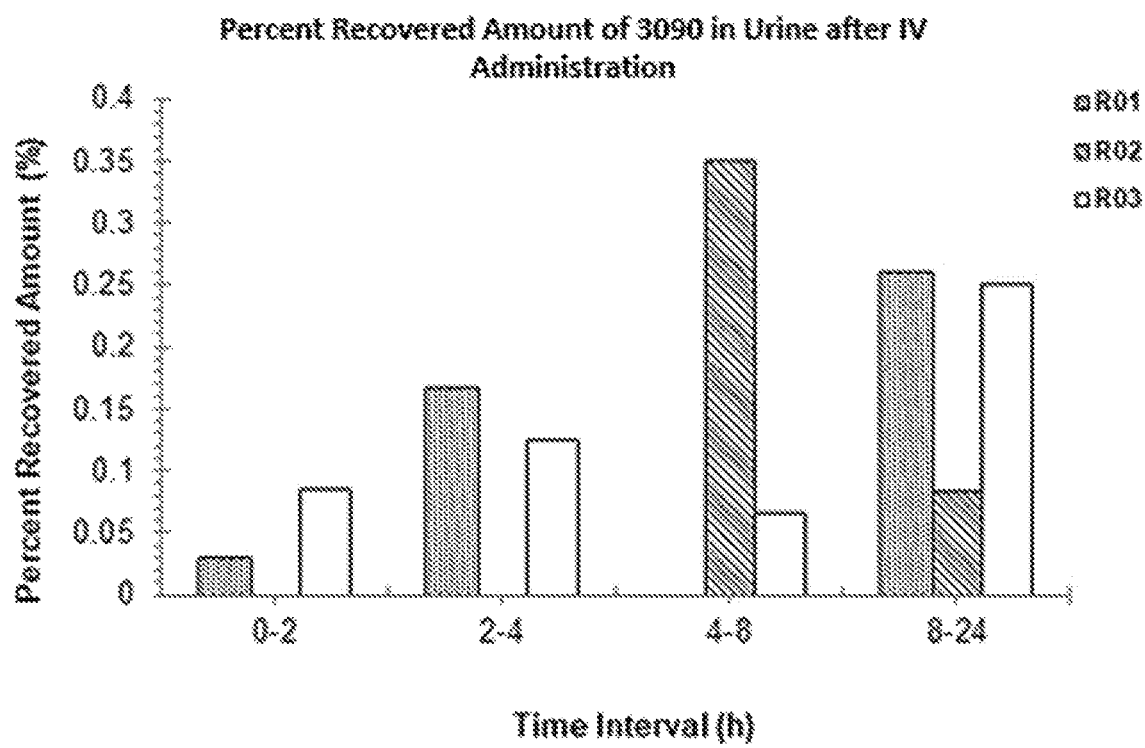

FIG. 16 shows bar graphs depicting the percent recovered amount of 3086 (panel A) or 3090 (panel B) in urine after IV administration at various time intervals after administration.

Figure 17:
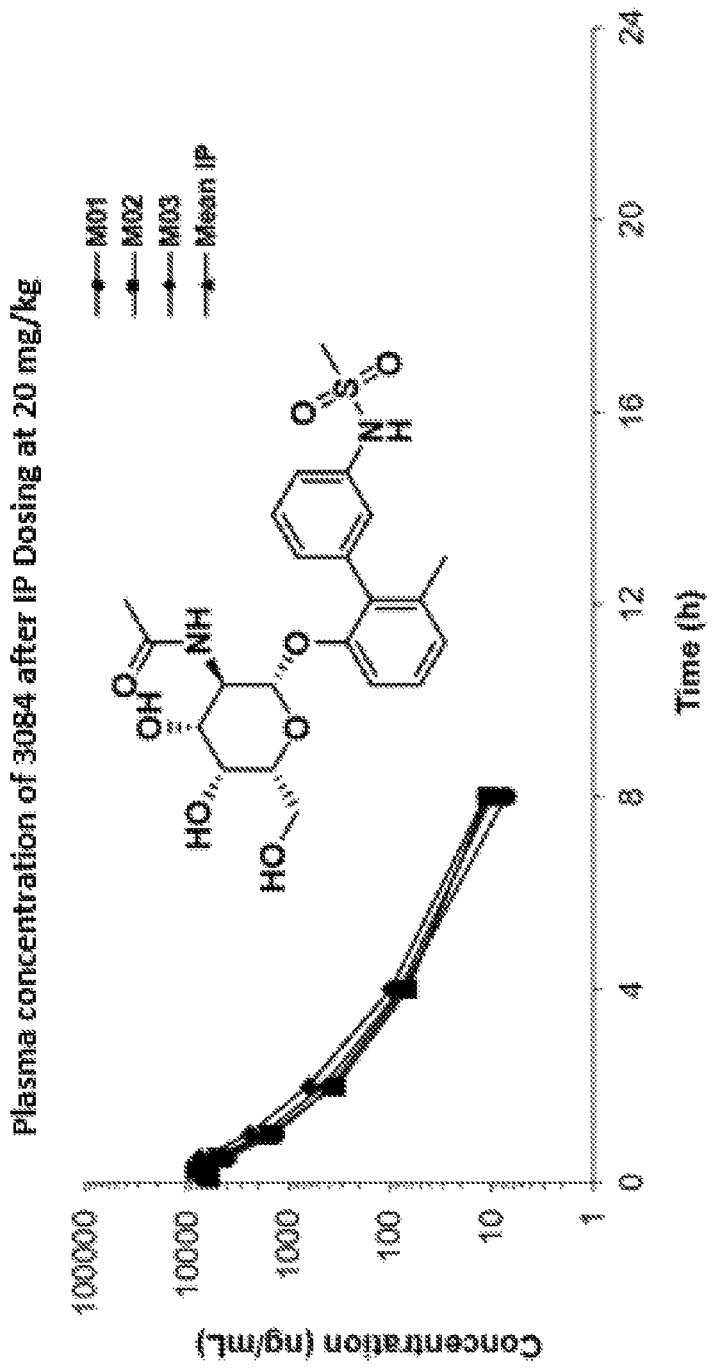

FIG. 17 is a graph depicting the plasma concentration of 3084 at various time points after IP dosing at 20 mg/kg.

Corresponding reference characters indicate corresponding parts throughout the drawings.

DETAILED DESCRIPTION OF THE INVENTION

Generally, the present invention is directed to various compounds, compositions, and methods for treating bacterial infections such as urinary tract infections (UTI).

Applicants have discovered various high-affinity galactosides (e.g., aryl galactosides and N-acetylgalactosaminosides) that bind to and inhibit FmlH, conferring significant therapeutic efficacy in the treatment of bacterial infections including chronic UTI. This discovery supports the mechanistic and therapeutic value of anti-virulence strategies that aim to define the structure-function relationships of diverse bacterial adhesins at the molecular level and to leverage these structural biology insights to high-affinity galactosides for the treatment of UTI and other bacterial infections.

Compounds:

In accordance with the present invention, various compounds useful for inhibiting FmlH include compounds of Formula (I) or salt or prodrug thereof:

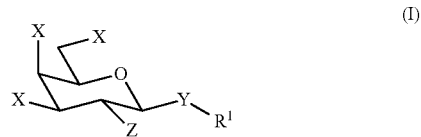
(I)

wherein:
each X is independently hydrogen, fluoro, or OR$^2$; each R$^2$ is independently hydrogen or substituted or unsubstituted hydrocarbyl;
Y is O, S, substituted or unsubstituted hydrocarbylene, substituted or unsubstituted amino, substituted or unsubstituted amido, substituted or unsubstituted thio, C(R$^3$)$_2$, (CH$_2$)$_m$, N(R$^3$), N(H)R$^3$, CO$_2$, COOR$^3$, SO$_2$, SO$_2$R$^3$, (CH$_2$)$_m$O, O(CH$_2$)$_m$, (CH$_2$)$_m$S, S(CH$_2$)$_m$, C(O), C(O)N(R$^3$), N(R$^3$)C(O), R$^3$N(R$^3$)C(O), C(O)N(R$^3$)R$^3$, SO$_2$N(R$^3$), or N(R$^3$)SO$_2$,
each R$^3$ is independently hydrogen or substituted or unsubstituted hydrocarbyl;
Z is hydrogen, OR$^4$, SR$^4$, or N(R$^4$)$_2$ (e.g., preferably NHR$^4$);
each R$^4$ is independently hydrogen or substituted or unsubstituted hydrocarbyl;
each m is independently an integer from 0 to 10; and
R$^1$ is a substituent of Formula (II), (III), (IV), (V), (VI), (VII), (VIII), (IX), (IXa), (X), (XI), (XII), or (XIII):

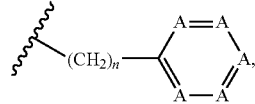
(II)

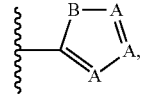
(III)

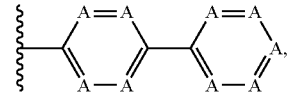
(IV)

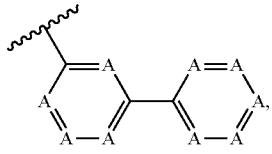
(V)

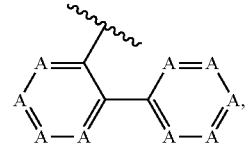
(VI)

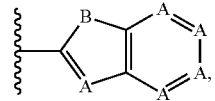
(VII)

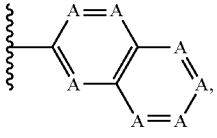
(VIII)

-continued

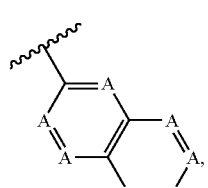
(IX)

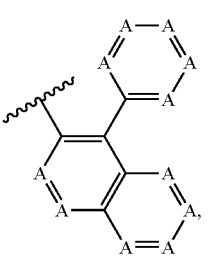
(IXa)

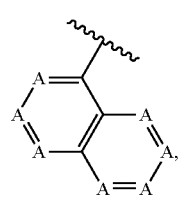
(X)

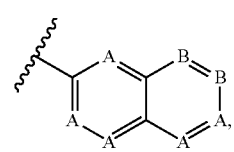
(XI)

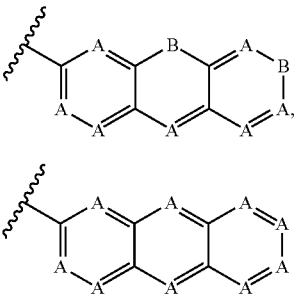
(XII)

(XIII)

wherein:
each A is independently $CR^5$ or N;
each B is independently O, S, C(O), $C(R^5)_2$, or $NR^6$;
each $R^5$ is independently hydrogen, oxygen, halo, substituted or unsubstituted amino, substituted or unsubstituted amido, substituted or unsubstituted haloalkyl, substituted or unsubstituted hydrocarbyl, substituted or unsubstituted aryl, $(CH_2)_pNO_2$, $(CH_2)_pCN$, $(CH_2)_pOR^7$, $(CH_2)_pC(R^7)_2OR^7$, $(CH_2)_pC(O)(R^7)_2$, $(CH_2)_pCO_2R^7$, $(CH_2)_pN(R^7)_2$, $(CH_2)_pSO_2R^7$, $(CH_2)_pN(SO_2R^7)_2$, $(CH_2)_pNR^7C(O)R^7$, $(CH_2)_pNR^7C(R^7)_2OR^7$, $(CH_2)_pNR^7CO_2R^7$, $(CH_2)_pNR^7C(O)N(R^7)_2$, $(CH_2)_pNR^7SO_2R^7$, $(CH_2)_pCON(R^7)_2$, $(CH_2)_pSO_2N(R^7)_2$, $(CH_2)_pN(R^7)SO_2N(R^7)_2$, or $(CH_2)_pOSO_2R'$;
each $R^6$ is independently hydrogen, substituted or unsubstituted haloalkyl, substituted or unsubstituted hydrocarbyl, substituted or unsubstituted aryl, $(CH_2)_pNO_2$, $(CH_2)_pCN$, $(CH_2)_pOR^7$, $(CH_2)_pC(R^7)_2OR^7$, $(CH_2)_pC(O)(R^7)_2$, $(CH_2)_pCO_2R^7$, $(CH_2)_pN(R^7)_2$, $(CH_2)_qN(SO_2R^7)_2$, $(CH_2)_pSO_2R^7$, $(CH_2)_qNR^7C(O)R^7$, $(CH_2)_qNR^7C(R^7)_2OR^7$, $(CH_2)_qNR^7CO_2R^7$, $(CH_2)_qNR^7C(O)N(R^7)_2$, $(CH_2)_qNR^7SO_2R^7$, $(CH_2)_pCON(R^7)_2$, $(CH_2)_pSO_2N(R^7)_2$, $(CH_2)_pN(R^7)SO_2N(R^7)_2$, or $(CH_2)_pOSO_2R^7$;
each $R^7$ is independently hydrogen or substituted or unsubstituted hydrocarbyl,
each n is independently an integer from 0 to 10,
each p is independently an integer from 0 to 10;
each q is independently an integer from 1 to 10 with the proviso that:
(a) when (i) each X is OH, (ii) Y is O, (iii) Z is $OR^4$, (iv) $R^4$ is hydrogen, (v) $R^1$ is a substituent of Formula (II), and (vi) n is 0, then $R^1$ is not unsubstituted phenyl and each $R^5$ is not nitro or amino;
(b) when (i) each X is OH, (ii) Y is O, (iii) Z is $OR^4$, (iv) $R^4$ is hydrogen, (v) $R^1$ is a substituent of Formula (VII), and (v) B is N, then $R^1$ is not unsubstituted indolyl and each $R^5$ is not chlorine;
(c) when (i) each X is OH, (ii) Y is O, (iii) Z is $OR^4$, (iv) $R^4$ is hydrogen, and (v) $R^1$ is a substituent of Formula (IX), then $R^1$ is not unsubstituted biphenyl;
(d) when (i) each X is OH, (ii) Y is O, (iii) Z is $OR^4$, (iv) $R^4$ is hydrogen, and (v) $R^1$ is a substituent of Formula (X), then $R^1$ is not

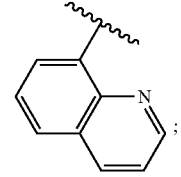 [SMILES: *c1cccc2cccnc12]

(e) when (i) each X is OH, (ii) Y is O, (iii) Z is $OR^4$, (iv) $R^4$ is hydrogen, and (v) $R^1$ is a substituent of Formula (XI) or (XII), then each B is not C(O);
(f) when (i) each X is OH, (ii) Y is S, (iii) Z is $OR^4$, (iv) $R^4$ is hydrogen, and (v) $R^1$ is a substituent of Formula (II), and (vi) n is 2, then $R^1$ is not unsubstituted phenyl; and
(g) when (i) each X is OH, (ii) Y is O, (iii) Z is $NHC(O)CH_3$, (iv) $R^1$ is a substituent of Formula (II), and (v) n is 0, then $R^1$ is not unsubstituted phenyl and each $R^5$ is not nitro.

In various embodiments, each X is independently OH. In various embodiments each X is independently $OR^2$ and each $R^2$ is independently hydrogen, substituted or unsubstituted $C_1$-$C_{30}$ alkyl. In some embodiments, $R^2$ is independently hydrogen or $C_1$-$C_{30}$ alkyl.

In various embodiments, Y is O, S, $C(R^3)_2$, $(CH_2)_m$, $N(R^3)$, $N(H)R^3$, $CO_2$, $COOR^3$, $SO_2$, $SO_2R^3$, $(CH_2)_mO$, $O(CH_2)_m$, $(CH_2)_mS$, $S(CH_2)_m$, C(O), $C(O)N(R^3)$, $N(R^3)C(O)$, $R^3N(R^3)C(O)$, $C(O)N(R^3)R^3$, $SO_2N(R^3)$, or $N(R^3)SO_2$. In some embodiments, m is an integer between 0 and 5. In these and other embodiments, each $R^3$ is independently hydrogen or substituted or unsubstituted $C_1$-$C_{30}$ alkyl. In some embodiments, each $R^3$ is independently hydrogen or $C(R^8)_2C(O)N(R^9)_2$, wherein each $R^8$ and $R^9$ are independently hydrogen, $C_1$-$C_{30}$ alkyl, or aryl. In certain embodiments, each $R^8$ and $R^9$ are independently hydrogen or $C_1$-$C_6$ alkyl.

In various embodiments, Z is $OR^4$ or $NHR^4$. In some embodiments, each $R^4$ is independently hydrogen or substituted or unsubstituted $C_1$-$C_{30}$ alkyl. In further embodiments, each $R^4$ is independently hydrogen or $C_1$-$C_{30}$ alkyl (e.g., $C_1$-$C_{20}$ alkyl, $C_1$-$C_{10}$ alkyl, or $C_1$-$C_6$ alkyl), $SO_2R^{10}$, or C(O)R$^{10}$, wherein R$^{10}$ is a C$_1$-C$_{10}$ alkyl or haloalkyl. In some embodiments, Z is OH, NHSO$_2$CF$_3$, NHC(O)CF$_3$, or NHC(O)CH$_3$. In certain embodiments, Z is NHC(O)CH$_3$.

In various embodiments, n is independently an integer from 0 to 3. In some embodiments, n is 2. In certain embodiments, p is independently an integer from 0 to 3 and/or q is independently an integer from 1 to 3. In some embodiments, p is 0.

In various embodiments, each A is CR$^5$ or N and each R$^5$ is independently H, O, CN, OR$^7$, NO$_2$, C(R$^7$)$_2$OR$^7$, C(O)(R$^7$)$_2$, CO$_2$R$^7$, N(R$^7$)$_2$, N(SO$_2$R$^7$)$_2$, SO$_2$R$^7$, NR$^7$C(O)R$^7$, NR$^7$C(R$^7$)$_2$OR$^7$, NR$^7$CO$_2$R$^7$, NR$^7$C(O)N(R$^7$)$_2$, NR$^7$SO$_2$R$^7$, CON(R$^7$)$_2$, SO$_2$N(R$^7$)$_2$, OSO$_2$R$^7$, N(R$^7$)SO$_2$N(R$^7$)$_2$, halo, substituted or unsubstituted haloalkyl, or substituted or unsubstituted aryl. In some embodiments, each R$^5$ is independently H, O, CN, NO$_2$, OR$^7$, CH$_2$OR$^7$, CO(R$^7$)$_2$, CO$_2$R$^7$, N(R$^7$)$_2$, SO$_2$R$^7$, NR$^7$C(O)R$^7$, NR$^7$CO$_2$R$^7$, NR$^7$SO$_2$R$^7$, CON(R$^7$)$_2$, OSO$_2$R$^7$, N(R$^7$)SO$_2$N(R$^7$)$_2$, N(SO$_2$R$^7$)$_2$, halo, haloalkyl, or substituted or unsubstituted aryl. In further embodiments, each R$^5$ is independently H, F, Cl, O, NO$_2$, CONHCH$_3$, OH, OCH$_3$, CO(CH$_3$)$_2$, CONH$_2$, CN, CF$_3$, NHSO$_2$CH$_3$, NHSO$_2$CF$_3$, NHSO$_2$N(R$^7$)$_2$CO$_2$H, CO$_2$CH$_3$, CO$_2$CH$_2$CH$_3$, SO$_2$CH$_3$, NHCOCH$_3$, OSO$_2$CH$_3$, NHSO$_2$R$^7$, N(SO$_2$R$^7$)$_2$, benzyl, phenyl, a hydroxyl-substituted phenyl (e.g., a radical of phenol, pyrocatechol or benzene-1,2,3-triol) or a alkoxyl-substituted phenyl (e.g., a radical of 2-methyoxyphenol).

In various embodiments, each B is independently O, S, C(O), or NR$^6$. In some embodiments, R$^6$ is independently hydrogen, substituted or unsubstituted haloalkyl, substituted or unsubstituted aryl, CN, OR$^7$, C(R$^7$)$_2$OR$^7$, C(O)R$^7$, CO$_2$R$^7$, CON(R$^7$)$_2$, SO$_2$R$^7$, C(O)R$^7$, SO$_2$N(R$^7$)$_2$, or OSO$_2$R$^7$. In certain embodiments, each R$^6$ is independently hydrogen, substituted or unsubstituted aryl, CN, OR$^7$, CH$_2$OR$^7$, C(O)(R$^7$)$_2$, CO$_2$R$^7$, CF$_3$, or CON(R$^7$)$_2$.

In various embodiments, each R$^7$ is independently hydrogen, substituted or unsubstituted C$_1$-C$_{30}$ alkyl, substituted or unsubstituted cycloalkyl, substituted or unsubstituted haloalkyl, substituted or unsubstituted aryl, or substituted or unsubstituted aralkyl. In some embodiments, each R$^7$ is independently hydrogen, phenyl, benzyl, halo-substituted phenyl, CF$_3$, C$_1$-C$_{30}$ alkyl, or a C$_3$-C$_{12}$ cycloalkyl (e.g., cyclopropyl, cyclobutyl, cyclopentyl, or cyclohexyl).

In various embodiments, when the compound of Formula (I) has the following structure:

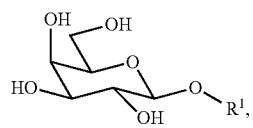

then R$^1$ is a substituent of Formula (III), (IV), (V), (VI), (VIII), (IXa), or (XIII):

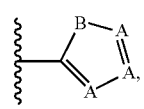

(III)

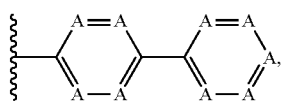

(IV)

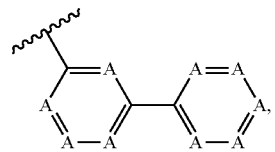

(V)

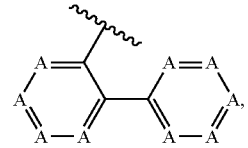

(VI)

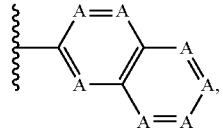

(VIII)

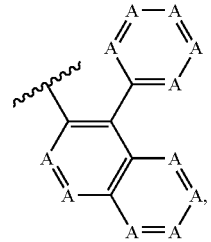

(IXa)

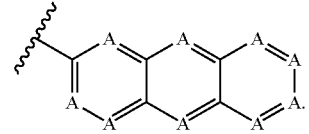

(XIII)

In other embodiments, when the compound of Formula (I) has the following structure:

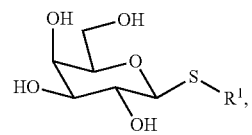

then R$^1$ is a substituent of Formula (III), (IV), (V), (VI), (VII), (VIII), (IX), (IXa), (X), (XI), (XII), or (XIII):

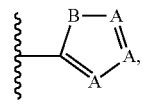

(III)

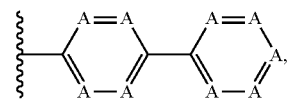

(IV)

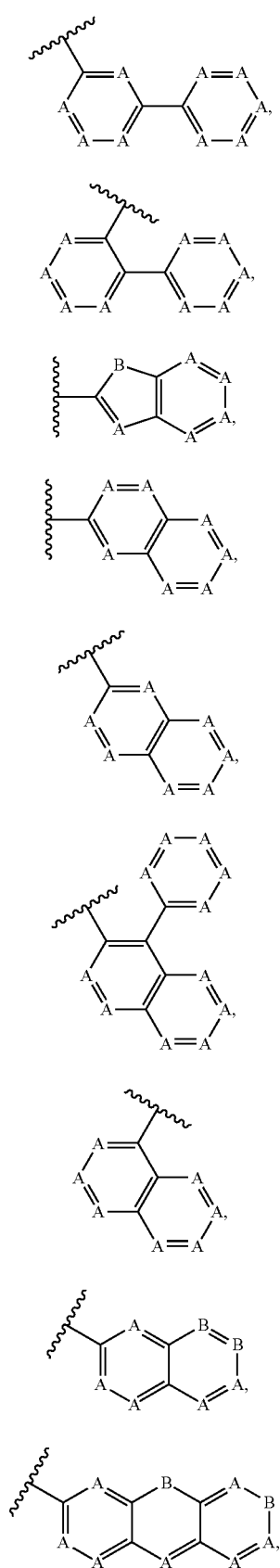
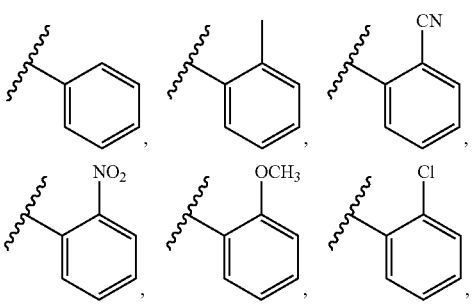
In various embodiments, $R^1$ is selected from the group consisting of:

-continued
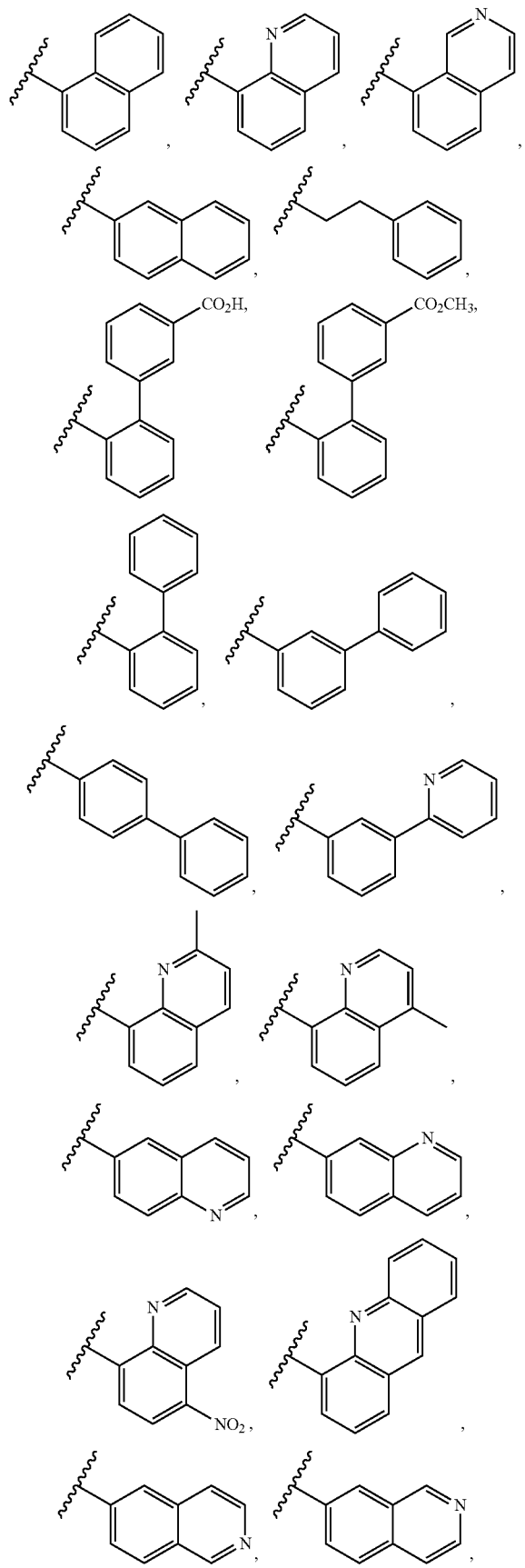
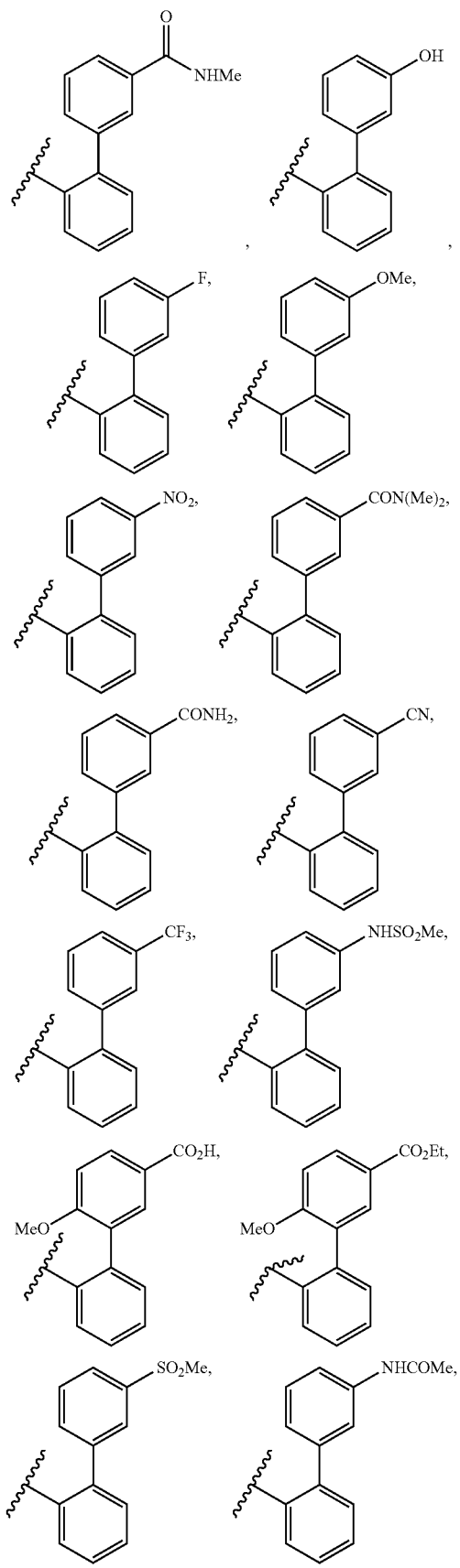

-continued
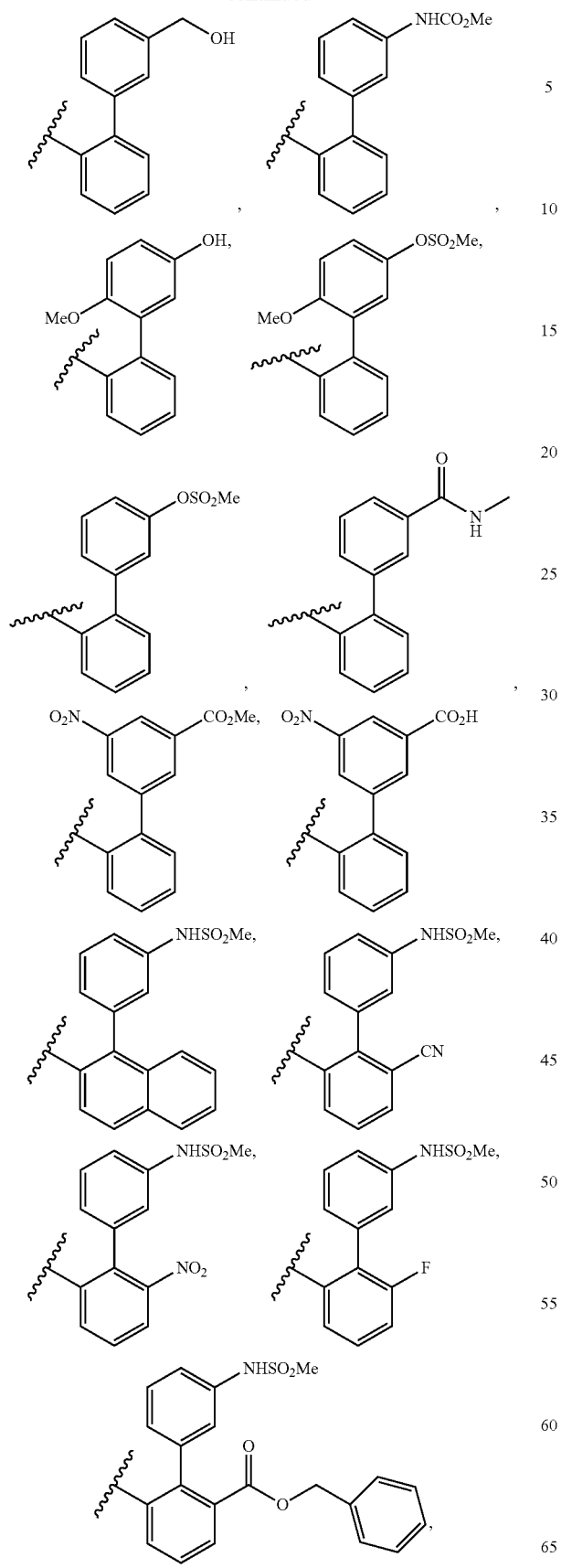
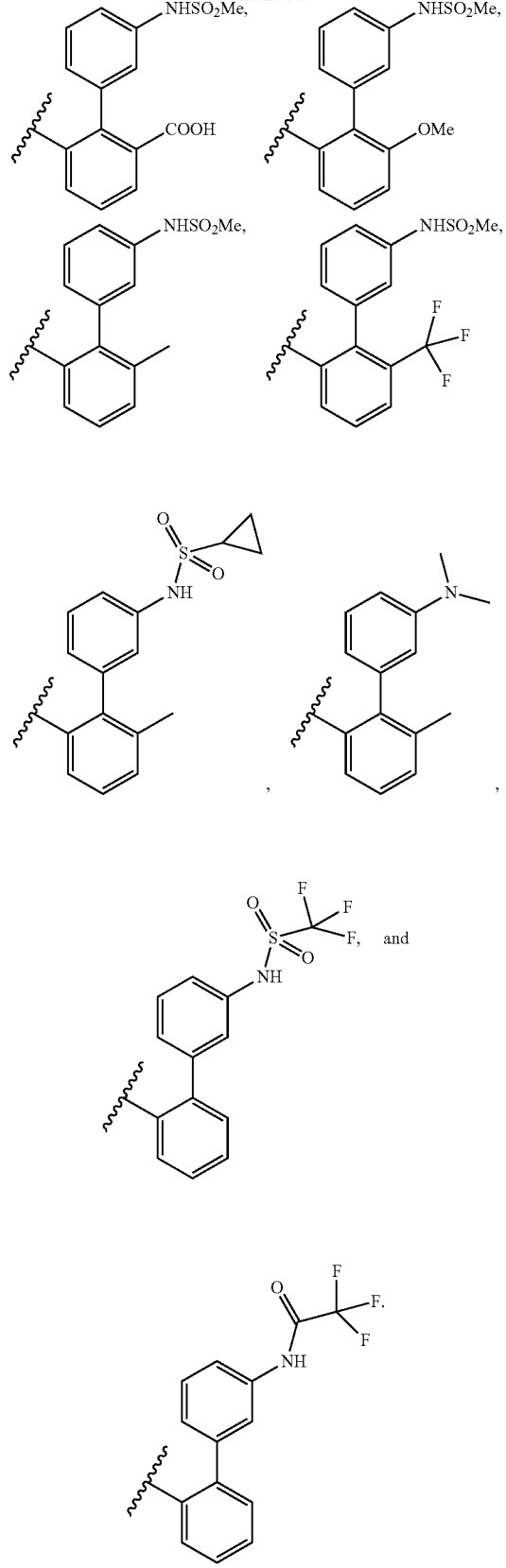
In various embodiments, $R^1$ is selected from the group consisting of:

-continued
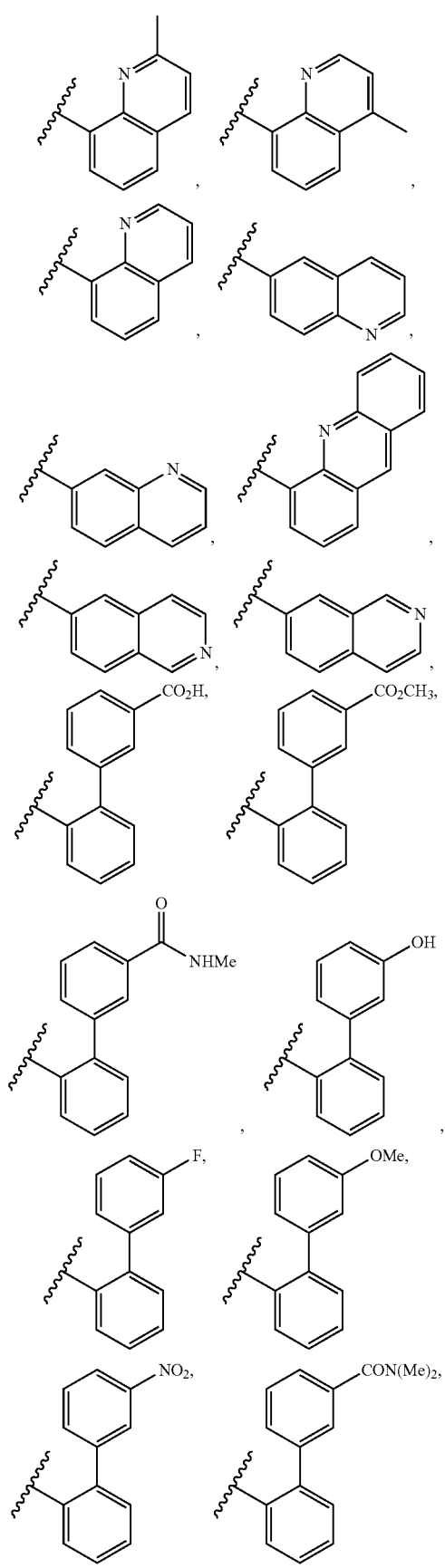
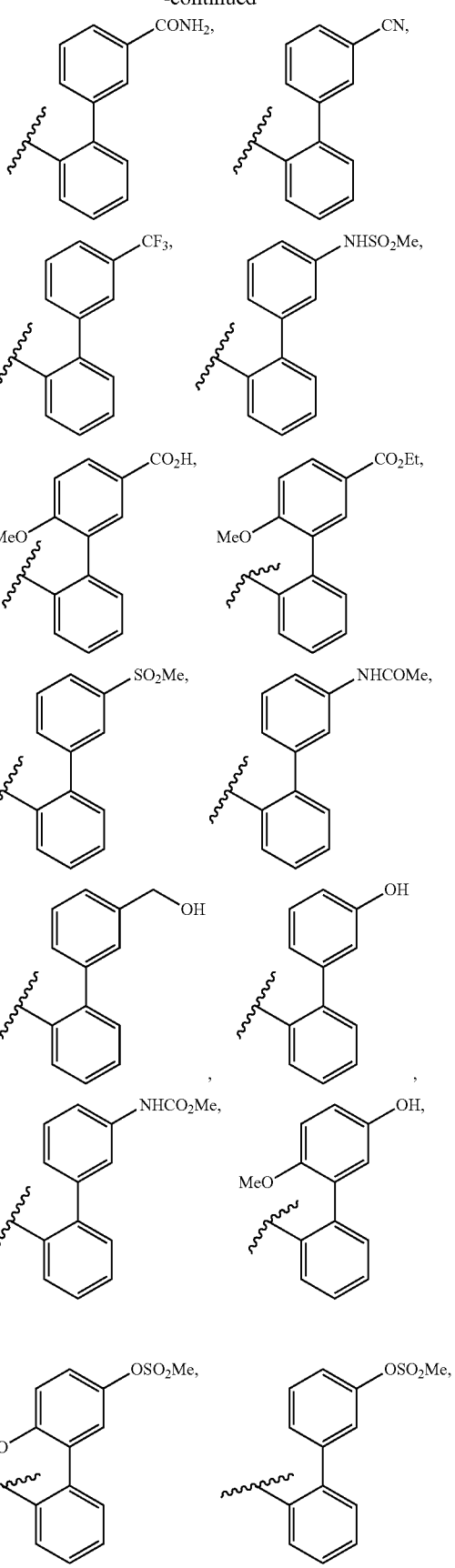

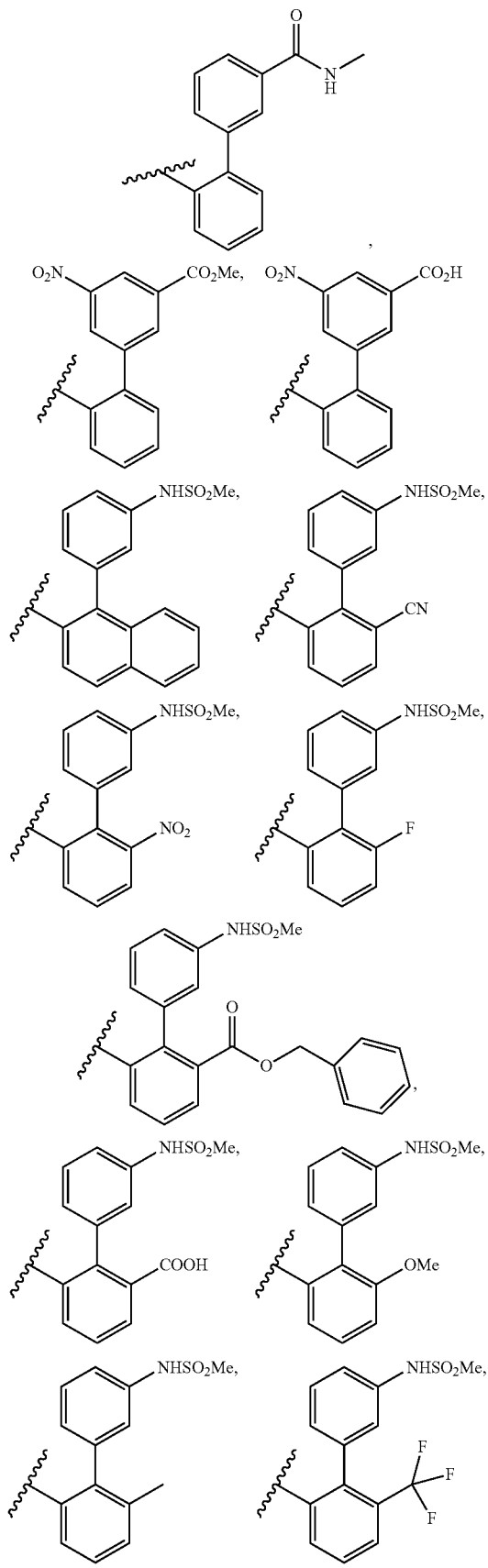
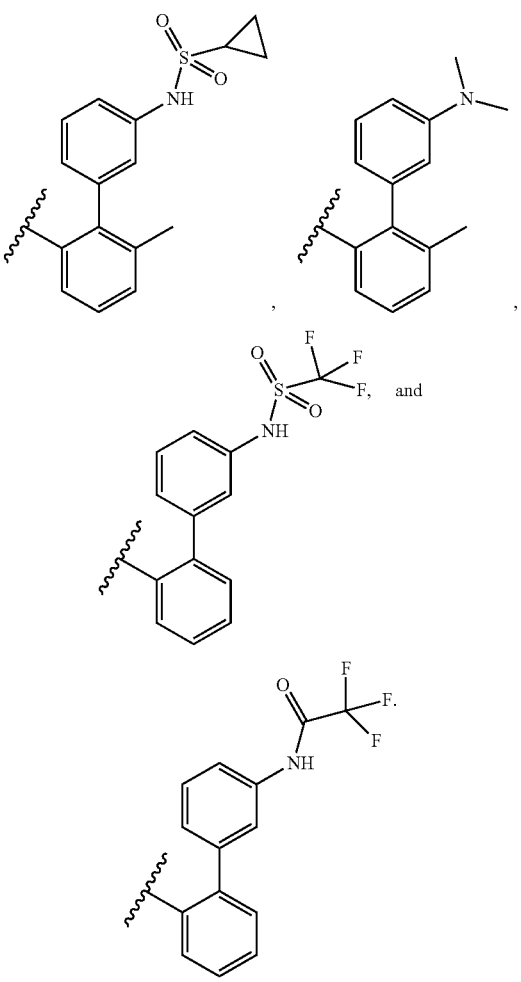
In various embodiments, the compound of Formula (I) is selected from the group consisting of:
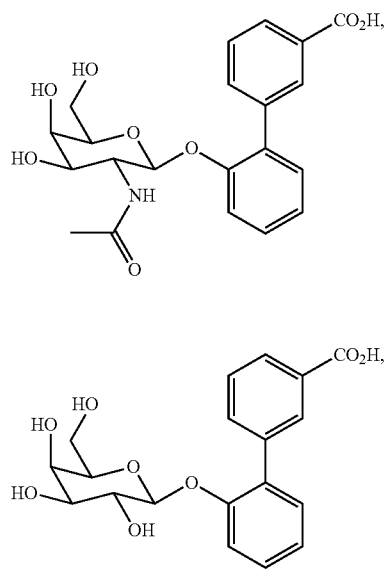

-continued
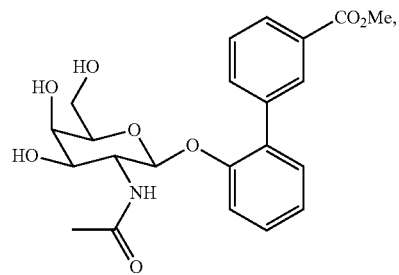
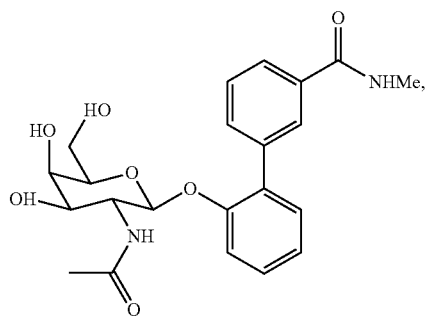
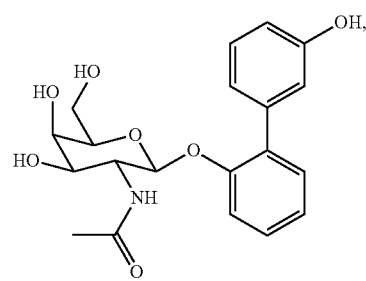
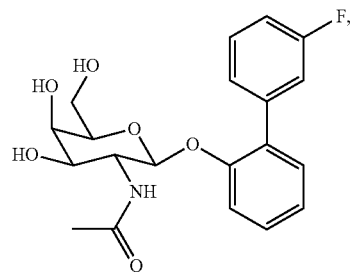
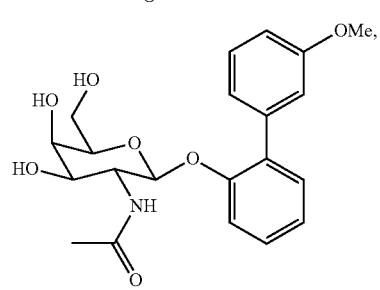
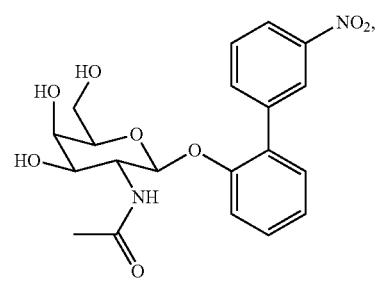
-continued
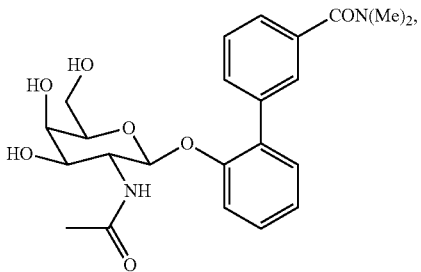
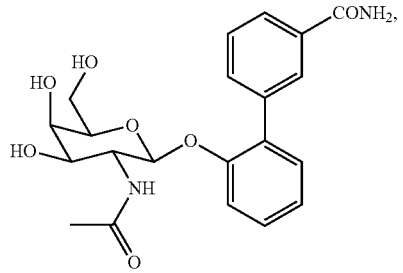
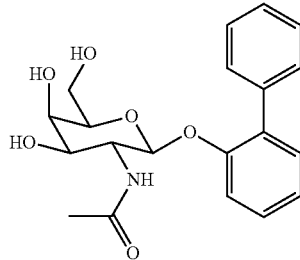
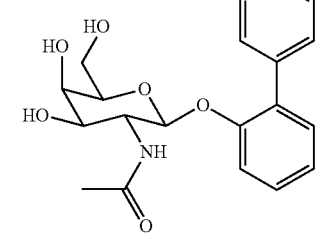
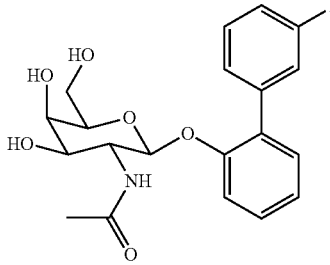
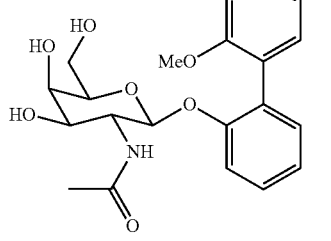

-continued
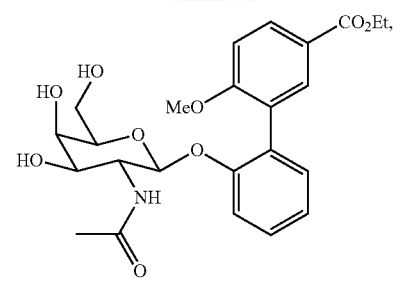
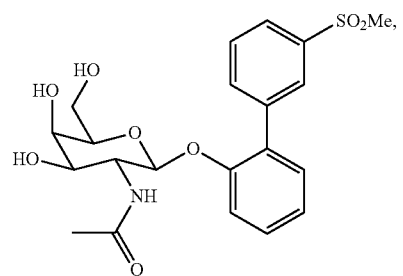
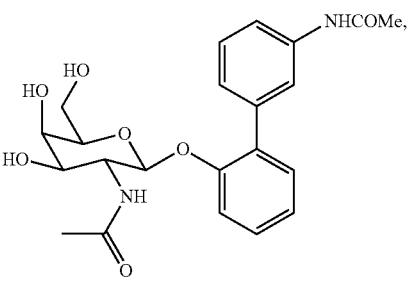
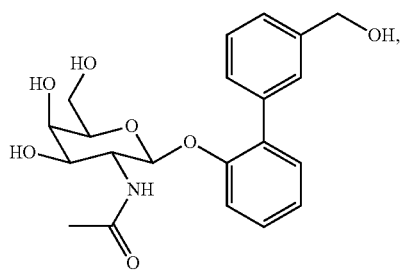
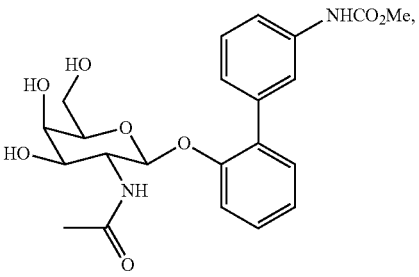
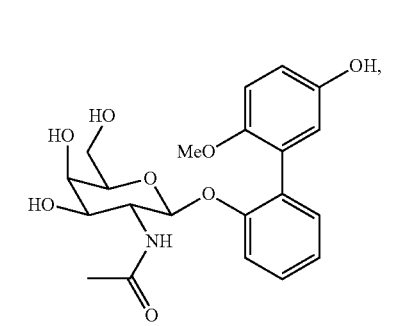
-continued
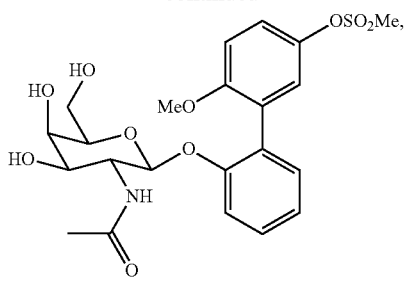
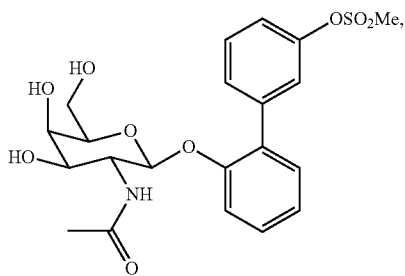
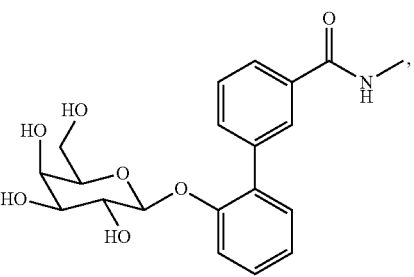
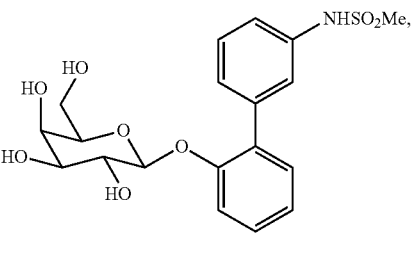
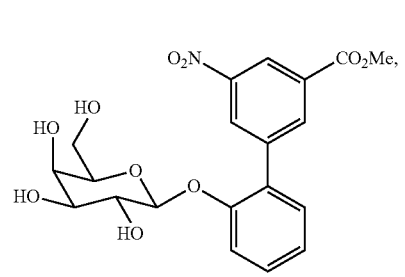
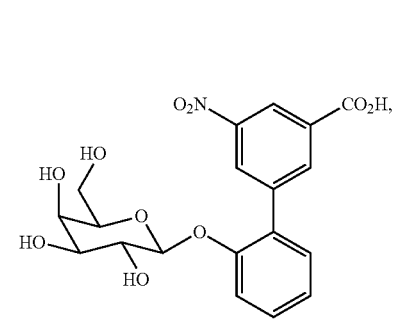

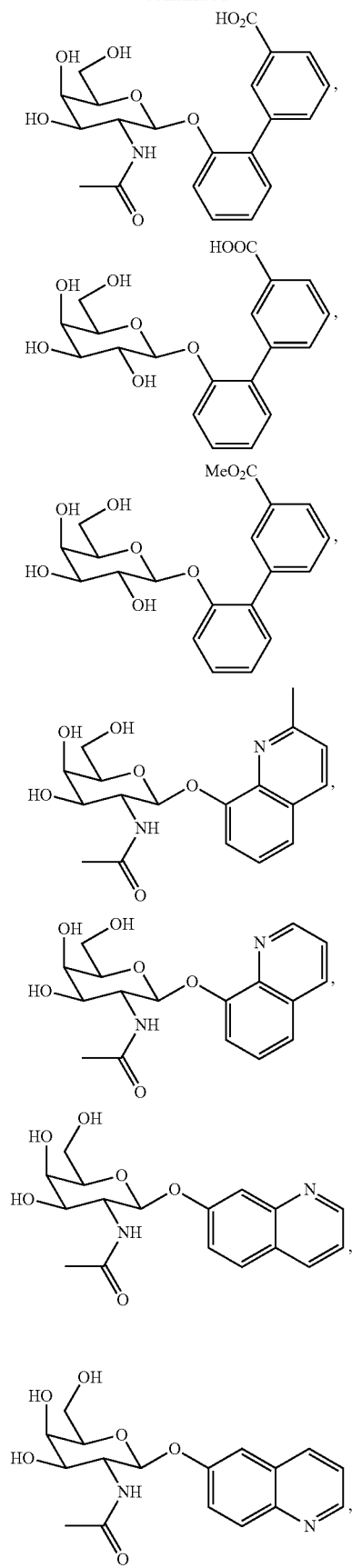
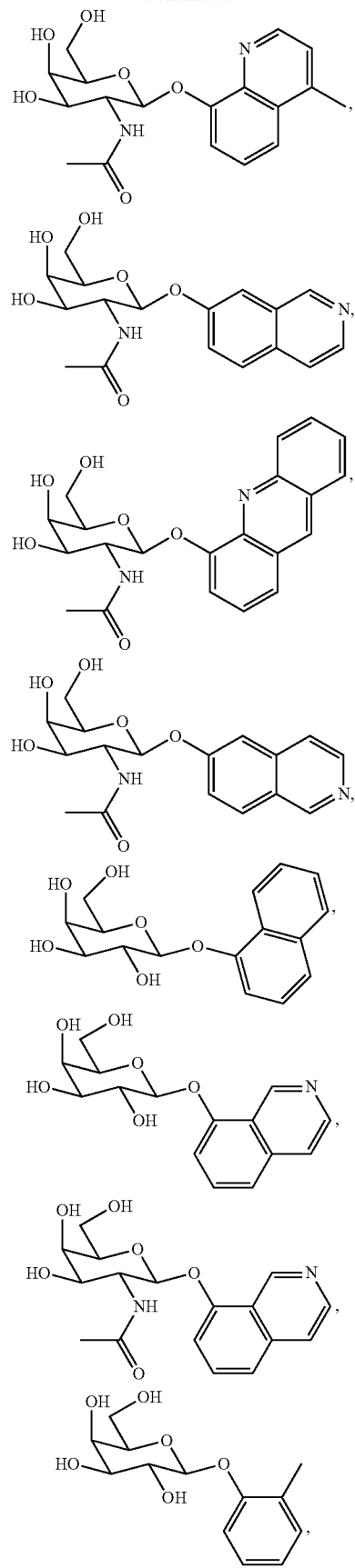

-continued
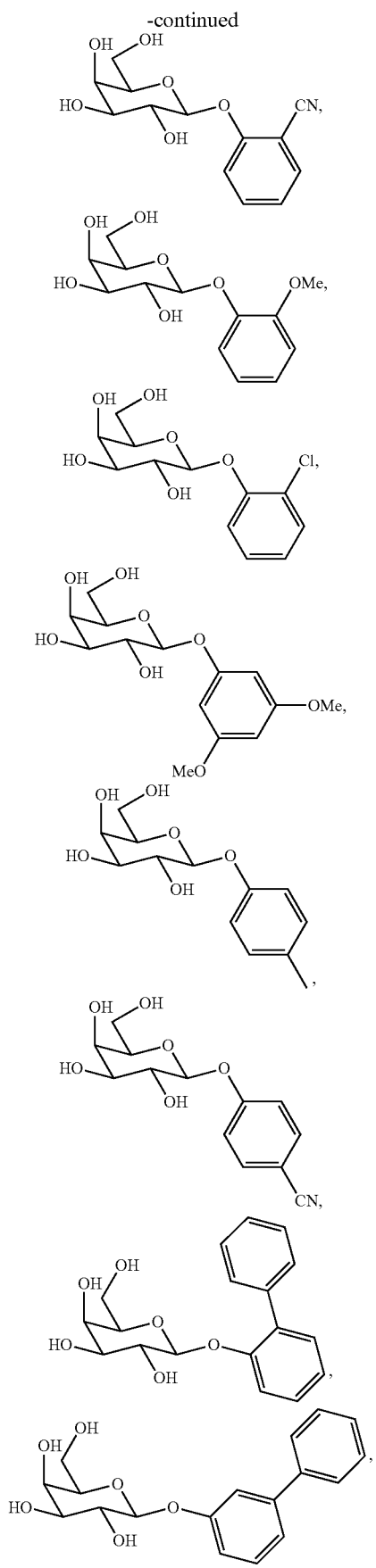
-continued
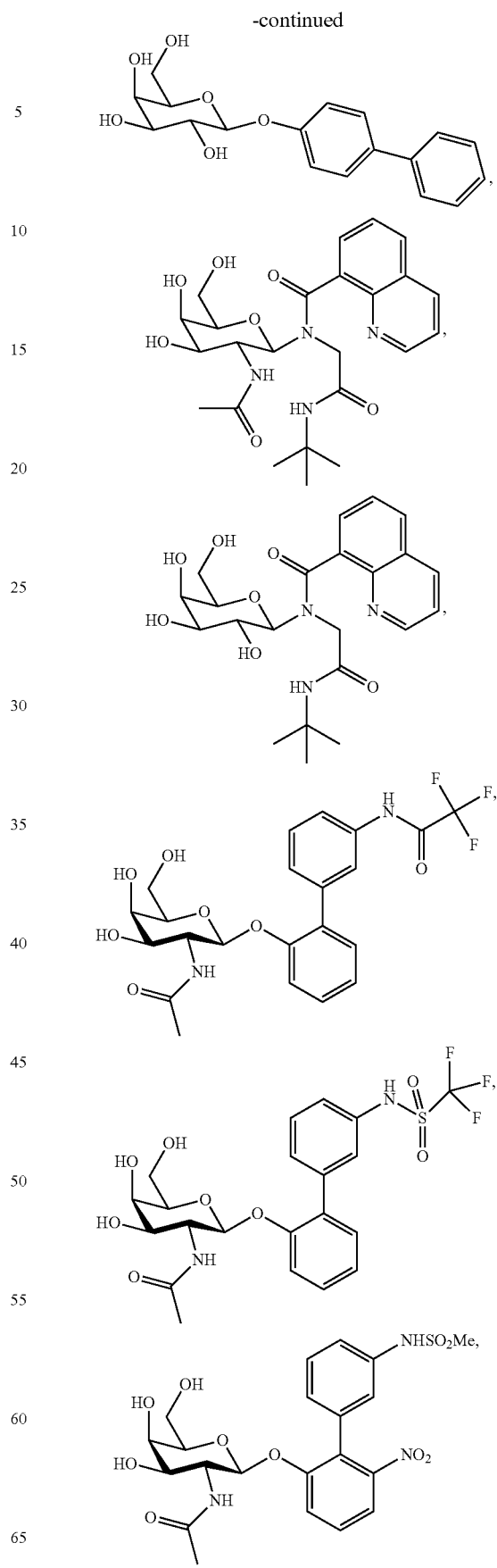

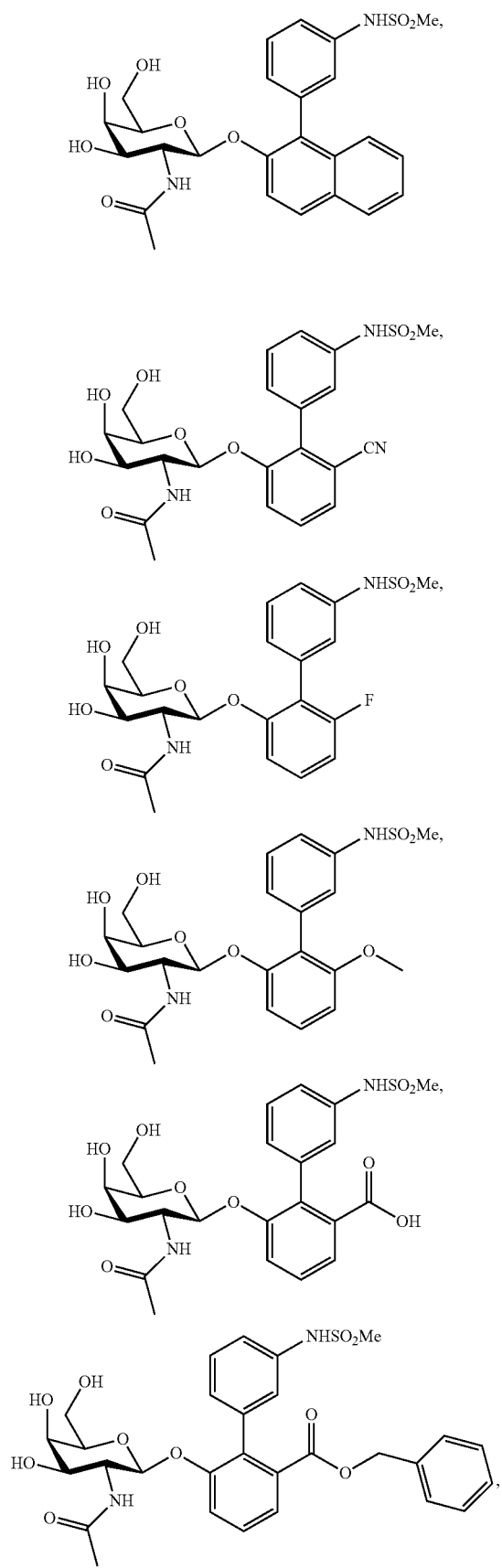
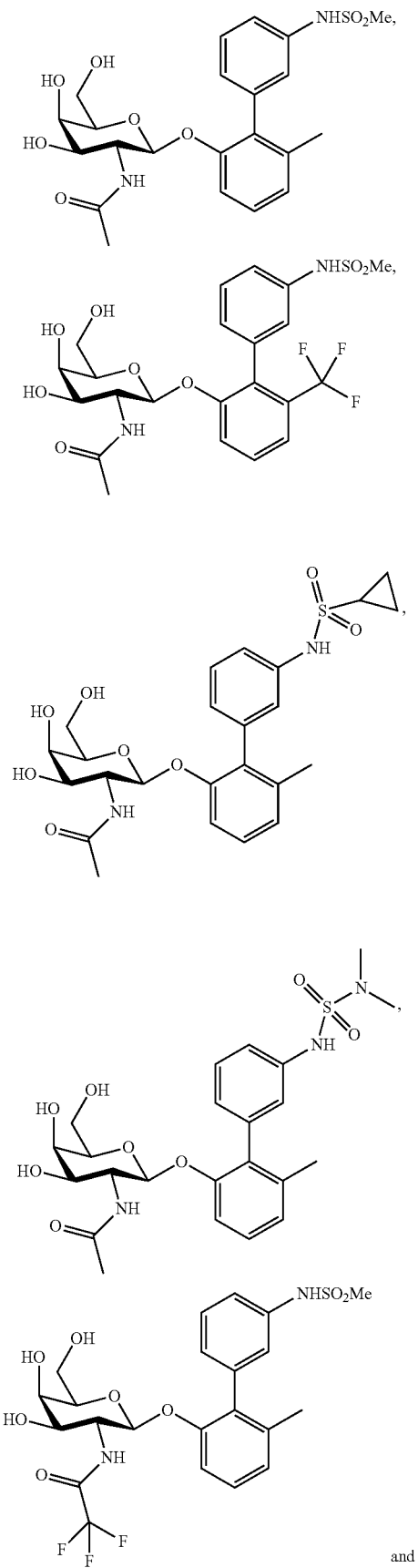

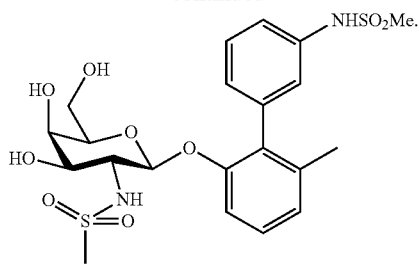
In various embodiments, the compound is selected from the group consisting of:
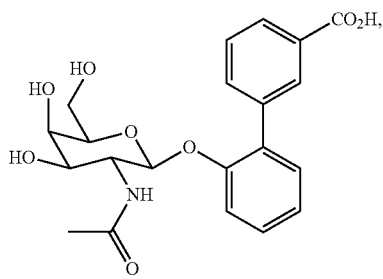
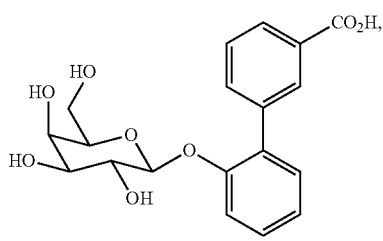
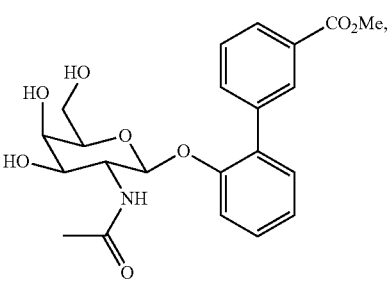
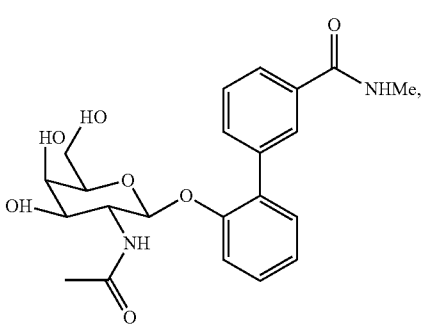
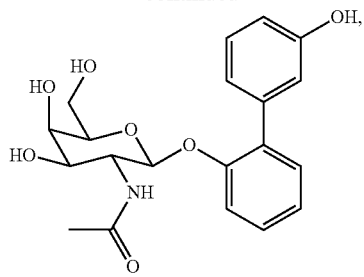
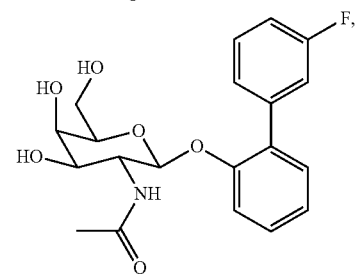
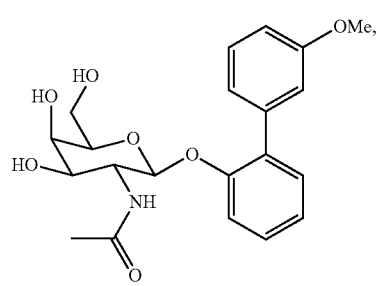
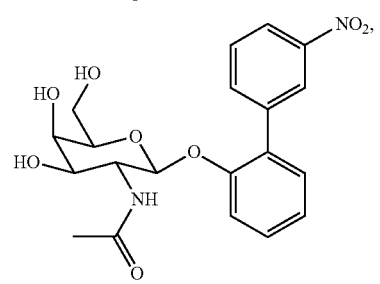
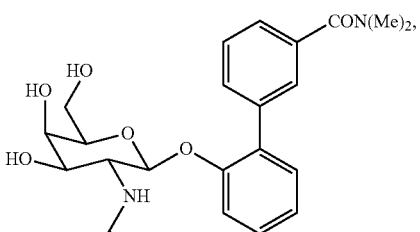
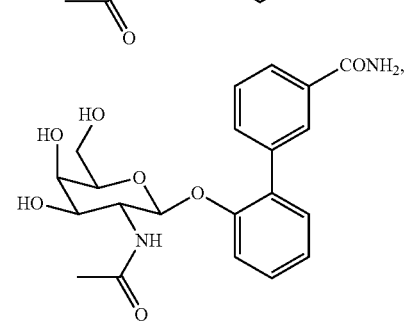

-continued
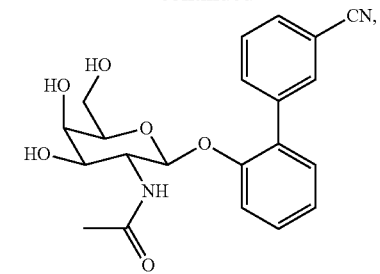
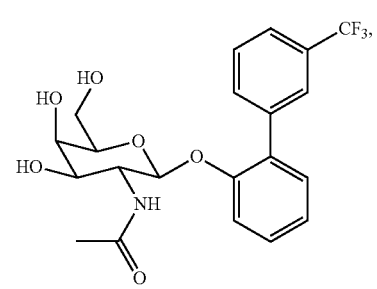
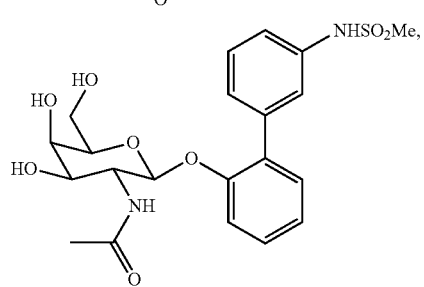
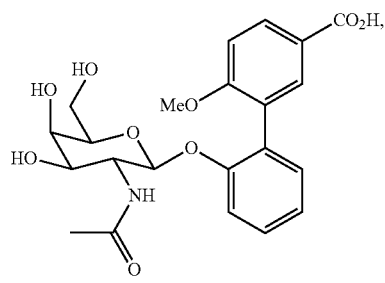
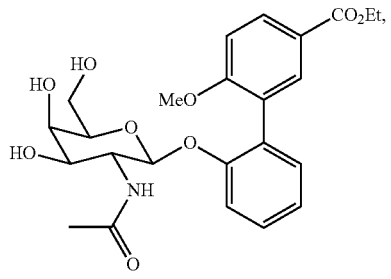
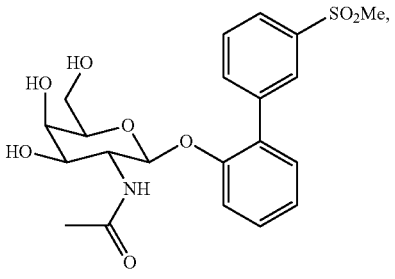
-continued

-continued
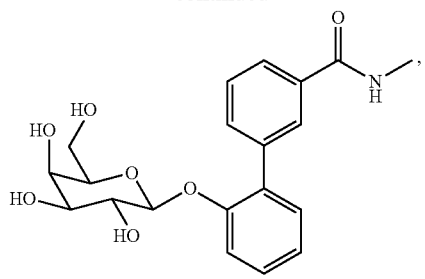
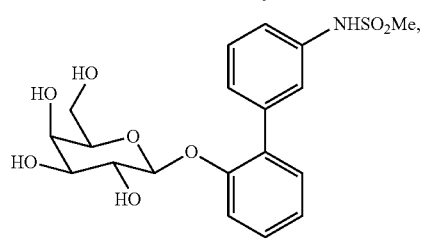
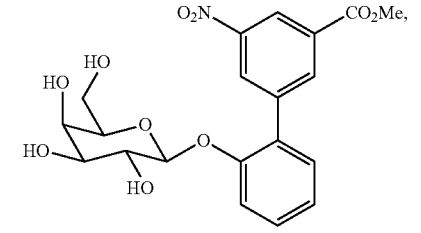
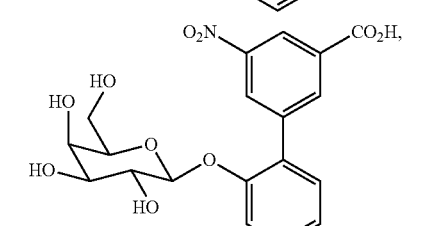
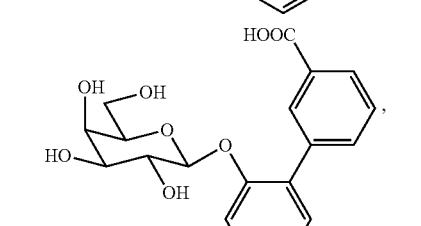
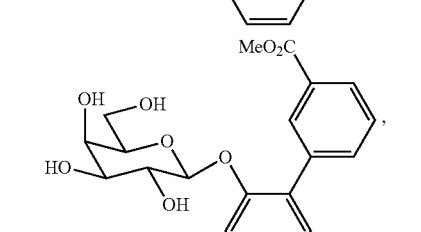
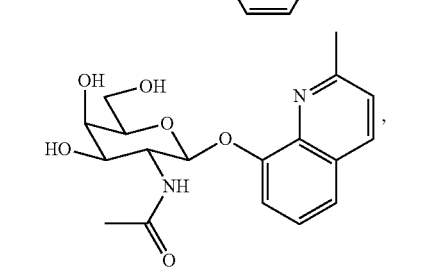
-continued
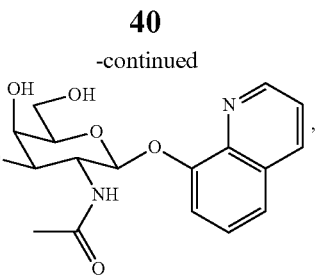
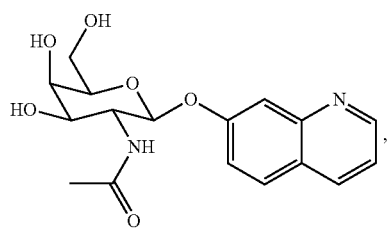
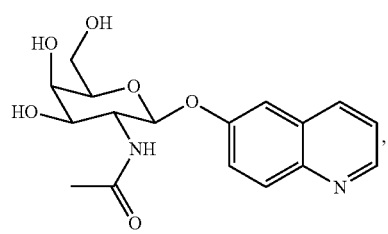
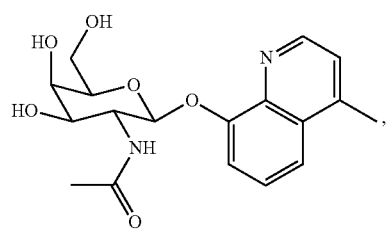
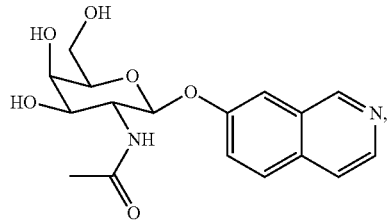
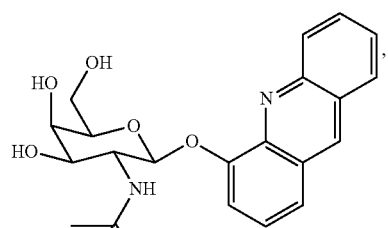
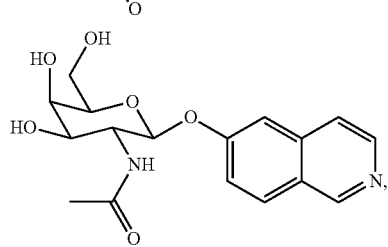

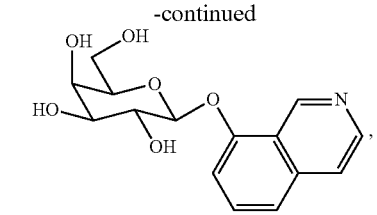
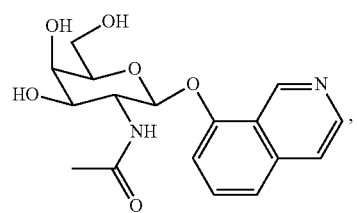
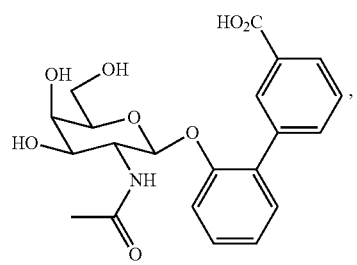
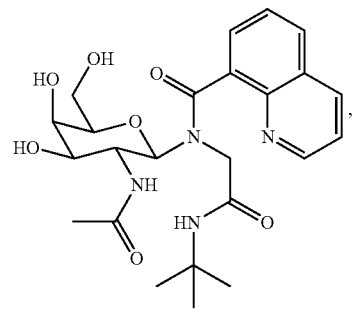
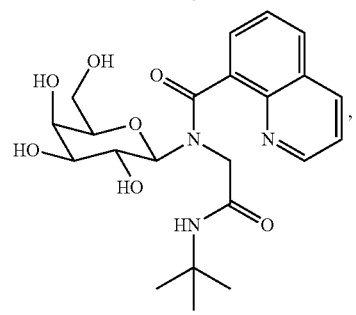
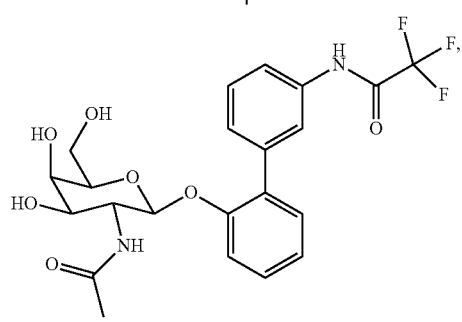
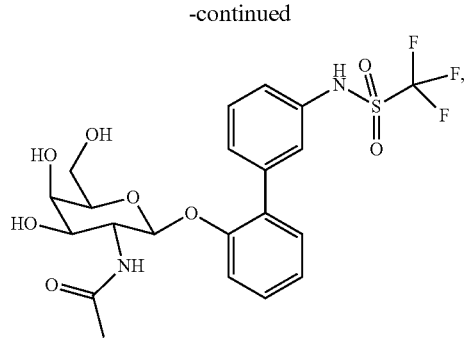
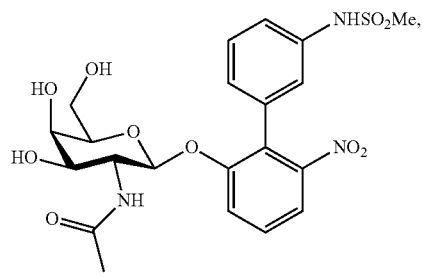
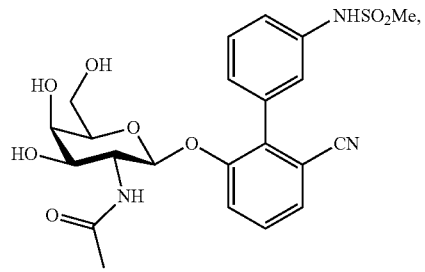
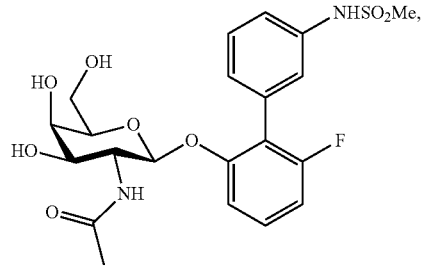
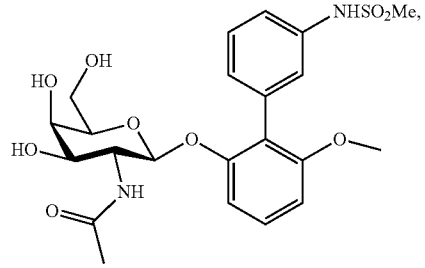

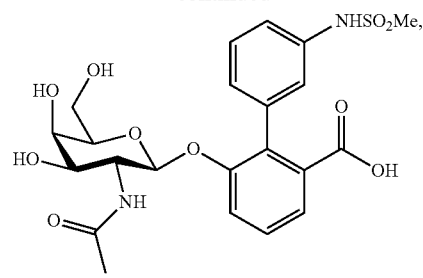
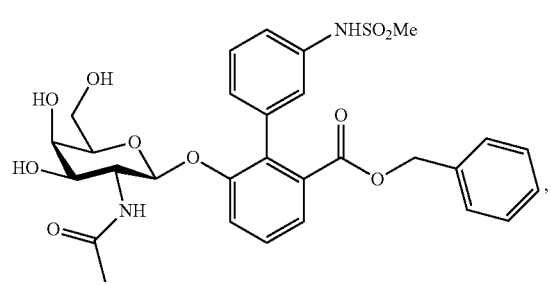
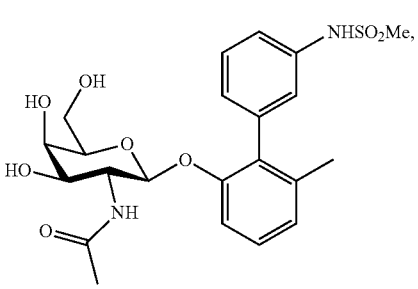
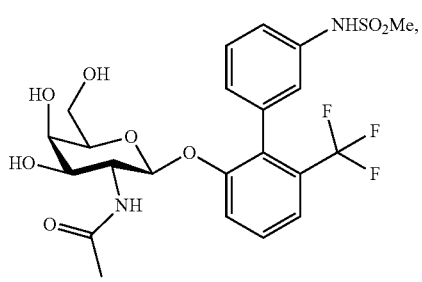
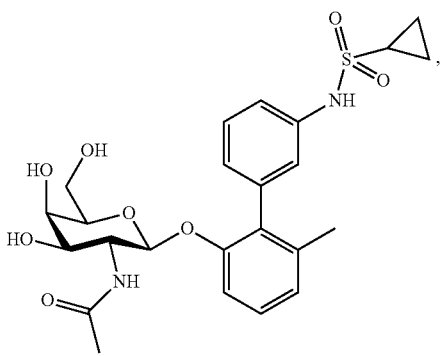
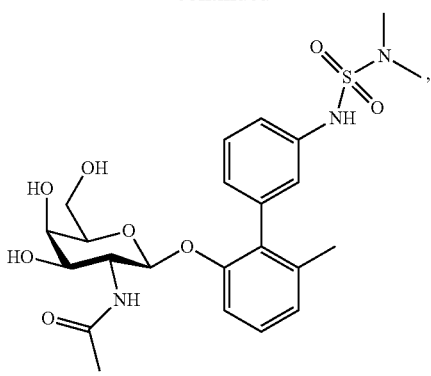
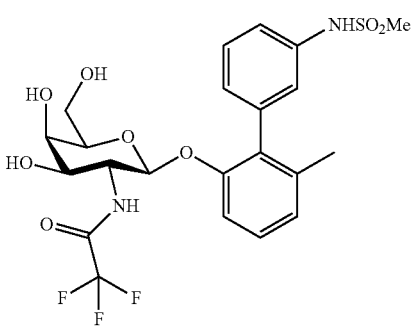
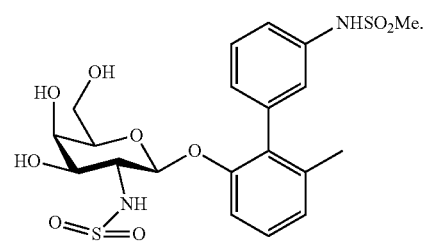
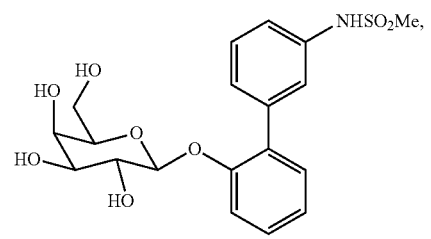
In various embodiments, the compound is selected from the group consisting of:
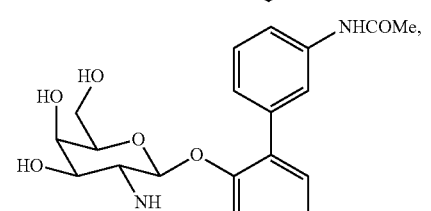
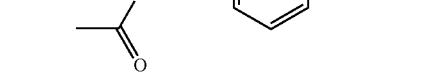

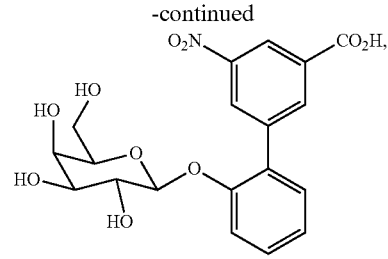
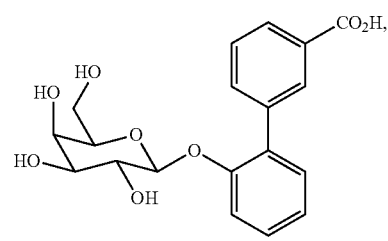
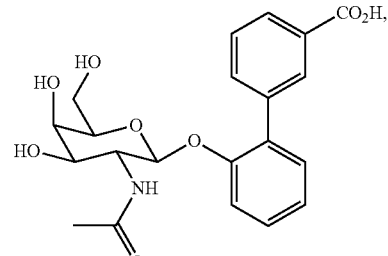
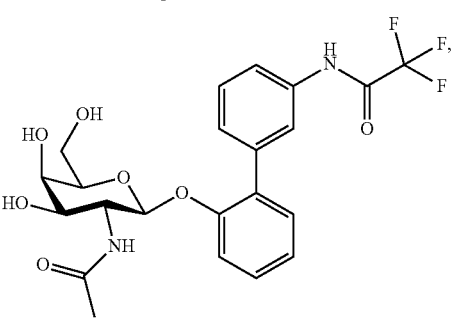
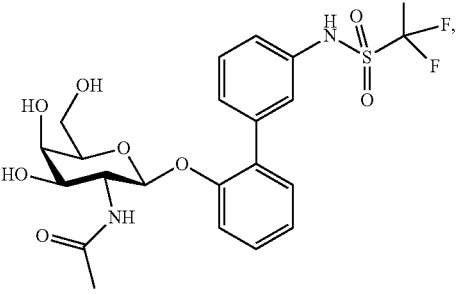
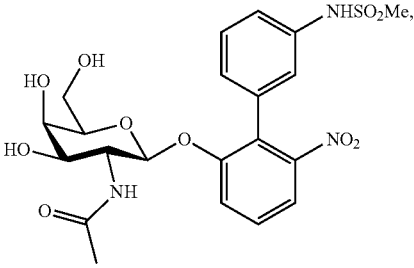
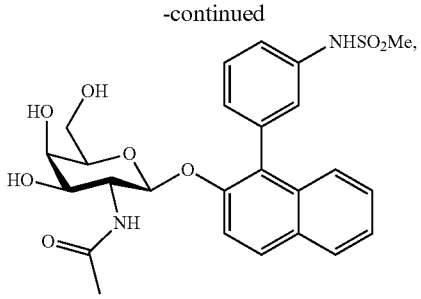
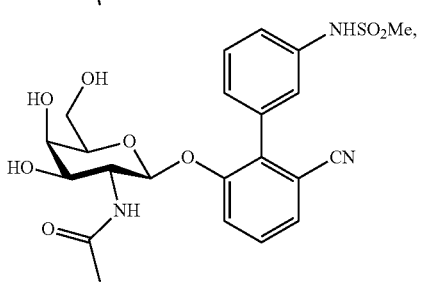
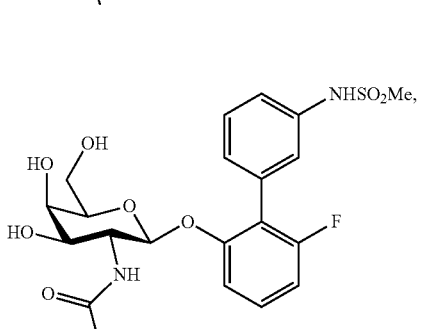
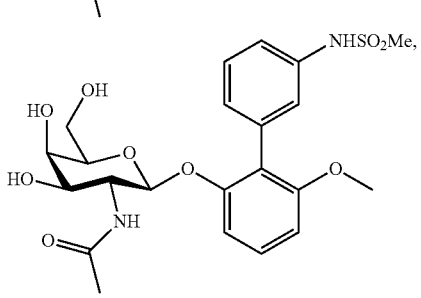
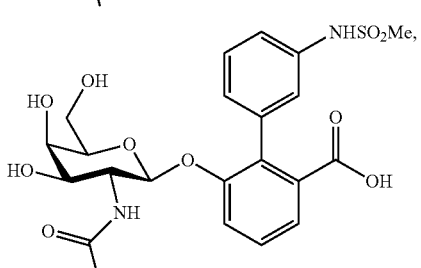
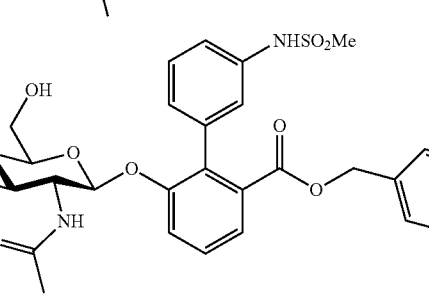

-continued

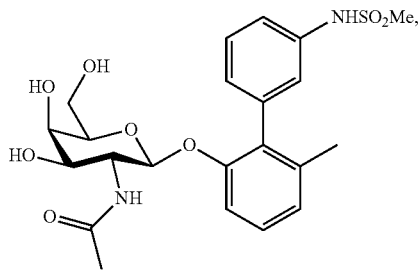

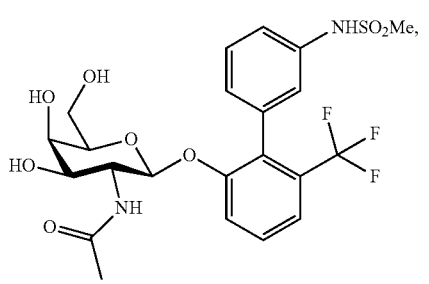

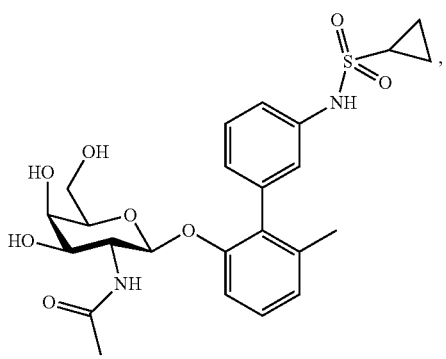

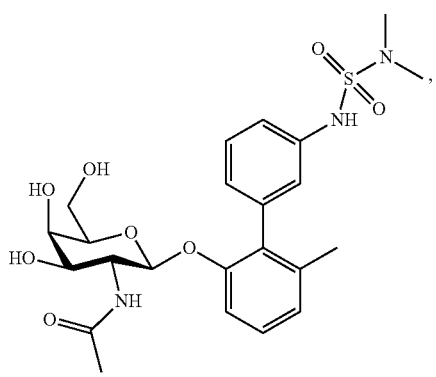

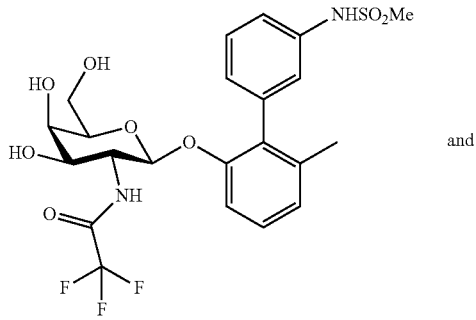

and

-continued

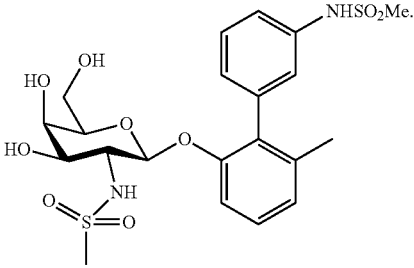

In various embodiments, the compound is capable of inhibiting FmlH. In some embodiments the compound can achieve at least 10% inhibition of FmlH. In some embodiments, the compound can achieve at least 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99% inhibition of FmlH at a concentration of 100 nM.

As used herein, the term "hydrocarbyl" refers to hydrocarbyl moieties containing, for example, 1 to about 50 carbon atoms, 1 to about 30 carbon atoms, or 1 to about 20 carbon atoms, including branched or unbranched species, saturated or unsaturated species, and cyclic or acyclic species. Preferred hydrocarbyl can be selected from the group consisting of alkyl, alkenyl, alkynyl, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted (i.e., "substituted hydrocarbyl). Hence, various hydrocarbyls can be further selected from substituted alkyl, substituted cycloalkyl, substituted aryl, and so on.

The term "hydrocarbylene" as used herein describes radicals joined at two ends thereof to other radicals in an organic compound, and which consists of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. These moieties can contain, for example, 1 to about 50 carbon atoms, 1 to about 30 carbon atoms, or 1 to about 20 carbon atoms.

The substituted hydrocarbyl and hydrocarbylene moieties described herein are substituted with at least one atom other than carbon, including moieties in which a carbon chain atom is substituted with a hetero atom such as nitrogen, oxygen, silicon, phosphorous, boron, sulfur, or a halogen atom.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. The term "aralkyl" as used herein denotes a group containing both alkyl and aryl structures such as benzyl.

Pharmaceutical Compositions

In various aspects, the present invention generally relates to pharmaceutical compositions comprising a therapeutically effective amount of at least one compound of Formula (I) or salt or prodrug thereof:

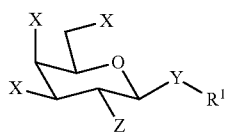

(I)

wherein:
  each X is independently hydrogen, fluoro, or OR²;
  each R² is independently hydrogen or substituted or unsubstituted hydrocarbyl;
  Y is O, S, substituted or unsubstituted hydrocarbylene, substituted or unsubstituted amino, substituted or unsubstituted amido, substituted or unsubstituted thio, $C(R^3)_2$, $(CH_2)_m$, $N(R^3)$, $N(H)R^3$, $CO_2$, $COOR^3$, $SO_2$, $SO_2R^3$, $(CH_2)_mO$, $O(CH_2)_m$, $(CH_2)_mS$, $S(CH_2)_m$, $C(O)$, $C(O)N(R^3)$, $N(R^3)C(O)$, $R^3N(R^3)C(O)$, $C(O)N(R^3)R^3$, $SO_2N(R^3)$, or $N(R^3)SO_2$,
  each R³ is independently hydrogen or substituted or unsubstituted hydrocarbyl;
  Z is hydrogen, OR⁴, SR⁴, or $N(R^4)_2$ (e.g., preferably NHR⁴);
  each R⁴ is independently hydrogen or substituted or unsubstituted hydrocarbyl;
  each m is independently an integer from 0 to 10; and
  R¹ is a substituent of Formula (II), (III), (IV), (V), (VI), (VII), (VIII), (IX), (IXa), (X), (XI), (XII) or (XIII):

(II)

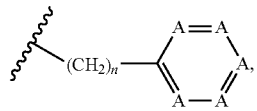

(III)

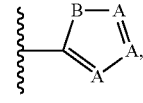

(IV)

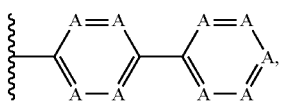

(V)

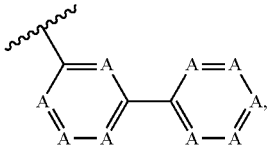

(VI)

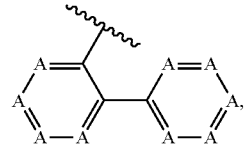

(VII)

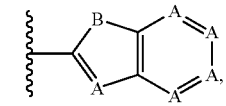

(VIII)

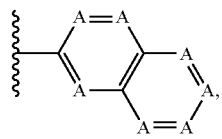

(IX)

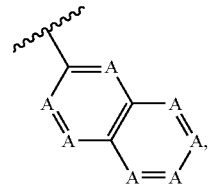

(IXa)

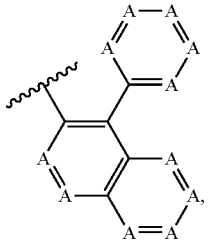

(X)

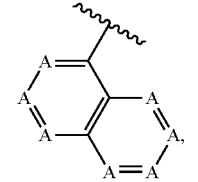

(XI)

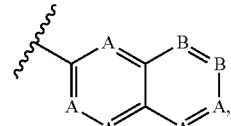

(XII)

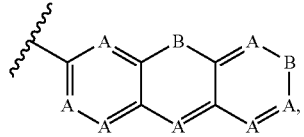

(XIII)

wherein:
  each A is independently CR⁵ or N;
  each B is independently O, S, C(O), $C(R^5)_2$, or NR⁶;
  each R⁵ is independently hydrogen, oxygen, halo, substituted or unsubstituted amino, substituted or unsubstituted amido, substituted or unsubstituted haloalkyl, substituted or unsubstituted hydrocarbyl, substituted or unsubstituted aryl, $(CH_2)_pNO_2$, $(CH_2)_pCN$, $(CH_2)_pOR^7$, $(CH_2)_pC(R^7)_2OR^7$, $(CH_2)_pC(O)(R^7)_2$, $(CH_2)_pCO_2R^7$, $(CH_2)_pN(R^7)_2$, $(CH_2)_pN(SO_2R^7)_2$, $(CH_2)_pSO_2R^7$, $(CH_2)_pNR^7C(O)R^7$, $(CH_2)_pNR^7C(R^7)_2OR^7$, $(CH_2)_pNR^7CO_2R^7$, $(CH_2)_pNR^7C(O)N(R^7)_2$, $(CH_2)_pNR^7SO_2R^7$, $(CH_2)_pCON(R^7)_2$, $(CH_2)_pSO_2N(R^7)_2$, $(CH_2)_pN(R^7)SO_2N(R^7)_2$ or $(CH_2)_pOSO_2R^7$;
  each R⁶ is independently hydrogen, substituted or unsubstituted haloalkyl, substituted or unsubstituted hydrocarbyl, substituted or unsubstituted aryl, $(CH_2)_qNO_2$, $(CH_2)_pCN$, $(CH_2)_pOR^7$, $(CH_2)_qN(SO_2R^7)_2$, $(CH_2)_pC(R^7)_2OR^7$, $(CH_2)_pC(O)(R^7)_2$, $(CH_2)_pCO_2R^7$, $(CH_2)_qN(R^7)_2$, $(CH_2)_pSO_2R^7$, $(CH_2)_qNR^7C(O)R^7$, $(CH_2)_pNR^7C(R^7)_2OR^7$, $(CH_2)_qNR^7CO_2R^7$, $(CH_2)_pNR^7C(O)N(R^7)_2$, $(CH_2)_qNR^7SO_2R^7$, $(CH_2)_pCON(R^7)_2$, $(CH_2)_pSO_2N(R^7)_2$, $(CH_2)_qN(R^7)SO_2N(R^7)_2$, or $(CH_2)_pOSO_2R^7$;

each $R^7$ is independently hydrogen or substituted or unsubstituted hydrocarbyl;

each n is independently an integer from 0 to 10;

each p is independently an integer from 0 to 10; and each q is independently an integer from 1 to 10.

In various embodiments, the pharmaceutical composition comprises at least one compound of Formula (I) wherein each X is independently OH or $CR^2$. In some embodiments, each $R^2$ is independently hydrogen or substituted or unsubstituted $C_1$-$C_{30}$ alkyl. In some embodiments each $R^2$ is independently hydrogen or a $C_1$-$C_{30}$ alkyl.

In various embodiments, the pharmaceutical composition comprises at least one compound of Formula (I) wherein Y is O, S, $C(R^3)_2$, $(CH_2)_m$, $N(R^3)$, $N(H)R^3$, $CO_2$, $COOR^3$, $SO_2$, $SO_2R^3$, $(CH_2)_mO$, $O(CH_2)_m$, $(CH_2)_mS$, $S(CH_2)_m$, $C(O)$, $C(O)N(R^3)$, $N(R^3)C(O)$, $R^3N(R^3)C(O)$, $C(O)N(R^3)R^3$, $SO_2N(R^3)$, or $N(R^3)SO_2$. In some embodiments, m is independently an integer between 0 and 5. In various embodiments, each $R^3$ is independently hydrogen or substituted or unsubstituted $C_1$-$C_{30}$ alkyl. In some embodiments each $R^3$ is independently hydrogen or $C(R^8)_2C(O)N(R^9)_2$, wherein each $R^8$ and $R^9$ are independently hydrogen, $C_1$-$C_{30}$ alkyl, or aryl. In some embodiments, $R^8$ and $R^9$ are independently hydrogen or $C_1$-$C_6$ alkyl. In some embodiments, Y is N-(tert-butyl)-2-(N-methylacetamido) acetamide.

In various embodiments, the pharmaceutical composition comprises at least one compound of Formula (I) wherein Z is $OR^4$ or $NHR^4$. In some embodiments, each $R^4$ is independently hydrogen or substituted or unsubstituted $C_1$-$C_{30}$ alkyl. In certain embodiments, each $R^4$ is independently hydrogen, $C_1$-$C_{30}$ alkyl (e.g., $C_1$-$C_{20}$ alkyl, $C_1$-$C_{10}$ alkyl, or $C_1$-$C_6$ alkyl), $SO_2R^{10}$, or $C(O)R^{10}$, wherein $R^{10}$ is a $C_1$-$C_{10}$ alkyl or haloalkyl. In some embodiments, Z is OH, $NHSO_2CF_3$, $NHC(O)CF_3$, or $NHC(O)CH_3$. In some embodiments, Z is $NHC(O)CH_3$.

In various embodiments, the pharmaceutical composition comprises at least one compound of Formula (I) wherein n is independently an integer from 0 to 3. In some embodiments, n is 2. In further embodiments, each p is independently an integer from 0 to 3 and/or each q is independently an integer from 1 to 3. In some embodiments, p is 0.

In various embodiments, the pharmaceutical composition comprises at least one compound of Formula (I) wherein each A is N or $CR^5$ and each $R^5$ is independently H, O, CN, $OR^7$, $NO_2$, $C(R^7)_2OR^7$, $C(O)(R^7)_2$, $CO_2R^7$, $N(R^7)_2$, $SO_2R^7$, $NR^7C(O)R^7$, $NR^7C(R^7)_2OR^7$, $NR^7CO_2R^7$, $NR^7C(O)N(R^7)_2$, $NR^7SO_2R^7$, $CON(R^7)_2$, $SO_2N(R^7)_2$, $OSO_2R^7$, $N(R^7)SO_2N(R^7)_2$, $N(SO_2R^7)_2$, halo, substituted or unsubstituted haloalkyl, or substituted or unsubstituted aryl. In some embodiments, each $R^5$ is independently H, O, CN, $NO_2$, $OR^7$, $CH_2OR^7$, $CO(R^7)_2$, $CO_2R^7$, $N(R^7)_2$, $SO_2R^7$, $NR^7C(O)R^7$, $NR^7CO_2R^7$, $NR^7SO_2R^7$, $CON(R^7)_2$, $OSO_2R^7$, $N(R')SO_2N(R^7)_2$, $N(SO_2R^7)_2$, halo, haloalkyl, or substituted or unsubstituted aryl. In further embodiments, each $R^5$ is independently H, F, Cl, O, $NO_2$, $CONHCH_3$, OH, $OCH_3$, $CO(CH_3)_2$, $CONH_2$, CN, $CF_3$, $NHSO_2CH_3$, $NHSO_2CF_3$, $CO_2H$, $CO_2CH_3$, $CO_2CH_2CH_3$, $SO_2CH_3$, $NHCOCH_3$, $OSO_2CH_3$, $NHSO_2R^7$, $N(SO_2R^7)_2$, benzyl, phenyl, a hydroxyl-substituted phenyl (e.g., a radical of phenol, pyro-catechol or benzene-1,2,3-triol) or a alkoxyl-substituted phenyl (e.g., a radical of 2-methoxyphenol).

In various embodiments, each B is independently O, S, C(O), or $NR^6$. In some embodiments, each $R^6$ is independently hydrogen, substituted or unsubstituted haloalkyl, substituted or unsubstituted aryl, CN, $OR^7$, $C(R^7)_2OR^7$, $C(O)R^7$, $CO_2R^7$, $CON(R^7)_2$, $SO_2R^7$, $C(O)R^7$, $SO_2N(R^7)_2$, or $OSO_2R^7$. In certain embodiments each $R^6$ is independently hydrogen, substituted or unsubstituted aryl, CN, $OR^7$, $CH_2OR^7$, $C(O)(R^7)_2$, $CO_2R^7$, $CF_3$, or $CON(R^7)_2$.

In further embodiments, $R^7$ is independently hydrogen, substituted or unsubstituted $C_1$-$C_{30}$ alkyl, substituted or unsubstituted cycloalkyl, substituted or unsubstituted haloalkyl, substituted or unsubstituted aryl, or substituted or unsubstituted aralkyl. In some embodiments, each $R^7$ is independently hydrogen, $C_1$-$C_{30}$ alkyl, $CF_3$, phenyl, benzyl, halo-substituted phenyl, or $C_3$-$C_{12}$ cycloalkyl (e.g., cyclopropyl, cyclobutyl, cyclopentyl, or cyclohexyl).

In various embodiments, the pharmaceutical composition comprises a compound of Formula (I) wherein $R^1$ of Formula (I) is selected from the group consisting of:

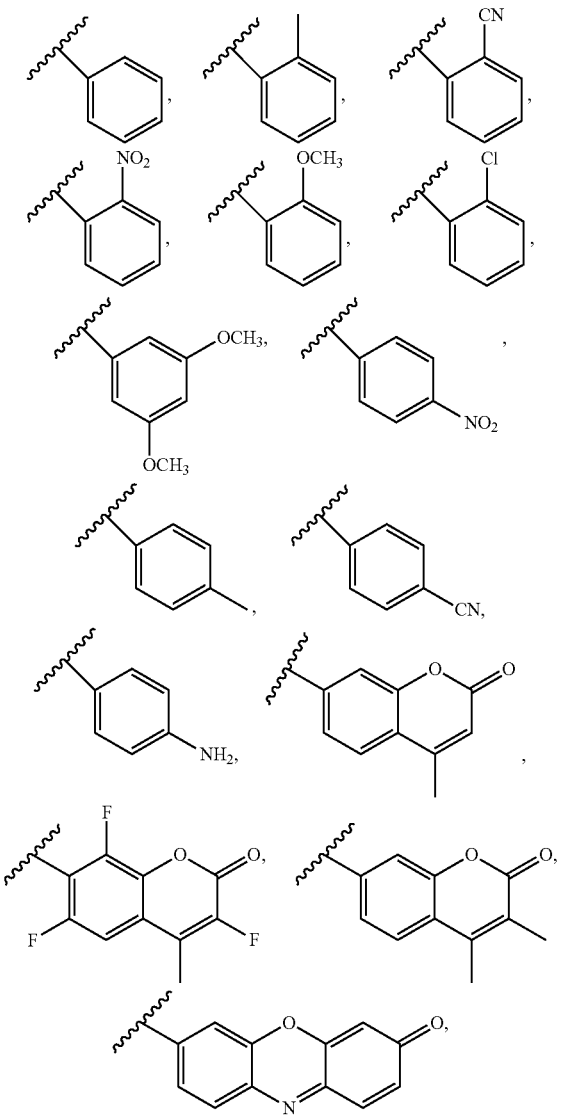

-continued
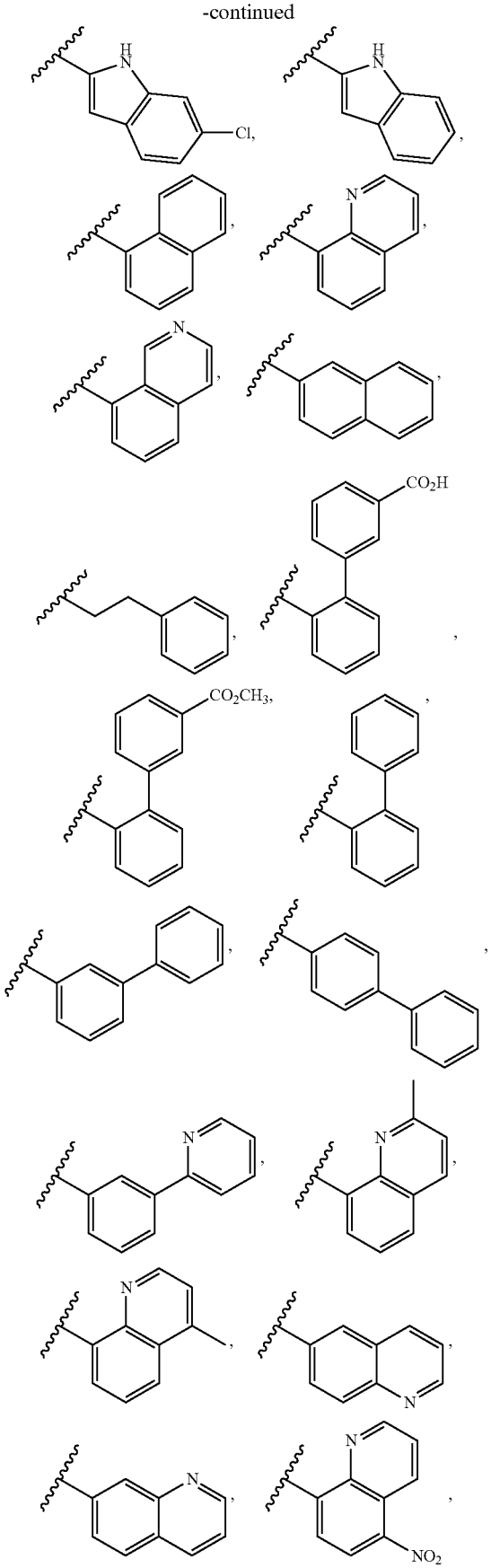
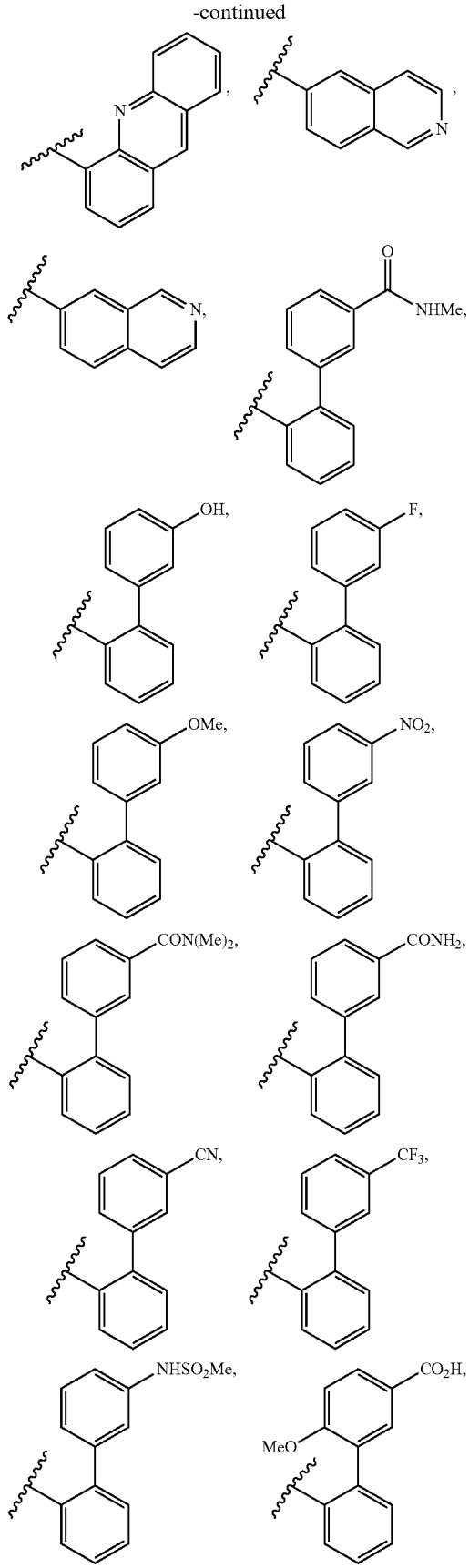

-continued
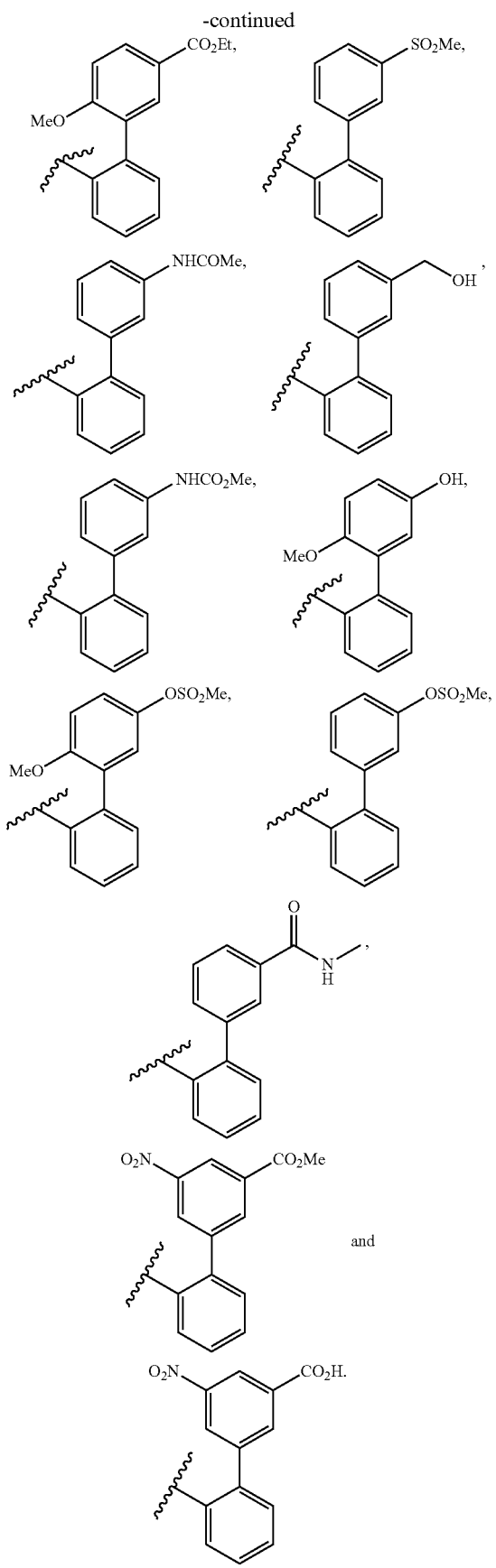
and
In various embodiments, the pharmaceutical composition comprises a therapeutically effective amount of a compound selected from the group consisting of:
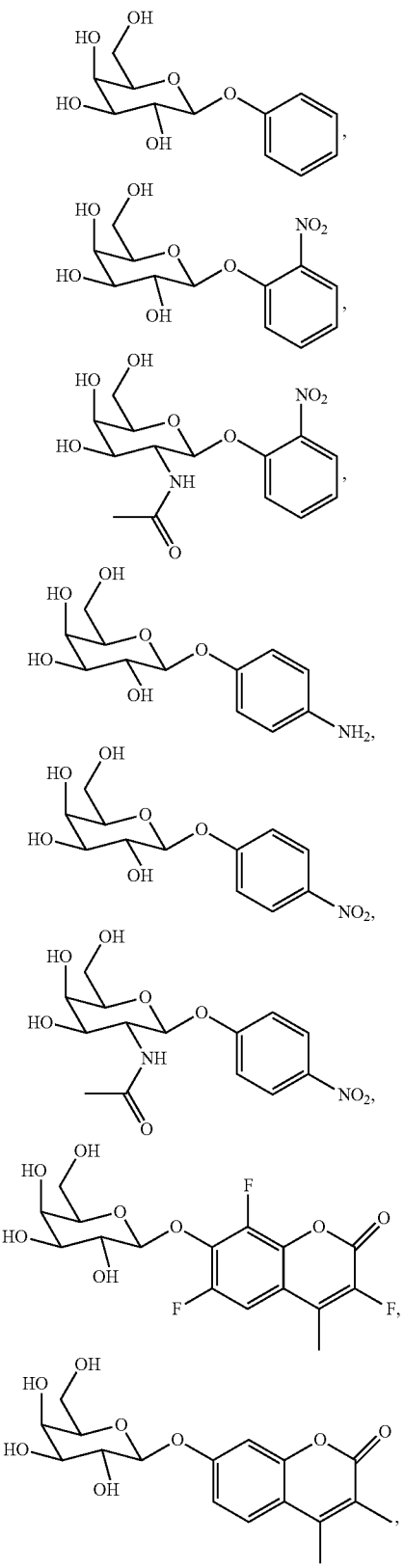

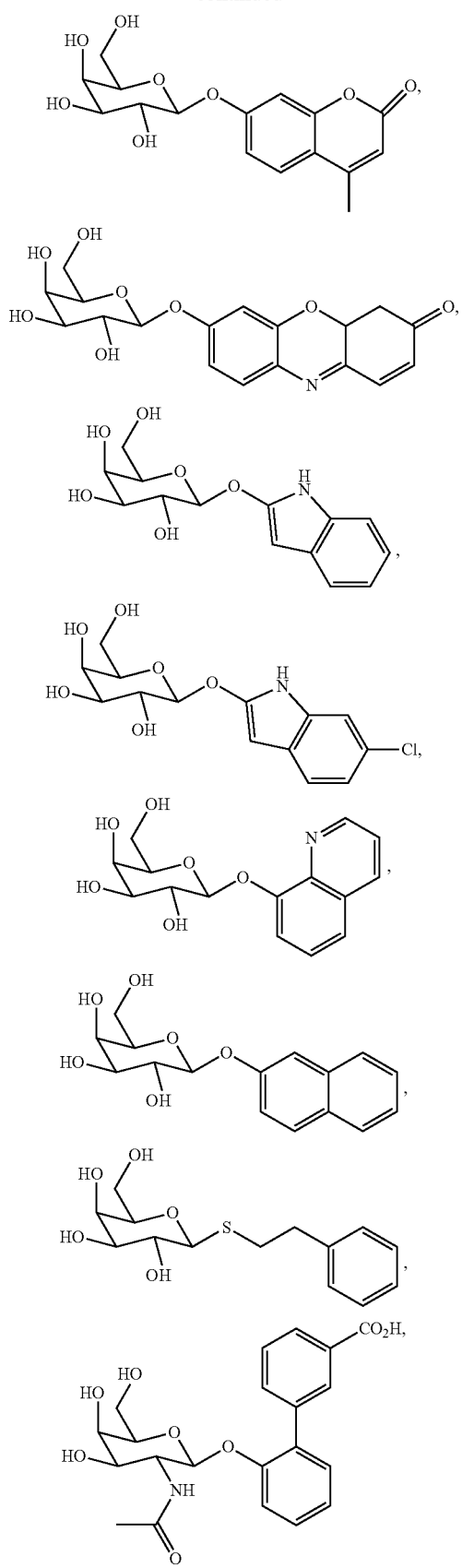
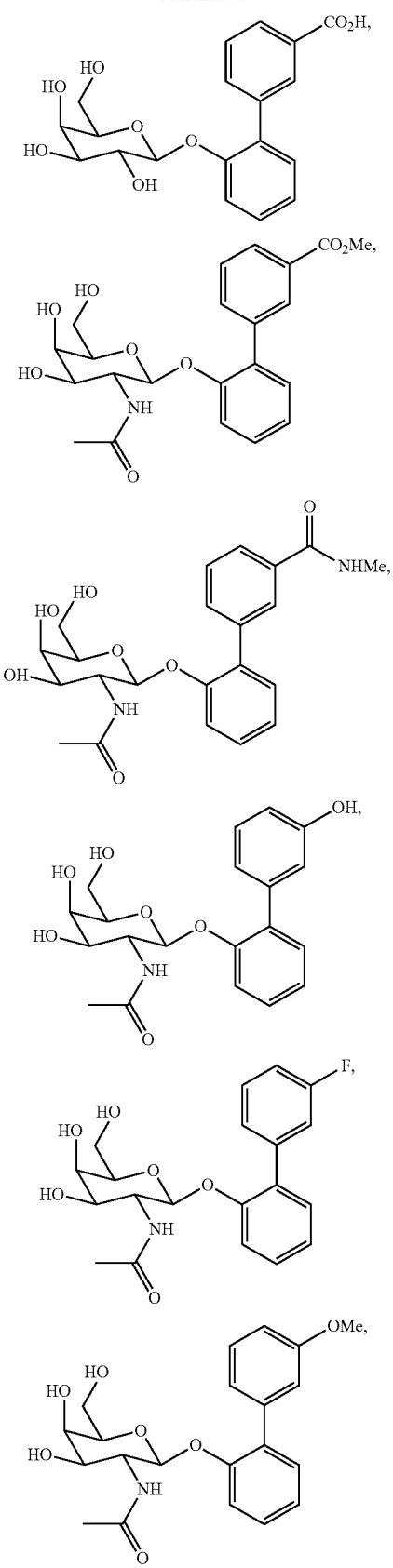

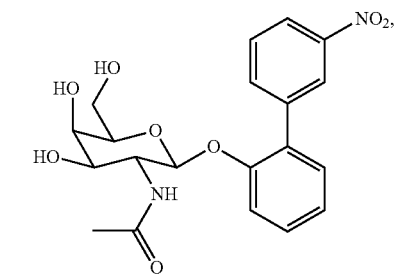
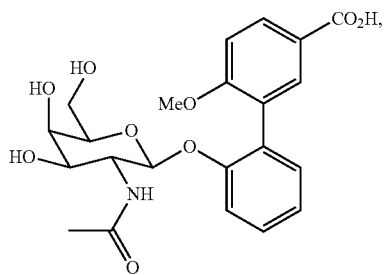
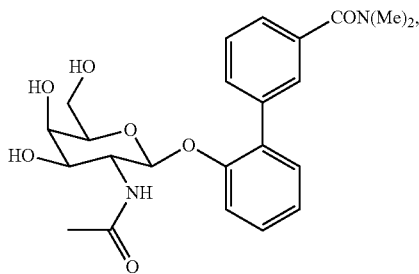
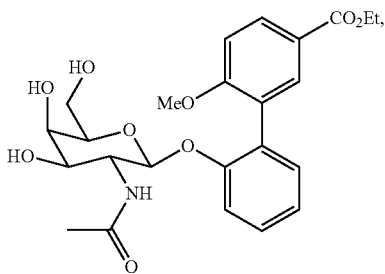
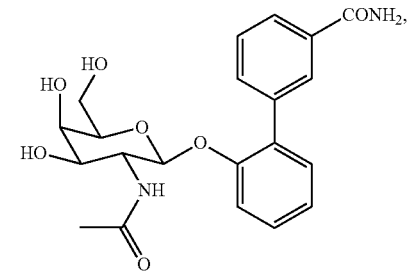
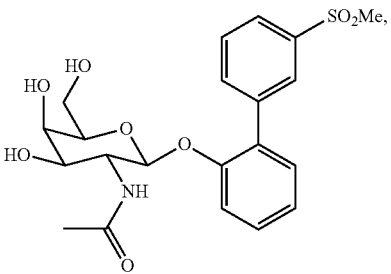
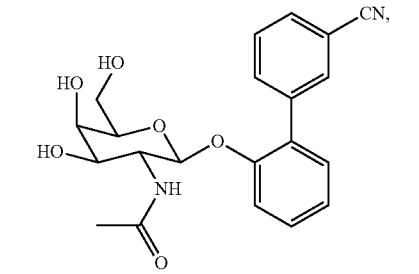
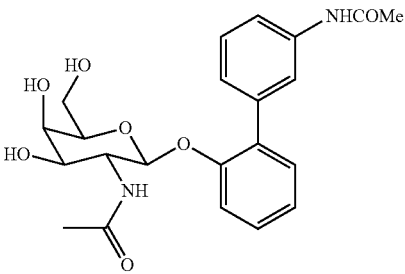
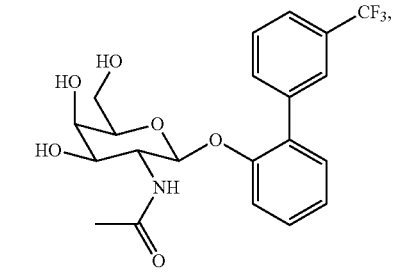
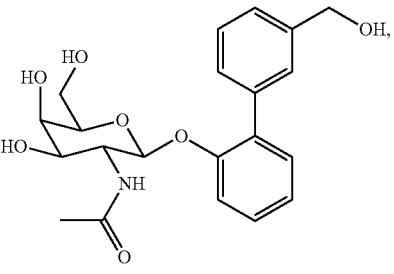
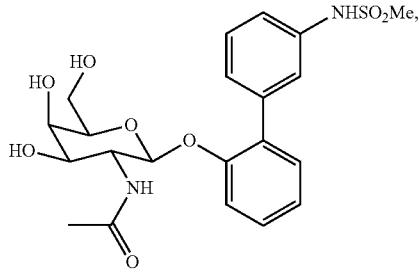
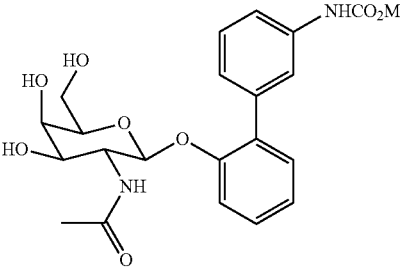

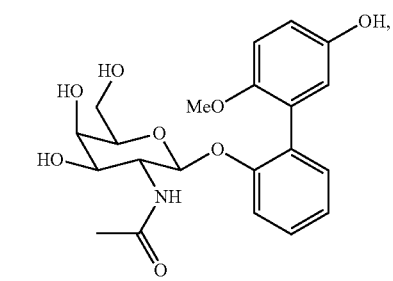
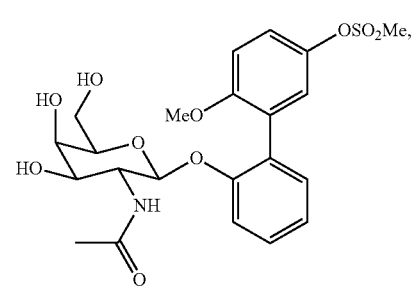
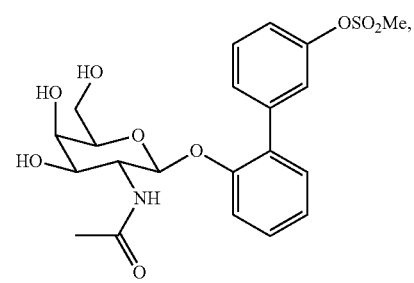
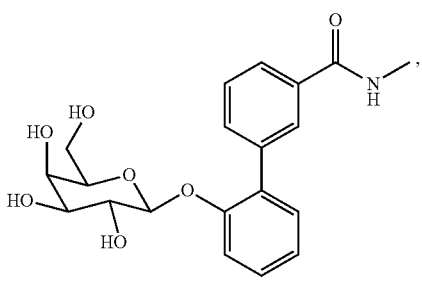
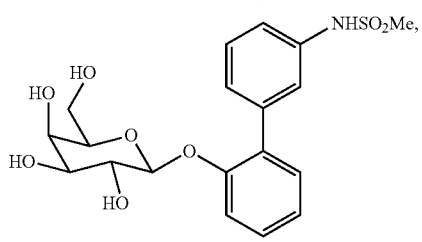
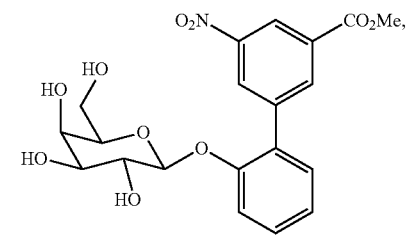
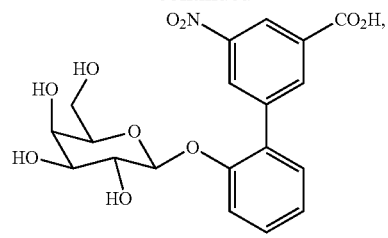
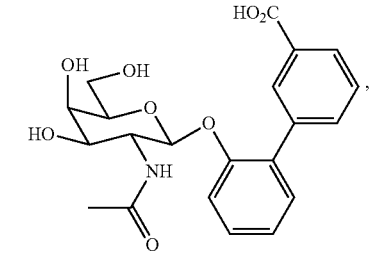
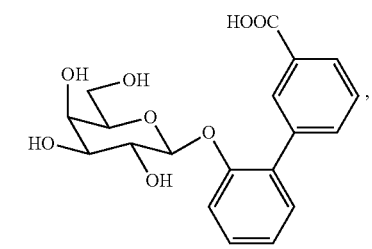
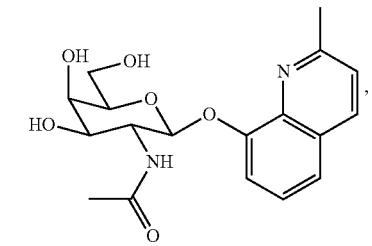
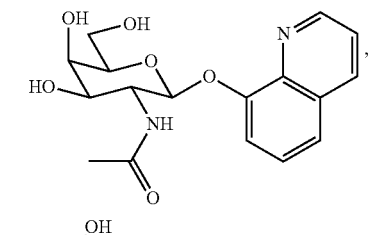
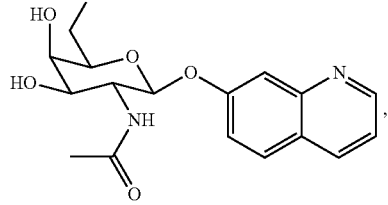

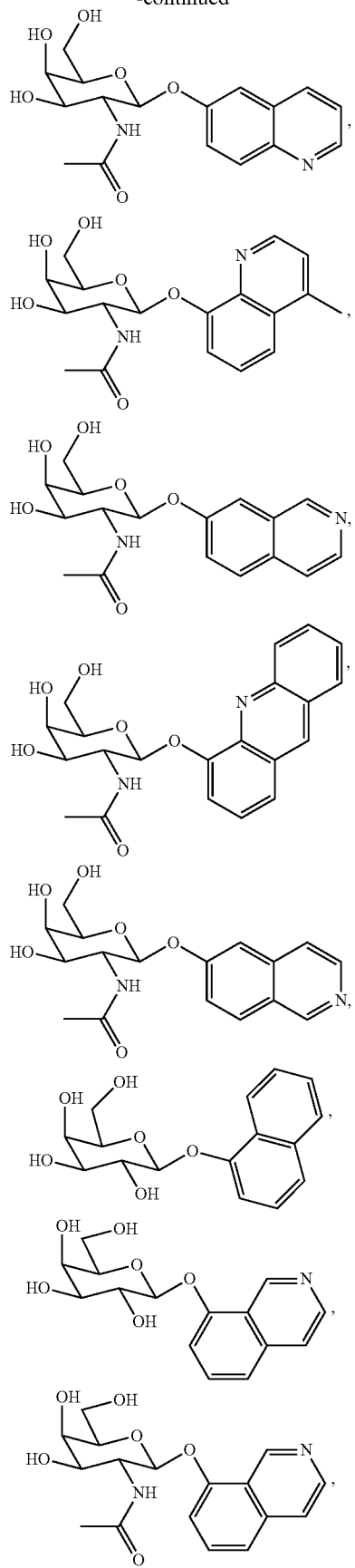
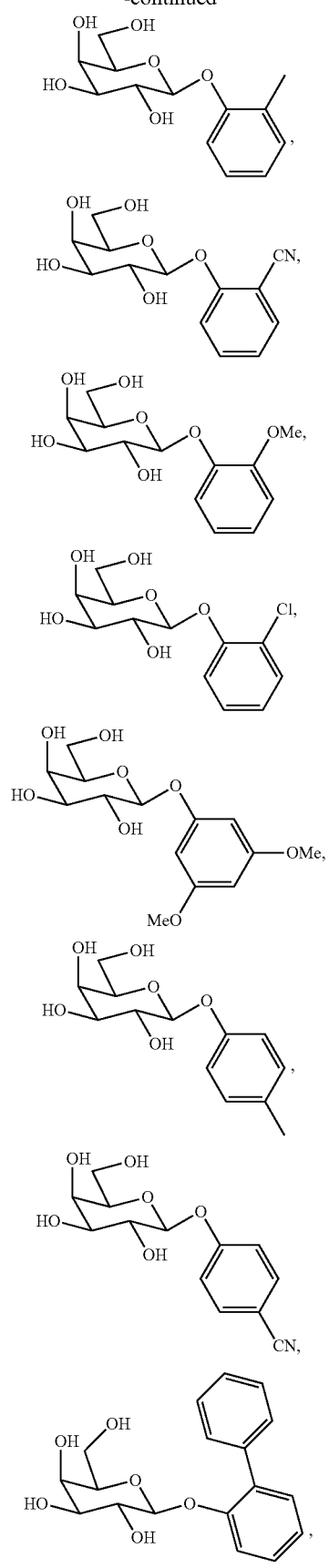

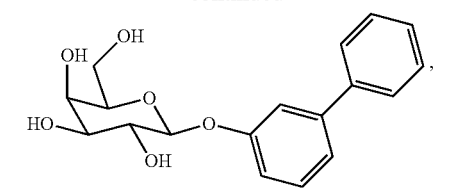
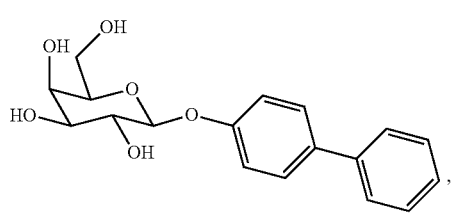
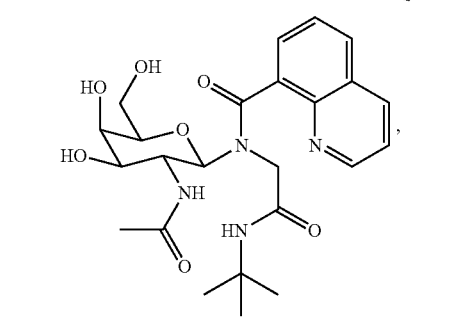
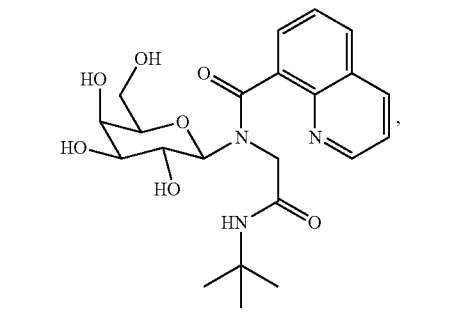
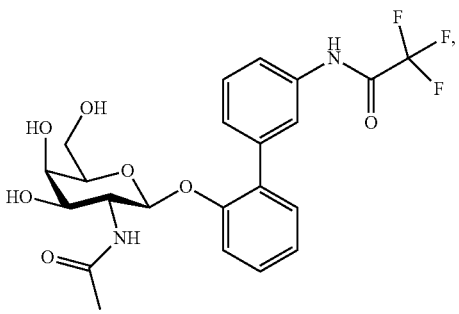
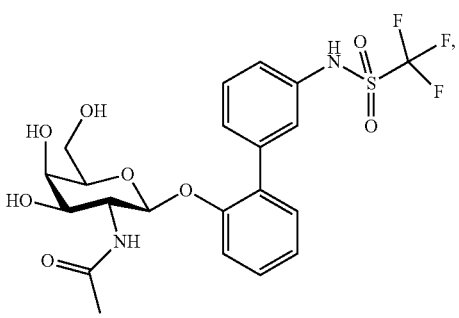
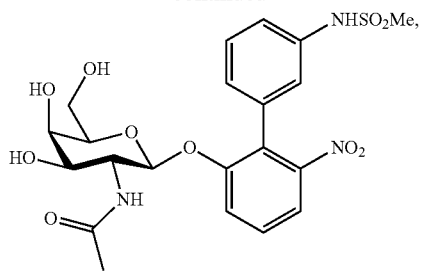
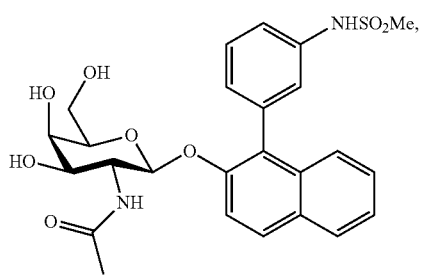
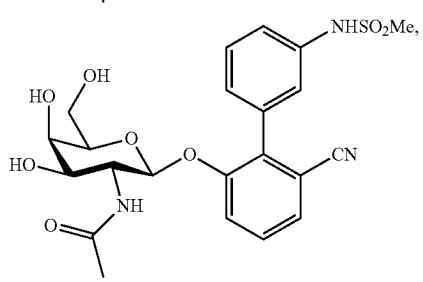
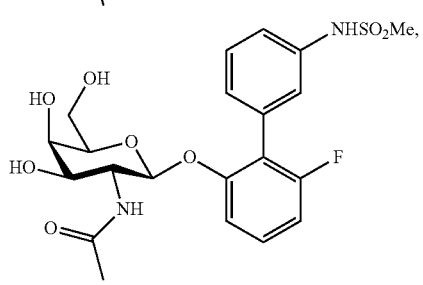
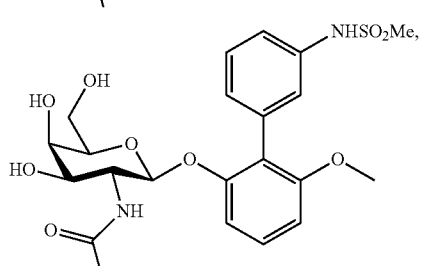
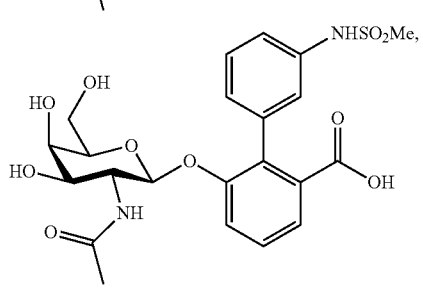

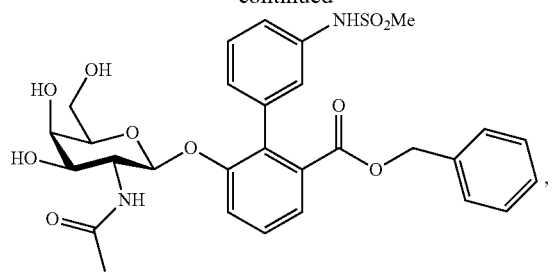
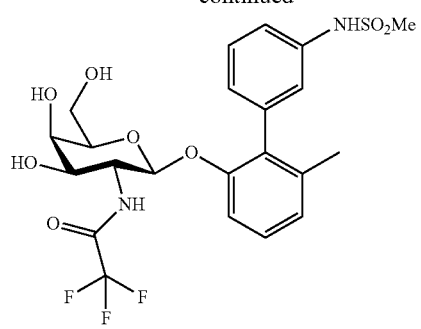
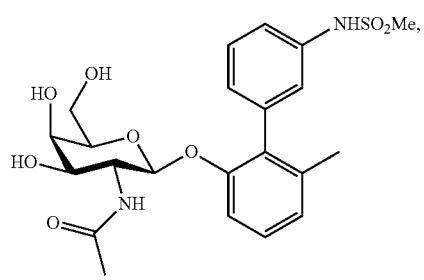
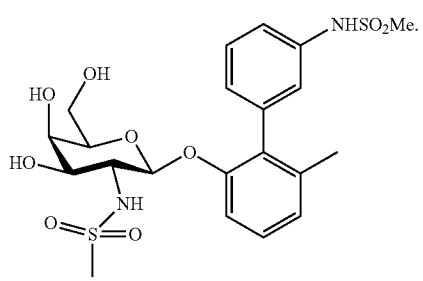
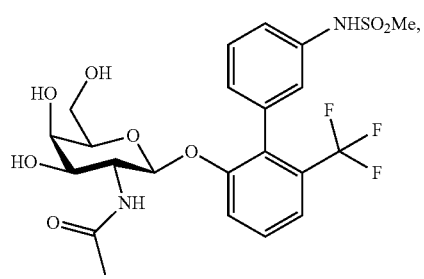
In various embodiments, the pharmaceutical composition comprises a compound selected from the group consisting of:
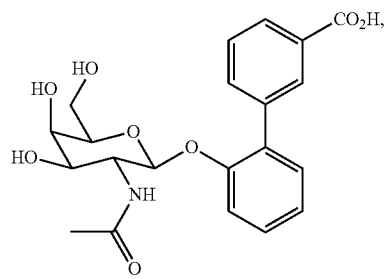
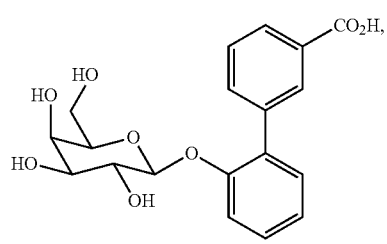
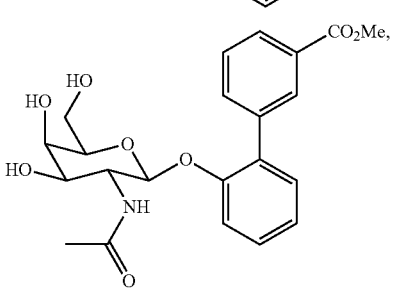
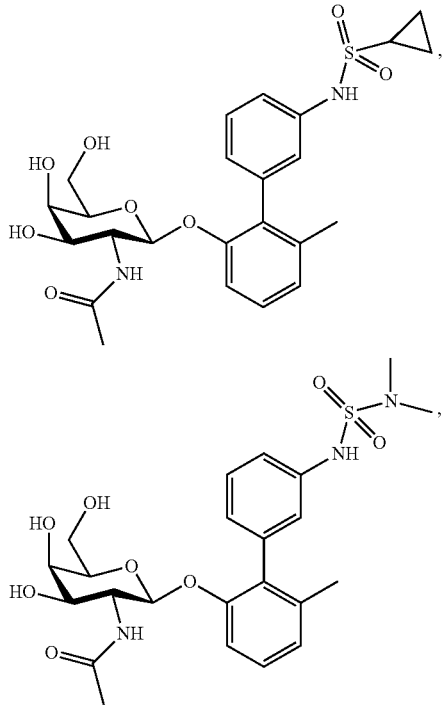

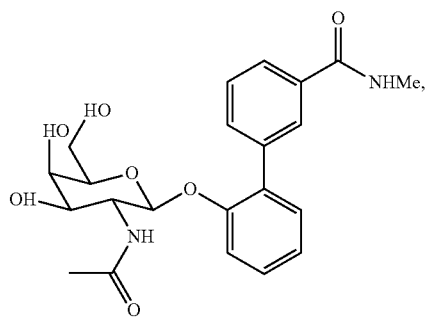
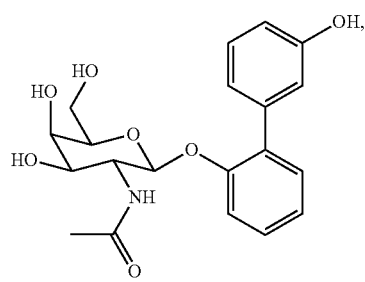
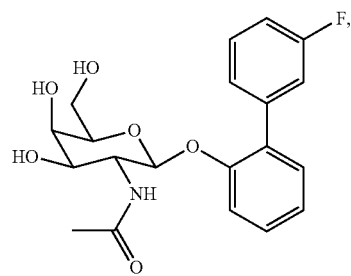
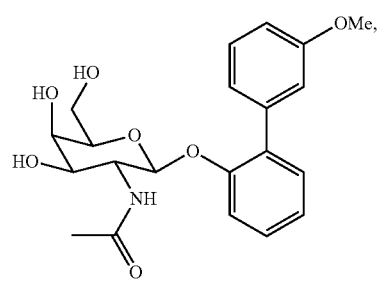
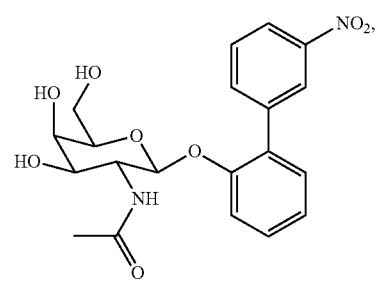
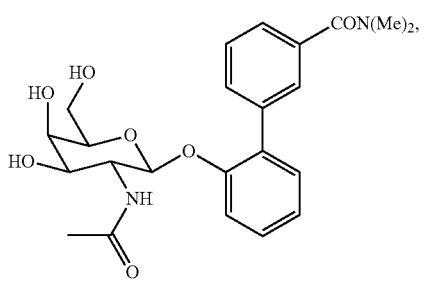
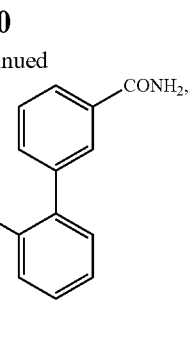
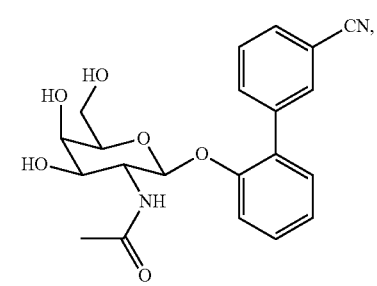
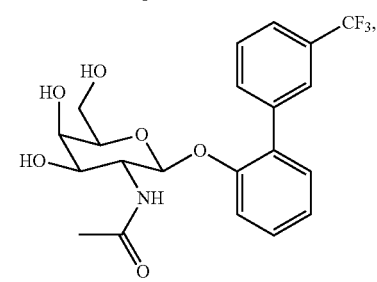
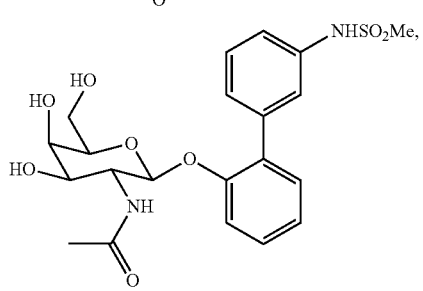
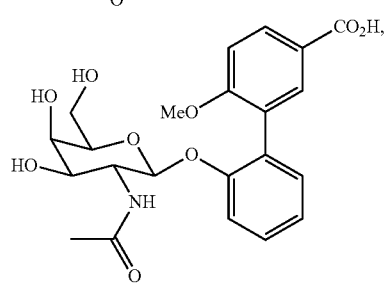
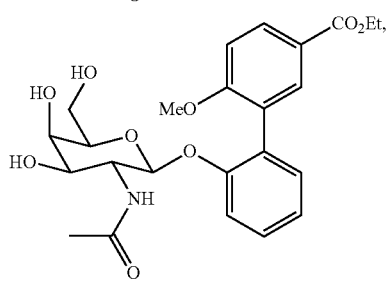

-continued
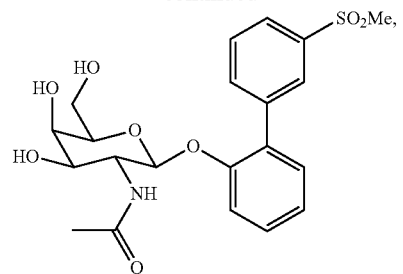
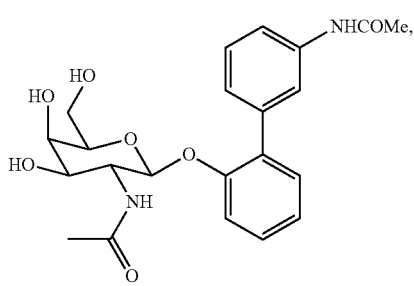
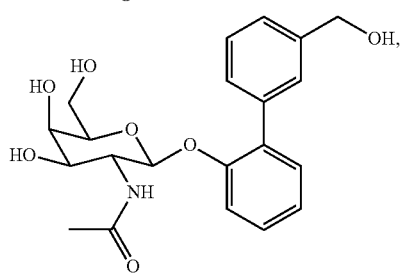
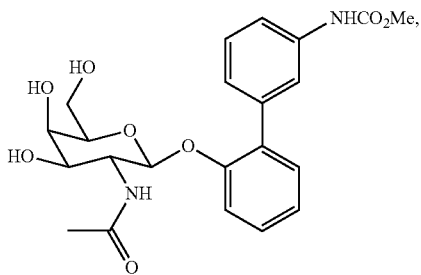
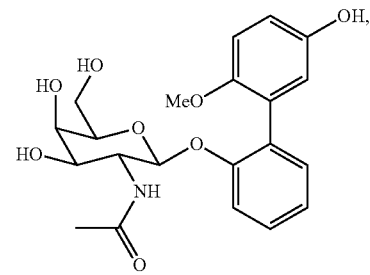
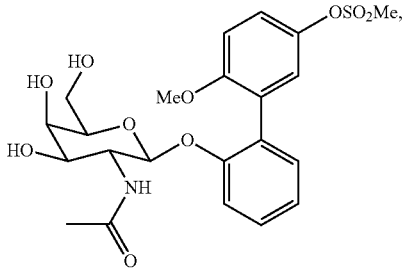
-continued
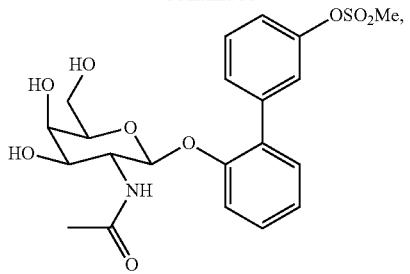
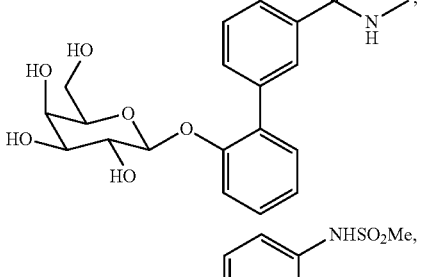
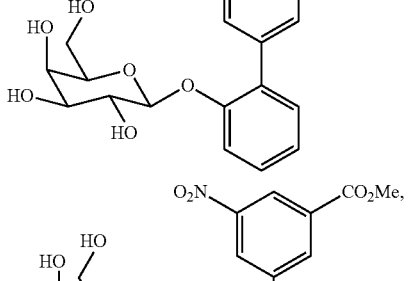
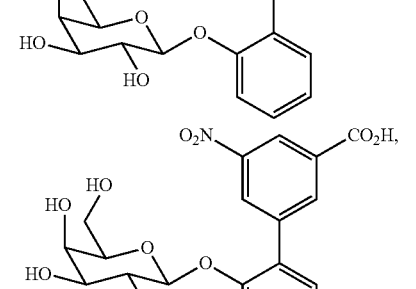
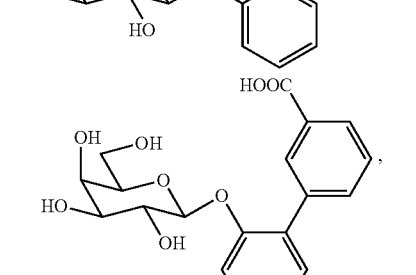
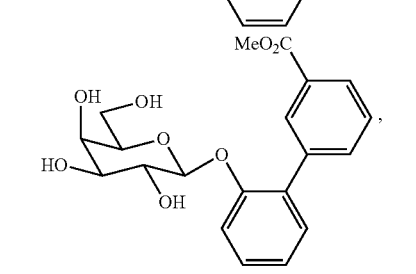

-continued
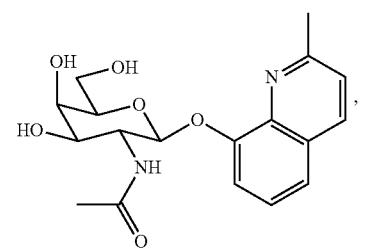
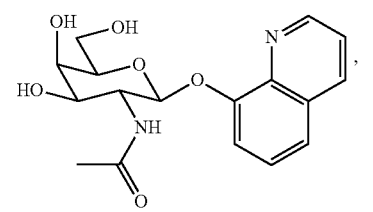
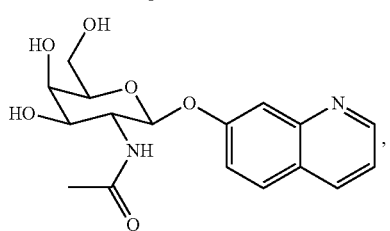
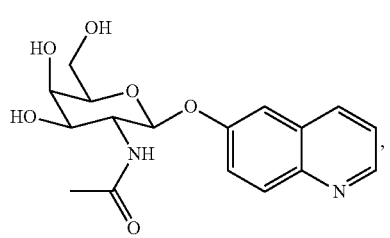
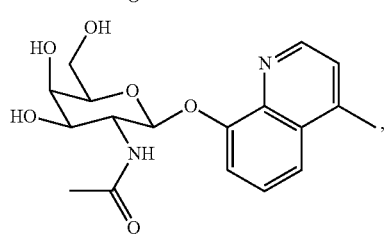
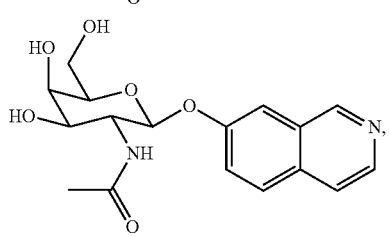
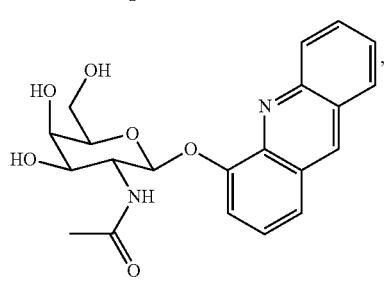
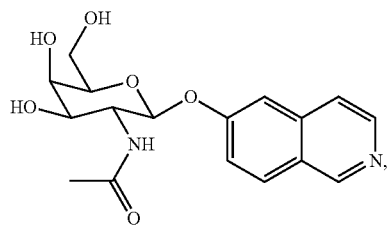
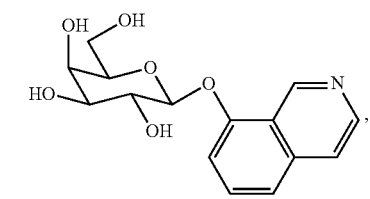
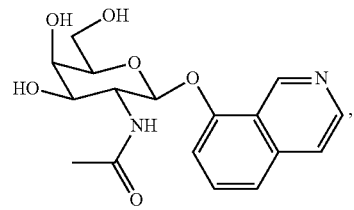
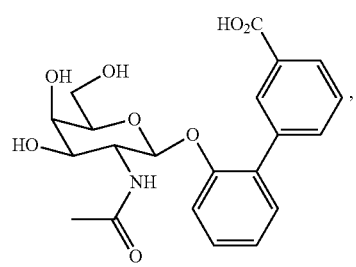
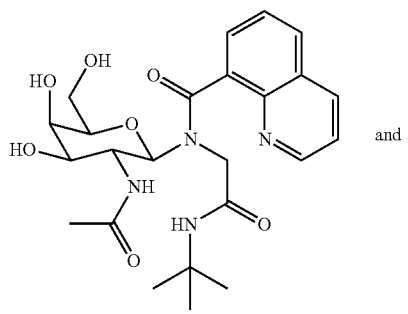
and
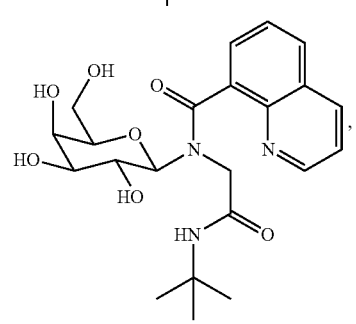

75
-continued
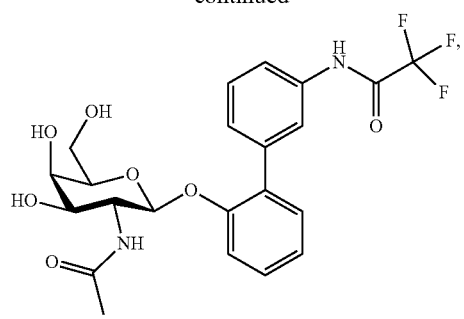
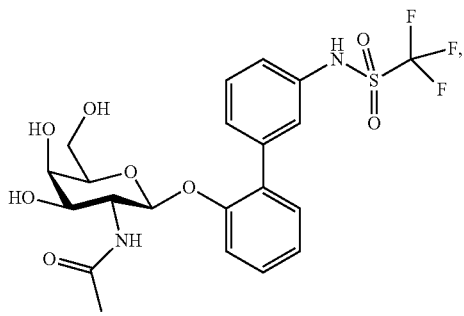
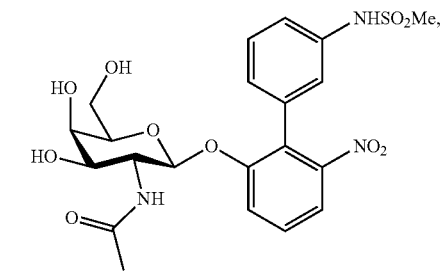
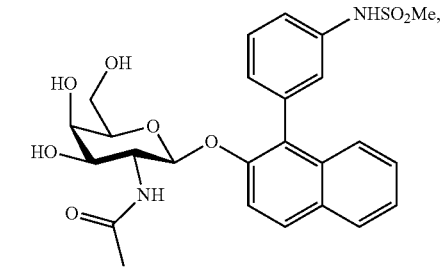
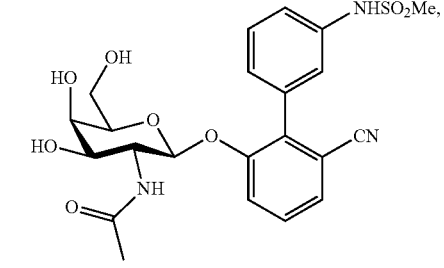
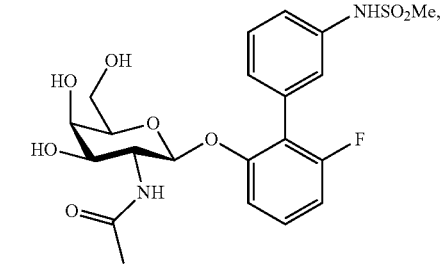
76
-continued
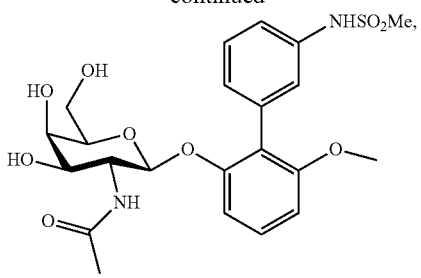
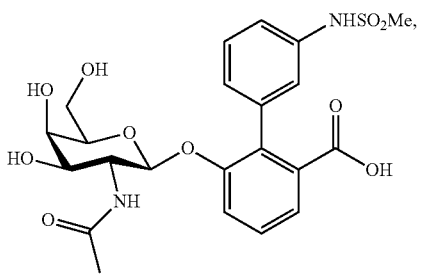
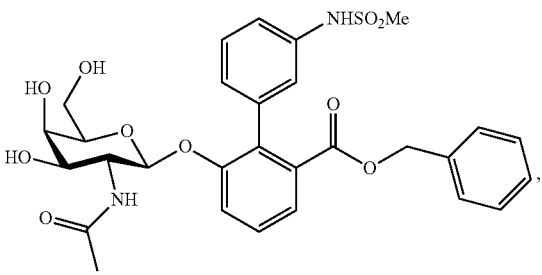
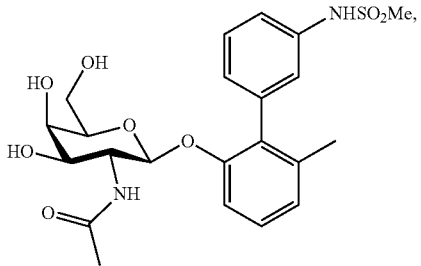
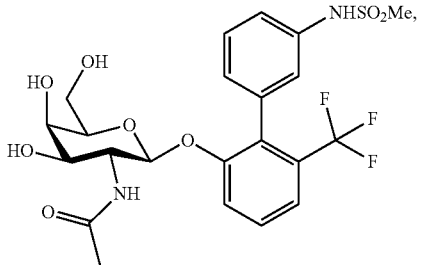
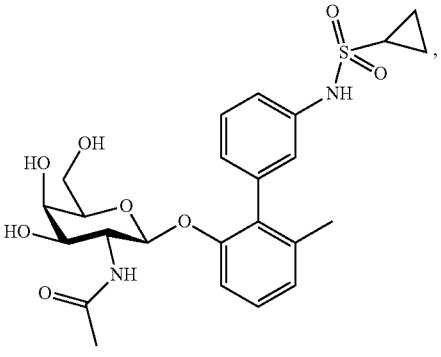

77
-continued
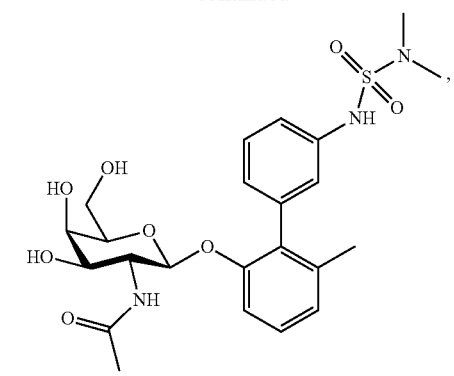
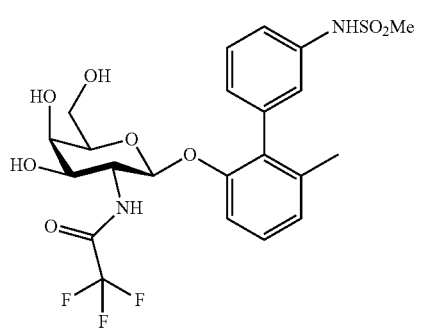
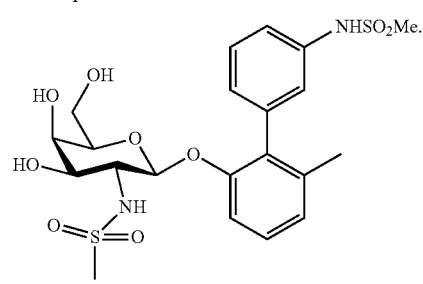
In various embodiments, the pharmaceutical composition comprises at least one compound selected from the group consisting of:
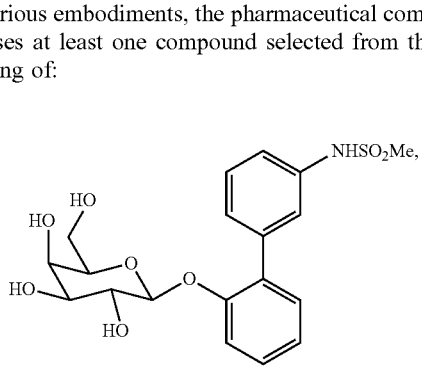
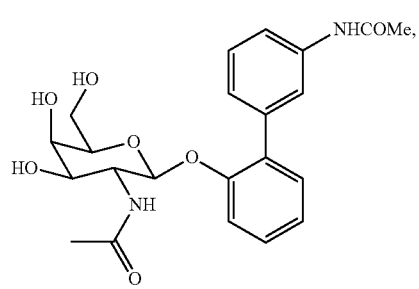
78
-continued
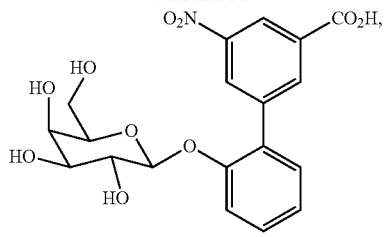
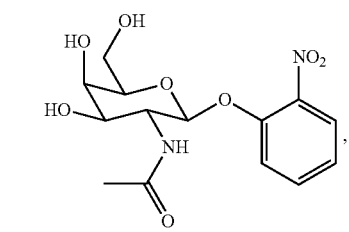
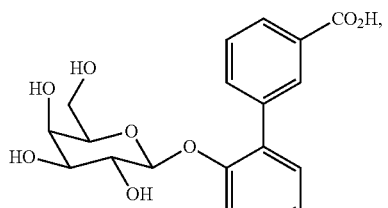
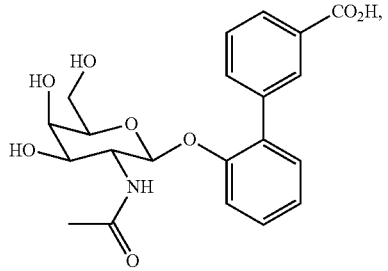
and
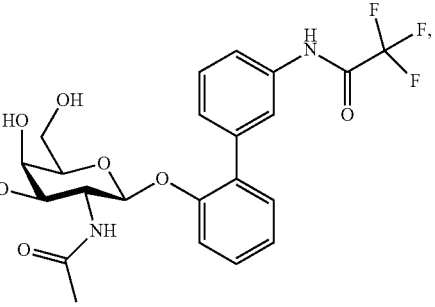
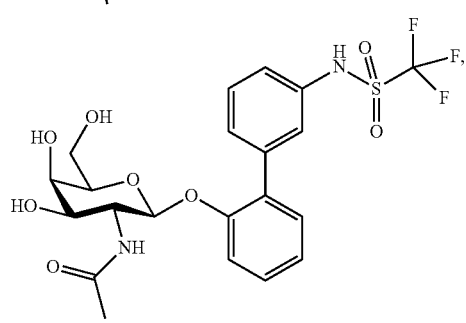

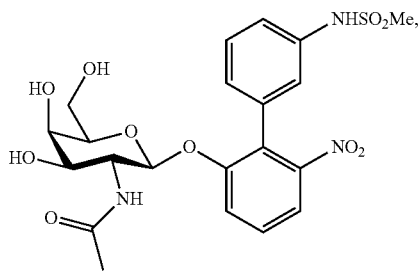
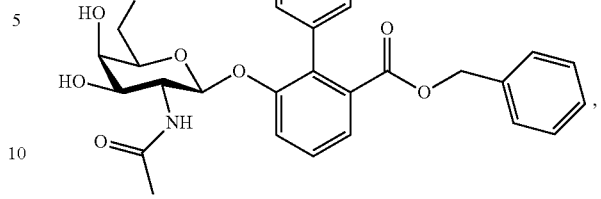
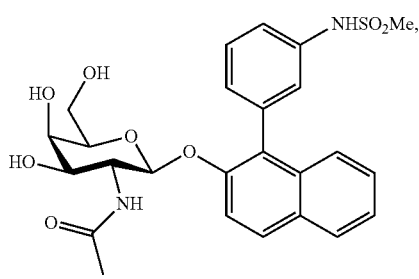
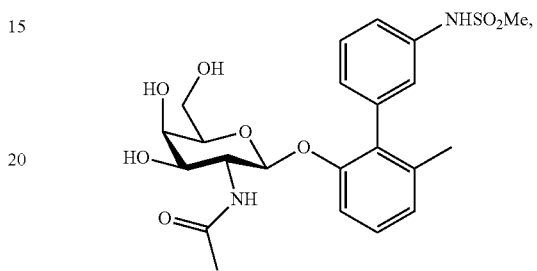
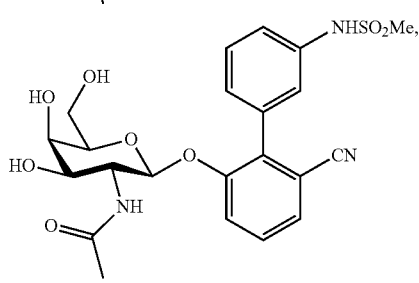
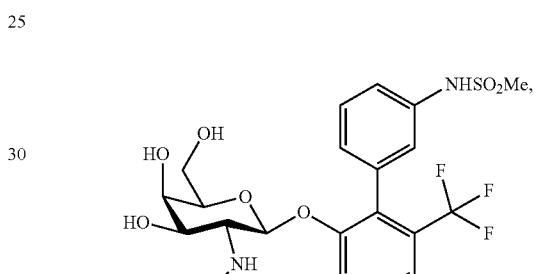
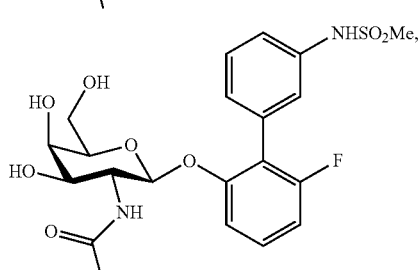
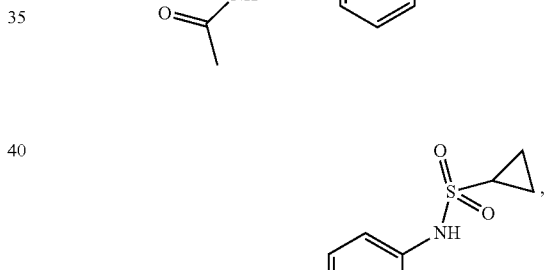
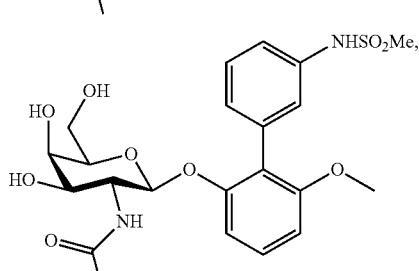
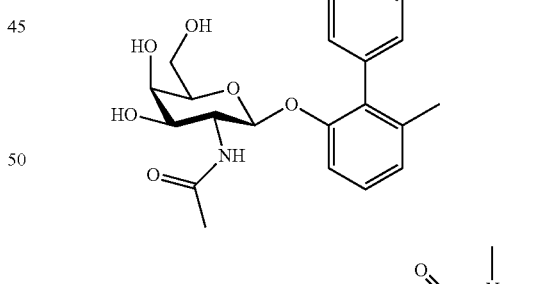
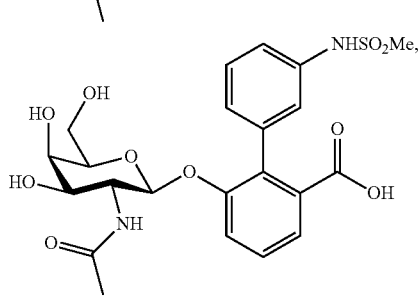
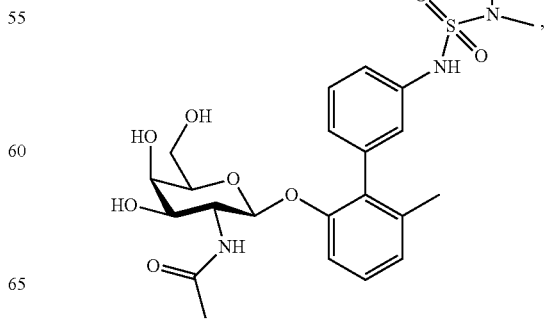

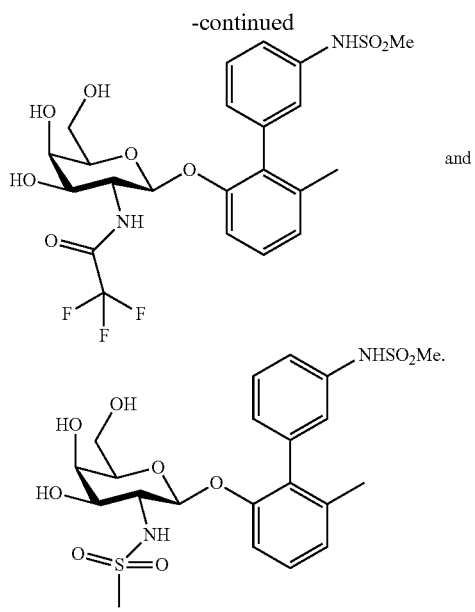

and

In various embodiments, the at least one compound is capable of inhibiting FmlH. In some embodiments the compound can achieve at least 10% inhibition of FmlH. In some embodiments, the compound can achieve at least 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99% inhibition of FmlH at a concentration of 100 nM.

In various embodiments, the pharmaceutical compositions can further comprise at least one additional active ingredient. In some embodiments, the active ingredient comprises an antibacterial. Antibacterials include, for example, trimethoprim, sulfamethoxazole, fosfomycin, nitrofurantoin, cephalexin, ceftriaxone, amoxicillin, ceftazidime, clavulanate, avibactam, ceftolozane, tazobactam or any combination thereof. In some embodiments, the antibacterial comprises at least one cephalosporin. In some embodiments, the cephalosporin comprises cefpodoxime, cefdinir, cefaclor or any combination thereof. In some embodiments, the antibacterial comprises at least one fluoroquinolone. In some embodiments, the fluoroquinolone comprises ciprofloxacin and/or levofloxacin.

In additional embodiments, the antibacterial comprises an inhibitor of FimH. Effective inhibitors of FimH include mannoside based compounds. Such mannoside inhibitors are described in U.S. Pat. Nos. 8,937,167; 9,567,362; and US 2017/0247401, which are hereby incorporated by reference herein.

Pharmaceutical compositions containing one or more of the compounds described herein can be formulated in any conventional manner. Proper formulation is dependent in part upon the route of administration selected. Routes of administration include, but are not limited to, oral, parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

As used herein, "a therapeutically effective amount" is an amount capable of causing a pharmaceutical effect in a subject thereof with minimal side effects. In various cases the pharmaceutical effect of "an effective amount" is a reduction or depletion in the colonization of any type of pathological bacteria in human tissue.

Typically, the normal dosage amount of the inhibitor can vary from about 0.05 to about 500 mg per kg body weight depending upon the route of administration. The active ingredient can be administered in a single dose per day, or alternatively, in divided doses (e.g., twice per day, three times a day, four times a day, etc). In general, lower doses can be administered when a parenteral route is employed. Thus, for example, for intravenous administration, a dose in the range, for example, from about 0.05 mg to about 30 mg, from about 0.1 mg to about 25 mg, or from about 0.1 mg to about 20 mg per kg body weight can be used.

In various embodiments, the pharmaceutical compositions can comprise at least one excipient. Pharmaceutically acceptable excipients for use in the compositions of the present invention are selected based upon a number of factors including the particular compound used, and its concentration, stability and intended bioavailability; the subject, its age, size and general condition; and the route of administration.

The pharmaceutical compositions can be formulated, for example, for oral administration. The pharmaceutical compositions can be formulated as tablets, dispersible powders, pills, capsules, gel-caps, granules, solutions, suspensions, emulsions, syrups, elixirs, troches, lozenges, or any other dosage form that can be administered orally. Pharmaceutical compositions can include one or more pharmaceutically acceptable excipients. Suitable excipients for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such solid dosage forms can be uncoated or can be coated to delay disintegration and absorption.

The pharmaceutical compositions can also be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

Pharmaceutically acceptable excipients are identified, for example, in *The Handbook of Pharmaceutical Excipients*, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

As used herein, the term "prodrug" refers to a derivative of a compound that can hydrolyze, oxidize, or otherwise react under biological conditions (in vitro or in vivo) to provide a compound as described herein. Prodrugs may only become active upon some reaction under biological conditions, but they may have activity in their unreacted forms. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 J. Pharm. Sci. 66:1-19). Prodrugs can typically be prepared using well-known methods, such as those described in Burger's Medicinal Chemistry and Drug Discovery (1995, Manfred E. Wolff ed., 5th ed. 172-178, 931-932).

"Salt" as used herein refers to pharmaceutically acceptable salts of the compounds described herein which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). Examples of pharmaceutically acceptable salts include, but are not limited to, nontoxic acid addition salts which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Methods of Use:

The compounds of Formula (I) are useful for inhibiting FmlH. FmlH is a component of F9 pilus, an important urovirulance factor employed by uropathogenic *E. coli* (UPEC) for the maintenance of urinary tract infections (UTI). Deletion of FmlH in the urosepsis isolate, CFT073, results in a competitive defect for UPEC to maintain UTI in mouse models of the disease.

Accordingly, in various embodiments, the invention is directed to methods of treating bacterial infections in a subject in need thereof comprising administering to the subject a therapeutically effective amount of at least one compound of Formula (I). In some embodiments, the method of treating bacterial infections in the subject comprises administering to the subject any pharmaceutical composition described herein.

In various embodiments, the method of treating bacterial infections further comprises administering one or more additional active ingredients. In various embodiments the method further comprises administering an antibacterial. The antibacterial can comprise any antibacterial understood by practitioners in the art to be suitable for the specific infection. In some embodiments, the antibacterial comprises trimethoprim, sulfamethoxazole, fosfomycin, nitrofurantoin, cephalexin, ceftriaxone, amoxicillin, ceftazidime, clavulanate, avibactam, ceftolozane, tazobactam or any combination thereof. In some embodiments, the antibacterial comprises at least one cephalosporin. In some embodiments, the cephalosporin comprises cefpodoxime, cefdinir, cefaclor or any combination thereof. In some embodiments, the antibacterial comprises at least one fluoroquinolone. In some embodiments, the fluoroquinolone comprises ciprofloxacin or levofloxacin.

In various embodiments, the antibacterial comprises an inhibitor of FimH. Effective inhibitors of FimH include mannoside based compounds as described herein.

In various embodiments, the bacterial infections to be treated by the methods described herein can be urinary tract infections (e.g., cystitis), kidney infections (e.g. pyelonephritis).

EXAMPLES

The following non-limiting examples are provided to further illustrate the present invention.

Overview of Examples

Design and Testing of Novel Galactoside Inhibitors of FmlH.

Figure 1:
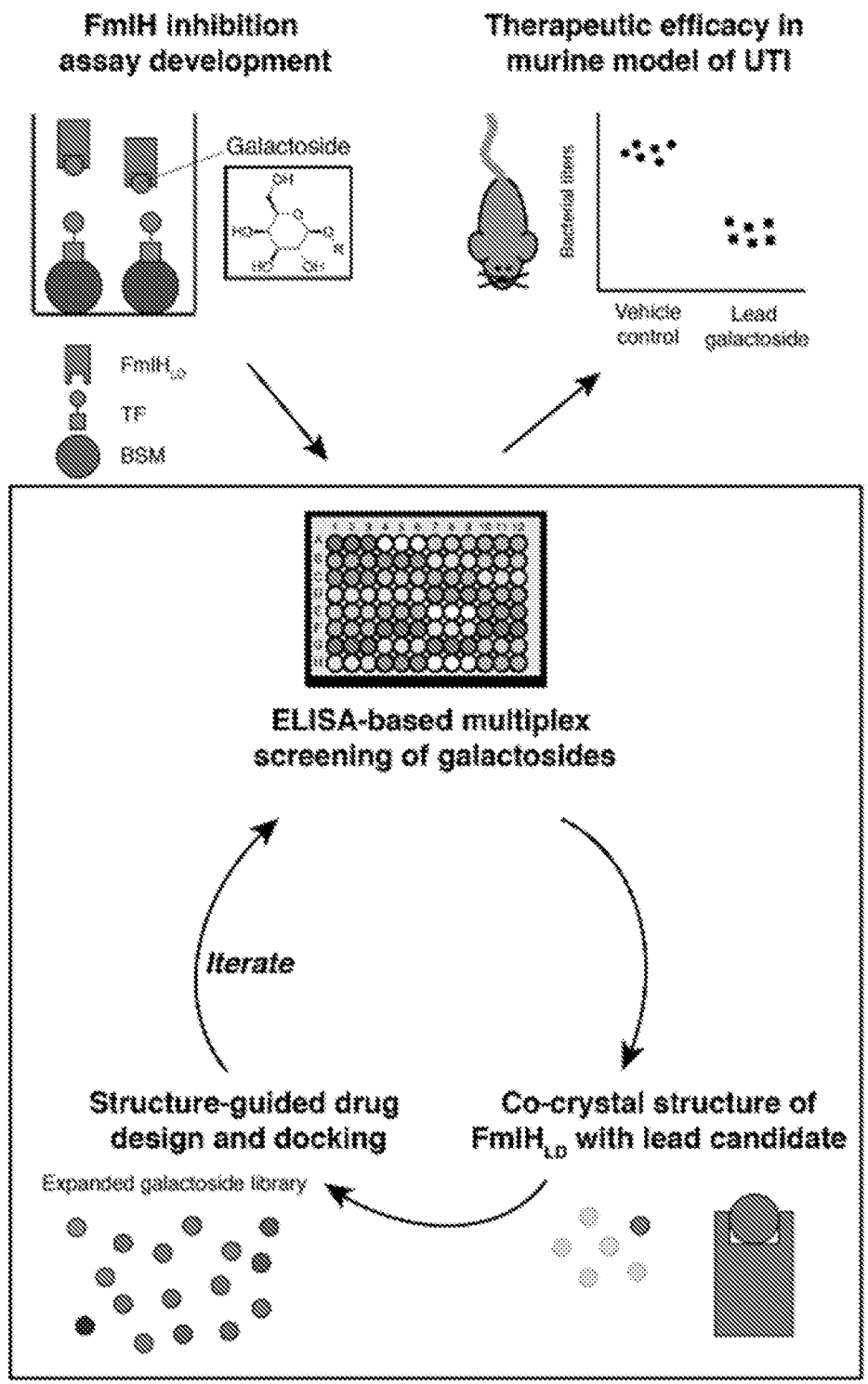
FIG. 1 diagrams the rational approach taken to design FmlH targeted inhibitors.

The following examples describe the steps employed to design and test the novel galactoside inhibitors of FmlH of the current invention. FIG. 1 diagrams the strategy employed. First, working from galactoside, a natural inhibitor of $FmlH_{LD}$, a variety of modified galactosides were produced and tested iteratively as inhibitors of $FmlH_{LD}$ binding to ds-BSM. The strongest candidates were further modified for enhance inhibition. Finally, the top candidates were tested in murine models of UTI.

Example 1: General Synthesis, Purification, and Analytical Chemistry Procedures

The compounds used in the following examples were synthesized and analyzed using the following protocols which will be referred to in later examples.

NMR and HPLC MS Analysis:

Starting materials, reagents, and solvents were purchased from commercial vendors unless otherwise noted. In general, anhydrous solvents were used for carrying out all reactions. 1H NMR spectra were measured on a Varian 400

MHz NMR instrument equipped with an auto sampler. The chemical shifts were reported as δ ppm relative to TMS using residual solvent peak as the reference unless otherwise noted. The following abbreviations were used to express the peak multiplicities: s=singlet; d=doublet; t=triplet; q=quartet; m=multiplet; br=broad. High-performance liquid chromatography (HPLC) was carried out on GILSON GX-281 using Waters C18 5 μM, 4.6*50 mm and Waters Prep C18 5 μM, 19*150 mm reverse phase columns, eluted with a gradient system of 5:95 to 95:5 acetonitrile:water with a buffer consisting of 0.05-0.1% TFA. Mass spectroscopy (MS) was performed on HPLC/MSD using a gradient system of 5:95 to 95:5 acetonitrile:water with a buffer consisting of 0.05-0.1% TFA on a C18 or C8 reversed phased column and electrospray ionization (ESI) for detection. All reactions were monitored by thin layer chromatography (TLC) carried out on either Merck silica gel plates (0.25 mm thick, 60F254) or Millipore Silica gel aluminum sheets (60F254) and visualized by using UV (254 nm) or dyes such as $KMnO_4$, p-Anisaldehyde and CAM (Hannesian's Stain). Molecular sieves (3 Å) were crushed and activated in vacuo at 390° C. overnight, then stored in a drying oven (300° C.) until just prior to use. Silica gel chromatography was carried out on a Teledyne ISCO CombiFlash purification system using pre-packed silica gel columns (12 g~330 g sizes). All compounds used for biological assays are greater than 95% pure based on NMR and HPLC by absorbance at 220 nm and 254 nm wavelengths.

Overall Synthesis Scheme:

The two main reaction schemes to synthesize the galactosides and galactosamines used in Examples 18-28 are summarized herein:

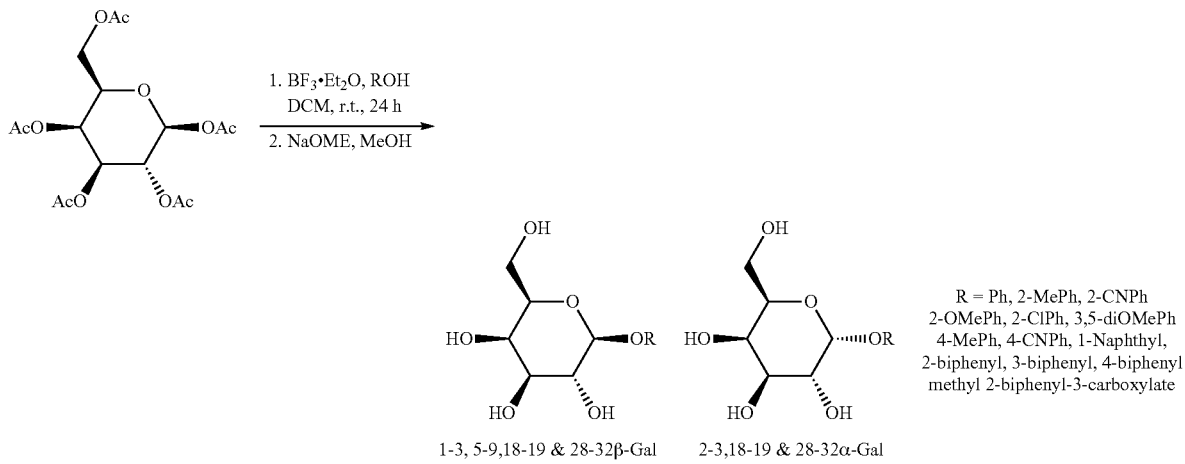

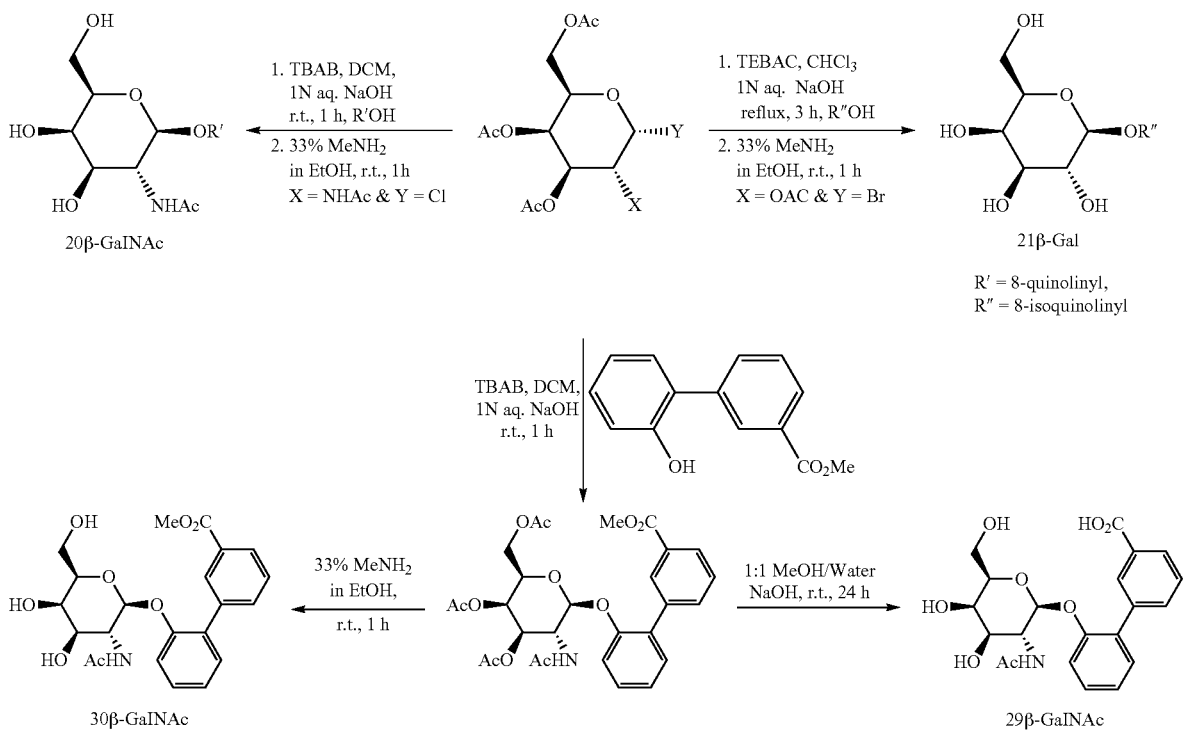

Reaction scheme A describes boron trifluoride promoted glycosidation of protected galactose followed by deprotection to yield galactosides. This process was used to synthesize compounds 1-3, 5-9, 18-19 and 28-32β-Gal and 2-3, 18-19 and 28-32α-Gal. Reaction scheme B shows the Koenigs-Knorr type reaction followed by deprotection for the substitution of a galactosyl halide with an alcohol to yield galactosides and galactosaminides. 20β-GalNac, 21β-Gal, 30β-GalNAc, and 29β-GalNac were produced using this procedure. The aglycone "R" groups that identify each of the galactosides/galactosamines are described in FIG. 2.

The common details of the glycosylation and deacetylation protocols used to synthesize these compounds are described below. Specific changes relevant to given compounds are described in later examples.

Glycosylation Protocol A: Starting from Galactose 1,2,3,4,6 Penta-O-Acetyl-β-D-Galactose.

Under nitrogen atmosphere, a solution of 1,2,3,4,6-penta-O-acetyl-β-D-galactose (0.25 mmol), phenol derivative (0.50 mmol), and 3 Å molecular sieves was stirred in either $CH_2Cl_2$ or 1,2-dichloroethane (5 mL) for 1 h. Boron trifluoride diethyl etherate (0.75 mmol) was then added dropwise, and the solution was stirred for the specified time and temperature, monitoring by TLC and LCMS. Upon completion, the reaction was cooled to room temperature (rt) and neutralized with $Et_3N$. The sieves were filtered off, and the remaining filtrate was washed with sat. aq. $NaHCO_3$ (2×1 mL), and brine (1×1 mL), dried over $Na_2SO_4$, and concentrated in vacuo. The resulting residue was then purified by silica gel chromatography with hexane/ethyl acetate combinations as eluent, to give the glycosylation product.

Glycosylation Protocol B: Starting from 2,3,4,6-Tetra-O-Acetyl-α-D-Galactopyranosyl Bromide Under nitrogen atmosphere, 1,2-dichloroethane (2 mL) was added to a flask containing 2,3,4,6-tetra-O-acetyl-α-D-galactopyranosyl bromide (103 mg, 0.25 mmol) and phenol derivative (0.75 mmol). Silver carbonate (0.50 mmol) was then added, and the solution was stirred for specified time and temperature, monitoring by TLC and LCMS. Upon completion, the reaction was cooled, filtered and concentrated in vacuo. The resulting residue was purified by silica gel chromatography with hexane/ethyl acetate combinations as eluent, to give the glycosylation product.

Glycosylation Protocol C: Starting from 2-Acetamido-3,4,6-Tri-O-Acetyl-2-Deoxy-α-D-Galactopyranosyl Chloride (Biphasic Conditions)

1N aqueous NaOH solution (1 mL) was added into a solution of 2-acetamido-3,4,6-tri-O-acetyl-2-deoxy-α-D-galactopyranosyl chloride (100 mg, 0.273 mmol), tetrabutylammonium bromide (88 mg, 0.273 mmol) and phenol derivative (0.546 mmol) in dichloromethane (2 mL) at room temperature. The reaction was stirred until the TLC indicated complete disappearance of chloride. The reaction was then diluted with dichloromethane (10 mL) and washed with water, followed by brine. The organic layer was collected, dried over $Na_2SO_4$ and concentrated in vacuo. The resulting residue was purified by silica gel chromatography with hexane/ethyl acetate combinations as eluent, to give the glycosylation product.

Glycosylation Protocol D: Starting from 2,3,4,6-Tetra-O-Acetyl-α-D-Galactopyranosyl Bromide (Biphasic Conditions)

1N aqueous NaOH solution (1 mL) was added into a solution of 2,3,4,6-tetra-O-acetyl-α-D-galactopyranosyl bromide (200 mg, 0.487 mmol), benzyltriethylammonium chloride (111 mg, 0.0.487 mmol) and phenol derivative (0.975 mmol) in chloroform (2 mL) at room temperature. The reaction was stirred at 60° C. until the TLC indicated complete disappearance of starting material. The reaction was cooled and diluted with dichloromethane (10 mL) and washed with water followed by brine. The organic layer was collected, dried over $Na_2SO_4$ and concentrated under vacuo. The resulting residue was purified by silica gel chromatography with hexane/ethyl acetate combinations as eluent, to give the glycosylation product.

Deprotection Protocol A: Using Sodium Methoxide

Acetyl esters were removed by dissolving the galactoside intermediate (0.5 mmol) in 20 mL of methanol, with a catalytic amount of sodium methoxide (0.02 M), and stirred overnight at room temperature. Upon completion, H+ exchange resin (DOWEX 50WX4-100) was added to neutralize the mixture. The resin was filtered off and the filtrate was concentrated and then dried in vacuo, and the residue was purified by HPLC (C18, 15*150 mm column; eluent: acetonitrile/water (0.05% TFA).

Deprotection Protocol B: Using Methylamine

33% Wt. Methylamine in absolute ethanol solution (5 mL) was added to the galactoside intermediate (0.105 mmol), and the reaction was stirred at room temperature (0.5-1 h) until TLC indicated complete disappearance of the staring material. Complete evaporation of the solvent provides the pure compound, which was further purified by HPLC (C18, 15*150 mm column; eluent: acetonitrile/water (0.05% TFA).

Example 2: Synthesis of 2-Methylphenyl α/β-D-Galactopyranoside (2α/β)

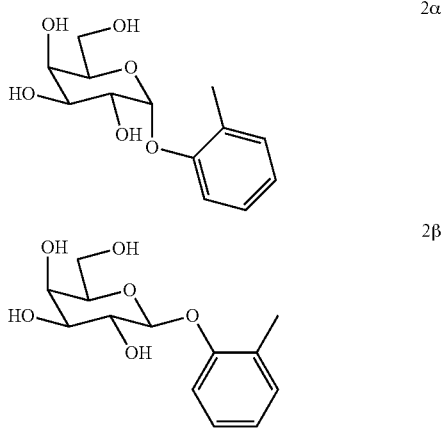

Following glycosylation protocol "A", described in Example 1, β-D-galactose pentaacetate (0.100 g, 0.26 mmol) was coupled with 2-methylphenol (0.052 mL, 0.51 mmol) in 1,2-dichloroethane (rt for 10 h), to give glycosylation product, 2-methylphenyl 2,3,4,6-tetra-O-acetyl-α/β-D-galactopyranoside, in 14% yield (alpha); and 6% yield (beta); ESI-MS [M+Na]+ calcd for $C_{21}H_{26}O_{10}Na+$ 461.14, found 461.3 (alpha) and 461.3 (beta). Subsequently, the acetates were removed using the deprotection protocol "A" described in Example 1 to give the title compounds (2α), and separately (2β), each in quantitative yield. Analytical data for (2α): 1H NMR (400 MHz, Methanol-d4) δ ppm 7.15-7.19 (m, 1H), 7.07-7.14 (m, 2H), 6.82-6.92 (m, 1H), 5.52 (d, J=2.7 Hz, 1H), 3.97-4.01 (m, 3H), 3.93 (t, J=6.1 Hz, 1H), 3.62-3.75 (m, 2H), 2.28 (s, 3H); ESI-MS [M+Na]+ calcd for $C_{13}H_{18}O_6Na+$ 293.10, found 293.3. Analytical data for (213): 1H NMR (400 MHz, Methanol-d4) δ ppm 7.05-7.20 (m, 3H), 6.86-6.94 (m, 1H), 4.85 (d, Hz, 1H), 3.89-3.93 (m, 1H), 3.83 (dd, J=9.8, 7.8 Hz, 1H), 3.76 (d, J=2.0 Hz, 1H), 3.75 (s, 1H), 3.63-3.67 (m, 1H), 3.57 (dd, J=9.8, 3.5 Hz, 1H), 2.27 (s, 3H); ESI-MS [M+Na]+ calcd for $C_{13}H_{18}O_6Na$+293.10, found 293.3.

Example 3: Synthesis of 2-cyanophenyl α/β-D-galactopyranoside (3α/β)

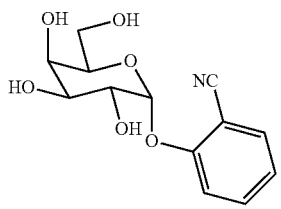

3α

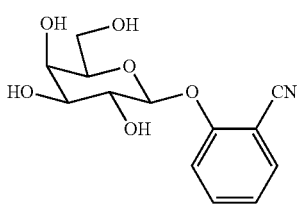

3β

Following glycosylation protocol "A", described in Example 1, β-D-galactose pentaacetate (0.100 g, 0.26 mmol) was coupled with 2-cyanophenol (0.061 g, 0.51 mmol) in 1,2-dichloroethane (rt for 10 h), to give glycosylation product, 2-cyanophenyl 2,3,4,6-tetra-O-acetyl-α/13-D-galactopyranoside, in 10% yield (alpha) and 10% yield (beta); ESI-MS [M+Na]+ calcd for $C_{21}H_{23}NO_{10}Na$+472.12, found 472.3 (alpha) and 472.3 (beta). The acetates were subsequently removed using the deprotection protocol "A" described in Example 1 to give the title compounds (3a), and separately (3β), each in quantitative yield. Analytical data for (3a): 1H NMR (400 MHz, Methanol-d4) δ ppm 7.56-7.66 (m, 2H), 7.42 (d, J=8.2 Hz, 1H), 7.10-7.17 (m, 1H), 5.78 (d, J=3.1 Hz, 1H), 4.03-4.10 (m, 2H), 4.00-4.03 (m, 1H), 3.93 (t, J=6.1 Hz, 1H), 3.61-3.72 (m, 2H); ESI-MS [M+H]+ calcd for $C_{13}H_{15}NO_6H$+282.10, found 282.3. Analytical data for (3β): 1H NMR (400 MHz, dimethylsulfoxide-d6) δ ppm 7.67 (dd, J=7.8, 1.6 Hz, 1H), 7.58 (ddd, J=8.9, 7.3, 1.8 Hz, 1H), 7.27 (d, J=8.6 Hz, 1H), 7.01-7.12 (m, 1H), 5.15 (d, J=5.5 Hz, 1H), 5.04 (d, J=7.8 Hz, 1H), 4.83 (d, J=5.9 Hz, 1H), 4.58 (t, J=5.5 Hz, 1H), 4.53 (d, J=4.3 Hz, 1H), 3.63-3.67 (m, 1H), 3.52-3.61 (m, 1H), 3.32-3.51 (m, 4H); ESI-MS [M+H]+ calcd for $C_{13}H_{15}NO_6H$+282.10, found 282.3

Example 4: Synthesis of 2-methoxyphenyl β-D-galactopyranoside (5β)

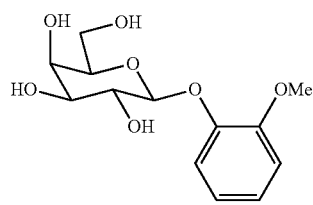

5β

Following glycosylation protocol "B", described in Example 1, acetobromogalactose tetraacetate (0.100 g, 0.24 mmol) was coupled with guaiacol (0.090 g, 0.73 mmol) in 1,2-dichloroethane (40° C. for 1 h), to give glycosylation product, 2-cyanophenyl 2,3,4,6-tetra-O-acetyl-β-D-galactopyranoside, in 16% yield; ESI-MS [M+Na]+ calcd for $C_{21}H_{26}O_{11}Na$+ 477.14, found 477.3. The acetates were subsequently removed via the deprotection protocol "A" described in Example 1 to give the title compound (5β) in quantitative yield. Analytical data for (513): 1H NMR (400 MHz, Methanol-d4) δ ppm 7.18 (d, J=7.4 Hz, 1H), 6.97-7.01 (m, 2H), 6.86-6.91 (m, 1H), 4.85 (d, 1H), 3.89 (d, J=3.5 Hz, 1H), 3.85 (s, 3H), 3.81-3.84 (m, 1H), 3.76 (d, J=2.0 Hz, 1H), 3.74 (s, 1H), 3.62-3.66 (m, 1H), 3.58 (dd, J=9.8, 3.5 Hz, 1H); ESI-MS [M+Na]+ calcd for $C_{13}H_{18}O_7Na$+309.10, found 309.3.

Example 5: Synthesis of 2-chlorophenyl β-D-galactopyranoside (6β)

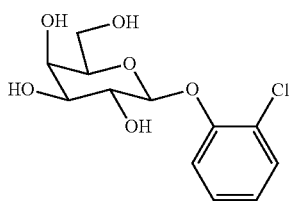

6β

Following glycosylation protocol "B", described in Example 1, acetobromogalactose tetraacetate (0.100 g, 0.24 mmol) was coupled with 2-chlorophenol (0.074 mL, 0.73 mmol) in 1,2-dichloroethane (40° C. for 1 h), to give the glycosylation product, 2-chlorophenyl 2,3,4,6-tetra-O-acetyl-β-D-galactopyranoside, in 23% yield; ESI-MS [M+Na]+ calcd for $C_{20}H_{23}ClO_{10}Na$+481.09, found 481.3. The acetates were subsequently removed via the deprotection protocol "A" described in Example 1 to give the title compound (6β) in quantitative yield. Analytical data for (6β): 1H NMR (400 MHz, Methanol-d4) δ ppm 7.32-7.38 (m, 1H), 7.19-7.29 (m, 2H), 6.93-7.02 (m, 1H), 4.95 (d, J=7.4 Hz, 1H), 3.92 (d, J=3.5 Hz, 1H), 3.88 (dd, J=9.4, 7.8 Hz, 1H), 3.72-3.82 (m, 2H), 3.66-3.71 (m, 1H), 3.59 (dd, J=9.4, 3.1 Hz, 1H); ESI-MS [M+Na]+ calcd for $C42H43N3O6Na$+ 313.05, found 313.2.

Example 6: 3,5-dimethoxyphenyl β-D-galactopyranoside (7β)

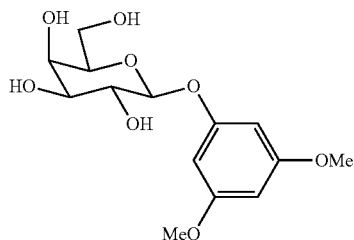

Following glycosylation protocol "B", described in Example 1, acetobromogalactose tetraacetate (0.100 g, 0.24 mmol) was coupled with 3,5-dimethoxyphenol (0.113 g, 0.73 mmol) in 1,2-dichloroethane (40° C. for 1 h), to give the glycosylation product, 3,5-dimethoxyphenyl 2,3,4,6-tetra-O-acetyl-β-D-galactopyranoside, in 8% yield; ESI-MS [M+Na]+ calcd for $C_{22}H_{28}O_{12}Na+507.15$, found 507.3. The acetates were then removed using the deprotection protocol "A", described in Example 1, to give the title compound (7β) in quantitative yield. Analytical data for (7β): 1H NMR (400 MHz, Methanol-d4) δ ppm 6.32 (d, J=2.0 Hz, 2H), 6.15 (t, J=2.2 Hz, 1H), 4.81 (d, J=7.8 Hz, 1H), 3.88 (d, J=3.1 Hz, 1H), 3.71-3.82 (m, 9H), 3.65-3.70 (m, 1H), 3.57 (dd, J=9.6, 3.3 Hz, 1H); ESI-MS [M+Na]+ calcd for C14H20O8Na+ 339.11, found 339.3.

Example 7: 4-methylphenyl β-D-galactopyranoside (8β)

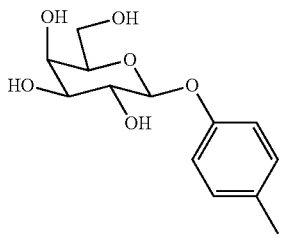

Following glycosylation protocol "B", described in Example 1, acetobromogalactose tetraacetate (0.100 g, 0.24 mmol), was coupled with p-cresol (0.077 mL, 0.73 mmol) in 1,2-dichloroethane (40° C. for 1 h), to give the glycosylation product, 4-methylphenyl 2,3,4,6-tetra-O-acetyl-β-D-galactopyranoside, in 3% yield; ESI-MS [M+Na]+ calcd for $C_{21}H_{26}O_{10}Na+461.14$, found 461.3. The acetates were then removed via the deprotection protocol "A" described in Example 1 to give the title compound (8β) in quantitative yield. Analytical data for (8β): 1H NMR (400 MHz, Methanol-d4) δ ppm 7.04-7.09 (m, 2H), 6.96-7.01 (m, 2H), 4.79 (d, J=7.8 Hz, 1H), 3.88-3.91 (m, 1H), 3.71-3.80 (m, 3H), 3.62-3.67 (m, 1H), 3.54-3.59 (m, 1H), 2.26 (s, 3H); ESI-MS [M+Na]+ calcd for $C_{13}H_{18}O_6Na+293.10$, found 293.2.

Example 8: 4-cyanophenyl β-D-galactopyranoside (9β)

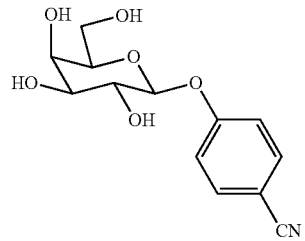

Following glycosylation protocol "B", described in Example 1, acetobromogalactose tetraacetate (0.100 g, 0.24 mmol) was coupled with 4-cyanophenol (0.087 g, 0.73 mmol) in 1,2-dichloroethane (40° C. for 1 h), to give the glycosylation product, 4-cyanophenyl 2,3,4,6-tetra-O-acetyl-β-D-galactopyranoside, in 16% yield; ESI-MS [M+Na]+ calcd for $C_{21}H_{23}NO_{10}Na+472.12$, found 472.3. The acetates were subsequently removed via the deprotection protocol "A" described in Example 1 to give the title compound (9β) in quantitative yield. Analytical data for (9β): 1H NMR (400 MHz, Methanol-d4) δ ppm 7.66 (d, J=9.0 Hz, 2H), 7.23 (d, J=8.6 Hz, 2H), 4.97 (d, J=7.8 Hz, 1H), 3.91 (d, J=3.5 Hz, 1H), 3.70-3.86 (m, 4H), 3.60 (dd, J=9.8, 3.5 Hz, 1H); ESI-MS [M+H]+ calcd for $C_{13}H_{15}NO_6H+282.10$, found 282.2

Example 9: 1-naphthalenyl α/β-D-galactopyranoside (18α/β)

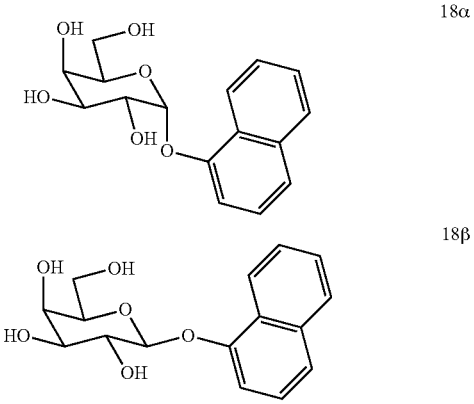

Following glycosylation protocol "A", described in Example 1, β-D-galactose pentaacetate (0.100 g, 0.26 mmol) was coupled with 1-naphthol (0.074 g, 0.51 mmol) in CH$_2$Cl$_2$ (rt for 48 h), to give glycosylation product, 1-naphthalenyl 2,3,4,6-tetra-O-acetyl-α/β-D-galactopyranoside, in 14% yield (alpha), and 40% yield (beta); ESI-MS [M+Na]+ calcd for $C_{24}H_{26}O_{10}Na+497.14$, found 497.3 (alpha) and 497.3 (beta). The acetates were then removed via the deprotection protocol "A" described in Example 1 to give the title compounds (18a), and separately (1813), each in quantitative yield. Analytical data for (18α): 1H NMR (400 MHz, Methanol-d4) δ ppm 8.38 (ddt, J=6.3, 3.6, 0.8 Hz, 1H), 7.83-7.77 (m, 1H), 7.53-7.27 (m, 5H), 5.72 (d, J=3.7 Hz, 1H), 4.20-4.05 (m, 2H), 4.04 (dd, J=3.4, 1.3 Hz, 1H), 3.98 (td, J=6.1, 5.6, 1.3 Hz, 1H), 3.75-3.64 (m, 2H); ESI-MS [M+Na]+ calcd for $C_{16}H_{18}O_6Na$+329.10, found 329.3. Analytical data for (18β): 1H NMR (400 MHz, Methanol-d4) δ ppm 8.43-8.36 (m, 1H), 7.83-7.76 (m, 1H), 7.53-7.41 (m, 3H), 7.37 (t, J=8.0 Hz, 1H), 7.22 (dd, J=7.7, 0.9 Hz, 1H), 5.07 (d, J=7.8 Hz, 1H), 4.02-3.92 (m, 2H), 3.84-3.70 (m, 3H), 3.63 (dd, J=9.7, 3.4 Hz, 1H); ESI-MS [M+Na]+ calcd for $C_{16}H_{18}O_6Na$+329.10, found 329.3.

Example 10: 8-isoquinolinyl β-D-galactopyranoside (21β)

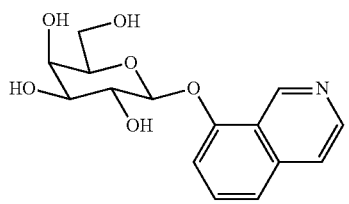

21β

Following glycosylation protocol "D", described in Example 1, 2,3,4,6-tetra-O-acetyl-α-D-galactopyranosyl bromide (200 mg, 0.487 mmol) was coupled with 8-hydroxy isoquinoline (141.53 mg, 0.975 mmol), to give glycosylation product, 8-isoquinolinyl 2,3,4,6-tetra-O-acetyl-β-D-galactopyranoside, in 86% yield; ESI-MS [M+H]+ calcd for $C_{23}H_{25}NO_{10}H$+476.16, found 476.3 The acetates were then removed via deprotection protocol "B" to give the title compound (21β) in 87% yield. Analytical data for (21β): 1H NMR (400 MHz, Methanol-d4) δ ppm 9.69 (s, 1H), 8.44 (d, J=5.5 Hz, 2H), 7.89-7.90 (m, 1H), 7.68-7.81 (m, 2H), 7.57 (d, J=8.2 Hz, 1H), 7.40 (d, J=7.8 Hz, 1H), 5.16 (d, J=7.8 Hz, 1H), 3.99-4.07 (m, 1H), 3.97 (d, J=3.5 Hz, 1H), 3.76-3.85 (m, 3H), 3.67 (dd, J=9.8, 3.1 Hz, 1H); ESI-MS [M+H]+ calcd for $C_{15}H_{17}NO_6H$+308.11, found 308.3.

Example 11: [1,1'-biphenyl]-2-yl α/β-D-galactopyranoside (28α/β)

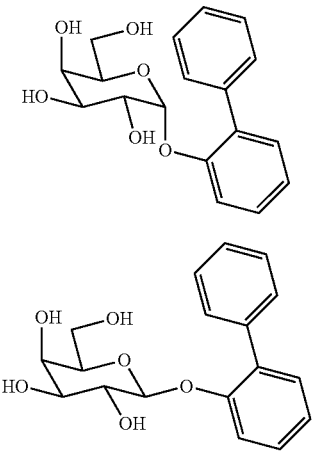

Following glycosylation protocol "A", described in Example 1, β-D-galactose pentaacetate (0.100 g, 0.26 mmol) was coupled with 2-phenylphenol (0.087 g, 0.51 mmol) in $CH_2Cl_2$ (rt for 48 h), to give glycosylation product, [1,1'-biphenyl]-2-yl 2,3,4,6-tetra-O-acetyl-α/β-D-galactopyranoside, in 38% yield (alpha) and 15% yield (beta); ESI-MS [M+Na]+ calcd for C26H28O10Na+ 523.16, found 523.4 (alpha) and 523.4 (beta). The acetates were then removed via deprotection protocol "A", to give the title compounds (28α), and separately (28β), each in quantitative yield. Analytical data for (28α): 1H NMR (400 MHz, Methanol-d4) δ ppm 7.60-7.54 (m, 2H), 7.40 (t, J=7.6 Hz, 2H), 7.36-7.28 (m, 4H), 7.09 (m, 1H), 5.61 (d, J=3.7 Hz, 1H), 3.90 (m, 1H), 3.80 (d, J=3.4 Hz, 1H), 3.70 (m, 1H), 3.61-3.47 (m, 3H); ESI-MS [M+Na]+ calcd for $C_{18}H_{20}O_6Na$+355.12, found 355.3. Analytical data for (28β): 1H NMR (400 MHz, Methanol-d4) δ ppm 7.62-7.58 (m, 2H), 7.40-7.34 (m, 2H), 7.31-7.25 (m, 4H), 7.07 (m, 1H), 5.00 (d, J=7.7 Hz, 1H), 3.88 (dd, J=3.3, 1.0 Hz, 1H), 3.79-3.65 (m, 4H), 3.54 (dd, J=9.6, 3.4 Hz, 1H); ESI-MS [M+Na]+ calcd for $C_{18}H_{20}O_6Na$+355.12, found 355.3.

Example 12: 2'-(α/β-D-galactopyranosyloxy)-[1,1'-Biphenyl]-3-carboxylic acid methyl ester (30α/β)

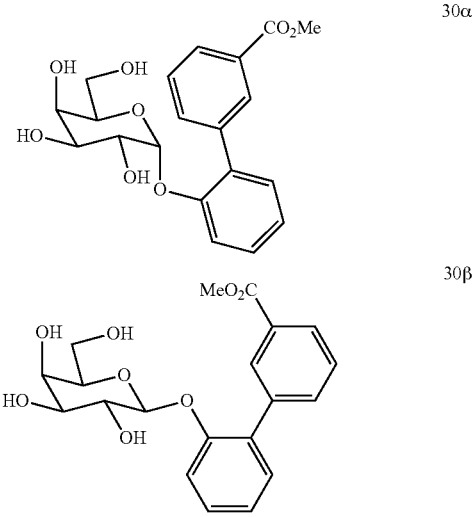

Following glycosylation protocol "A", described in Example 1, β-D-galactose pentaacetate (0.200 g, 0.51 mmol) was coupled with 2'-hydroxy[1,1'biphenyl]-3-carboxylic acid methyl ester (0.234 g, 1.02 mmol) in $CH_2Cl_2$ (rt for 1.5 h), to give glycosylation product, 2'-(2,3,4,6-tetra-O-acetyl-α/β-D-galactopyranosyloxy)-[1,1'-Biphenyl]-3-carboxylic acid methyl ester, in 5% yield (alpha) and 18% yield (beta); ESI-MS [M+Na]+ calcd for $C_{28}H_{30}O_{12}Na$+ 581.16, found 581.4 (alpha) and 581.4 (beta). The acetates were then removed via deprotection protocol "A" to give the title compounds (30α) and separately (30β), each in quantitative yield. Analytical data for (30α): 1H NMR (400 MHz, Methanol-d4) δ 8.23 (m, 1H), 7.97 (m, 1H), 7.86 (m, 1H), 7.53 (tt, J=7.7, 0.7 Hz, 1H), 7.39-7.31 (m, 3H), 7.11 (m, 1H), 5.65 (d, J=3.7 Hz, 1H), 3.95-3.90 (m, 4H), 3.85 (d, J=3.4 Hz, 1H), 3.73 (dd, J=10.1, 3.4 Hz, 1H), 3.66-3.52 (m, 4H); ESI-MS [M+Na]+ calcd for $C_{20}H_{22}O_8Na$+413.12, found 413.3. Analytical data for (30β): 1H NMR (400 MHz, Methanol-d4) δ 8.24 (m, 1H), 7.92 (m, 1.0 Hz, 2H), 7.50 (td, J=7.8, 0.6 Hz, 1H), 7.37-7.30 (m, 3H), 7.14-7.08 (m, 1H), 5.03 (d, J=7.7 Hz, 1H), 3.92 (d, J=0.8 Hz, 3H), 3.88 (dd, J=3.5, 0.9 Hz, 1H), 3.80-3.66 (m, 4H), 3.56 (ddd, J=9.6, 3.4, 0.7 Hz, 1H); ESI-MS [M+Na]+ calcd for $C_{20}H_{22}O_8Na+$ 413.12, found 413.3.

Example 13: 2'-(α/β-D-galactopyranosyloxy)-[1,1'-Biphenyl]-3-carboxylic acid (29α/β)

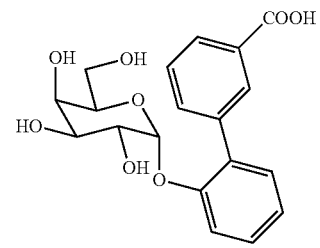

29α

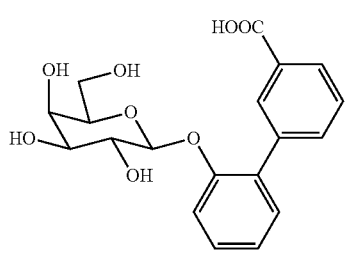

29β

Compound 30α (38 mg, 0.097 mmol) and separately 30β (38 mg, 0.097 mmol), produced as described in Example 12, were each dissolved in MeOH (2 mL) at rt. Then, [0.5 M] NaOH aq. (2 mL) was added dropwise, and the reactions were monitored by LCMS. After 24 h, the reactions were acidified with [0.2 N] HCl aq. to a pH of ~3-4. The solvents were then evaporated under reduced pressure, and the compounds were purified by HPLC (C18, 15*150 mm column; eluent: acetonitrile/water (0.05% TFA) to give the title compounds (29α) in 5% yield, and separately (29β) in 88% yield. Analytical data for (29α): 1H NMR (300 MHz, methanol-d4) δ ppm 8.22 (d, J=1.6 Hz, 1H), 7.84-8.02 (m, 2H), 7.53 (td, J=7.7, 4.5 Hz, 1H), 7.29-7.40 (m, 3H), 7.06-7.16 (m, 1H), 5.63-5.69 (m, 1H), 3.89-3.96 (m, 1H), 3.85 (br. s., 1H), 3.72-3.78 (m, 1H), 3.54-3.67 (m, 3H); ESI-MS [M+Na]+ calcd for $C_{19}H_{20}O_8Na+399.11$, found 399.6. Analytical data for (29β): 1H NMR (300 MHz, methanol-d4) δ ppm 8.16 (s, 1H), 7.87 (d, J=7.8 Hz, 1H), 7.81 (d, J=7.8 Hz, 1H), 7.41 (t, J=7.8 Hz, 1H), 7.19-7.30 (m, 3H), 6.98-7.06 (m, 1H), 4.94 (d, J=7.8 Hz, 1H), 3.80 (d, J=3.1 Hz, 1H), 3.55-3.72 (m, 4H), 3.48 (dd, J=9.6, 3.3 Hz, 1H); 13C NMR (100 MHz, methanol-d4) δ 170.1, 155.7, 140.1, 135.6, 132.0, 131.7, 131.6, 130.2, 129.1, 123.6, 116.6, 102.6, 77.0, 75.2, 72.3, 70.2, 62.4; ESI-MS [M+Na]+ calcd for $C_{19}H_{20}O_8Na+399.11$, found 399.6.

Example 14: Synthesis of 2'-(2-acetamido-2-deoxy-β-D-galactopyranosyloxy)-[1,1'-Biphenyl]-3-carboxylic acid methyl ester (30β-Nac)

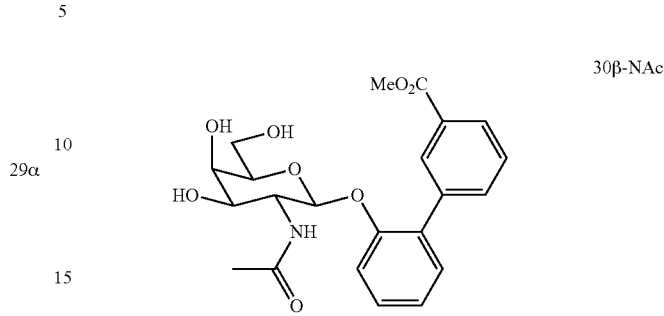

30β-NAc

Following glycosylation protocol "C", described in Example 1, 2-acetamido-3,4,6-tri-O-acetyl-2-deoxy-α-D-galactopyranosyl chloride (100 mg, 0.273 mmol), was coupled with 2'-hydroxy[1,1'biphenyl]-3-carboxylic acid methyl ester (0.125 g, 0.546 mmol), to give glycosylation product, 2'-(2-acetamido-3,4,6-tri-O-acetyl-2-deoxy-β-D-galactopyranosyloxy)-[1,1'-Biphenyl]-3-carboxylic acid methyl ester. The acetates were removed via deprotection protocol B, to give the title compound (30β-Nac) in 80% yield. Analytical data for (30β-Nac): 1H NMR (400 MHz, Methanol-d4) δ ppm 8.08 (s, 1H), 7.94 (d, J=7.4 Hz, 1H), 7.72 (d, J=7.4 Hz, 1H), 7.43-7.49 (m, 1H), 7.27-7.38 (m, 3H), 7.10 (t, J=7.2 Hz, 1H), 5.06 (d, J=8.6 Hz, 1H), 4.04 (t, J=9.6 Hz, 1H), 3.90 (s, 3H), 3.72-3.87 (m, 4H), 3.57-3.69 (m, 3H), 1.60 (s, 3H); ESI-MS [M+Na]+ calcd for $C_{22}H_{25}NO_8Na^+$ 454.15, found 454.3.

Example 15: Synthesis of 2'-(2-acetamido-2-deoxy-β-D-galactopyranosyloxy)-[1,1'-Biphenyl]-3-carboxylic acid (29β-NAc)

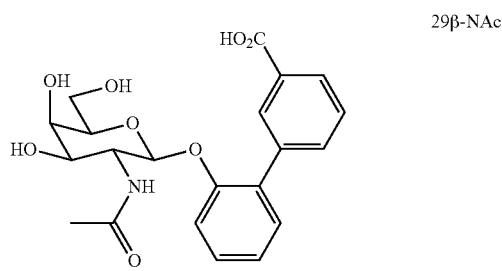 [SMILES: COC(=O)c1cccc(-c2ccccc2OC2OC(CO)C(O)C(O)C2NC(C)=O)c1]

29β-NAc

NaOH (79 mg, 1.97 mmol) was added into a solution of 30β-NAc (Example 13, 110 mg, 0.197 mmol) in 50% water in methanol (10 mL) at room temperature. The reaction was stirred at the same temperature (15 h) until the TLC indicated complete disappearance of the staring material. The reaction solution was neutralized with 6N aqueous HCl and the MeOH was evaporated in vacuo. The aqueous solution was adjusted to a pH~2 with 6N aqueous HCl and the product was extracted with ethyl acetate (3×10 mL). The organic layers were combined and washed with brine, dried over $Na_2SO_4$, and concentrated in vacuo. The resulting residue was purified by silica gel chromatography with dichloromethane/methanol combinations as eluent provide the title compound (29β-NAc) in 67% yield. Analytical data for (29β-NAc): 1H NMR (300 MHz, methanol-d4) δ ppm 8.00 (s, 1H), 7.87 (d, J=7.8 Hz, 1H), 7.64 (d, J=7.4 Hz, 1H), 7.35-7.42 (m, 1H), 7.21-7.29 (m, 3H), 6.98-7.07 (m, 1H), 5.01 (d, J=8.6 Hz, 1H), 3.94 (dd, J=10.6, 8.6 Hz, 1H), 3.78 (d, J=3.1 Hz, 1H), 3.64-3.76 (m, 2H), 3.54-3.61 (m, 2H), 1.55 (s, 3H); ESI-MS [M+Na]+ calcd for $C_{21}H_{23}NO_8Na+$ 440.13, found 440.3

Example 16: Synthesis of [1,1'-biphenyl]-3-yl α/β-D-galactopyranoside (31α/β)

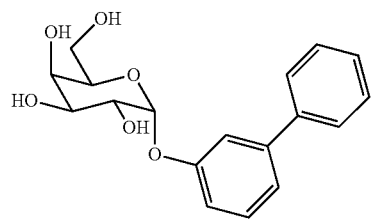

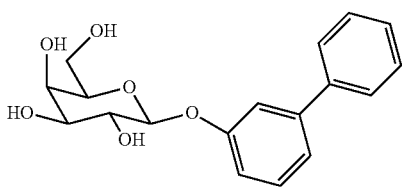

Following glycosylation protocol "A", described in Example 1, β-D-galactose pentaacetate (0.100 g, 0.26 mmol) was coupled with 3-phenylphenol (0.087 g, 0.51 mmol) in $CH_2Cl_2$ (rt for 72 h), to give glycosylation product, [1,1'-biphenyl]-3-yl 2,3,4,6-tetra-O-acetyl-α/β-D-galactopyranoside, in 36% yield (alpha) and 23% yield (beta). Analytical data for [1,1'-biphenyl]-3-yl 2,3,4,6-tetra-O-acetyl-α-D-galactopyranoside: ESI-MS [M+Na]+ calcd for $C_{26}H_{28}O_{10}Na+523.16$, found 523.4. Analytical data for [1,1'-biphenyl]-3-yl 2,3,4,6-tetra-O-acetyl-α/β-D-galactopyranoside: ESI-MS [M+Na]+ calcd for $C_{26}H_{28}O_{10}Na+$ 523.16, found 523.3. The acetates were removed via deprotection protocol A, to give the title compounds (31α), and separately (31β), each in quantitative yield. Analytical data for (31α): 1H NMR (400 MHz, Methanol-d4) δ ppm 7.49 (m, 2H), 7.35-7.13 (m, 6H), 7.06 (m, 1H), 5.46 (d, J=2.7 Hz, 1H), 3.94-3.83 (m, 4H), 3.66-3.55 (m, 2H); ESI-MS [M+Na]+ calcd for $C_{18}H_{20}O_6Na+355.12$, found 355.3. Analytical data for (31β): 1H NMR (400 MHz, Methanol-d4) δ ppm 7.61-7.56 (m, 2H), 7.42-7.22 (m, 6H), 7.08 (m, 1H), 4.91 (d, J=7.7 Hz, 1H), 3.89 (dd, J=3.5, 0.9 Hz, 1H), 3.84-3.66 (m, 4H), 3.58 (dd, J=9.7, 3.4 Hz, 1H); ESI-MS [M+Na]+ calcd for $C_{18}H_{20}O_6Na+$ 355.12, found 355.3.

Example 17: Synthesis of [1,1'-biphenyl]-4-yl α/β-D-galactopyranoside (32α/β)

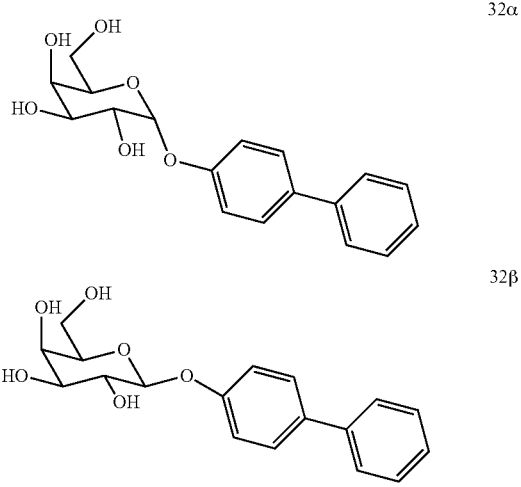

Following glycosylation protocol "A", described in Example 1, β-D-galactose pentaacetate (0.100 g, 0.26 mmol) was coupled with 4-phenylphenol (0.087 g, 0.51 mmol) in $CH_2Cl_2$ (rt for 72 h), to give glycosylation product, [1,1'-biphenyl]-4-yl 2,3,4,6-tetra-O-acetyl-α/β-D-galactopyranoside, in 26% yield (alpha) and 14% yield (beta). Analytical data for [1,1'-biphenyl]-4-yl 2,3,4,6-tetra-O-acetyl-α-D-galactopyranoside: ESI-MS [M+Na]+ calcd for $C_{26}H_{28}O_{10}Na+523.16$, found 523.3. Analytical data for [1,1'-biphenyl]-4-yl 2,3,4,6-tetra-O-acetyl-α/β-D-galactopyranoside: ESI-MS [M+Na]+ calcd for $C_{26}H_{28}O_{10}Na+$ 523.16, found 523.3. Step 2: The acetates were removed via deprotection protocol A, to give the title compounds (32α), and separately (32β), each in quantitative yield. Analytical data for (32α): 1H NMR (400 MHz, Methanol-d4) δ ppm 7.59-7.49 (m, 4H), 7.44-7.36 (m, 2H), 7.31-7.19 (m, 3H), 5.54 (d, J=2.7 Hz, 1H), 4.03-3.92 (m, 4H), 3.70 (dd, J=6.3 Hz, 2H); ESI-MS [M+Na]+ calcd for $C_{18}H_{20}O_6Na+355.12$, found 355.3. Analytical data for (32β): 1H NMR (400 MHz, Methanol-d4) δ ppm 7.61-7.56 (m, 2H), 7.42-7.22 (m, 6H), 7.08 (m, 1H), 4.91 (d, J=7.7 Hz, 1H), 3.89 (dd, J=3.5, 0.9 Hz, 1H), 3.84-3.66 (m, 4H), 3.58 (dd, J=9.7, 3.4 Hz, 1H); ESI-MS [M+Na]+ calcd for $C_{18}H_{20}O_6Na+355.12$, found 355.3.

Example 18: Competitive Inhibition Assay of Galactosidase Compounds Against FmlH An ELISA-based competition assay was performed to detect binding of $FmlH_{LD}$ to surface-immobilized desialylated bovine submaxillary mucin (ds-BSM) in the presence or absence of soluble compounds at 1 and 0.1 mM (unless otherwise noted): galactosidase (gal), N-acetyl galactosidase (GalNAc), TF, mannose (1 mM only), glucose (1 mM only), lactose (galactose-(β1-4-glucose, 1 mM only), o-nitrophenyl β-galactoside (ONPG, 0.1 mM only) and isopropyl β-thio-galactoside (IPTG, 0.1 mM only). Immulon 4HBX 96-well plates were coated overnight with 1 μg bovine submaxillary mucin (Sigma). Coated wells were then treated with 100 μl of *Arthrobacter ureafaciens* sialidase (AUS) (10 mU/ml) diluted in PBS for 1 hour at 37° C. Thereafter, wells were incubated with 200 μl blocking buffer (PBS+1% BSA) for 2 hours at 23° C., followed by incubation with 100 µl biotinylated $FmlH_{LD}$ diluted in blocking buffer to 20 µg/ml in the presence or absence of the tested compounds for 1 hr at 23° C. After washing 3× with PBS+0.05% TWEEN-20, 100 µl Streptavidin-HRP conjugate (BD Biosciences; 1:2000 dilution in blocking buffer) was added to each well for 1 hr at 23° C. After a final round of washing, plates were developed with 100 µl Tetramethylbenzidine (TMB, BD Biosciences) substrate, quenched within 1-2 min with 50 µl M H2SO4, and absorbance measured at 450 nm. The results are summarized in FIG. 5. 1 mM Gal, GalNAc, and TF were each capable of inhibiting $FmlH_{LD}$, with GalNAc exerting greater inhibitory potency than TF or Gal, while 1 mM mannose (Man) or glucose (Glc) had no effect on the ability of $FmlH_{LD}$ to bind ds-BSM. Lactose (Lac) was also incapable of inhibiting $FmlH_{LD}$, demonstrating the high selectivity with which $FmlH_{LD}$ engages Gal-containing glycans. While IPTG exerted minor inhibitory activity at 100 µM, ONPG was found to block $FmlH_{LD}$ from interacting with ds-BSM more effectively than Gal, GalNAc, or TF at a low concentration. The strong inhibitory potency of ONPG suggested that β-galactosides could be rationally designed with higher affinity by specifically targeting residues within and surrounding the sugar binding pocket of FmlH.

Example 19: X-Ray Crystallography of Apo and Ligand-Bound $FmlH_{LD}$

To further understand the $FmlH_{LD}$ binding pocket to further the design of appropriate inhibitors, X-ray crystallography was implemented to elucidate the three-dimensional structures of apo and ligand-bound $FmlH_{LD}$. The parameters used for data collection and analysis are summarized in Table 1, and described in detail below.

TABLE 1

|  | apo $FmlH_{LD}$ (6AOW) | $FmlH_{LD}$: TF (6AOX) | $FmlH_{LD}$: ONPG (6AOY) | $FmlH_{LD}$: 4β (6ARM) | $FmlH_{LD}$: 5β (6ARN) | $FmlH_{LD}$: 20β (6ARO) | $FmlH_{LD}$: 29β-NAc (6AS8) |
|---|---|---|---|---|---|---|---|
| Data collection | | | | | | | |
| Space group | C2 | C 2 2 21 | C2 | P 2 21 21 | P 21 21 2 | P 21 21 2 | P 2 21 21 |
| Cell dimensions | | | | | | | |
| a, b, c (Å) | 65.5, 78.3, 58.5 | 67.4, 78.1, 105.5 | 66.2, 78.3, 58.5 | 50.0, 51.3, 114.6 | 51.3, 116.1, 50.3 | 51.3, 116.3, 50.6 | 51.0, 51.5, 117.5 |
| α, β, γ (°) | 90.0, 97.0, 90.0 | 90.0, 90.0, 90.0 | 90.0, 97.5, 90.0 | 90.0, 90.0, 90.0 | 90.0, 90.0, 90.0 | 90.0, 90.0, 90.0 | 90.0, 90.0, 90.0 |
| Resolution (Å) | 50.0-1.6 (1.63-1.60) | 52.8-2.1 (2.21-2.10) | 40.0-1.8 (1.90-1.80) | 57.3-1.25 (1.53-1.50) | 51.3-1.25 (1.27-1.25) | 58.1-1.15 (1.17-1.15) | 50.0-2.10 (2.14-2.10) |
| $R_{merge}$ (%)[a] | 9.3 (139) | 27.2 (189) | 8.1 (67.8) | 6.8 (137) | 6.5 (192) | 11.4 (86.9) | 14.6 (51.3) |
| $R_{pim}$ (%)[b] | 5.7 (87.6) | 8.0 (55.7) | 3.2 (32.2) | 2.8 (68.7) | 2.7 (102) | 4.8 (63.7) | 4.1(26.0) |
| I/σI | 8.7 (0.9) | 8.0 (1.6) | 15.6 (2.8) | 16.0 (0.8) | 15.0 (0.7) 9.2 (1.0) | | 16.1 (1.5) |
| Completeness (%) | 98.5 (99.8) | 99.6 (99.9) | 99.6 (98.5) | 96.4 (78.3) | 99.2 (91.5) | 93.6 (58.5) | 87.7 (44.2) |
| Multiplicity | 3.5 (3.4) | 12.0 (12.0) | 6.9 (5.1) | 6.2 (4.1) | 6.5 (4.2) | 6.0 (2.6) | 10.7 (2.5) |
| $CC_{1/2}$ | 1.0 (0.38) | 0.99 (0.39) | 1.0 (0.79) | 1.0 (0.28) | 1.0 (0.31) | 0.99 (0.46) | 0.99 (0.82) |
| Total/Unique reflections | 134,257/ 38,073(6,454/ 1,891) | 199,439/ 16,562(28,511/ 2,379) | 188,555/ 27,380(19,891/ 3,397) | 288,591/ 46,203(7,374/ 1,811) | 544,119/ 83,215(15,705/ 3,708) | 610,631/ 101,126(7,812/ 3,048) | 176,770/16,455 (932/412) |
| Refinement | | | | | | | |
| $R_{work}$[c]/$R_{free}$[d] | 19.5/23.3 | 22.5/25.9 | 18.5/22.0 | 20.1/24.0 | 20.8/22.4 | 17.6/19.0 | 20.1/24.0 |
| No. atoms | | | | | | | |
| Protein | 2307 | 2247 | 2345 | 2309 | 2321 | 2431 | 2322 |
| Ligand/ion | 15 | 52 | 26 | 47 | 45 | 49 | 60 |
| Water | 262 | 140 | 263 | 326 | 350 | 513 | 126 |
| B-factors | | | | | | | |
| Protein | 24.9 | 35.6 | 26.9 | 23.2 | 19.7 | 14.5 | 30.2 |
| Ligand/ion | 40.6 | 31.5 | 40.1 | 25.2 | 19.4 | 14.7 | 32.3 |
| Water | 35.5 | 38.2 | 32.8 | 30.8 | 29.5 | 30.5 | 32.6 |
| R.m.s. deviations | | | | | | | |
| Bond lengths (Å) | 0.009 | 0.004 | 0.008 | 0.008 | 0.006 | 0.013 | 0.011 |
| Bond angles (°) | 1.19 | 0.98 | 1.11 | 1.19 | 1.10 | 1.54 | 0.81 |
| Ramachandran plot | | | | | | | |
| favored (%) | 97.0 | 98.0 | 96.0 | 94.0 | 97.0 | 97.0 | 96.0 |
| allowed (%) | 3.0 | 2.0 | 3.0 | 5.7 | 2.3 | 2.7 | 3.7 |
| outliers (%) | 0 | 0 | 1.0 | 0.3 | 0.7 | 0.3 | 0.3 |
| Clashscore | 2.6 | 1.6 | 3.9 | 9.1 | 6.1 | 3.5 | 0.4 |

Figure 4:
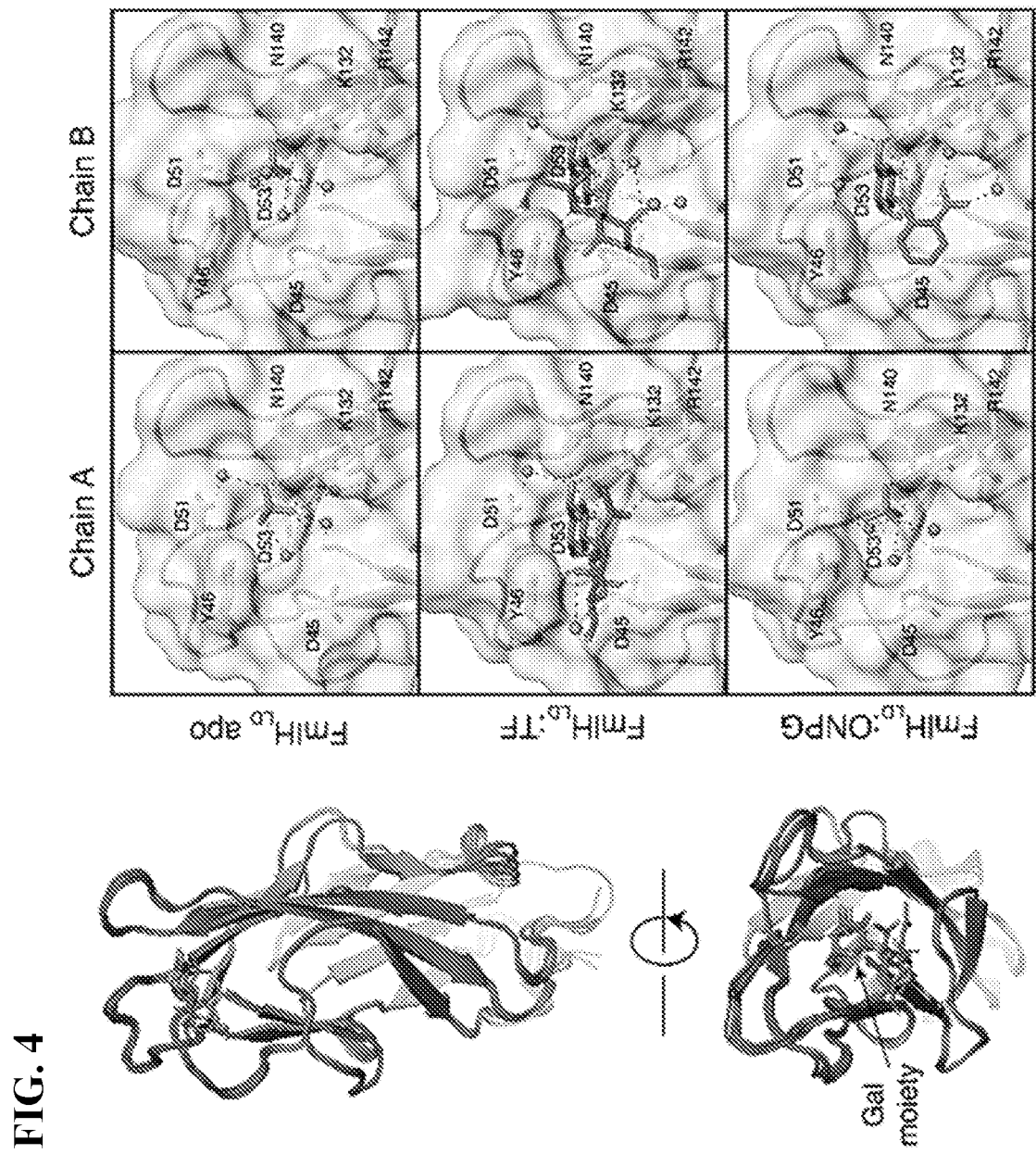
FIG. 4 is directed to the structural characterization of galactoside antagonists of FmlH. Panel A shows the structural alignment of $FmlH_{LD}$ from an apo $FmlH_{LD}$ crystal structure (PDB ID 6AOW), a $FmlH_{LD}$-TF co-crystal structure (PDB ID 6AOX), and a $FmlH_{LD}$-ONPG co-crystal structure (PDB ID 6AOY). Panel B shows crystal structures of sulfate ions or ligands bound in the $FmlH_{LD}$ binding pocket, with H-bonding (black dashed lines) indicated between sulfate ions (yellow sticks), ligands (green sticks), water molecules (red spheres), or side chains (pink sticks).

[a] $R_{merge} = \Sigma_{hkl} \Sigma_i |I_i(hkl)-<I(hkl)>|/\Sigma_{hkl} \Sigma_i I_i(hkl)$, where the sum i is over all separate measurements of the unique reflection hkl.
[b] $R_{pim} = \Sigma_{hkl} [1/(n-1)]^{1/2} \Sigma_i|I_i(hkl)-<I(hkl)>|/\Sigma_{hkl} \Sigma_i I_i(hkl)$
[b] $R_{work} = \Sigma_{hkl} ||F_{obs}| - |F_{calc}||/\Sigma_{hkl} |F_{obs}|$
[c] $R_{free}$, calculated the same as for $R_{work}$ but on the 5% data randomly excluded from the refinement calculation.
Values in parentheses indicate the highest resolution shell First, a crystal structure of apo FmlH$_{LD}$ was solved at 1.6 Å resolution by molecular replacement (MR) using FmlH$_{LD}$ (PDB ID 3MCY) as the search model. Briefly, crystals of apo FmlH$_{LD}$ in 10 mM Hepes pH 7.5, 50 mM NaCl were grown by mixing 2 µl protein (6 mg/ml) with 2 µl of mother liquor (0.2 M ammonium sulfate, 0.1M NaCl, 0.1 M MES (pH 5.6), 28% PEG 3350) and equilibrated against 1 ml mother liquor in the reservoir. Additional co-crystals of FmlH$_{LD}$ bound to TF or ONPG were grown by mixing 2 µl protein (6 mg/ml) in the presence of 5 mM compound with 2 µl of mother liquor (0.2 M ammonium sulfate, 0.1M NaCl, 0.1 M MES (pH 5.6), 32% PEG 3350). These crystals were transferred into cryoprotectant (0.2 M ammonium sulfate, 0.1M NaCl, 0.1 M MES (pH 5.6), 35% PEG 4000, 10% glycerol) and then flash frozen in liquid nitrogen. Diffraction data for FmlH$_{LD}$ apo and TF were collected at 100 K at an in-house facility equipped with a rotating anode Rigaku MicroMax 007 generator, a Rayonix Marmux X-ray source (Evanston, IL), and a Mar345 image plate detector. Diffraction data for FmlH$_{LD}$ apo, ONPG were collected at 100 K at the ALS Beamline 4.2.2. Data were indexed and integrated in iMosflm [43], XDS [44], or HKL2000 and scaled by Scala [45]. The phase problem was solved by molecular replacement (MR) using Phaser-MR in PHENIX [46] with FmlH$_{LD}$ from PDB ID 3MCY. Several rounds of refinements were performed in PHENIX to improve the final models. Within this structure, two copies of FmlH$_{LD}$ are found in the asymmetric unit, each of which adopts a canonical I3-sandwich fold, with three distinct binding loops (Loop 1: residues 10-15; Loop 2: residues 44-53; Loop 3: residues 132-142) that form a wide, shallow, solvent-exposed binding pocket (FIG. 4, panels A and B). Within the binding pocket of both copies resides a sulfate ion, which interacts with residues implicated in Gal binding (FIG. 4, panel B). Co-crystal structures of FmlH$_{LD}$ bound to TF and FmlH$_{LD}$ bound to ONPG were also solved to 2.1 Å and 1.8 Å, respectively. Structural overlay of the apo and ligated crystal structures yields root-mean-square deviation (RMSD) values that fall within 0.6 Å, suggesting that FmlH$_{LD}$ adopts the same active or functional conformation state in the absence or presence of ligand (FIG. 4, panel A), which is structurally homologous to the high-affinity conformation of FimH [27, 28].

The co-crystal structure of FmlH$_{LD}$-TF reveals two copies of FmlH$_{LD}$-TF in the unit cell, in which each TF adopts a distinct ligand conformation (FIG. 4, panel B). In both copies, the terminal Gal in TF occupies the cleft of the binding pocket through direct polar interactions with residues F1, D53, K132, and N140. In contrast, the orientation of the GalNAc in TF differs significantly between the two copies of FmlH. In chain A, the GalNAc sugar points toward Loop 3, with the carbonyl group of GalNAc forming a hydrogen bond (H-bond) with the guanidinium group of R142. In chain B, however, the GalNAc packs against and forms a H-bond with the hydroxyl group of Y46. Accordingly, the differences in the orientation of bound ligand across the two copies are accompanied by slight differences in orientation of the side chains of the interacting residues Y46 and R142. The multiple binding modes observed for a single ligand suggests that the wide, shallow nature of the galactose binding pocket in FmlH would enable galactosides to potentially bind FmlH with diverse interactions and conformations.

The FmlH$_{LD}$-ONPG co-crystal structure also shows two copies of FmlH$_{LD}$ in the unit cell, in which a sulfate ion occupies the binding pocket of chain A while ONPG occupies the binding pocket of chain B (FIG. 4, panel B). As expected, the Gal component of ONPG resides in the cleft of the binding pocket, while the solvent-exposed nitrophenyl group mediates a polar or salt bridge interaction with R142 through an intricate network of H-bonds with water molecules. Furthermore, the positioning of the Gal component of ONPG aligns with that of the Gal residue of TF (FIG. 4, panel A). Moreover, the conformation of the FmlH binding pocket observed in this FmlH$_{LD}$-ONPG co-crystal structure resembles the binding pocket conformation in the FmlH$_{LD}$-TF co-crystal structure, reflecting a high-affinity binding orientation that can be targeted for drug discovery. Together, these observations suggested that FmlH$_{LD}$ from the FmlH$_{LD}$-ONPG co-crystal structure represented an appropriate structural candidate for use in virtual screening to inform the design of galactoside compounds specific for FmlH.

Example 20: Virtual Screen and Identification of FmlH-Targeting Galactosides

Figure 5:
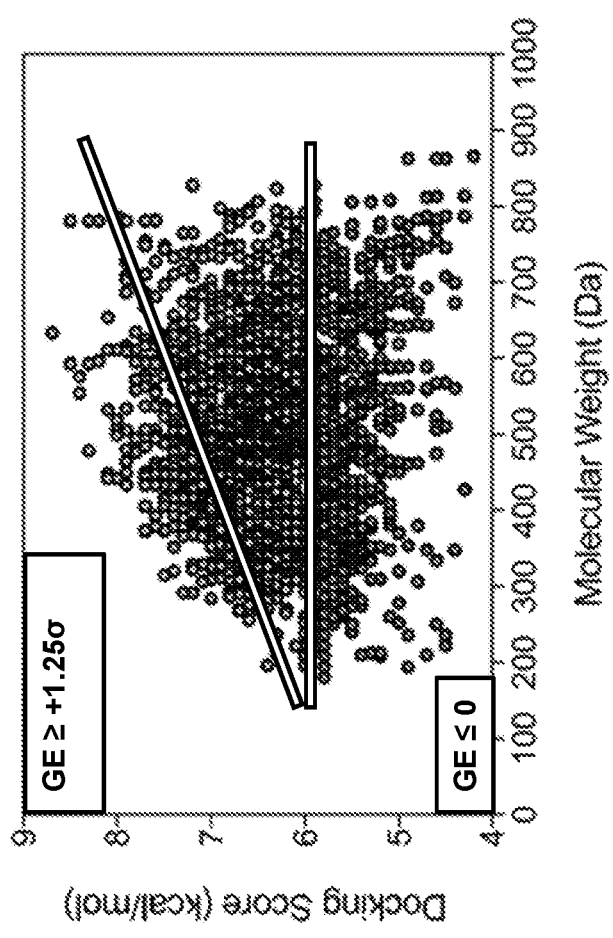
FIG. 5A presents the results of a virtual screen of galactoside compounds against $FmlH_{LD}$. Panel A shows a scatter plot of the docking score (GE) of the top predicted binding mode for each compound plotted against the molecular weight for each galactoside. The white lines divide compounds with GE values 1.256 above the mean (above top line) from compounds with GE values below 0 (under bottom line). Panel B shows the surface representation of $FmlH_{LD}$ with hot spot residues Y46, K132, and R142 labeled.
Figure 5:
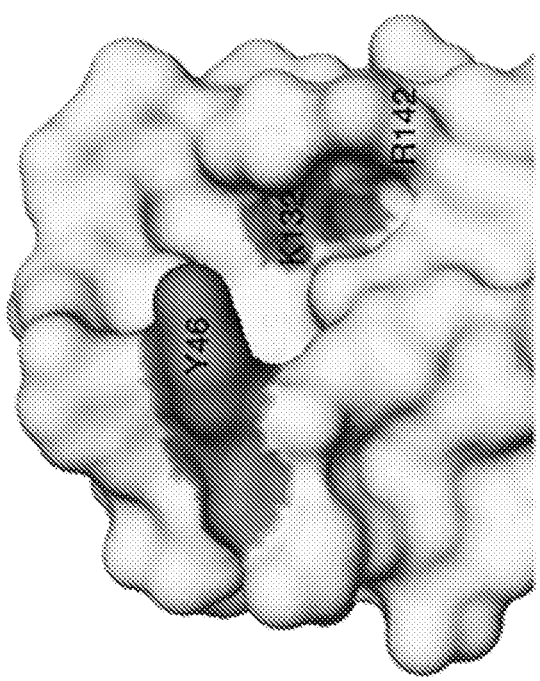
Figure 5:
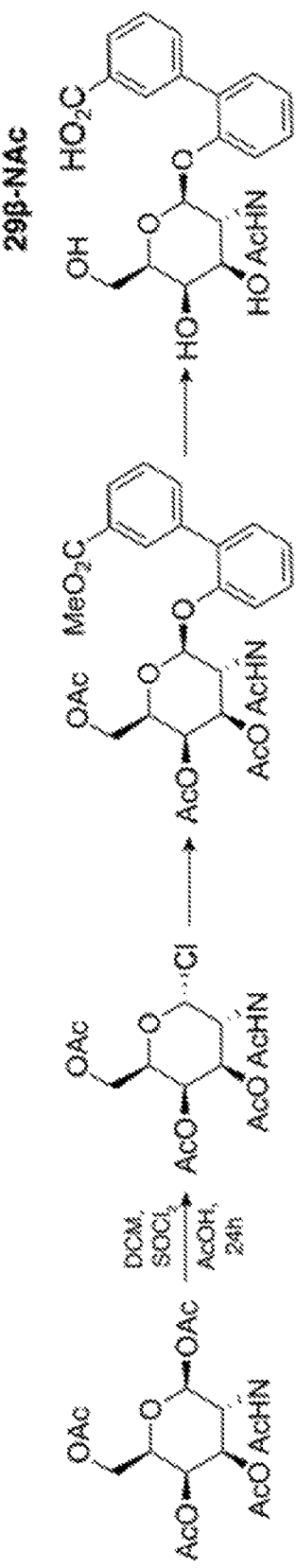

A virtual library composed of approximately 1800 known galactosides was assembled by mining the ZINC12 database [29] for all known galactose sub-structures. Thereafter, an exhaustive virtual screen was performed using AutoDock Vina to computationally dock the galactoside library in the binding pocket of FmlH$_{LD}$ (from a FmlH$_{LD}$-ONPG co-crystal structure; PDB ID 6AOY), generating a ranked list of top binding poses and associated docking scores for each galactoside. To identify top hits, the inventors abstained from directly comparing raw binding scores, as large, lipophilic molecules tend to have artificially high predicted binding interactions due to their contribution to hydrophobic interactions as calculated by the empirical scoring function of AutoDock Vina. Instead, the results of the virtual screen were evaluated per group efficiency (GE), which, in this context, measures the contribution of the aglycone group within each galactoside (X) to docking score (DS) with respect to the number of heavy atoms (HA) present in the aglycone group [GE=(DSX-DSGal)/(HAX-HAGal)]. Data are presented in FIG. 5, panel A as a scatter plot of the docking score of the top predicted binding mode plotted against the molecular weight for each galactoside. Compounds with GE values 1.256 above the mean are colored blue while compounds with GE values below 0 are colored red. Virtual screening of this library, which comprised galactosides ranging from 150-900 Da in molecular weight, yielded a mean docking score of 6.3 kcal/mol with a standard deviation of 0.73 kcal/mol and a range of 4-9 kcal/mol (FIG. 5, panel A). Top hits were defined as galactosides with a GE value greater than 1.25 times the standard deviation ($\sigma$=0.0016 kcal/mol/HA) above the library mean ($\mu$=0.0011 kcal/mol/HA), which constituted the top ~10% of highest-scoring galactosides (FIG. 5, panel A).

Thereafter, the binding poses of top hits were visually inspected to inform structure-guided drug design. In addition to the canonical binding observed for the Gal moiety of top-scoring galactosides in the cleft of the binding pocket, most top hits also interacted with specific hot spot residues near the galactose binding pocket, which were sought to leverage for lead optimization. These hot spot residues included (i) residue Y46, which caps the top of the binding pocket and can contribute hydrophobic interactions, (ii) residue K132, which lies at the bottom of the sugar binding pocket and can engage polar groups linked to the Gal sugar, and (iii) residue R142, which points towards an empty, solvent-exposed cleft near the binding pocket and can contribute electrostatic interactions (FIG. 5, panel B).

Example 21: Design and Synthesis of FmlH-Targeting Galactoside Antagonists

Figure 2:
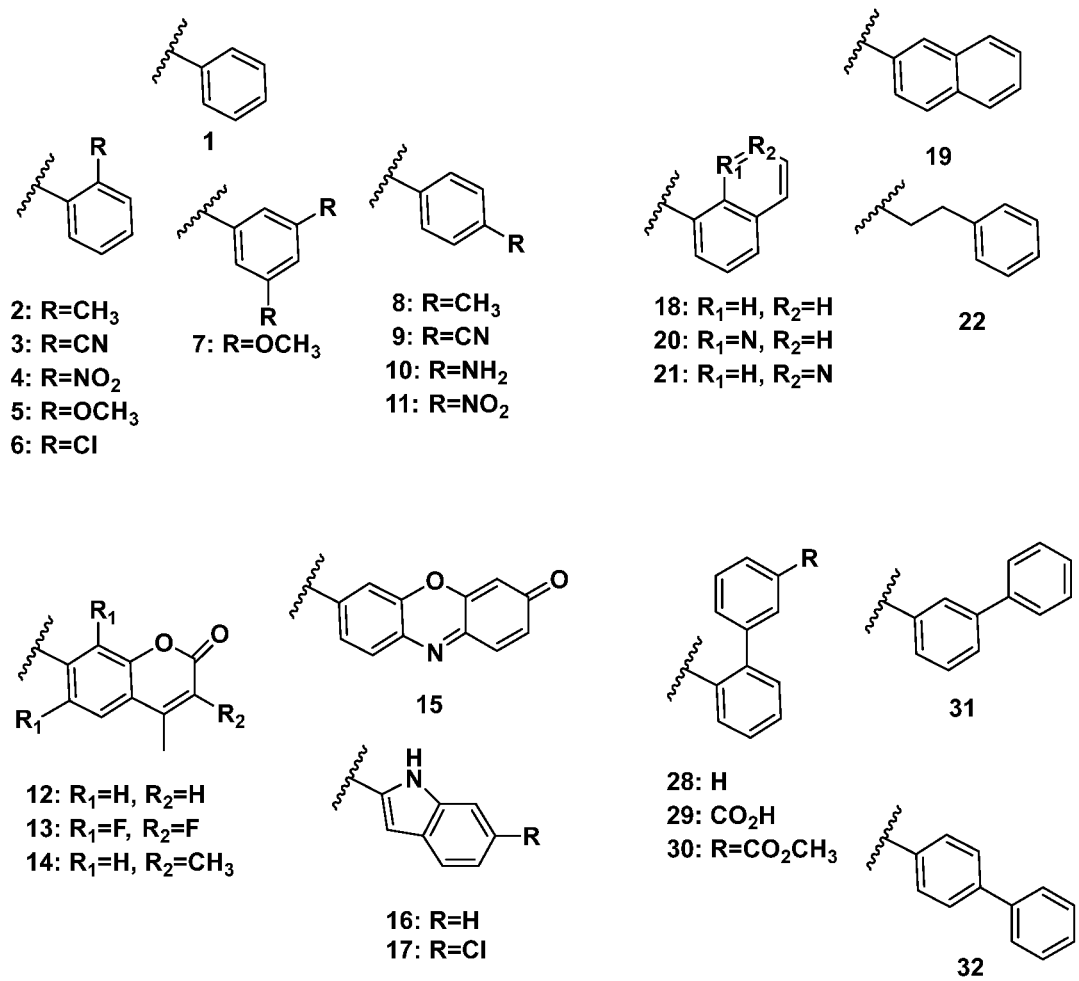
FIG. 2 shows structures for the aglycone portion of each galactoside tested.
Figure 3:
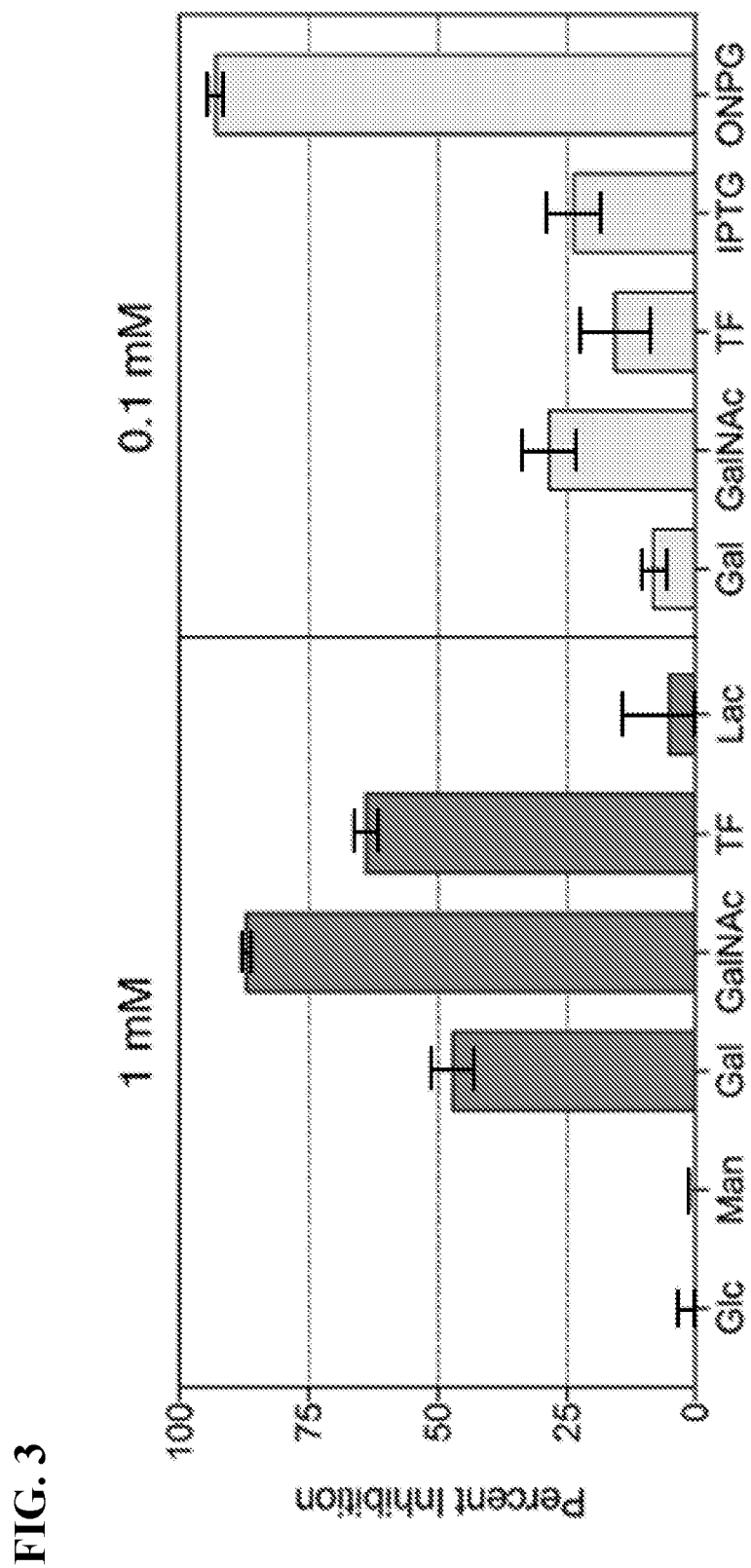
FIG. 3 presents bar graphs showing the percent inhibition (y-axis) of FmlH binding to surface immobilized desialylated bovine submaxillary mucin (ds-BSM) in the presence or absence of 1 mM (left) or 0.1 mM (right) of soluble compounds (x-axis).

To explore structure-activity relationships (SAR), a large library of galactoside analogs were acquired or synthesized (FIG. 2, panels A-E, Examples 1-17) and tested. Based on the docking results, it was predicted that β-Gal isomers would be preferred over α-Gal and that ortho positioning of functional groups on a phenyl scaffold would best facilitate interactions with specific sites within the binding pocket, namely hot spot residues Y46 and R142. Accordingly, small sets of phenyl galactosides with ortho substituted functional groups were synthesized and evaluated (2-6; FIG. 2, panel A). Compounds were synthesized as described in Examples 1-17. In addition, other phenyl galactosides, which had meta or para substituents on the aglycone ring (7-11; FIG. 2, panel A), and other aryl and heterocyclic galactosides (12-22; FIG. 2, panels B-C), were acquired to derive meaningful SAR information to inform further design and optimization of improved galactosides. Furthermore, the promising activity of the simple galactoside ONPG (413) in the initial screen (Example 18) led to synthesis of a compound series containing biphenyl aglycones (28-32; FIG. 2, panel D), such as 29β-NAc, the N-acetyl-β-galactosaminoside with an m-carboxylic acid on the B ring designed to directly interact with the hot spot residue R142 (FIG. 5, panels B and C). To confirm the predicted preference for the β-Gal isomers, many corresponding α-Gal isomers were also synthesized and tested. Compounds were synthesized as described in Examples 1-17 using two different synthetic glycosylation methods involving either a reaction between galactose pentaacetate and phenols promoted by boron trifluoride or a Koenigs-Knorr type reaction between galactosyl halide and aryl alcohols.

Example 22: Biochemical Characterization of FmlH Antagonists

Select top hit compounds and few low-scoring analogs from the virtual screening, as well as synthetic galactosides, were tested in the ELISA-based competition assay for their ability to inhibit binding of $FmlH_{LD}$ to ds-BSM. The ELISA assay was performed using the protocol described in Example 18. Direct comparison of inhibitory potency among galactosides led to delineation of basic SAR (Table 2, below). All compounds were tested at 100 µM; a subset was tested at 10 µM; and the strongest subset was additionally tested at 1 µM. The summary of the results are in Table 2. Percent inhibition (PI) values are reported as the mean with standard error of the mean for galactosides tested at 100 µM (PI100), 10 µM (PI10), and 1 µM (PI1) in the ELISA-based competition assay. Compounds indicated in the table are shown in FIG. 2 and/or described in previous examples except: 33 (p-nitrophenyl Gal-β1-3-GalNAc), 34 (p-nitrophenyl Gal-β1-3-GlcNAc), 35 (p-nitrophenyl Gal-β1-6-Gal), and 36β-thio (IPTG). The "thio" designation indicates a sulfur linkage between the sugar and the aglycone group, the "phospho" designation indicates a phosphate group attached the C6-hydroxyl group on the sugar, and the "uro" designation indicates galacturonide as the sugar.

TABLE 2

| | Galactoside inhibition of Fm1H. | | | |
|---|---|---|---|---|
| Name | Structure | $PI_{100}$ | $PI_{10}$ | $PI_1$ |
| 29β-NAc | | 99.5 ± 2.2 | 93.0 ± 1.5 | 54.7 ± 2.8 |
| 4β-NAc | | 99.4 ± 1.3 | 87.2 ± 1.7 | 28.6 ± 4.5 |

TABLE 2-continued

Galactoside inhibition of Fm1H.

| Name | Structure | $PI_{100}$ | $PI_{10}$ | $PI_1$ |
|---|---|---|---|---|
| 29β | 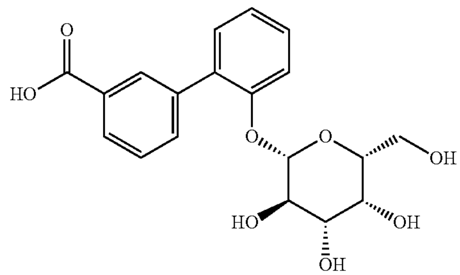 [SMILES: O=C(O)c1cccc(-c2ccccc2O[C@@H]2O[C@H](CO)[C@H](O)[C@H](O)[C@H]2O)c1] | 99.0 ± 1.3 | 75.1 ± 1.0 | 22.9 ± 5.1 |
| 5β | 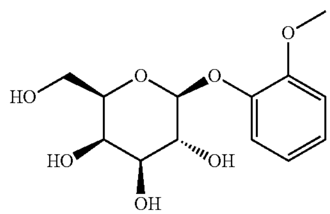 [SMILES: COc1ccccc1O[C@@H]1O[C@H](CO)[C@H](O)[C@H](O)[C@H]1O] | 97.2 ± 0.4 | 55.7 ± 1.6 | 10.0 ± 4.3 |
| 20β | 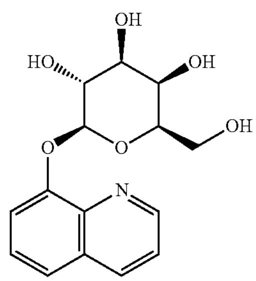 [SMILES: OC[C@H]1O[C@@H](Oc2cccc3cccnc23)[C@H](O)[C@@H](O)[C@H]1O] | 95.1 ± 1.1 | 48.1 ± 2.0 | 19.2 ± 2.8 |
| 3β | 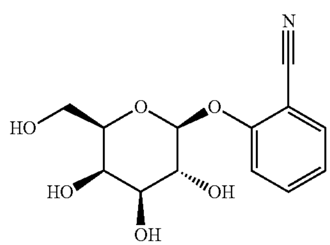 [SMILES: N#Cc1ccccc1O[C@@H]1O[C@H](CO)[C@H](O)[C@H](O)[C@H]1O] | 94.5 ± 0.3 | 30.4 ± 1.8 | 12.1 ± 6.3 |
| 4β (ONPG) | 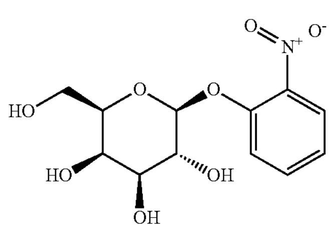 | 93.0 ± 1.4 | 31.1 ± 3.3 | 16.5 ± 3.8 |
| 28β | 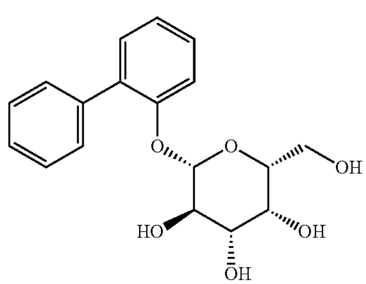 [SMILES: OC[C@H]1O[C@@H](Oc2ccccc2-c2ccccc2)[C@H](O)[C@@H](O)[C@H]1O] | 91.1 ± 1.2 | 31.0 ± 2.1 | 8.1 ± 6.0 |

TABLE 2-continued

Galactoside inhibition of Fm1H.

| Name | Structure | $PI_{100}$ | $PI_{10}$ | $PI_1$ |
|------|-----------|------------|-----------|--------|
| 6β | 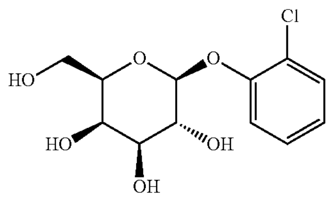 [SMILES: OC[C@H]1O[C@@H](Oc2ccccc2Cl)[C@H](O)[C@@H](O)[C@H]1O] | 90.5 ± 0.6 | 20.7 ± 5.5 | 8.0 ± 4.0 |
| 14β | 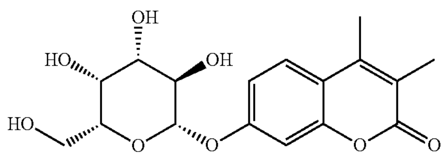 [SMILES: Cc1c(C)c2ccc(O[C@@H]3O[C@H](CO)[C@H](O)[C@H](O)[C@H]3O)cc2oc1=O] | 89.2 ± 0.4 | 19.8 ± 3.8 | 10.2 ± 4.3 |
| 2β | 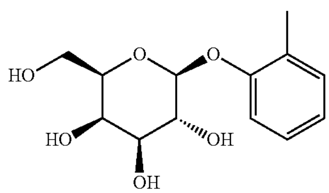 [SMILES: Cc1ccccc1O[C@@H]1O[C@H](CO)[C@H](O)[C@H](O)[C@H]1O] | 87.3 ± 3.7 | 28.2 ± 1.8 | 1.8 ± 5.7 |
| 30β | 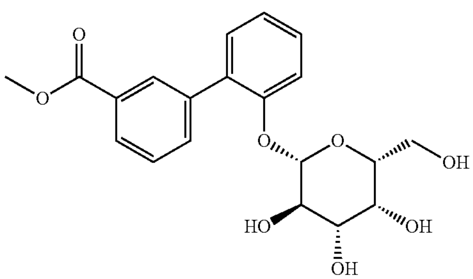 [SMILES: COC(=O)c1cccc(-c2ccccc2O[C@@H]2O[C@H](CO)[C@H](O)[C@H](O)[C@H]2O)c1] | 86.6 ± 0.8 | 22.4 ± 2.6 | 3.7 ± 3.5 |
| 32α | 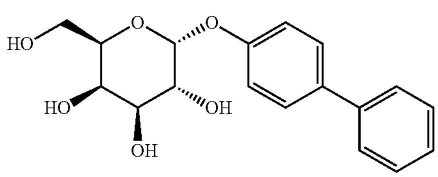 [SMILES: OC[C@H]1O[C@H](Oc2ccc(-c3ccccc3)cc2)[C@H](O)[C@@H](O)[C@H]1O] | 86.5 ± 1.7 | 22.6 ± 3.9 | |
| 8β | 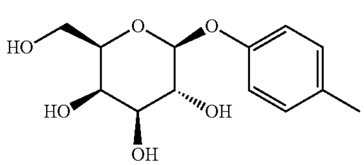 [SMILES: Cc1ccc(O[C@@H]2O[C@H](CO)[C@H](O)[C@H](O)[C@H]2O)cc1] | 85.8 ± 0.7 | 16.5 ± 3.3 | 4.6 ± 7.9 |
| 9β | 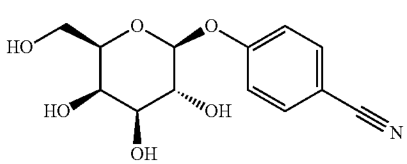 [SMILES: N#Cc1ccc(O[C@@H]2O[C@H](CO)[C@H](O)[C@H](O)[C@H]2O)cc1] | 85.7 ± 1.6 | 19.2 ± 4.8 | 9.5 ± 3.7 |
| 12β | 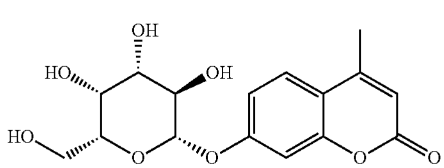 [SMILES: Cc1cc(=O)oc2cc(O[C@@H]3O[C@H](CO)[C@H](O)[C@H](O)[C@H]3O)ccc12] | 85.3 ± 0.7 | 19.7 ± 4.2 | 8.7 ± 3.1 |

TABLE 2-continued

Galactoside inhibition of Fm1H.

| Name | Structure | $PI_{100}$ | $PI_{10}$ | $PI_1$ |
|---|---|---|---|---|
| 11α-NAc | 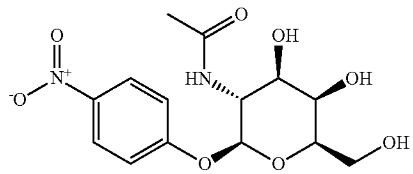 | 82.0 ± 2.7 | 6.3 ± 3.7 | |
| 15β | 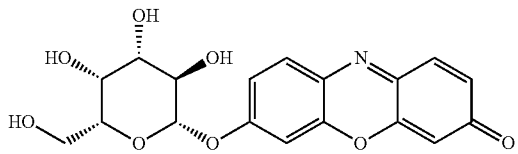 [SMILES: O=c1ccc2nc3ccc(O[C@@H]4O[C@H](CO)[C@H](O)[C@H](O)[C@H]4O)cc3oc-2c1] | 80.4 ± 6.6 | 24.0 ± 3.2 | |
| 19β | 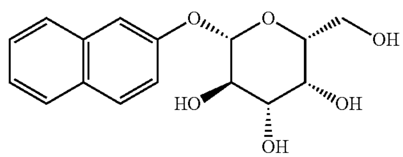 [SMILES: OC[C@H]1O[C@@H](Oc2ccc3ccccc3c2)[C@H](O)[C@@H](O)[C@H]1O] | 78.8 ± 2.1 | 14.6 ± 3.1 | |
| 11β | 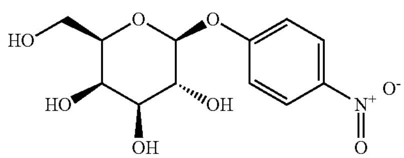 | 78.1 ± 0.6 | 13.7 ± 5.3 | |
| 1β | 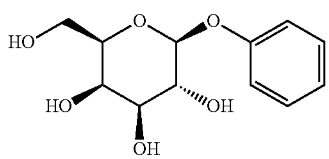 [SMILES: OC[C@H]1O[C@@H](Oc2ccccc2)[C@H](O)[C@@H](O)[C@H]1O] | 76.9 ± 0.4 | 15.5 ± 4.2 | |
| 7β | 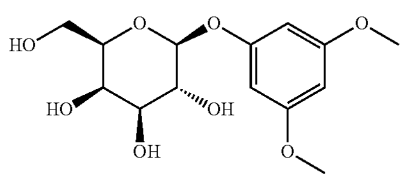 [SMILES: COc1cc(OC)cc(O[C@@H]2O[C@H](CO)[C@H](O)[C@H](O)[C@H]2O)c1] | 76.4 ± 2.4 | 11.7 ± 2.7 | |
| 11β-thio | 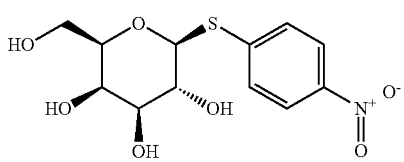 | 72.5 ± 0.9 | 17.0 ± 3.7 | |
| 10β | 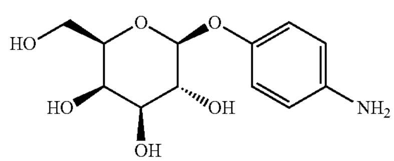 [SMILES: Nc1ccc(O[C@@H]2O[C@H](CO)[C@H](O)[C@H](O)[C@H]2O)cc1] | 65.1 ± 1.4 | 9.8 ± 3.9 | |
| 31β | 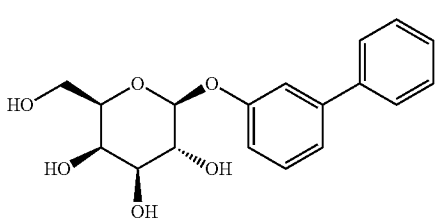 [SMILES: OC[C@H]1O[C@@H](Oc2cccc(-c3ccccc3)c2)[C@H](O)[C@@H](O)[C@H]1O] | 56.9 ± 6.2 | 7.8 ± 5.5 | |

TABLE 2-continued

Galactoside inhibition of Fm1H.

| Name | Structure | PI$_{100}$ | PI$_{10}$ | PI$_{1}$ |
|---|---|---|---|---|
| 22β-thio | 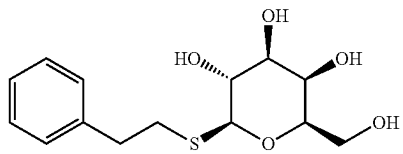 [SMILES: OC[C@H]1O[C@@H](SCCc2ccccc2)[C@H](O)[C@@H](O)[C@H]1O] | 49.8 ± 2.5 | 2.3 ± 2.5 | |
| 13β | 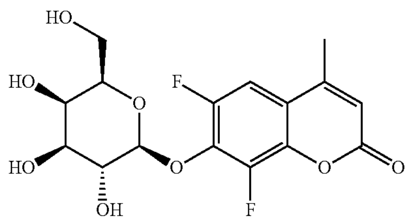 [SMILES: Cc1cc(=O)oc2c(F)c(O[C@@H]3O[C@H](CO)[C@H](O)[C@H](O)[C@H]3O)c(F)cc12] | 49.7 ± 4.5 | 0.8 ± 3.1 | |
| 18β | 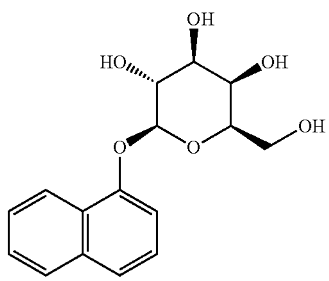 [SMILES: OC[C@H]1O[C@@H](Oc2cccc3ccccc23)[C@H](O)[C@@H](O)[C@H]1O] | 45.9 ± 3.7 | | |
| 31α | 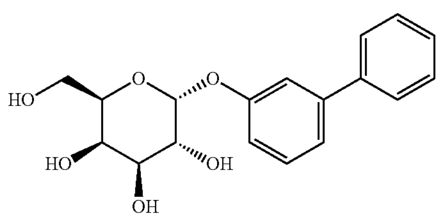 [SMILES: OC[C@H]1O[C@H](Oc2cccc(-c3ccccc3)c2)[C@H](O)[C@@H](O)[C@H]1O] | 45.6 ± 2.5 | | |
| 17β | 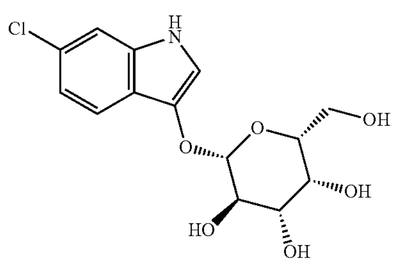 [SMILES: OC[C@H]1O[C@@H](Oc2c[nH]c3cc(Cl)ccc23)[C@H](O)[C@@H](O)[C@H]1O] | 41.2 ± 3.4 | | |
| 2α | 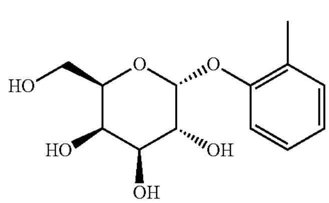 [SMILES: Cc1ccccc1O[C@H]1O[C@H](CO)[C@H](O)[C@H](O)[C@H]1O] | 30.0 ± 5.4 | | |
| 32β | 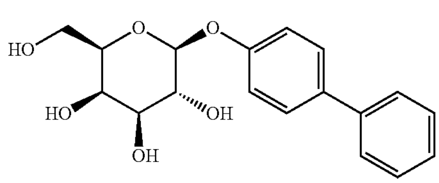 [SMILES: OC[C@H]1O[C@@H](Oc2ccc(-c3ccccc3)cc2)[C@H](O)[C@@H](O)[C@H]1O] | 30.0 ± 3.9 | | |

TABLE 2-continued

Galactoside inhibition of Fm1H.

| Name | Structure | PI$_{100}$ | PI$_{10}$ | PI$_1$ |
| --- | --- | --- | --- | --- |
| GalNAc | 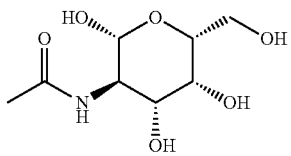 | 28.5 ± 5.2 | | |
| 18α | 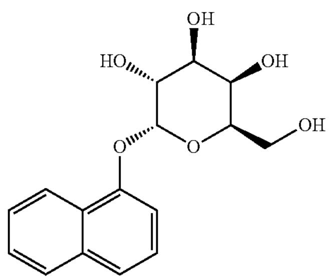 [SMILES: OC[C@H]1O[C@H](Oc2cccc3ccccc23)[C@H](O)[C@@H](O)[C@H]1O] | 28.1 ± 3.4 | | |
| 29α | 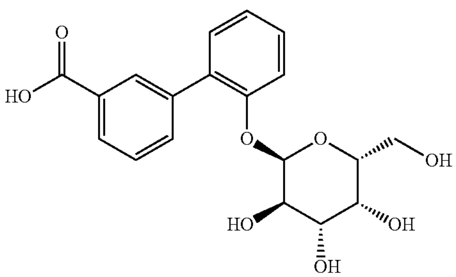 [SMILES: O=C(O)c1cccc(-c2ccccc2O[C@H]2O[C@H](CO)[C@H](O)[C@H](O)[C@H]2O)c1] | 26.2 ± 5.9 | | |
| 36β-thio (IPTG) | 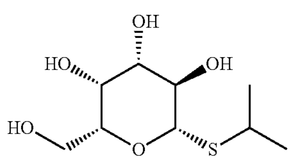 | 23.7 ± 5.3 | | |
| 16β | 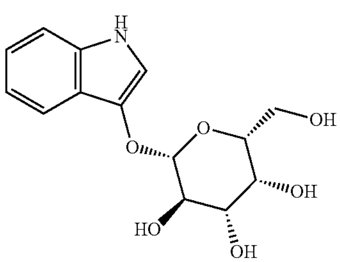 [SMILES: OC[C@H]1O[C@@H](Oc2c[nH]c3ccccc23)[C@H](O)[C@@H](O)[C@H]1O] | 21.7 ± 2.4 | | |
| 35 | 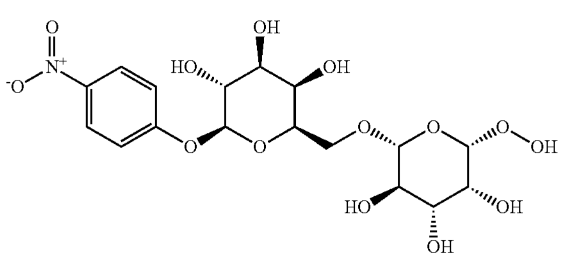 | 19.4 ± 1.6 | | |

TABLE 2-continued

Galactoside inhibition of Fm1H.

| Name | Structure | PI$_{100}$ | PI$_{10}$ | PI$_1$ |
|---|---|---|---|---|
| 28α | 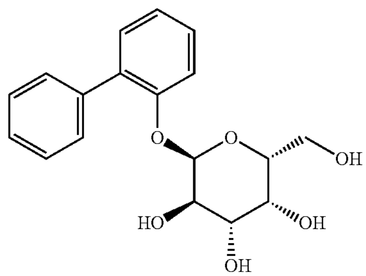 [SMILES: OC[C@H]1O[C@H](Oc2ccccc2-c2ccccc2)[C@H](O)[C@@H](O)[C@H]1O] | 19.2 ± 3.0 | | |
| 3α | 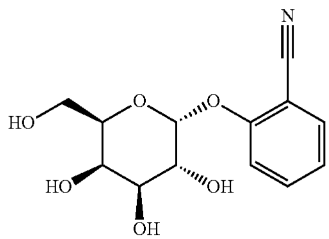 [SMILES: N#Cc1ccccc1O[C@H]1O[C@H](CO)[C@H](O)[C@H](O)[C@H]1O] | 17.8 ± 6.3 | | |
| TF | 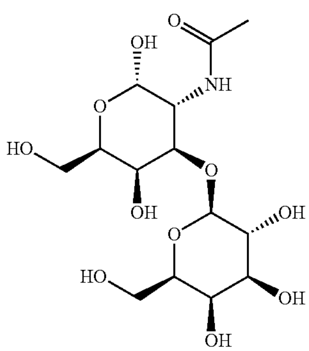 [SMILES: CC(=O)N[C@@H]1[C@@H](O[C@@H]2O[C@H](CO)[C@H](O)[C@H](O)[C@H]2O)[C@@H](O)[C@@H](CO)O[C@@H]1O] | 15.5 ± 6.7 | | |
| 33 | 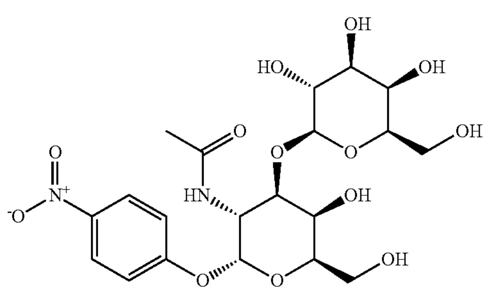 | 15.3 ± 3.1 | | |
| 21β | 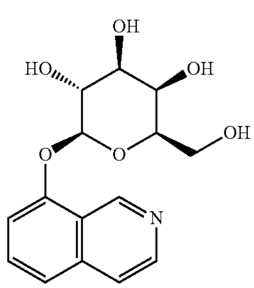 [SMILES: OC[C@H]1O[C@@H](Oc2cccc3ccncc23)[C@H](O)[C@@H](O)[C@H]1O] | 15.2 ± 7.1 | | |

TABLE 2-continued

Galactoside inhibition of Fm1H.

| Name | Structure | PI$_{100}$ | PI$_{10}$ | PI$_1$ |
|---|---|---|---|---|
| 30α | 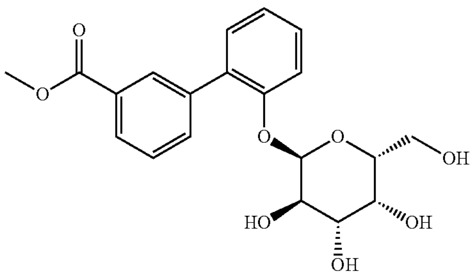 [SMILES: COC(=O)c1cccc(-c2ccccc2O[C@H]2O[C@H](CO)[C@H](O)[C@H](O)[C@H]2O)c1] | 13.1 ± 7.6 | | |
| Gal | 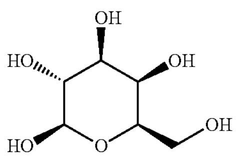 [SMILES: OC[C@H]1O[C@@H](O)[C@H](O)[C@@H](O)[C@H]1O] | 8.1 ± 2.6 | | |
| 4β-phospho | 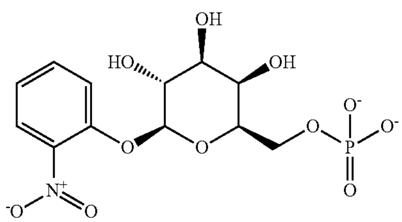 | 1.3 ± 4.7 | | |
| 11β-uro | 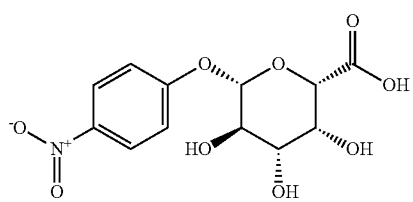 | −2.4 ± 5.2 | | |
| 34 | 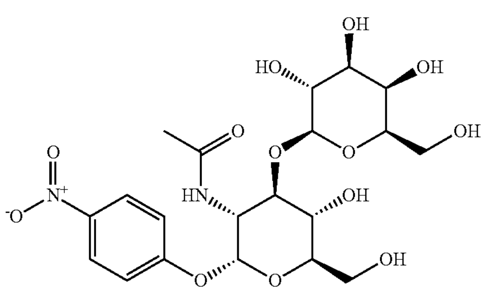 | −3.6 ± 1.0 | | |
| Gal-β1-3-GalNAc | 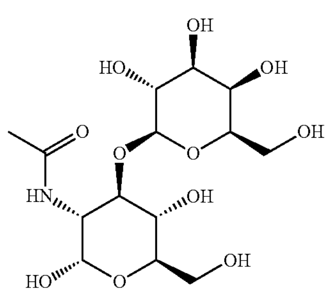 [SMILES: CC(=O)N[C@@H]1[C@@H](O[C@@H]2O[C@H](CO)[C@H](O)[C@H](O)[C@H]2O)[C@H](O)[C@@H](CO)O[C@@H]1O] | | | |

When tested at 100 µM, phenyl β-galactoside 1β (beta isomer of 1) exhibited significantly higher binding inhibition (77%) than Gal (8.1%), indicating that the phenyl group enhances binding to FmlH$_{LD}$ (Table 2). Various ortho-substituents on the phenyl ring additionally conferred substantial improvements in inhibitory potency, as observed with 2β (87%), 3β (95%), 4β (ONPG; 93%), 5β (97%), and 6β (90%). In contrast, the meta methoxy groups in compound 7β (76%) did not enhance binding strength compared to 1β. Further, para-substituted functional groups displayed variable inhibitory potencies relative to 1β, with enhancements observed in 8β (86%) and 9O (86%), no significant effect observed in 11β (78%) or 11β-thio (72%), and reduction observed in 1013 (65%). Thus, ortho-substituted phenyl β-galactosides generally outperformed other simple phenyl galactosides.

Complex heterocyclic galactosides, such as coumarins 12β (85%) and 14β (89%), which differ only by a methyl group, displayed significant inhibitory potencies against FmlH$_{LD}$, while the related galactoside 13β (50%) displayed reduced inhibitory activity likely because of its fluoro-substituents (FIG. 2, panel B). Resorufin galactoside 15β (80%) also displayed no greater potency than phenyl galactoside 1β. Together, these results suggest that the substituents of 1213 are responsible for augmenting affinity relative to 1β. In contrast, indoles 16β (22%) and 17β (41%) performed poorly as inhibitors of FmlH$_{LD}$. Naphthyl galactosides 18β (46%) and 19β (79%), in addition to isoquinoline 21β (15%), showed no improvement in activity relative to 1β. However, quinoline 20β (95%) displayed significantly higher inhibition than 1β and 18β. This suggested that the electron-pair-donating nitrogen atom in 20β makes a specific interaction with FmlH. This observation is consistent with the pattern of SAR indicating that the ortho position is key to enhancing inhibitory potency against FmlH$_{LD}$.

Moreover, the tested GalNAc-derived compounds possessed significantly higher inhibitory potency compared to their Gal-derived counterparts, as observed with 4β-NAc (87%) relative to 4β (31%) when tested for inhibition at 10 µM (Table 2). These results suggested that the N-acetyl group together with other functional groups contributes to binding by targeting distinct components of the binding pocket of FmlH. In contrast, galactosides with α-linkages (28-30α) or disaccharides with aglycone moieties (33-35) were generally poor inhibitors of FmlH, except for 11α-NAc (82%) (Table 2).

Consistent with the above-mentioned SAR, the ortho-biphenyl galactoside 28β (91%) was more potent than the meta 31β (57%) or para 32β (30%) analogs (Table 2). This inhibition was enhanced with the addition of a carboxylate group at the meta position on the biphenyl B-ring (29β), intended to target the pocket formed by N140 and R142, and which resulted in a compound (29β) that exhibited greater inhibition (99%) compared to 28β when tested at 100 µM (Table 2). This difference in activity was further highlighted when these compounds were tested for inhibition at 10 µM and 1 µM (Table 2). Importantly, 30β, the methyl ester of 29β (87%), tested at 100 µM results in a reduction in binding, suggesting that the negative charge of the carboxylic acid likely mediates a critical electrostatic interaction with R142 of FmlH$_{LD}$. Finally, the GalNAc version of 2913 was synthesized (Example 15) to increase its binding affinity and found that 29β-NAc (93%) had significant improvement in activity over 29β (75%) when tested at 10 µM. Final evaluation of the highest performing galactosides in the ELISA-based competition assay at a concentration of 10 µM and 1 µM allowed for a clearer ranking of compounds, where 29β-NAc clearly stood out as the most potent (Table 2).

Example 23: Determination of FmlH-Galactoside Binding Affinities

Bio-layer interferometry (BLI) was used to quantitate the binding affinity of select galactosides to FmlH.

Bio-layer interferometry (BLI) protocol: Streptavidin (SA) pins were first dipped in a baseline in PBS (pH 7.4) for 120 s, followed by loading of 5-10 µg/mL biotinylated ser-TF (Toronto Research Chemicals) in PBS for 300 s, quenching by 10 µg/mL biocytin in PBS for 240 s, and another baseline step in PBS for 120 s. Thereafter, pins were dipped in PBS for 120 s and transferred to protein samples (varying concentration of FmlH$_{LD}$ or fixed concentration of FmlH$_{LD}$ with varying concentration of galactoside compounds) for association for 300-600 s. Equilibrium binding response values were used to determine the affinity of interaction between FmlH$_{LD}$ and immobilized ser-TF or between FmlH$_{LD}$ and galactosides in solution.

Steady-state analysis of binding responses from incubation of biotinylated serine-linked TF (ser-TF) immobilized on Streptavidin pins with varied titrations of FmlH$_{LD}$ in solution revealed a dissociation constant, K$_D$, of 15.0±0.8 µM (FIG. 6, panel A). Then, immobilized ser-TF was incubated in solutions comprising a fixed concentration of FmlH$_{LD}$ but varying concentrations of galactosides to determine their inhibitory constants, K$_d$ (FIG. 6, panel B, Table 3). The BLI-based affinity determinations correlated well with the relative binding strengths measured in the ELISA-based competition assay (Table 3 vs. Table 2). The two lead compounds 29β-NAc and 29β bound tightly to FmlH$_{LD}$ with K$_d$ values of ~90 nM and 2.1 KM, respectively, which represent a ~7,800-fold and ~330-fold enhancement in binding affinity relative to Gal. Another promising compound, 4β-NAc, bound FmlH$_{LD}$ with a K$_d$ value of 2.3 µM.

TABLE 3

Inhibitory constants of galactoside inhibitors of Fm1H.

| Name | Structure | K$_d$ (µM) |
|---|---|---|
| 29β-NAc | 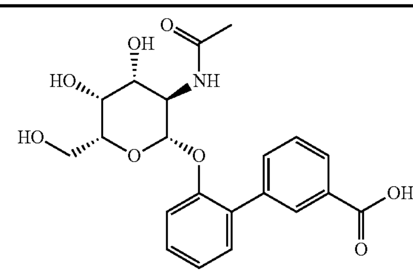 | 0.089 ± 0.4 |
| 4β-NAc | 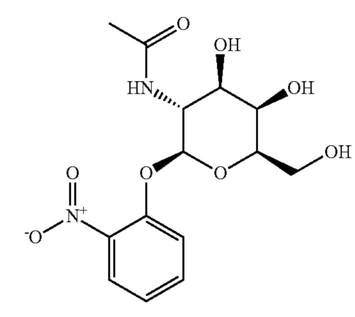 | 2.3 ± 1.4 |

TABLE 3-continued

Inhibitory constants of galactoside inhibitors of Fm1H.

| Name | Structure | $K_d$ (μM) |
|---|---|---|
| 29β | 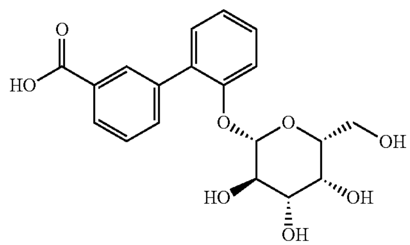 [SMILES: O=C(O)c1cccc(-c2ccccc2O[C@@H]2O[C@H](CO)[C@H](O)[C@H](O)[C@H]2O)c1] | 2.1 ± 0.9 |
| 5β | 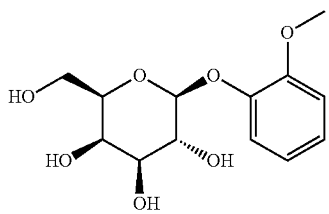 [SMILES: COc1ccccc1O[C@@H]1O[C@H](CO)[C@H](O)[C@H](O)[C@H]1O] | 6.5 ± 1.4 |
| 20β | 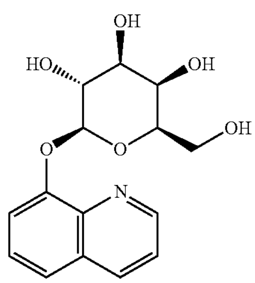 [SMILES: OC[C@H]1O[C@@H](Oc2cccc3cccnc23)[C@H](O)[C@@H](O)[C@H]1O] | 7.1 ± 2.3 |
| 4β (ONPG) | 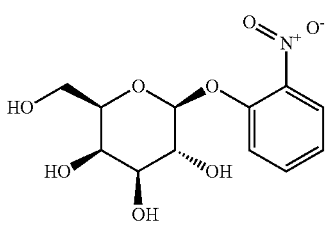 | 10.6 ± 4.6 |
| GalNAc | 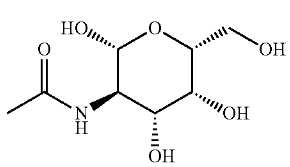 | 189 ± 22.9 |
| Gal | 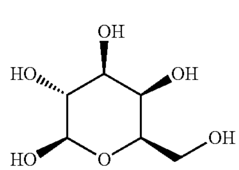 [SMILES: OC[C@H]1O[C@@H](O)[C@H](O)[C@@H](O)[C@H]1O] | 694 ± 56.1 |
| Gal-β1-GalNAc | | 248 ± 20.3 |

Example 24: Structural Basis of Galactoside Inhibition of FmlH

To elucidate the molecular basis for galactoside inhibition of FmlH, co-crystal structures of FmlH$_{LD}$ bound to 4β, 5β, 20β, and 29β-NAc were determined (FIG. 7, panels A-B).

Protein Crystallization and Analysis Protocol:

Crystals of apo FmlH$_{LD}$ in 10 mM Hepes pH 7.5, 50 mM NaCl were grown by mixing 2 μl protein (6 mg/ml) with 2 μl of mother liquor (0.2 M ammonium sulfate, 0.1M NaCl, 0.1 M MES (pH 5.6), 28% PEG 3350) and equilibrated against 1 ml mother liquor in the reservoir. Co-crystals of FmlH$_{LD}$ bound to TF or galactosides 4β (in space group P 2 21 21), 5β, and 20β were grown by mixing 2 μl protein (6 mg/ml) in the presence of 5 mM compound with 2 μl of mother liquor (0.2 M ammonium sulfate, 0.1M NaCl, 0.1 M MES (pH 5.6), 32% PEG 3350). These crystals were transferred into cryoprotectant (0.2 M ammonium sulfate, 0.1M NaCl, 0.1 M MES (pH 5.6), 35% PEG 4000, 10% glycerol) and then flash frozen in liquid nitrogen. Co-crystals of FmlH$_{LD}$ bound to galactoside 29β-NAc were grown by mixing 2 μl protein (10 mg/ml) with 2 μl of mother liquor (0.7 M LiSO4, 2% PEG8000). These crystals were transferred into cryoprotectant (1 M LiSO4, 10% PEG8000, 25% glycerol). Diffraction data for FmlH$_{LD}$ TF, 4β (in space group C 1 2 1), and 29β-NAc structures were collected at 100 K at an in-house facility equipped with a rotating anode Rigaku MicroMax 007 generator, a Rayonix Marmux X-ray source (Evanston, IL), and a Mar345 image plate detector. Diffraction data for FmlH$_{LD}$ apo, 4β, 5β, and 20β structures were collected at 100 K at the ALS Beamline 4.2.2. Data were indexed and integrated in iMosflm [43], XDS [44], or HKL2000 and scaled by Scala [45]. The phase problem was solved by molecular replacement (MR) using Phaser-MR in PHENIX [46] with FimH$_{LD}$ from PDB ID 3MCY. Several rounds of refinements were performed in PHENIX to improve the final models.

The galactosides examined (4β, 5β, and 20β, and 29β) share a common aglycone motif consisting of a phenyl ring with an ortho-substituted functional group. As predicted from computational studies, the sugar portion of these galactosides all resided within the cleft of the binding pocket. The phenyl groups directly attached to the sugar portion of all four compounds lie along the same three-dimensional plane. In this nearly-identical conformation, the phenyl ring was found to be oriented perpendicularly to the side chain of residue Y46, revealing edge-to-face π-stacking which likely contributed to the enhanced affinity observed for all β-galactosides. For 4β, 5β, and 20β, the ortho-substituents pointed toward R142 but were too distant (>7 Å) for direct interaction and instead formed H-bonds with water molecules that in turn interacted with residues K132 and R142 (FIG. 7, panel A). Thus, it was deduced that the marked affinity enhancement observed for 4β, 5β, and 20β was due to a combination of (i) indirect interactions between the ortho-substituent and residues K132 and R142 formed by an intricate network of water-mediated H-bonds and (ii) edge-to-face π-stacking between the phenyl ring and residue Y46.

In contrast, the biphenyl scaffold of 29β-NAc presented the carboxylic acid to engage in a direct charge-charge interaction with the guanidinium side chain of R142 (FIG. 7 panel B). The lower potency of methyl ester derivative 30β was further evidence that the charge-charge interaction likely drove the observed affinity enhancement (FIG. 7 panel C). The improved affinity of 29β-NAc relative to 29β was also due to additional interactions mediated by the N-acetyl group in H-bonding to a water molecule captured by the biphenyl aglycone and the side chain of residue K132 (FIG. 7, panels B-C). Altogether, analysis of all X-ray crystal structures of ligand-bound FmlH revealed two general mechanisms for the significant enhancement in binding affinity of galactosides relative to Gal: edge-to-face π-stacking with Y46 and polar or electrostatic charge-charge interactions with K132 and R142.

Example 25: Assessment of Mutant FmlH to Bind Ds-BSM In Vitro

To confirm the importance of the binding pocket explored extensively in previous examples, a target mutation (K132Q) was made to produce a putative binding-null mutant FmlH. The ability of K132Q-FmlH to bind ds-BSM in vitro was compared to native FmlH in an ELISA assay using the procedure described in Example 18. Data is summarized in FIG. 8. K132Q FmlH showed no binding to sialidase-treated BSM even at high concentrations.

Example 26: Use of FmlH Antagonists to Treat Murine UTI In Vivo

To assess therapeutic efficacy, galactosides were evaluated for their ability to reduce bacterial burdens in the urinary tracts of C3H/HeN mice during chronic UTI. 7-8 week old female C3H/HeN mice were obtained from Envigo (Indianapolis, IN). Mice were anesthetized and inoculated via transurethral catheterization with 50 μl of CFT073 bacterial suspension (~1-2*$10^8$ CFU in total) in phosphate-buffered saline (PBS). Chronic cystitis in C3H/HeN mice was defined as urine titers of >$10^4$ CFU/ml lasting at least two to four weeks, as well as bladder inflammation and edema at euthanasia [30]. Further, C3H/HeN mice are genetically predisposed to vesicoureteral reflux (retrograde flow of urine from the bladder to the kidneys), which can lead to bacterial colonization of the kidneys, renal abscess formation, scarring and atrophy {Murawski, 2010 #4776}. Accordingly, high levels of CFT073 kidney colonization were also observed in control (vehicle-treated) animals.

Mice meeting the criteria for chronic cystitis (high titers of bacteriuria (>$10^4$ CFU/ml) and edematous and inflamed bladders after 2 weeks) were then transurethrally inoculated either with 50 mg/kg compound or vehicle control (10% DMSO). Compounds tested were: 29β-NAc (50 mg/kg), mannoside 4Z269 (a type 1 pilus adhesin FimH inhibitor, 50 mg/kg), or 29β-NAc+4Z269. Mice were sacrificed 6 hours post treatment and bacteria colonizing the bladder or kidney were plated for quantification. Data are presented in FIG. 9, panels A and B, as bacterial titers of CFT073 in each organ in each condition. The horizontal lines represent the means. Asterisks indicate significance (*$P<0.05$, $P<0.01$, *$P<0.001$, ****$P<0.0001$, two-tailed Mann-Whitney U test). Each condition was measured in two or three independent experiments with 4 or 5 mice per group per experiment.

Treatment of mice experiencing chronic cystitis with 50 mg/kg 29β-NAc through transurethral delivery 6 hours prior to euthanasia led to a significant reduction of CFT073 in the bladders of infected mice relative to vehicle control (FIG. 10, panel A) and even greater clearance of CFT073 from the kidneys (FIG. 9, panel B). For comparison, mannoside 4Z269, which inhibits the type 1 pilus adhesin FimH, also substantially reduced titers of CFT073 from the bladders and kidneys of infected mice relative to vehicle control. When administered together, 29β-NAc and 4Z269 substantially reduced bacterial titers in the bladder and eradicated bacteria from the kidney in nearly all mice, suggesting that FimH mannosides and FmlH galactosides may function synergistically to target distinct bacterial adhesins or communities within the kidney habitat.

Example 27: Galactoside Inhibition of $FmlH_{LD}$ Binding to Human Bladder and Kidney Tissues The relevance of FmlH and FmlH-targeting galactosides in human UTI was assessed by performing immunofluorescence analysis of wild-type (WT) $FmlH_{LD}$ or mutant (K132Q) $FmlH_{LD}$ binding to human bladder and non-malignant kidney biopsied tissue in the presence or absence of 29β-NAc. The mutant $FmlH_{LD}$(K132Q) was shown to have reduced inhibition in previous Example 25.

Frozen, de-identified human bladder and kidney sections were obtained from the Tissue Procurement Core and stored stably at −80° C. These tissue section slides were removed from the freezer and allowed to thaw at room temperature for 10-20 min. After applying a hydrophobic barrier pen around the tissue, slides were rehydrated in 200 μl buffer (5% BSA, 0.2% Triton X-100 in PBS) for 10 min. Buffer was gently aspirated and slides were blocked for 1 hr at room temperature with 200 μl buffer. Thereafter, buffer was gently aspirated and slides were incubated with 200 μl sample overnight at 4° C. Samples diluted in buffer included 50 μg/ml $FmlH_{LD}$ wild-type (WT), 50 μg/ml $FmlH_{LD}$ K132Q, and 50 μg/ml $FmlH_{LD}$ WT incubated with 100 μM 29β-NAc. Samples were gently aspirated and slides were washed three times in buffer for 5 min each. Next, slides were incubated with a mouse anti-FmlH polyclonal antibody (1:500 dilution in buffer) for 1 hr at room temperature. Slides were washed again three times in buffer and then incubated in the dark with donkey anti-mouse IgG, Alexa Fluor 594 and Wheat Germ Agglutinin, Alexa Fluor 633 (each 1:500 dilution in buffer) for 1 hr at room temperature. Slides were washed once with buffer and then incubated in the dark with DAPI (1:1000 dilution in buffer) for 5 min at room temperature. After washing twice with buffer, coverslips were mounted using 80 μl mounting media. Slides were loaded onto a Zeiss LSM 880 Confocal Laser Scanning Microscope (Carl Zeiss Inc., Thornwood, NY) equipped with a diode 405-430 laser, a HeNe 543 laser, and a HeNe 633 laser. Images were acquired with a 20×, 0.8 numerical aperture Zeiss Plan Apochromat objective using ZEN 2 imaging software.

Representative images are depicted in FIG. 10. Panels are labeled to the left and across the top with the tissue type and the treatment applied. Green corresponds to FmlH, red corresponds to Wheat Germ Agglutinin (a cell membrane marker) and blue corresponds to DAPI (a nuclear stain). While $FmlH_{LD}$ did not appear to bind to healthy human bladder tissue, $FmlH_{LD}$ did bind to healthy human kidney tissue, particularly in regions resembling the collecting ducts and distal tubules of the kidney (FIG. 10). As a negative control, the binding null mutant $FmlH_{LD}$ K132Q, which lacks the ability to bind ds-BSM in vitro (Example 25), was incapable of binding either healthy human bladder or kidney tissue, suggesting that $FmlH_{LD}$ specifically recognized receptors naturally present in human kidney tissue (FIG. 10). These observations are consistent with the previously reported binding phenotypes in mice, in which FmlH can bind naïve mouse kidney tissue but not naïve mouse bladder tissue and that FmlH binds to receptors in inflamed bladder tissue induced during the later stages of UTI pathogenesis [27]. Moreover, incubation of 29β-NAc with $FmlH_{LD}$ prevented binding to human kidney tissue, suggesting that 29β-NAc may be efficacious in treating human pyelonephritis.

Example 28: Synthesis of galactosides or n-acetyl galactosides with an "N-(tert-butyl)-2-(N-methylacetamido) acetamide" linkage The Ugi reaction was used to combine an aldehyde, amine, carboxylic acid, and isocyanide into a galactoside containing an "N-(tert-butyl)-2-(N-methylacetamido) acetamide" linkage as described in the General Scheme outlined below.

General Scheme (A)

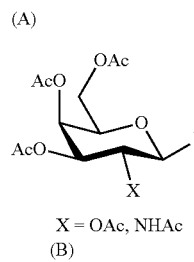

X = OAc, NHAc (B)

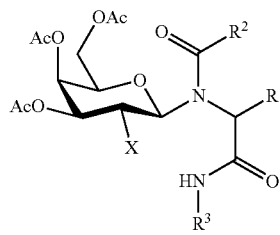

X = OAc, NHAc

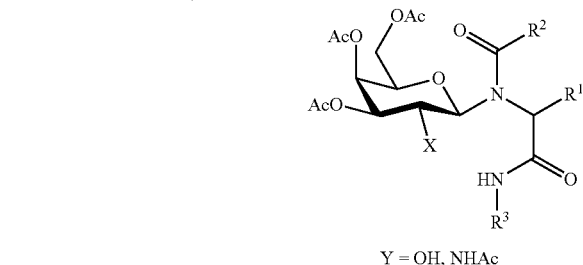

Y = OH, NHAc $R^1 = R^2 = R^3$ = Alkyl or Aryl

Using the following reactants, specific quinoline containing galactosides with the "N-(tert-butyl)-2-(N-methylacetamido) acetamide" linkage were synthesized: β-GalNAc-amine (2R,3R,4R,5R,6R)-5-acetamido-2-(acetoxymethyl)-6-aminotetrahydro-2H-pyran-3,4-diyl diacetate), f3-Gal amine ((2R,3S,4S,5R,6R)-2-(acetoxymethyl)-6-aminotetrahydro-2H-pyran-3,4,5-triyl triacetate), carboxylic acid (quinoline-8-carboxylic acid), and isocyanide (2-isocyano-2-methylpropane). The specific reaction protocols are diagrammed and described below:

Specific Scheme

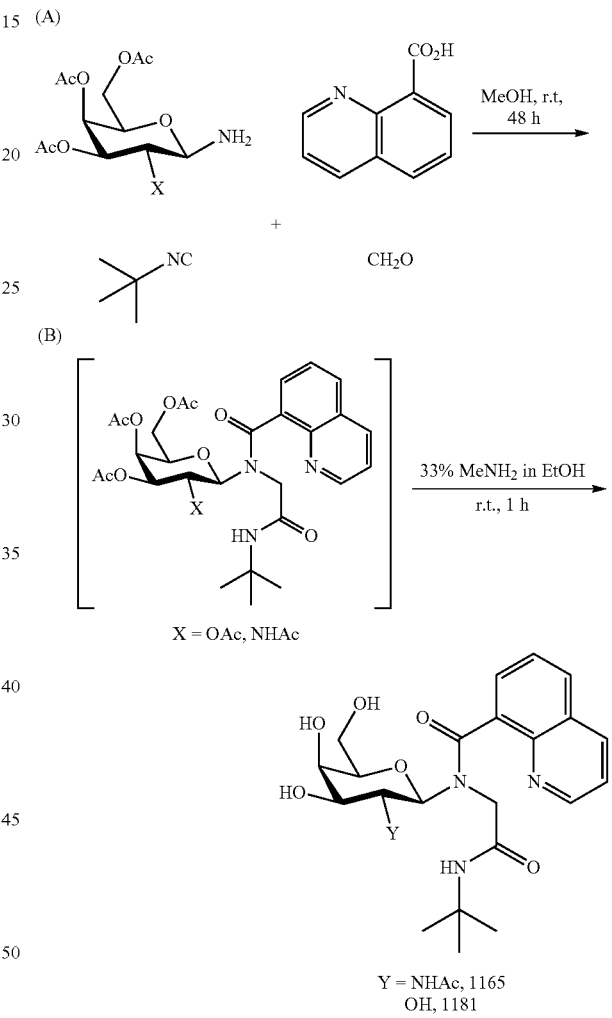

Y = NHAc, 1165
OH, 1181

(A) General Ugi Reaction Procedure with β-GalNAc/β-Gal Amine

Into a solution of aldehyde (38 mg, 0.650 mmol) in methanol (5 mL), β-GalNAc or β-Gal amine (400 mg, 0.650 mmol) was added and stirred for 5 minutes at room temperature. Then, carboxylic acid (200 mg, 0.650 mmol), and isocyanide (130 µL, 0.650 mmol) were added. The reaction was continually stirred until no noticeable starting reagents were visualized using TLC. Upon completion of the reaction, methanol was evaporated under reduced pressure and the crude compound subjected to flash column chromatography (EtOAc/Hexanes) to yield pure compound ((2R,3R,4R,5R,6R)-5-acetamido-2-(acetoxymethyl)-6-(N-(2-(tert-butylamino)-2-oxoethyl)quinoline-8-carboxamido) tetrahydro-2H-pyran-3,4-diyl diacetate and (2R,3S,4S,5R, 6R)-2-(acetoxymethyl)-6-(N-(2-(tert-butylamino)-2-oxoethyl)quinoline-8-carboxamido)tetrahydro-2H-pyran-3, 4,5-triyl triacetate).

(B) General Procedure for Deacetylation

33% Wt. Methylamine in absolute ethanol solution (5 mL) was added to (2R,3S,4S,5R,6R)-2-(acetoxymethyl)-6-(N-(2-(tert-butylamino)-2-oxoethyl)quinoline-8-carboxamido)tetrahydro-2H-pyran-3,4,5-triyl triacetate (100 mg, 0.163 mmol). The reaction solution was stirred at the same temperature (0.5-1 h) until TLC indicated complete disappearance of staring material. Complete evaporation of the solvent provided the pure compound.

N-((2R,3R,4R,5R,6R)-3-acetamido-4,5-dihydroxy-6-(hydroxymethyl)tetrahydro-2H-pyran-2 yl)-N-(2-"(tert-butylamino)-2-oxoethyl)quinoline-8-carboxamide (1165)"

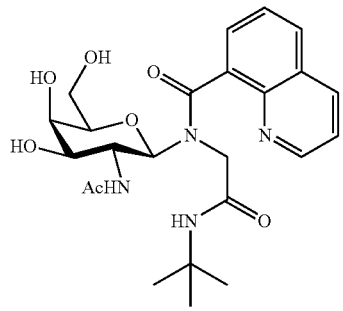

Compound was isolated as a white solid, 55 mg in 69% yield; $^1$H NMR (400 MHz, DMSO-d$_6$) δ ppm 8.87-8.93 (m, 1H), 8.53 (d, J=7.8 Hz, 1H), 8.12 (d, J=8.6 Hz, 1H), 7.57-7.77 (m, 4H), 5.74 (d, J=9.8 Hz, 1H), 4.08 (d, J=16.4 Hz, 2H), 3.85 (br. s., 2H), 3.77 (d, J=10.6 Hz, 1H), 3.42-3.52 (m, 3H), 3.34 (br. s., 1H), 3.14 (d, J=9.8 Hz, 1H), 1.83 (br. s., 3H), 1.32 (s, 9H); LCMS (ESI): found [M+H]$^+$, 489.4.

N-(2-(tert-butylamino)-2-oxoethyl)-N-((2R,3R,4S, 5R,6R)-3,4,5-trihydroxy-6-(hydroxymethyl)tetrahydro-2H-pyran-2-yl)quinoline-8-carboxamide (1181)

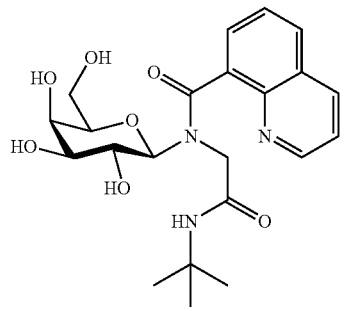

Compound was isolated as a white solid, 51 mg in 58% yield; $^1$H NMR (400 MHz, DMSO-d$_6$) δ ppm 8.88 (d, J=3.9 Hz, 1H), 8.47 (d, J=8.6 Hz, 1H), 8.08 (d, J=9.4 Hz, 1H), 7.68 (br. s., 1H), 7.62 (dd, J=8.2, 4.3 Hz, 2H), 5.54 (d, J=9.0 Hz, 1H), 4.05 (d, J=8.6 Hz, 3H), 3.68 (br. s., 3H), 3.36-3.61 (m, 6H), 2.93 (dd, J=9.4, 2.7 Hz, 1H), 1.33 (s, 9H); LCMS (ESI): found [M+H]$^+$, 448.4.

Example 29: Synthesis of Bi-Aryl Galactosides and Bi-Aryl N-Acetyl Galactosides

Using the reaction scheme described below, a variety of substituted biaryl galactosides and bi-aryl N-acetyl galactosides were synthesized. The detailed experimental protocols for each method illustrated (Method A, Method B, Suzuki reaction, Deacetylation) are outlined below.

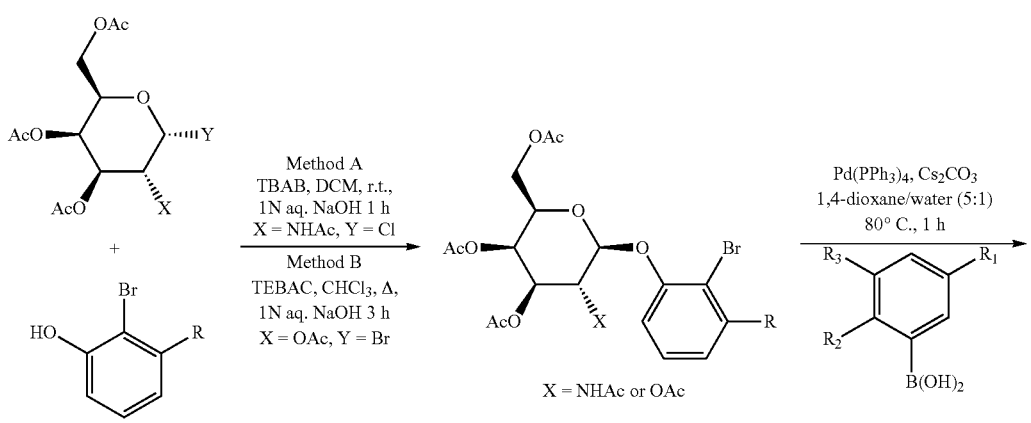

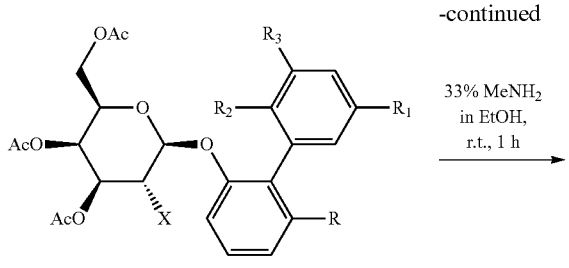
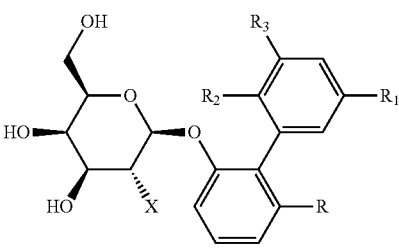

X = NHAc or OAc

X = NHAc, R = H, R$_1$ = CONHMe, R$_2$ = H, R$_3$ = H; 1189
X = NHAc, R = H, R$_1$ = OH, R$_2$ = H, R$_3$ = H; 2021
X = NHAc, R = H, R$_1$ = F, R$_2$ = H, R$_3$ = H; 2028
X = NHAc, R = H, R$_1$ = OMe, R$_2$ = H, R$_3$ = H; 2029
X = NHAc, R = H, R$_1$ = NO$_2$, R$_2$ = H, R$_3$ = H; 2030
X = NHAc, R = H, R$_1$ = CO(Me)$_2$, R$_2$ = H, R$_3$ = H; 2032
X = NHAc, R = H, R$_1$ = CONH$_2$, R$_2$ = H, R$_3$ = H; 2033
X = NHAc, R = H, R$_1$ = CN, R$_2$ = H, R$_3$ = H; 2035
X = NHAc, R = H, R$_1$ = CF$_3$, R$_2$ = H, R$_3$ = H; 2037
X = NHAc, R = H, R$_1$ = NHSO$_2$Me, R$_2$ = H, R$_3$ = H; 2038
X = NHAc, R = H, R$_1$ = CO$_2$H, R$_2$ = OME, R$_3$ = H; 2051

X = NHAc or OH

X = NHAc, R = H, R$_1$ = CO$_2$Et, R$_2$ = OMe, R$_3$ = H; 2053
X = NHAc, R = H, R$_1$ = SO$_2$Me, R$_2$ = H, R$_3$ = H; 2059
X = NHAc, R = H, R$_1$ = NHCOMe, R$_2$ = H, R$_3$ = H; 2062
X = NHAc, R = H, R$_1$ = CH$_2$OH, R$_2$ = H, R$_3$ = H; 2064
X = NHAc, R = H, R$_1$ = NHCO$_2$Me, R$_2$ = H, R$_3$ = H; 2065
X = NHAc, R = H, R$_1$ = OH, R$_2$ = OMe, R$_3$ = H; 2073
X = NHAc, R = H, R$_1$ = OSO$_2$Me, R$_2$ = OMe, R$_3$ = H; 2077
X = NHAc, R = H, R$_1$ = OSO2Me, R$_2$ = H, R$_3$ = H; 2078
X = OH, R = H, R$_1$ = CONHMe, R$_2$ = H, R$_3$ = H; 2042
X = OH, R = H, R$_1$ = NHSO$_2$Me, R$_2$ = H, R$_3$ = H; 2043
X = OH, R = H, R$_1$ = CO$_2$Me, R$_2$ = H, R$_3$ = NO$_2$; 2049
X = OH, R = H, R$_1$ = COOH, R$_2$ = H, R$_3$ = NO$_2$; 2050

General Procedure for Glycosylation (Method A).

1N aqueous NaOH solution (1 mL) was added into a solution of 2-acetamido-3,4,6,-tri-O-acetyl-1-chloro-1,2-dideoxy-α-D-galactopyranose (100 mg, 0.273 mmol), tetrabutylammonium bromide (88 mg, 0.273 mmol) and 2-bromo phenol (79 mg, 0.546 mmol) in dichloromethane (2 mL) at room temperature. The reaction solution was stirred at the same temperature until the TLC indicated complete disappearance of chloride. The reaction mass was then diluted with dichloromethane (10 mL) and washed with water followed by brine. The organic layer was collected, dried over Na$_2$SO$_4$ and concentrated under vacuo. The resulting residue was purified by silica gel chromatography with hexane/ethyl acetate combinations as eluent, giving rise to the 129 mg of Product A ((2R,3R,4R,5R,6S)-5-acetamido-2-(acetoxymethyl)-6-(2-bromophenoxy)tetrahydro-2H-ran-3,4-diyl diacetate) as a white solid.

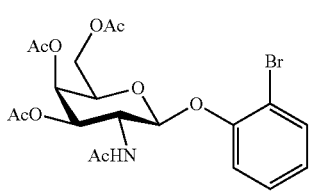

(Product A)

General Procedure for Glycosylation (Method B)

1N aqueous NaOH solution (1 mL) was added into a solution of (2R,3S,4S,5R,6R)-2-(acetoxymethyl)-6-bromo-tetrahydro-2H-pyran-3,4,5-triyl triacetate (200 mg, 0.487 mmol), benzyltriethylammonium chloride (111 mg, 0.0.487 mmol) and 2-bromo phenol (79 mg, 0.975 mmol) in chloroform (2 mL) at room temperature. The reaction solution was stirred at 60° C. temperature until the TLC indicated complete disappearance of starting material. The reaction solution was then cooled and diluted with the dichloromethane (10 mL) and washed with water followed by brine. The organic layer was collected, dried over Na$_2$SO$_4$ and concentrated under vacuo. The resulting residue was purified by silica gel chromatography with hexane/ethyl acetate combinations as eluent, giving rise to the 200 mg of Product B ((2R,3S,4S,5R,6S)-2-(acetoxymethyl)-6-(2-bromophenoxy) tetrahydro-2H-pyran-3,4,5-triyl triacetate) as a white solid.

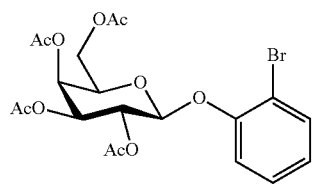

(Product B)

General Procedure for Suzuki Reaction

Under nitrogen atmosphere (2R,3R,4R,5R,6S)-5-acetamido-2-(acetoxymethyl)-6-(2-bromophenoxy) tetrahydro-2H-pyran-3,4-diyl diacetate (100 mg, 0.199 mmol), 3-(N-methyl amino carbonyl) phenyl boronic acid (78 mg, 0.298 mmol), Pd(PPh$_3$)$_4$ (23 mg, 0.0199 mmol) and Cesium carbonate (211 mg, 0.597 mmol) were added to a reaction vial followed by a dioxane/water mixture (5:1, 3.6 mL), before heating the reaction solution to 80° C. The reaction mixture was stirred at 80° C. until TLC indicated complete disappearance of staring material (1 h). The reaction solution was then cooled and diluted with dichloromethane (10 mL) and washed with water followed by brine. The organic layer was collected, dried over Na$_2$SO$_4$ and concentrated under vacuo. The resulting residue was purified by column chromatography with hexane/ethyl acetate combinations as eluent, giving rise to the desired product.

General Procedure for Deacetylation

33% Wt. Methylamine in absolute ethanol solution was added into (2R,3R,4R,5R,6S)-5-acetamido-2-(acetoxymethyl)-6-(quinolin-8-yloxy)tetrahydro-2H-pyran-3,4-diyl diacetate (50 mg, 0.105 mmol). The reaction solution was stirred at the same temperature (0.5-1 h) until TLC indicated complete disappearance of staring material. Complete evaporation of the solvent provided the pure compound.

These procedures were repeated using a variety of substituted reactants to produce Compounds 1189, 2021 and 2028-2050. The chemical identity and spectral characteristics for each compound are described in the following examples (Examples 31-53).

Example 30: 2'-(((2S,3R,4R,5R,6R)-3-acetamido-4,5-dihydroxy-6-(hydroxymethyl)tetrahydro-2H-pyran-2-yl)oxy)-N-methyl-[1,1'-biphenyl]-3-carboxamide (1189)

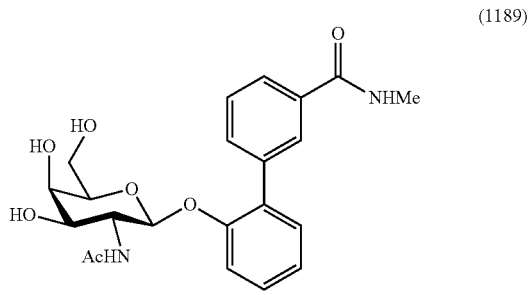

(1189)

Compound was isolated as a white solid, 62 mg in 73% yield; $^1$H NMR (400 MHz, CD$_3$OD) δ ppm 7.93 (d, J=3.91 Hz, 1H), 7.73 (t, J=5.09 Hz, 1H), 7.65 (t, J=5.87 Hz, 1H), 7.44-7.50 (m, 1H), 7.36 (d, J=4.70 Hz, 3H), 7.09-7.16 (m, 1H), 5.07-5.13 (m, 1H), 4.10-4.17 (m, 1H), 3.74-3.93 (m, 3H), 3.64-3.73 (m, 2H), 2.96 (d, J=5.09 Hz, 3H), 1.64 (d, J=4.70 Hz, 3H); $^{13}$C NMR (100 MHz, CD$_3$OD) δ ppm 174.03, 156.12, 140.03, 135.80, 133.90, 131.92, 130.44, 129.54, 126.83, 123.96, 116.96, 101.53, 77.41, 73.27, 69.79, 62.64, 54.23, 27.12, 22.82; LCMS (ESI): found [M+Na]$^+$, 453.3.

Example 31: N-((2S,3R,4R,5R,6R)-4,5-dihydroxy-2-((3'-hydroxy-[1,1'-biphenyl]-2-yl)oxy)-6-(hydroxymethyl)tetrahydro-2H-pyran-3-yl)acetamide (2021)

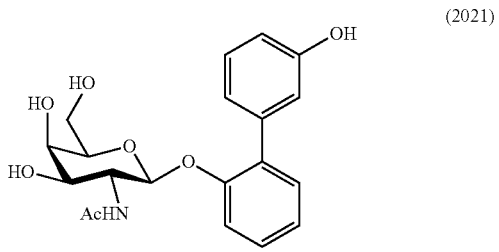

(2021)

Compound was isolated as a white solid, 30 mg in 70% yield; $^1$H NMR (400 MHz, CD$_3$OD) δ ppm 7.25-7.36 (m, 3H), 7.10-7.23 (m, 2H), 6.83-7.09 (m, 4H), 5.06 (d, J=8.6 Hz, 1H), 4.11 (dd, J=10.4, 8.8 Hz, 1H), 3.88 (d, J=3.1 Hz, 1H), 3.74-3.86 (m, 2H), 3.60-3.72 (m, 2H), 1.73 (s, 3H); $^{13}$C NMR (100 MHz, CD$_3$OD) δ ppm 174.31, 158.05, 156.13, 140.97, 132.87, 131.78, 129.79, 123.74, 122.35, 117.86, 117.09, 115.08, 101.44, 77.35, 73.63, 69.81, 62.63, 54.36, 22.96; LCMS (ESI): found [M+Na]$^+$, 412.3.

Example 32: N-((2S,3R,4R,5R,6R)-2-((3'-fluoro-[1,1'-biphenyl]-2-yl)oxy)-4,5-dihydroxy-6-(hydroxymethyl)tetrahydro-2H-pyran-3-yl)acetamide (2028)

(2028)

Compound was isolated as a white solid, 32 mg in 85% yield; 41 NMR (400 MHz, CD$_3$OD) δ ppm 7.24-7.41 (m, 5H), 7.20 (dd, J=10.4, 1.8 Hz, 1H), 7.07-7.14 (m, 1H), 7.00-7.07 (m, 1H), 5.06 (d, J=8.2 Hz, 1H), 4.10-4.19 (m, 1H), 3.89 (d, J=3.1 Hz, 1H), 3.75-3.87 (m, 2H), 3.67-3.72 (m, 1H), 3.61 (dd, J=11.0, 3.1 Hz, 1H), 1.72 (s, 3H); $^{13}$C NMR (100 MHz, CD$_3$OD) δ ppm 173.95, 165.19, 162.76156.03, 141.98, 131.78, 131.54, 130.82, 130.74, 130.47, 126.70, 126.67, 123.85, 117.70, 117.48, 116.99, 114.82, 114.61, 101.42, 77.41, 73.74, 69.81, 62.62, 54.12, 22.83; LCMS (ESI): found [M+Na]$^+$, 414.3.

Example 33: N-((2S,3R,4R,5R,6R)-4,5-dihydroxy-6-(hydroxymethyl)-2-((3'-methoxy-[1,1'-biphenyl]-2-yl)oxy)tetrahydro-2H-pyran-3-yl)acetamide (2029)

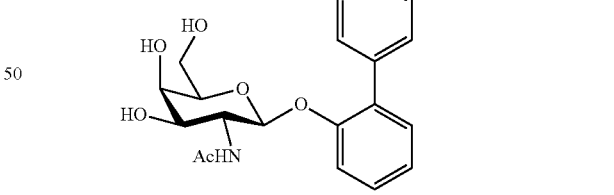

(2029)

Compound was isolated as a white solid, 20 mg in 87% yield; $^1$H NMR (400 MHz, CD$_3$OD) δ ppm 7.34-7.39 (m, 1H), 7.22-7.33 (m, 4H), 7.00-7.12 (m, 3H), 6.86 (d, J=8.2 Hz, 1H), 5.03 (d, J=8.2 Hz, 1H), 4.12 (t, J=9.8 Hz, 1H), 3.85-3.91 (m, 1H), 3.83 (s, 3H), 3.74-3.81 (m, 1H), 3.64-3.71 (m, 1H), 3.60 (dd, J=10.6, 2.3 Hz, 1H), 2.55 (s, 1H), 1.65 (s, 3H); $^{13}$C NMR (100 MHz, CD$_3$OD) δ ppm 174.07, 160.81, 156.24, 141.06, 132.95, 131.84, 129.96, 123.85, 123.23, 117.29, 116.47, 113.80, 101.85, 77.40, 73.79, 69.82, 62.64, 55.83, 54.25, 22.80; LCMS (ESI): found [M+Na]$^+$, 426.3.

Example 34: N-((2S,3R,4R,5R,6R)-4,5-dihydroxy-6-(hydroxymethyl)-2-((3'-nitro-[1,1'-biphenyl]-2-yl)oxy)tetrahydro-2H-pyran-3-yl)acetamide (2030)

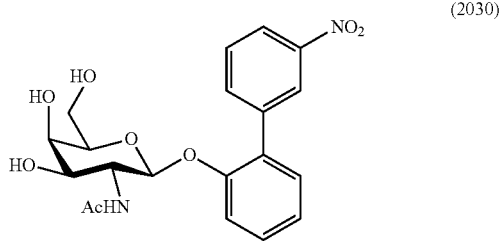

(2030)

Compound was isolated as a white solid, 35 mg in 91% yield; ¹H NMR (400 MHz, CD$_3$OD) δ ppm 8.33 (s, 1H), 8.19 (d, J=8.2 Hz, 1H), 7.87 (d, J=7.8 Hz, 1H), 7.62 (t, J=8.0 Hz, 1H), 7.35-7.41 (m, 3H), 7.13-7.18 (m, 1H), 5.07 (d, J=8.6 Hz, 1H), 4.08-4.14 (m, 1H), 3.89 (d, J=2.7 Hz, 1H), 3.75-3.87 (m, 3H), 3.67-3.73 (m, 1H), 3.61 (dd, J=10.6, 3.1 Hz, 1H), 2.55 (s, 1H), 1.63 (s, 3H); ¹³C NMR (100 MHz, CD$_3$OD) δ ppm 173.74, 156.05, 149.62, 141.30, 137.07, 131.66, 131.20, 130.38, 125.60, 124.06, 122.87, 117.01, 101.51, 77.43, 73.50, 69.77, 62.62, 54.04, 22.77; LCMS (ESI): found [M+Na]⁺, 441.3.

Example 35: 2'-(((2S,3R,4R,5R,6R)-3-acetamido-4,5-dihydroxy-6-(hydroxymethyl)tetrahydro-2H-pyran-2-yl)oxy)-N,N-dimethyl-[1,1'-biphenyl]-3-carboxamide (2032)

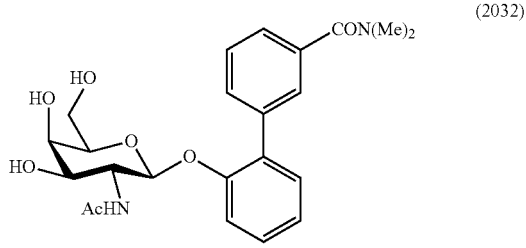

(2032)

Compound was isolated as a white solid, 29 mg in 86% yield; ¹H NMR (400 MHz, CD$_3$OD) δ ppm 7.55-7.60 (m, 2H), 7.47 (t, J=7.8 Hz, 1H), 7.29-7.39 (m, 4H), 7.08-7.14 (m, 1H), 5.17 (d, J=8.2 Hz, 1H), 3.98-4.06 (m, 1H), 3.89 (d, J=2.7 Hz, 1H), 3.73-3.84 (m, 2H), 3.65-3.73 (m, 2H), 3.12 (d, J=5.1 Hz, 6H), 1.74 (s, 3H); ¹³C NMR (100 MHz, CD$_3$OD) δ ppm 173.94, 156.03, 140.15, 136.96, 132.31, 131.84, 130.44, 129.66, 129.41, 126.62, 123.90, 116.88, 101.05, 77.35, 73.42, 69.77, 62.63, 54.49, 40.58, 35.88, 23.01; LCMS (ESI): found [M+Na]⁺, 445.3.

Example 36: 2'-(((2S,3R,4R,5R,6R)-3-acetamido-4,5-dihydroxy-6-(hydroxymethyl)tetrahydro-2H-pyran-2-yl)oxy)-[1,1'-biphenyl]-3-carboxamide (2033)

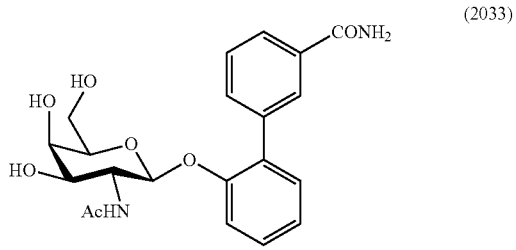

(2033)

Compound was isolated as a white solid, 13 mg in 85% yield; ¹H NMR (400 MHz, CD$_3$OD) δ ppm 7.99 (s, 1H), 7.79 (d, J=7.83 Hz, 1H), 7.68 (d, J=7.83 Hz, 1H), 7.45-7.50 (m, 1H), 7.31-7.39 (m, 4H), 7.12 (t, J=6.85 Hz, 1H), 5.11 (d, J=8.22 Hz, 1H), 4.10 (dd, J=8.80, 10.37 Hz, 1H), 3.89 (d, J=3.13 Hz, 1H), 3.75-3.87 (m, 3H), 3.64-3.72 (m, 3H), 1.64 (s, 3H); ¹³C NMR (100 MHz, CD$_3$OD) δ ppm 174.01, 172.99, 156.13, 140.02, 135.11, 134.37, 131.91, 130.44, 129.96, 129.41, 127.24, 123.97, 117.00, 101.50, 77.41, 73.26, 62.63, 54.32, 22.82; LCMS (ESI): found [M+Na]⁺, 439.3.

Example 37: N-((2S,3R,4R,5R,6R)-2-((3'-cyano-[1,1'-biphenyl]-2-yl)oxy)-4,5-dihydroxy-6-(hydroxymethyl)tetrahydro-2H-pyran-3-yl)acetamide (2035)

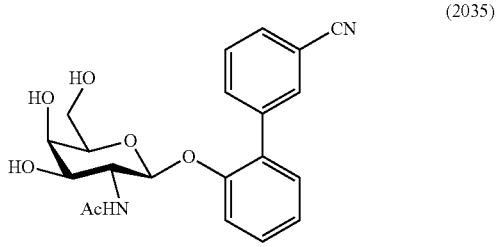

(2035)

Compound was isolated as a white solid, 16 mg in 84% yield; ¹H NMR (400 MHz, CD$_3$OD) δ ppm 7.77-7.82 (m, 2H), 7.67 (d, J=9.00 Hz, 1H), 7.53-7.59 (m, 1H), 7.31-7.40 (m, 3H), 7.10-7.17 (m, 1H), 5.07 (d, J=8.22 Hz, 1H), 4.10-4.18 (m, 1H), 3.90 (d, J=3.13 Hz, 1H), 3.74-3.87 (m, 2H), 3.67-3.73 (m, 1H), 3.61 (dd, J=2.54, 10.76 Hz, 1H), 1.70 (s, 3H); ¹³C NMR (100 MHz, CD$_3$OD) δ ppm 173.77, 155.97, 141.05, 135.62, 134.28, 131.72, 131.03, 130.36, 123.99, 120.08, 116.88, 113.37, 101.38, 77.42, 73.58, 69.77, 62.61, 54.01, 22.87; LCMS (ESI): found [M+Na]⁺, 421.3.

Example 38: N-((2S,3R,4R,5R,6R)-4,5-dihydroxy-6-(hydroxymethyl)-2-((3'-(trifluoromethyl)-[1,1'-biphenyl]-2-yl)oxy)tetrahydro-2H-pyran-3-yl)acetamide (2037)

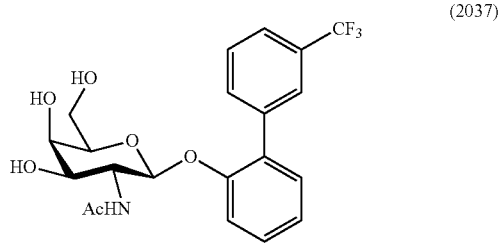

(2037)

Compound was isolated as a white solid, 14 mg in 86% yield; $^1$H NMR (400 MHz, CD$_3$OD) δ ppm 7.78 (d, J=7.4 Hz, 1H), 7.68 (s, 1H), 7.53-7.63 (m, 2H), 7.36-7.39 (m, 2H), 7.30-7.36 (m, 1H), 7.11-7.17 (m, 1H), 5.07 (d, J=8.6 Hz, 1H), 4.11 (dd, J=10.4, 8.8 Hz, 1H), 3.89 (br. s., 1H), 3.75-3.86 (m, 2H), 3.66-3.73 (m, 1H), 3.61 (dd, J=10.8, 3.3 Hz, 1H), 1.63 (s, 3H); $^{13}$C NMR (100 MHz, CD$_3$OD) δ ppm 173.39, 156.11, 140.70, 135.02, 131.74, 131.33, 130.81, 129.92, 126.95, 124.75, 117.02, 101.53, 77.44, 73.72, 69.78, 62.62, 54.13, 22.73; LCMS (ESI): found [M+Na]$^+$, 464.3.

Example 39: N-((2S,3R,4R,5R,6R)-4,5-dihydroxy-6-(hydroxymethyl)-2-((3'-(methylsulfonamido)-[1,1'-biphenyl]-2-yl)oxy)tetrahydro-2H-pyran-3-yl)acetamide (2038)

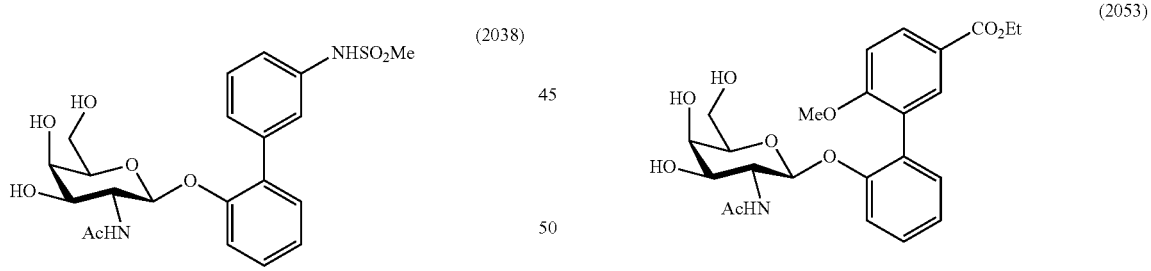

(2038)

Compound was isolated as a white solid, 34 g in 96% yield; 1H NMR (400 MHz, CD3OD) δ ppm 7.40 (s, 1H), 7.36 (s, 1H), 7.32 (d, J=5.87 Hz, 3H), 7.22-7.29 (m, 2H), 7.07-7.12 (m, 1H), 5.12 (d, J=8.61 Hz, 1H), 4.11 (dd, J=8.61, 10.56 Hz, 1H), 3.89 (d, J=3.13 Hz, 1H), 3.73-3.85 (m, 2H), 3.63-3.71 (m, 2H), 3.03 (s, 3H), 1.73 (s, 3H); 13C NMR (100 MHz, CD3OD) δ ppm 174.06, 155.99, 140.93, 139.06, 131.97, 130.27, 127.25, 123.82, 120.68, 116.69, 101.09, 77.35, 73.46, 62.60, 54.24, 39.58, 23.04; LCMS (ESI): found [M+Na]$^+$, 489.2.

Example 40: 2'-(((2S,3R,4R,5R,6R)-3-acetamido-4,5-dihydroxy-6-(hydroxymethyl)tetrahydro-2H-pyran-2-yl)oxy)-6-methoxy-[1,1'-biphenyl]-3-carboxylic acid (2051)

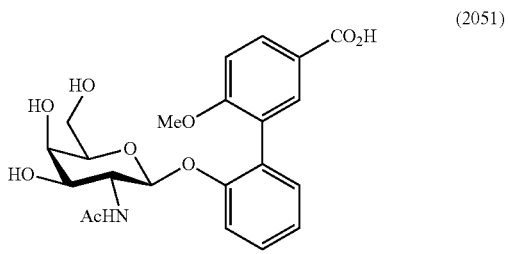

(2051)

Compound was isolated as a white solid, 49 mg in 65% yield; 1H NMR (400 MHz, CD3OD) δ ppm 8.03 (dd, J=1.96, 8.61 Hz, 1H), 7.78 (d, J=2.35 Hz, 1H), 7.29-7.36 (m, 2H), 7.15 (d, J=7.43 Hz, 1H), 7.03-7.10 (m, 2H), 4.95 (d, J=8.22 Hz, 1H), 3.96 (dd, J=8.80, 10.37 Hz, 1H), 3.83-3.88 (m, 1H), 3.82 (s, 3H), 3.73-3.80 (m, 1H), 3.62-3.67 (m, 1H), 3.58 (dd, J=3.13, 10.56 Hz, 1H), 1.62 (s, 3H); 13C NMR (100 MHz, CD3OD) δ ppm 173.77, 170.06, 162.78, 156.91, 134.12, 132.47, 132.33, 130.16, 129.56, 129.31, 123.58, 123.31, 116.78, 112.06, 111.59, 101.61, 77.29, 73.49, 69.80, 62.62, 56.50, 54.20, 22.87; LCMS (ESI): found [M+Na]$^+$, 470.3.

Example 41: ethyl 2'-(((2S,3R,4R,5R,6R)-3-acetamido-4,5-dihydroxy-6-(hydroxymethyl)tetrahydro-2H-pyran-2-yl)oxy)-6-methoxy-[1,1'-biphenyl]-3-carboxylate (2053)

(2053)

Compound was isolated as a white solid, 36 mg in 91% yield; 1H NMR (400 MHz, CD3OD) δ ppm 8.02 (dd, J=8.6, 2.0 Hz, 1H), 7.77 (d, J=2.0 Hz, 1H), 7.29-7.37 (m, 2H), 7.14 (d, J=7.4 Hz, 1H), 7.04-7.11 (m, 2H), 4.94 (d, J=8.2 Hz, 1H), 4.34 (q, J=7.0 Hz, 2H), 3.96 (dd, J=10.4, 8.8 Hz, 1H), 3.83-3.87 (m, 2H), 3.82 (s, 3H), 3.74-3.80 (m, 1H), 3.62-3.67 (m, 1H), 3.57 (dd, J=11.0, 3.1 Hz, 1H), 1.60 (s, 3H), 1.37 (t, J=7.2 Hz, 3H); 13C NMR (100 MHz, CD3OD) δ ppm 174.08, 168.72, 163.27, 157.34, 134.21, 132.57, 130.64, 129.92, 123.74, 117.21, 112.52, 102.09, 77.72, 73.94, 70.20, 63.04, 62.39, 56.93, 54.5623.30, 15.26; LCMS (ESI): found [M+Na]$^+$, 498.3.

Example 42: N-((2S,3R,4R,5R,6R)-4,5-dihydroxy-6-(hydroxymethyl)-2-((3'-(methylsulfonyl)-[1,1'-biphenyl]-2-yl)oxy)tetrahydro-2H-pyran-3-yl)acetamide (2059)

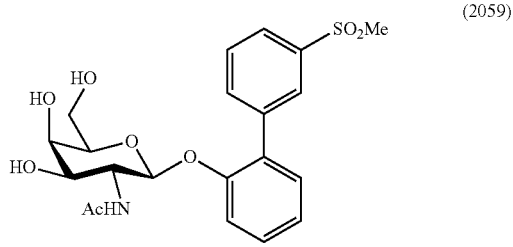

(2059)

Compound was isolated as a white solid, 14 mg in 60% yield; $^{1}$H NMR (400 MHz, CD$_3$OD) δ ppm 8.10 (s, 1H), 7.90 (d, J=7.8 Hz, 1H), 7.81 (d, J=7.8 Hz, 1H), 7.62-7.69 (m, 1H), 7.34-7.42 (m, 3H), 7.12-7.18 (m, 1H), 5.14 (d, J=8.2 Hz, 1H), 4.06 (dd, J=10.6, 8.6 Hz, 1H), 3.89 (d, J=3.1 Hz, 1H), 3.75-3.87 (m, 3H), 3.63-3.71 (m, 2H), 3.24 (s, 2H), 1.68 (s, 3H); $^{13}$C NMR (100 MHz, CD$_3$OD) δ ppm 173.81, 156.05, 141.91, 141.01, 136.05, 131.77, 131.06, 130.44, 129.69, 126.80, 124.10, 116.95, 101.46, 77.44, 73.41, 69.77, 62.61, 54.27, 44.65, 22.93; LCMS (ESI): found [M+Na]$^+$, 474.3.

Example 43: N-(2'-(((2S,3R,4R,5R,6R)-3-acetamido-4,5-dihydroxy-6-(hydroxymethyl)tetrahydro-2H-pyran-2-yl)oxy)-[1,1'-biphenyl]-3-yl)acetamide (2062)

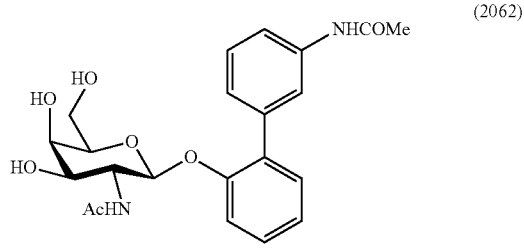

(2062)

Compound was isolated as a white solid, 38 mg in 96% yield; 1H NMR (400 MHz, CD3OD) δ ppm 7.63 (t, J=1.8 Hz, 1H), 7.56 (d, J=9.0 Hz, 1H), 7.28-7.36 (m, 5H), 7.23 (s, 1H), 7.09 (td, J=7.2, 1.6 Hz, 1H), 5.11 (d, J=8.6 Hz, 1H), 4.13 (dd, J=10.6, 8.6 Hz, 1H), 3.89 (d, J=3.1 Hz, 1H), 3.74-3.85 (m, 2H), 3.65-3.70 (m, 2H), 2.16 (s, 3H), 1.70 (s, 3H); 13C NMR (100 MHz, CD3OD) δ ppm 174.17, 171.86, 155.99, 140.15, 139.38, 132.16, 131.78, 130.08, 129.58, 126.81, 132.83, 123.23, 120.35, 116.84, 101.05, 77.32, 73.37, 69.80, 62.63, 54.32, 24.01, 23.02; LCMS (ESI): found [M+Na]$^+$, 453.3.

Example 44: N-((2S,3R,4R,5R,6R)-4,5-dihydroxy-6-(hydroxymethyl)-2-((3'-(hydroxymethyl)-[1,1'-biphenyl]-2-yl)oxy)tetrahydro-2H-pyran-3-yl)acetamide (2064)

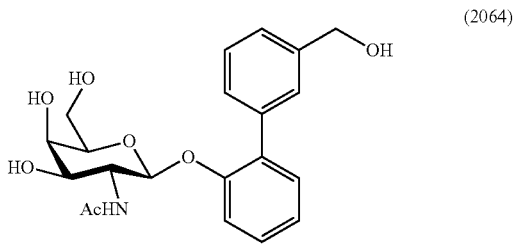

(2064)

Compound was isolated as a white solid, 33 mg in 87% yield; 1H NMR (400 MHz, CD3OD) δ ppm 7.53 (s, 1H), 7.27-7.40 (m, 6H), 7.06-7.12 (m, 1H), 4.97 (d, J=8.61 Hz, 1H), 4.63 (s, 2H), 4.18 (dd, J=8.61, 10.56 Hz, 1H), 3.88 (d, J=3.52 Hz, 1H), 3.82-3.86 (m, 1H), 3.76-3.81 (m, 1H), 3.66-3.71 (m, 1H), 3.59 (dd, J=3.13, 10.56 Hz, 1H), 1.54 (s, 3H); 13C NMR (100 MHz, CD3OD) δ ppm 174.24, 156.32, 142.22, 132.65, 131.80, 130.32, 129.99, 129.65, 129.33, 127.18, 123.90, 117.10, 101.91, 77.42, 73.47, 69.82, 65.84, 62.68, 54.09, 22.70; LCMS (ESI): found [M+Na]$^+$, 426.3.

Example 45: methyl (2'-(((2S,3R,4R,5R,6R)-3-acetamido-4,5-dihydroxy-6-(hydroxymethyl)tetrahydro-2H-pyran-2-yl)oxy)-[1,1'-biphenyl]-3-yl)carbamate (2065)

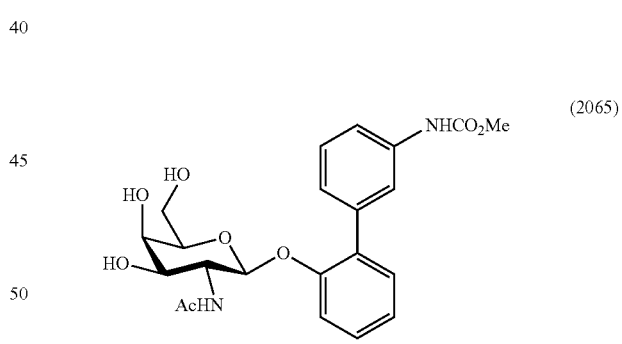

(2065)

Compound was isolated as a white solid, 34 mg in 87% yield; 1H NMR (400 MHz, CD3OD) δ ppm 7.53 (br. s., 1H), 7.41 (d, J=8.61 Hz, 1H), 7.27-7.35 (m, 4H), 7.16 (d, J=7.83 Hz, 1H), 7.06-7.11 (m, 1H), 5.11 (d, J=8.61 Hz, 1H), 4.09 (dd, J=8.61, 10.56 Hz, 1H), 3.88 (d, J=3.13 Hz, 1H), 3.77-3.85 (m, 2H), 3.74 (s, 3H), 3.68 (dd, J=3.13, 10.56 Hz, 2H), 1.70 (s, 3H); 13C NMR (100 MHz, CD3OD) δ ppm 174.17, 156.01, 140.27, 132.46, 131.85, 130.00, 129.57, 125.88, 123.39, 116.89, 101.08, 77.32, 73.34, 69.83, 62.61, 54.42, 52.67, 22.96; LCMS (ESI): found [M+Na]$^+$, 469.2.

Example 46: N-((2S,3R,4R,5R,6R)-4,5-dihydroxy-2-((5'-hydroxy-2'-methoxy-[1,1'-biphenyl]-2-yl)oxy)-6-(hydroxymethyl)tetrahydro-2H-pyran-3-yl)acetamide (2073)

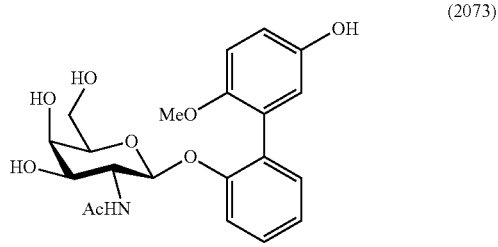

(2073)

Compound was isolated as a white solid, 21 mg in 91% yield; $^1$H NMR (400 MHz, CD$_3$OD) δ ppm 7.14 (dd, J=7.4, 1.2 Hz, 1H), 7.03 (t, J=6.8 Hz, 1H), 6.86 (d, J=9.0 Hz, 1H), 6.73 (dd, J=8.8, 2.9 Hz, 1H), 6.60 (d, J=3.1 Hz, 1H), 4.95 (d, J=8.2 Hz, 1H), 4.00 (dd, J=10.6, 8.6 Hz, 1H), 3.86 (d, J=2.7 Hz, 1H), 3.80-3.84 (m, 1H), 3.74-3.79 (m, 1H), 3.66 (s, 3H), 3.61-3.64 (m, 1H), 3.56-3.61 (m, 2H), 1.73 (s, 3H); $^{13}$C NMR (100 MHz, CD$_3$OD) δ ppm 174.15, 156.75, 152.19, 151.93, 132.55, 130.44, 129.68, 123.21, 119.49, 117.10, 115.98, 114.77, 101.70, 77.25, 73.62, 69.80, 62.61, 57.44, 54.32, 23.02; LCMS (ESI): found [M+Na]$^+$, 442.3.

Example 47: 2'-(((2S,3R,4R,5R,6R)-3-acetamido-4,5-dihydroxy-6-(hydroxymethyl)tetrahydro-2H-pyran-2-yl)oxy)-6-methoxy-[1,1'-biphenyl]-3-yl methanesulfonate (2077)

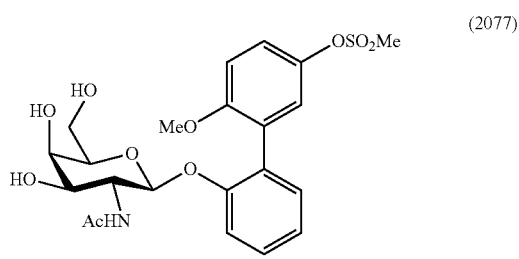

(2077)

Compound was isolated as a white solid, 13 mg in 82% yield; $^1$H NMR (400 MHz, CD$_3$OD) δ ppm 7.25-7.34 (m, 3H), 7.20 (d, J=7.4 Hz, 1H), 7.14 (d, J=2.7 Hz, 1H), 7.02-7.10 (m, 2H), 5.01 (d, J=8.2 Hz, 1H), 3.93-4.01 (m, 1H), 3.83-3.89 (m, 1H), 3.79-3.83 (m, 1H), 3.74 (s, 1H), 3.64 (t, J=6.1 Hz, 2H), 3.23 (s, 3H), 1.72 (s, 3H); $^{13}$C NMR (100 MHz, CD$_3$OD) δ ppm 173.87, 156.47, 143.93, 132.69, 128.77, 126.45, 123.27, 116.95, 113.58, 101.39, 77.30, 73.34, 69.75, 62.59, 56.79, 54.31, 37.38, 23.05; LCMS (ESI): found [M+Na]$^+$, 520.2.

Example 48: 2'-(((2S,3R,4R,5R,6R)-3-acetamido-4,5-dihydroxy-6-(hydroxymethyl)tetrahydro-2H-pyran-2-yl)oxy)-[1,1'-biphenyl]-3-yl methanesulfonate (2078)

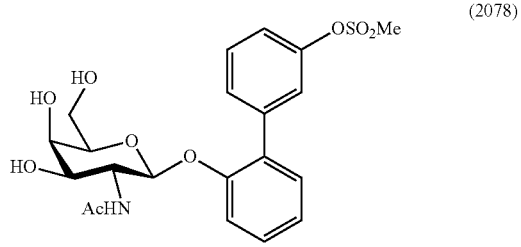

(2078)

Compound was isolated as a white solid, 30 mg in 94% yield; $^1$H NMR (400 MHz, CD$_3$OD) δ ppm 7.46-7.51 (m, 2H), 7.32-7.38 (m, 2H), 7.27-7.32 (m, 1H), 7.10-7.16 (m, 1H), 5.15 (d, J=8.22 Hz, 1H), 4.05 (dd, J=8.41, 10.76 Hz, 1H), 3.89 (d, J=3.13 Hz, 1H), 3.75-3.84 (m, 2H), 3.66-3.73 (m, 2H), 3.29 (s, 3H), 1.71 (s, 3H); $^{13}$C NMR (100 MHz, CD$_3$OD) δ ppm 173.98, 156.04, 150.72, 141.82, 131.81, 131.30, 130.72, 129.89, 124.60, 124.02, 121.79, 117.10, 101.35, 77.43, 73.27, 69.79, 62.61, 54.47, 37.77, 22.96; LCMS (ESI): found [M+Na]$^+$, 490.3.

Example 49: N-methyl-2'-(((2S,3R,4S,5R,6R)-3,4,5-trihydroxy-6-(hydroxymethyl)tetrahydro-2H-pyran-2-yl)oxy)-[1,1'-biphenyl]-3-carboxamide (2042)

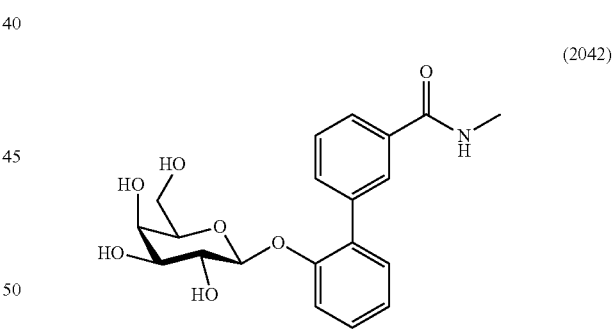

(2042)

Compound was isolated as a white solid, 34 mg in 97% yield; $^1$H NMR (400 MHz, CD$_3$OD) δ ppm 8.19 (s, 1H), 7.75 (dd, J=13.5, 8.0 Hz, 2H), 7.49 (t, J=7.6 Hz, 1H), 7.32-7.40 (m, 3H), 7.11 (ddd, J=7.7, 5.2, 3.1 Hz, 1H), 5.05 (d, J=7.8 Hz, 1H), 3.90 (d, J=3.5 Hz, 1H), 3.67-3.80 (m, 4H), 3.61 (d, J=3.5 Hz, 1H), 3.58 (d, J=3.5 Hz, 1H), 2.94 (s, 3H); $^{13}$C NMR (100 MHz, CD$_3$OD) δ ppm 170.95, 155.94, 140.12, 135.01, 133.79, 131.78, 130.37, 129.92, 126.89, 123.76, 116.84, 102.98, 77.17, 75.33, 72.62, 70.38, 62.54, 27.14; LCMS (ESI): found [M+Na]$^+$, 412.3.

141

Example 50: N-(2'-(((2S,3R,4S,5R,6R)-3,4,5-trihydroxy-6-(hydroxymethyl)tetrahydro-2H-pyran-2-yl)oxy)-[1,1'-biphenyl]-3-yl)methanesulfonamide (2043)

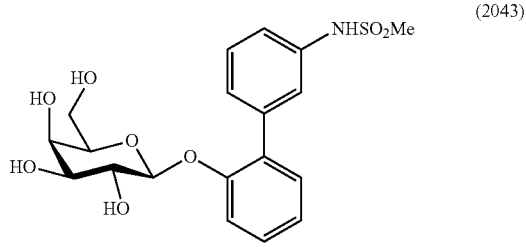

(2043)

Compound was isolated as a white solid, 33 mg in 93% yield; $^1$H NMR (400 MHz, CD$_3$OD) δ ppm 7.54 (s, 1H), 7.27-7.39 (m, 5H), 7.19-7.26 (m, 1H), 7.06-7.12 (m, 1H), 5.06 (d, J=7.8 Hz, 1H), 3.89 (d, J=3.1 Hz, 1H), 3.72-3.77 (m, 2H), 3.66-3.72 (m, 2H), 3.57 (dd, J=9.6, 3.3 Hz, 1H), 3.01 (s, 3H); $^{13}$C NMR (100 MHz, CD$_3$OD) δ ppm 153.37, 141.09, 138.77, 131.72, 129.98, 127.19, 123.71, 123.36, 120.63, 116.29, 101.96, 76.91, 75.02, 72.17, 70.15, 62.2739.16; LCMS (ESI): found [M+Na]$^+$, 448.2.

Example 51: methyl 5-nitro-2'-(((2S,3R,4S,5R,6R)-3,4,5-trihydroxy-6-(hydroxymethyl)tetrahydro-2H-pyran-2-yl)oxy)-[1,1'-biphenyl]-3-carboxylate (2049)

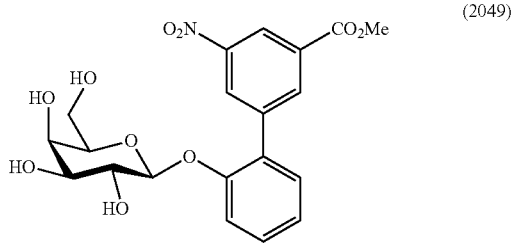

(2049)

Compound was isolated as a white solid, 42 mg in 89% yield; 1H NMR (400 MHz, CD3OD) δ ppm 8.64 (d, J=2.0 Hz, 1H), 8.59-8.61 (m, 1H), 8.55 (s, 1H), 7.37-7.49 (m, 3H), 7.16-7.22 (m, 1H), 5.05 (d, J=7.4 Hz, 1H), 3.91 (d, J=3.5 Hz, 1H), 3.75-3.83 (m, 2H), 3.67-3.74 (m, 2H), 3.60 (dd, J=9.8, 3.5 Hz, 1H), 2.98 (s, 3H); 13C NMR (100 MHz, CD3OD) δ ppm 168.34, 156.06, 149.96, 141.95, 136.66, 135.53, 131.66, 131.59, 129.82, 127.91, 124.16, 121.76, 117.42, 103.41, 77.28, 75.27, 72.54, 70.36, 62.54, 27.27; LCMS (ESI): found [M+Na]$^+$, 457.2.

142

Example 52: 5-nitro-2'-(((2S,3R,4S,5R,6R)-3,4,5-trihydroxy-6-(hydroxymethyl)tetrahydro-2H-pyran-2-yl)oxy)-[1,1'-biphenyl]-3-carboxylic acid (2050)

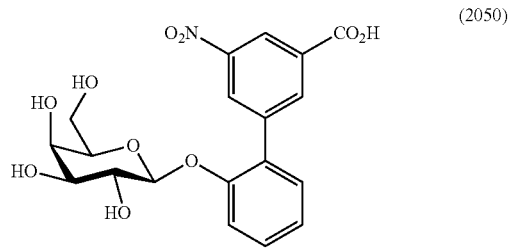

(2050)

Compound was isolated as a white solid, 62 mg in 88% yield; 1H NMR (400 MHz, CD3OD) δ ppm; 8.73 (s, 2H), 8.58 (s, 1H), 7.37-7.46 (m, 4H), 7.15-7.21 (m, 1H), 5.01 (d, J=7.4 Hz, 1H), 3.89 (d, J=3.5 Hz, 1H), 3.74-3.83 (m, 2H), 3.66-3.72 (m, 2H), 3.56 (dd, J=9.6, 3.3 Hz, 1H); 13C NMR (100 MHz, CD3OD) δ ppm 167.88, 156.03, 149.75, 142.10, 137.57, 133.60, 131.57, 129.73, 124.13, 123.66, 117.52, 103.33, 77.27, 75.31, 72.33, 70.3562.51; LCMS (ESI): found [M+Na]+, 444.3.

Example 53: Synthesis of Quionoline and Isoinoline Containing Galactosides

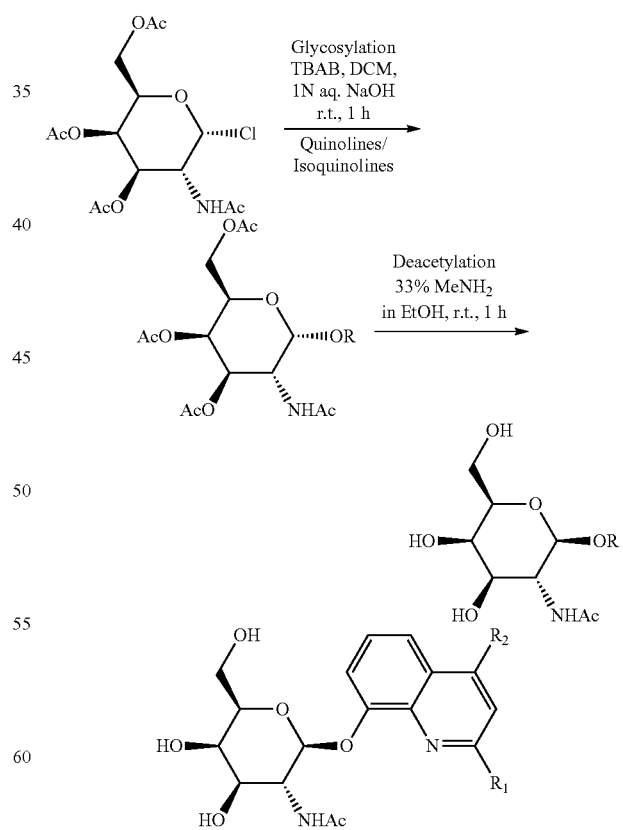

R$_1$ = H, R$_2$ = H; 1176
R$_1$ = Me, R$_2$ = H; 1179
R$_1$ = H, R$_2$ = Me; 1192

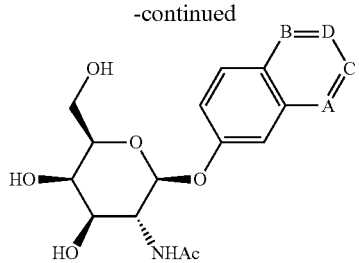

A = H, B = H, C = H, D = H; 1180
A = H, B = N, C = H, D = H; 1184
A = H, B = H, C = N, D = H; 2002
A = H, B = H, C = H, D = N; 2007

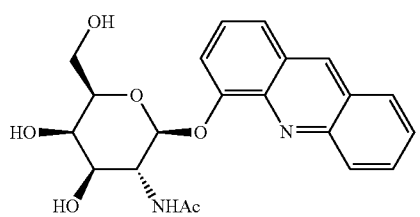

2003

General Procedure for Glycosylation.

1N aqueous NaOH solution (1 mL) was added into a solution of 2-Acetamido-3,4,6,-tri-O-acetyl-1-chloro-1,2-dideoxy-α-D-galactopyranose (100 mg, 0.273 mmol), tetrabutylammonium bromide (88 mg, 0.273 mmol) and 8-hydroxy quinoline (79 mg, 0.546 mmol) in dichloromethane (2 mL) at room temperature. The reaction solution was stirred at the same temperature until the TLC indicated complete disappearance of chloride. The reaction mass was then diluted with dichloromethane (10 mL) and washed with water followed by brine. The organic layer was collected, dried over Na2SO4 and concentrated under vacuo. The resulting residue was purified by silica gel chromatography with hexane/ethyl acetate combinations as eluent, giving rise to the 129 mg of (2R,3R,4R,5R,6S)-5-acetamido-2-(acetoxymethyl)-6-(quinolin-8-yloxy)tetrahydro-2H-pyran-3,4-diyl diacetate as a white solid.

General Procedure for Deacetylation

33% Wt. Methylamine in absolute ethanol solution was added into (2R,3R,4R,5R,6S)-5-acetamido-2-(acetoxymethyl)-6-(quinolin-8-yloxy)tetrahydro-2H-pyran-3,4-diyl diacetate (50 mg, 0.105 mmol). The reaction solution was stirred at the same temperature (0.5-1 h) until TLC indicates complete disappearance of staring material. Complete evaporation of the solvent provided the pure compound.

These procedures were repeated using different quinolines/isoquinolines in place of 8-hydroxyquinoline to produce compounds 1179, 1192, 1180, 1184, 2002, 2003, and 2007. The chemical/spectral properties for each isolated compound are described in the following Examples 54-60.

Example 54: N-((2S,3R,4R,5R,6R)-4,5-dihydroxy-6-(hydroxymethyl)-2-((2-methylquinolin-8-yl)oxy)tetrahydro-2H-pyran-3-yl)acetamide (1179)

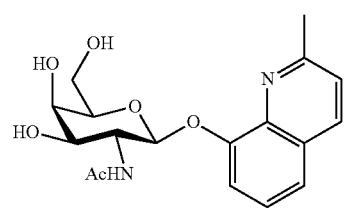

(1179)

Compound was isolated as a white solid, 24 mg in 65% yield; 1H NMR (400 MHz, DMSO-d6) δ ppm 8.20 (d, J=8.2 Hz, 1H), 7.55 (d, J=7.4 Hz, 1H), 7.34-7.47 (m, 3H), 5.29 (d, J=8.6 Hz, 1H), 4.07 (t, J=9.2 Hz, 1H), 3.73 (br. s., 2H), 3.42-3.63 (m, 4H), 2.65 (s, 3H), 1.80 (s, 3H); 13C NMR (100 MHz, DMSO-d6) δ ppm 171.17, 158.45, 136.81, 127.82, 126.17, 123.08, 121.92, 114.67, 109.98, 99.94, 76.01, 71.56, 67.79, 60.73, 53.07, 25.11, 23.44; LCMS (ESI): found [M+H]$^+$, 363.3.

Example 55: N-((2S,3R,4R,5R,6R)-4,5-dihydroxy-6-(hydroxymethyl)-2-(quinolin-7-yloxy)tetrahydro-2H-pyran-3-yl)acetamide (1180)

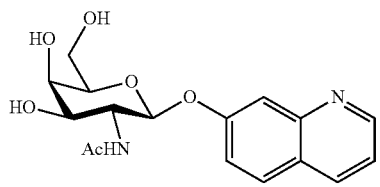

(1180)

Compound was isolated as a white solid, 24 mg in 54% yield; 1H NMR (400 MHz, CD3OD) δ ppm 8.77 (d, J=3.5 Hz, 1H), 8.29 (d, J=7.8 Hz, 1H), 7.87 (d, J=9.0 Hz, 1H), 7.58 (br. s., 1H), 7.42 (dd, J=8.2, 4.3 Hz, 1H), 7.34 (d, J=7.8 Hz, 1H), 5.27 (d, J=8.2 Hz, 1H), 4.31 (t, J=9.4 Hz, 1H), 3.98 (br. s., 1H), 3.75-3.88 (m, 4H), 2.00 (s, 3H); 13C NMR (100 MHz, CD3OD) δ ppm 174.40, 160.31, 151.64, 150.11, 138.26, 130.68, 126.14, 121.37, 121.06, 111.80, 100.98, 77.32, 73.12, 69.62, 62.38, 54.24, 23.15; LCMS (ESI): found [M+H]$^+$, 371.1.

Example 56: N-((2S,3R,4R,5R,6R)-4,5-dihydroxy-6-(hydroxymethyl)-2-(quinolin-6-yloxy)tetrahydro-2H-pyran-3-yl)acetamide (1184)

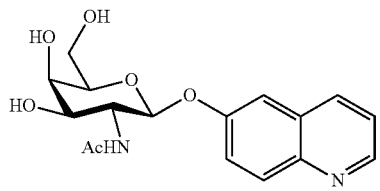

(1184)

Compound was isolated as a white solid, 22 mg in 68% yield; 1H NMR (400 MHz, CD3OD) δ ppm 8.71 (d, J=3.5 Hz, 1H), 8.28 (d, J=8.2 Hz, 1H), 7.95 (d, J=9.0 Hz, 1H), 7.46-7.54 (m, 3H), 5.22 (d, J=8.2 Hz, 1H), 4.24-4.31 (m, 1H), 3.95 (d, J=3.1 Hz, 1H), 3.84-3.90 (m, 1H), 3.76-3.83 (m, 3H), 2.00 (s, 3H); 13C NMR (100 MHz, CD3OD) δ ppm 174.43, 157.36, 149.55, 145.41, 137.77, 131.01, 130.64, 124.19, 122.95, 111.95, 101.27, 77.54, 73.09, 69.82, 62.75, 54.35, 23.17; LCMS (ESI): found [M+H]+, 371.4.

Example 57: N-((2S,3R,4R,5R,6R)-4,5-dihydroxy-6-(hydroxymethyl)-2-((4-methylquinolin-8-yl)oxy)tetrahydro-2H-pyran-3-yl)acetamide (1192)

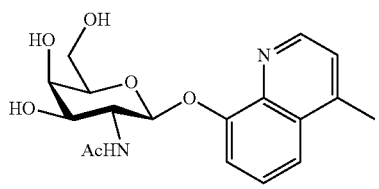

(1192)

Compound was isolated as a white solid, 57 mg in 96% yield; 1H NMR (400 MHz, DMSO-d6) δ ppm 8.55 (d, J=4.3 Hz, 1H), 7.58 (d, J=8.2 Hz, 1H), 7.38 (t, J=8.2 Hz, 1H), 7.22-7.28 (m, 2H), 5.14 (d, J=8.2 Hz, 1H), 3.86 (t, J=9.2 Hz, 1H), 3.51-3.59 (m, 2H), 3.30-3.41 (m, 3H), 2.35 (br. s., 3H), 1.66 (s, 3H); 13C NMR (100 MHz, DMSO-d6) δ ppm 171.03, 153.33, 149.16, 144.73, 139.81, 129.28, 126.78, 122.69, 118.20, 114.48, 99.68, 75.90, 71.66, 67.62, 60.60, 53.23, 23.32, 18.86; LCMS (ESI): found [M+H]+, 363.3.

Example 58: N-((2S,3R,4R,5R,6R)-4,5-dihydroxy-6-(hydroxymethyl)-2-(isoquinolin-7-yloxy)tetrahydro-2H-pyran-3-yl)acetamide (2002)

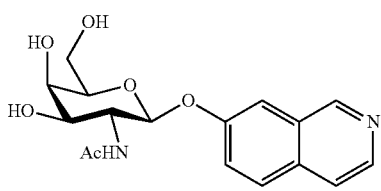

(2002)

Compound was isolated as a white solid, 50 mg in 85% yield; 1H NMR (400 MHz, CD3OD) δ ppm 9.13 (s, 1H), 8.31 (d, J=5.5 Hz, 1H), 7.87 (d, J=8.6 Hz, 1H), 7.75 (d, J=5.5 Hz, 1H), 7.66 (s, 1H), 7.49 (d, J=9.0 Hz, 1H), 5.24 (d, J=8.6 Hz, 1H), 4.29 (t, J=9.6 Hz, 1H), 3.95 (br. s., 1H), 3.75-3.91 (m, 4H), 1.99 (s, 3H); 13C NMR (100 MHz, CD3OD) δ ppm 174.43, 158.08, 152.36, 141.50, 133.87, 131.34, 129.50, 125.70, 122.21, 11.36, 101.15, 77.56, 73.08, 69.82, 62.76, 54.26, 23.16; LCMS (ESI): found [M+H]+, 371.3.

Example 59: N-((2S,3R,4R,5R,6R)-2-(acridin-4-yloxy)-4,5-dihydroxy-6-(hydroxymethyl)tetrahydro-2H-pyran-3-yl)acetamide (2003)

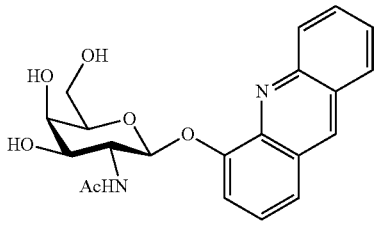

(2003)

Compound was isolated as a yellow solid, 95 mg in 86% yield; 1H NMR (400 MHz, CD3OD) δ ppm 9.90 (br. s., 1H), 8.67 (d, J=8.6 Hz, 1H), 8.50 (d, J=8.6 Hz, 1H), 8.33 (t, J=7.6 Hz, 1H), 8.14 (d, J=8.6 Hz, 1H), 7.93-8.00 (m, 2H), 7.81-7.89 (m, 1H), 5.41 (d, J=8.2 Hz, 1H), 4.54 (t, J=10.2 Hz, 1H), 4.01 (br. s., 1H), 3.78-3.91 (m, 4H), 2.01 (s, 3H); 13C NMR (100 MHz, CD3OD) δ ppm 176.11, 131.33, 129.67, 129.38, 124.31, 120.09, 103.16, 77.72, 72.38, 69.46, 62.66, 54.37, 23.55; LCMS (ESI): found [M+H]+, 399.3.

Example 60: N-((2S,3R,4R,5R,6R)-4,5-dihydroxy-6-(hydroxymethyl)-2-(isoquinolin-6-yloxy)tetrahydro-2H-pyran-3-yl)acetamide (2007)

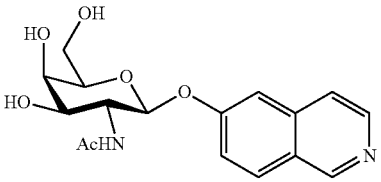

(2007)

Compound was isolated as a white solid, 57 mg in 78% yield; 1H NMR (400 MHz, DMSO-d6) δ ppm 9.18 (s, 1H), 8.41 (d, J=5.9 Hz, 1H), 8.06 (d, J=9.0 Hz, 1H), 7.79 (d, J=9.0 Hz, 1H), 7.69 (d, J=5.5 Hz, 1H), 7.43 (s, 1H), 7.29 (d, J=10.2 Hz, 1H), 5.19 (d, J=8.2 Hz, 1H), 4.80 (d, J=6.3 Hz, 1H), 4.67-4.76 (m, 2H), 4.00-4.12 (m, 1H), 3.77 (br. s., 1H), 3.50-3.69 (m, 4H), 1.80 (s, 3H); 13C NMR (100 MHz, DMSO-d6) δ ppm 169.63, 158.41, 151.62, 143.23, 136.81, 129.61, 124.54, 120.09, 119.74, 108.56, 99.05, 75.80, 71.16, 67.46, 60.35, 51.64, 23.11; LCMS (ESI): found[M+H]+, 371.3.

Example 61: Biochemical Characterization of Substituted Bi-Phenyl Galactosides and Substituted Quionoline and Isoinoline Containing Galactosides The compounds synthesized in Examples 30 to 60 were tested in the ELISA-based competition assay for their ability to inhibit binding of FmlH$_{LD}$ to ds-BSM. The ELISA assay was performed using the protocol described in Example 18. All compounds were tested at 1 μM and a subset was additionally tested at 100 nM. Results are summarized in Table 4. Average percent inhibition (PI) values are reported for compounds tested at 1 μM (PI$_1$) and 100 nM (PI$_{0.1}$).

TABLE 4

Galactoside Inhibition of Fm1H

| Compound Name | Structure | $PI_{(1)}$ | $PI_{(0.1)}$ |
|---|---|---|---|
| AM2003 | 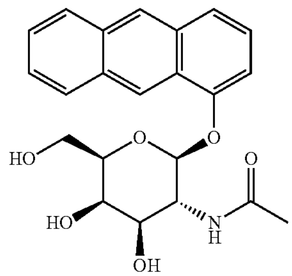 | 15.44 | N/A |
| AM1179 | 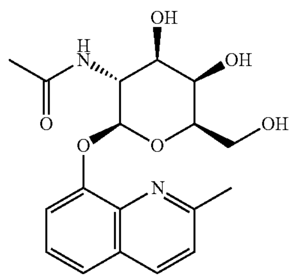 [SMILES: CC(=O)N[C@H]1[C@H](Oc2cccc3ccc(C)nc23)O[C@H](CO)[C@H](O)[C@@H]1O] | 25.22 | N/A |
| AM1192 | 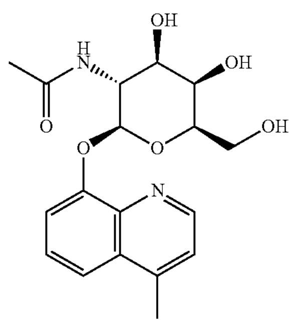 [SMILES: CC(=O)N[C@H]1[C@H](Oc2cccc3c(C)ccnc23)O[C@H](CO)[C@H](O)[C@@H]1O] | 16.83 | N/A |
| AM1176 | 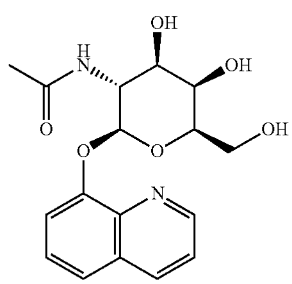 [SMILES: CC(=O)N[C@H]1[C@H](Oc2cccc3cccnc23)O[C@H](CO)[C@H](O)[C@@H]1O] | 20.96 | N/A |
| AM1180 | 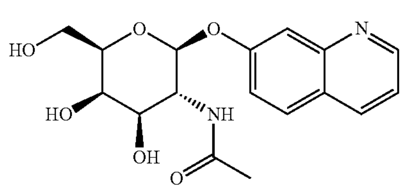 [SMILES: CC(=O)N[C@H]1[C@H](Oc2ccc3cccnc3c2)O[C@H](CO)[C@H](O)[C@@H]1O] | 15.39 | N/A |
| AM1184 | 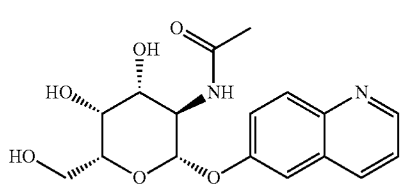 [SMILES: CC(=O)N[C@H]1[C@H](Oc2ccc3ncccc3c2)O[C@H](CO)[C@H](O)[C@@H]1O] | 7.56 | N/A |

TABLE 4-continued

Galactoside Inhibition of Fm1H

| Compound Name | Structure | PI$_{(1)}$ | PI$_{(0.1)}$ |
|---|---|---|---|
| AM2007 | 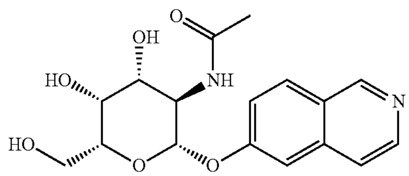 [SMILES: CC(=O)N[C@H]1[C@H](Oc2ccc3cnccc3c2)O[C@H](CO)[C@H](O)[C@@H]1O] | 12.59 | N/A |
| AM1186 | 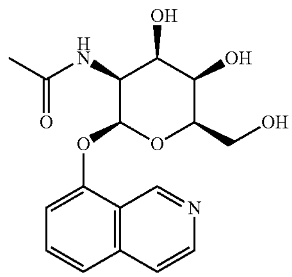 [SMILES: CC(=O)N[C@@H]1[C@H](Oc2cccc3ccncc23)O[C@H](CO)[C@H](O)[C@@H]1O] | 23.51 | N/A |
| AM2002 | 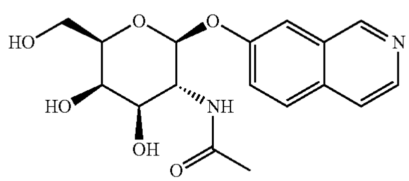 [SMILES: CC(=O)N[C@H]1[C@H](Oc2ccc3ccncc3c2)O[C@H](CO)[C@H](O)[C@@H]1O] | 20.24 | N/A |
| AM1189 | 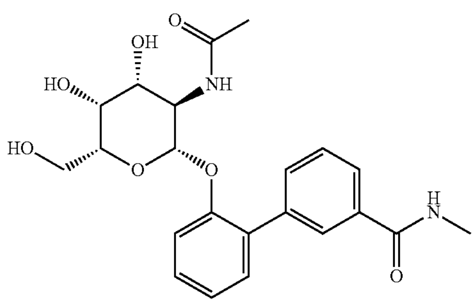 [SMILES: CNC(=O)c1cccc(-c2ccccc2O[C@@H]2O[C@H](CO)[C@H](O)[C@H](O)[C@H]2NC(C)=O)c1] | 12.32 | N/A |
| AM2035 | 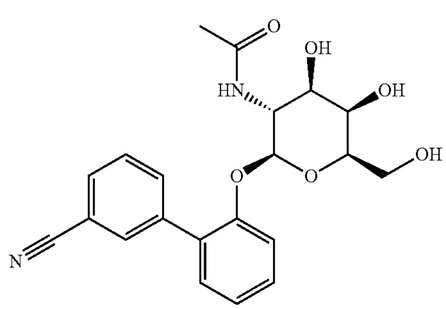 [SMILES: CC(=O)N[C@H]1[C@H](Oc2ccccc2-c2cccc(C#N)c2)O[C@H](CO)[C@H](O)[C@@H]1O] | 20.93 | N/A |
| AM2029 | 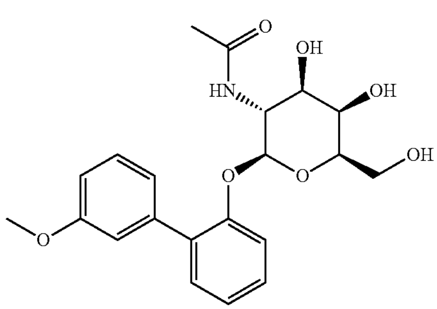 [SMILES: COc1cccc(-c2ccccc2O[C@@H]2O[C@H](CO)[C@H](O)[C@H](O)[C@H]2NC(C)=O)c1] | 15.54 | N/A |

TABLE 4-continued

| Compound Name | Structure | PI$_{(1)}$ | PI$_{(0.1)}$ |
|---|---|---|---|
| AM2028 | 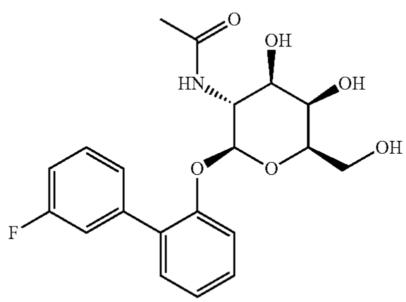 [SMILES: CC(=O)N[C@H]1[C@H](Oc2ccccc2-c2cccc(F)c2)O[C@H](CO)[C@H](O)[C@@H]1O] | 11.76 | N/A |
| AM2037 | 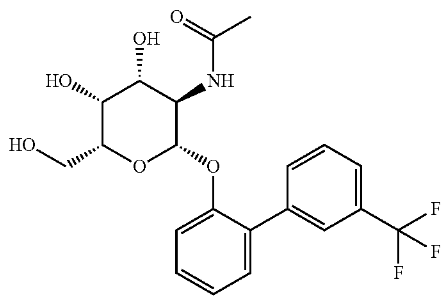 [SMILES: CC(=O)N[C@H]1[C@H](Oc2ccccc2-c2cccc(C(F)(F)F)c2)O[C@H](CO)[C@H](O)[C@@H]1O] | 15.72 | N/A |
| AM2038 | 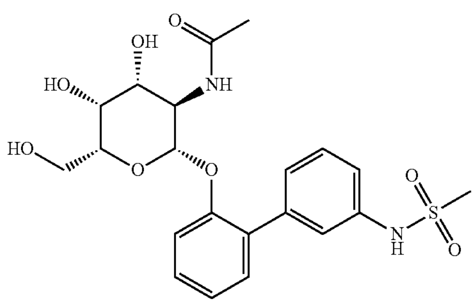 | 81.40 | 16.50 |
| AM2030 | 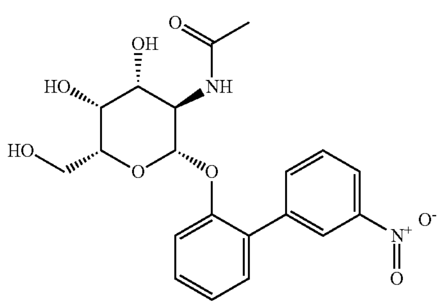 | 9.25 | N/A |
| AM2033 | 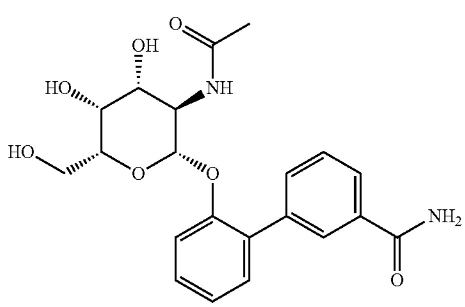 [SMILES: CC(=O)N[C@H]1[C@H](Oc2ccccc2-c2cccc(C(N)=O)c2)O[C@H](CO)[C@H](O)[C@@H]1O] | 3.52 | N/A |

TABLE 4-continued

Galactoside Inhibition of Fm1H

| Compound Name | Structure | PI$_{(1)}$ | PI$_{(0.1)}$ |
|---|---|---|---|
| AM2032 | 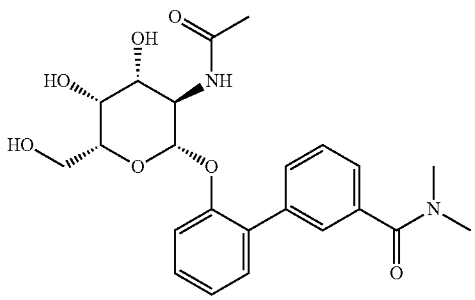 [SMILES: CC(=O)N[C@H]1[C@H](Oc2ccccc2-c2cccc(C(=O)N(C)C)c2)O[C@H](CO)[C@H](O)[C@@H]1O] | −3.61 | N/A |
| AM2021 | 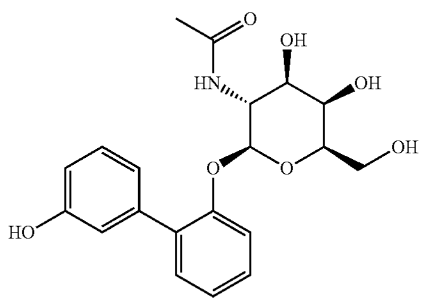 [SMILES: CC(=O)N[C@H]1[C@H](Oc2ccccc2-c2cccc(O)c2)O[C@H](CO)[C@H](O)[C@@H]1O] | 17.71 | N/A |
| AM1181 | 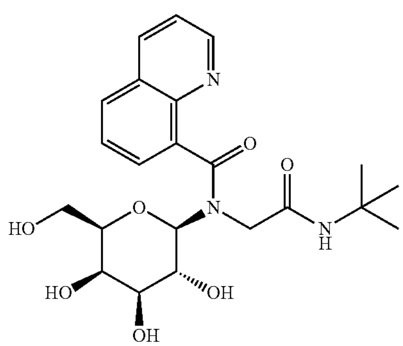 [SMILES: CC(C)(C)NC(=O)CN(C(=O)c1cccc2cccnc12)[C@@H]1O[C@H](CO)[C@H](O)[C@H](O)[C@H]1O] | 10.78 | N/A |
| AM1165 | 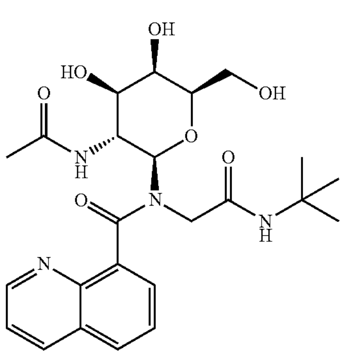 [SMILES: CC(=O)N[C@@H]1[C@@H](O)[C@@H](O)[C@@H](CO)O[C@H]1N(CC(=O)NC(C)(C)C)C(=O)c1cccc2cccnc12] | 5.57 | N/A |

TABLE 4-continued
| Galactoside Inhibition of Fm1H | | | |
|---|---|---|---|
| Compound Name | Structure | PI$_{(1)}$ | PI$_{(0.1)}$ |
| 2051 | 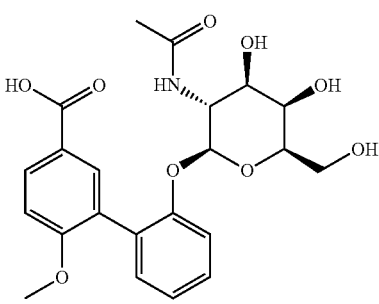 [SMILES: COc1ccc(C(=O)O)cc1-c1ccccc1O[C@@H]1O[C@H](CO)[C@H](O)[C@H](O)[C@H]1NC(C)=O] | 15.90 | 0.00 |
| AM2053 | 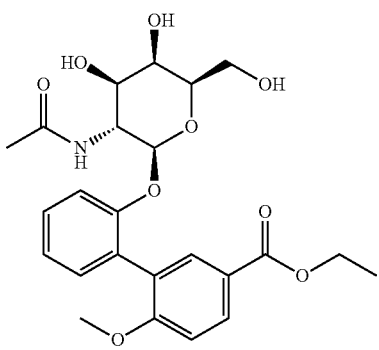 [SMILES: CCOC(=O)c1ccc(OC)c(-c2ccccc2O[C@@H]2O[C@H](CO)[C@H](O)[C@H](O)[C@H]2NC(C)=O)c1] | 13.70 | 0.00 |
| AM2059 | 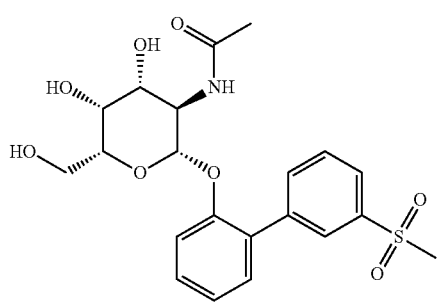 [SMILES: CC(=O)N[C@H]1[C@H](Oc2ccccc2-c2cccc(S(C)(=O)=O)c2)O[C@H](CO)[C@H](O)[C@@H]1O] | 23.30 | 0.10 |
| AM2062 | 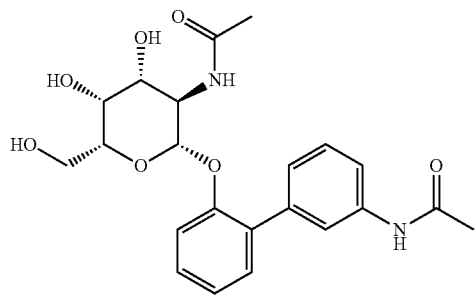 [SMILES: CC(=O)Nc1cccc(-c2ccccc2O[C@@H]2O[C@H](CO)[C@H](O)[C@H](O)[C@H]2NC(C)=O)c1] | 67.90 | 14.80 |

TABLE 4-continued
Galactoside Inhibition of Fm1H
| Compound Name | Structure | PI$_{(1)}$ | PI$_{(0.1)}$ |
|---|---|---|---|
| AM2065 | 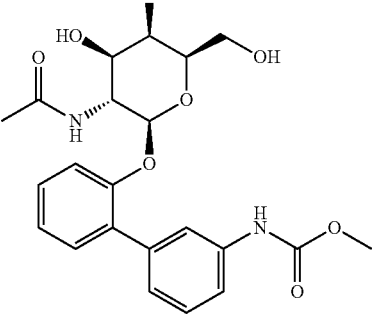 | 45.30 | 0.00 |
| AM2064 | 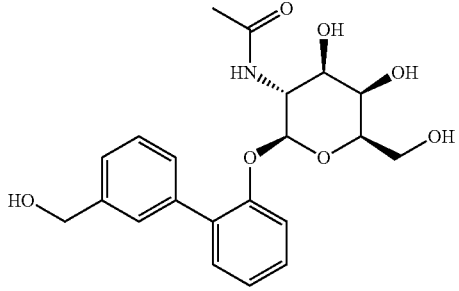 [SMILES: CC(=O)N[C@H]1[C@H](Oc2ccccc2-c2cccc(CO)c2)O[C@H](CO)[C@H](O)[C@@H]1O] | 38.90 | 2.00 |
| AM2078 | 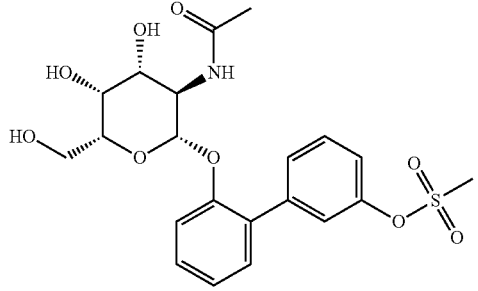 [SMILES: CC(=O)N[C@H]1[C@H](Oc2ccccc2-c2cccc(OS(C)(=O)=O)c2)O[C@H](CO)[C@H](O)[C@@H]1O] | 32.50 | 2.0 |
| AM2073 | 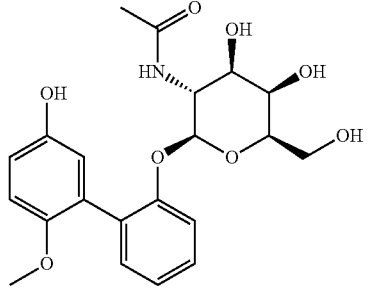 [SMILES: COc1ccc(O)cc1-c1ccccc1O[C@@H]1O[C@H](CO)[C@H](O)[C@H](O)[C@H]1NC(C)=O] | 34.20 | 7.10 |
| AM2077 | 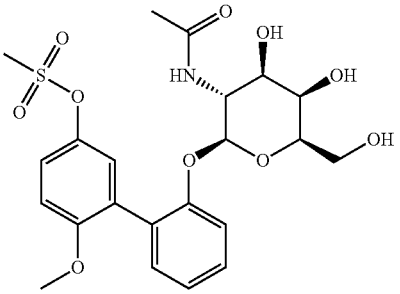 [SMILES: COc1ccc(OS(C)(=O)=O)cc1-c1ccccc1O[C@@H]1O[C@H](CO)[C@H](O)[C@H](O)[C@H]1NC(C)=O] | 0.00 | 2.50 |

TABLE 4-continued

Galactoside Inhibition of Fm1H

| Compound Name | Structure | PI$_{(1)}$ | PI$_{(0.1)}$ |
|---|---|---|---|
| AM2042 | 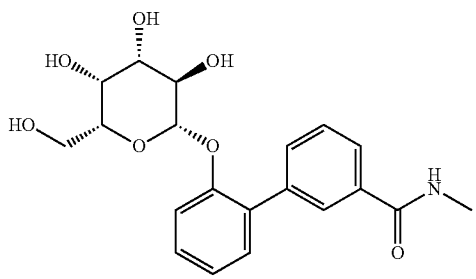 [SMILES: CNC(=O)c1cccc(-c2ccccc2O[C@@H]2O[C@H](CO)[C@H](O)[C@H](O)[C@H]2O)c1] | 16.60 | 0.00 |
| AM2043 | 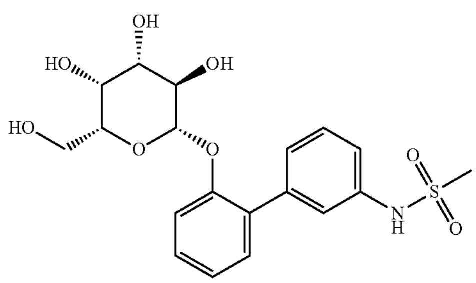 [SMILES: CS(=O)(=O)Nc1cccc(-c2ccccc2O[C@@H]2O[C@H](CO)[C@H](O)[C@H](O)[C@H]2O)c1] | 49.80 | 1.60 |
| AM2049 | 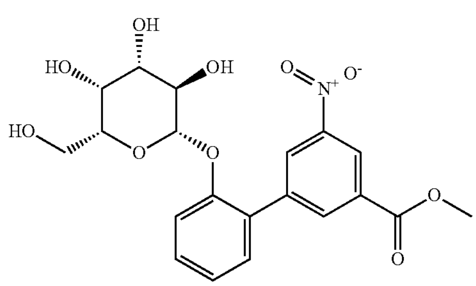 | 0.00 | 0.00 |
| AM2050 | 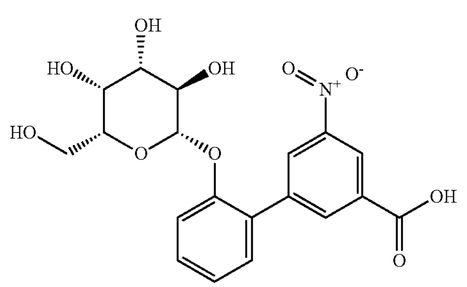 | 68.00 | 7.6 |

Example 62: Synthesis of Additional Substituted Bi-Aryl Galactosides and Bi-Aryl-N-Acetyl Galactosides The synthesis of substituted bi-aryl galactosides and bi-aryl N-acetyl galactosides, compounds 29β-NAc, 2050, 2051, 2021, 2078, 2073, 2077, 2028, 2029, 2030, 2035, 2037, 2059, 2064, 2062, 3044, 2065, 2032, 1189, 2033, 2038, and 2043, was previously described in Example 29 and the chemical identity provided in Examples 30-52. Using the same procedures (which a minor modification to the deacetylation step described below), three new compounds (3029, 3044, and 3049) were synthesized. For ease of reference, the general synthesis scheme for these compounds is depicted in Scheme 1, below. Note that it is identical to the reaction schemes described in Example 29. Briefly, reaction steps "a" and "d" refer to glycosylation Methods A and B, respectively, as described in Example 29. Reaction steps "b" refer to the Suzuki reaction described in Example 29. Reaction step "c" is deacetylation, which was performed using a 33 wt. % methylamine in absolute ethanol solution (for compounds 3044 and 3049), as described in Example 29, or using the following Deacetylation Procedure B (compounds 3029, 2050, 2051).

Deacetylation Procedure B (Compounds 2050, 2051 and 3029)

NaOH (27 mg, 0.66 mmol) was added into a solution of compound 6 (110 mg, 0.066 mmol) in methanol-water (1:1, 5 mL) at room temperature, stirred (15 h) until the TLC indicated complete disappearance of the staring material.

The reaction solution was acidified pH-2 with 3N aqueous HCl and the product was extracted with ethyl acetate (3×10 mL). The organic layers were combined and washed with brine, dried over Na$_2$SO$_4$, and concentrated in vacuo. The resulting residue was subjected for HPLC purification provided compound 3029 and followed the same procedure for compounds 2050, 2051.

Scheme 1.
Synthesis of biphenyl glycoside compounds (3029, 3044, 3049)$^a$.

A.

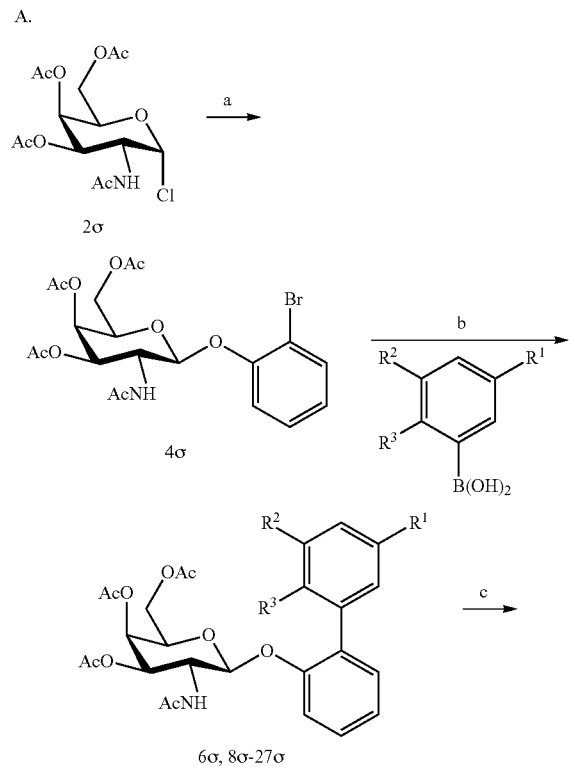

B.

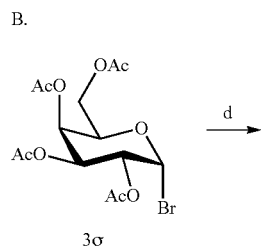

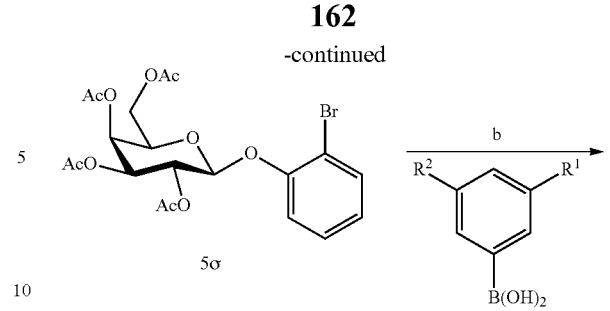

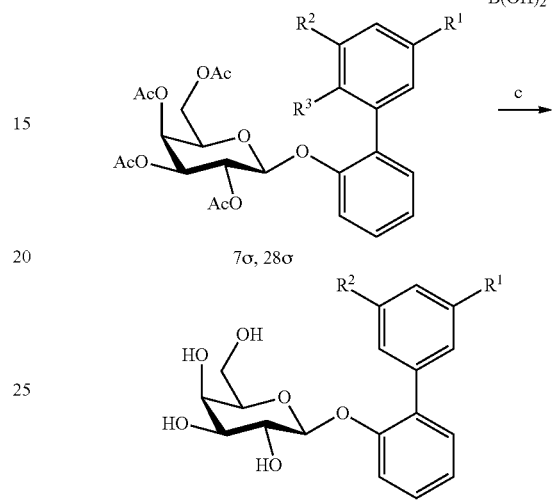

$^a$Reagents and conditions:
(a) DCM, IN NaOH, TBAB, 2-bromophenol, r.t., 1 h;
(b) Pd(PPh$_3$)$_4$, Cs$_2$CO$_3$, 1,4-dioxane/water (5:1), 80° C., 1 h;
(c) NaOH, methanol/water (1:1), r.t., overnight for 3029, 2050, and 2051 or 33% Methylamine in absolute ethanol, r.t., 1 h for 32-51;
(d) CHCl$_3$, IN NaOH, TEBAC, 2-bromophenol, r.t., 1 h. See Examples 62-64 and Table 5 for identity of R$^1$, R$^2$, and R$^3$.

The chemical identity of each new compound (3029, 3044 and 3049) and their spectral properties are described in Examples 63-65.

Example 63: 2'-(((2S,3S,4R,5R)-3-acetamido-4,5-dihydroxy-6-(hydroxymethyl)tetrahydro-2H-pyran-2-yl)oxy)-5-nitro-[1,1'-biphenyl]-3-carboxylic acid (3029)

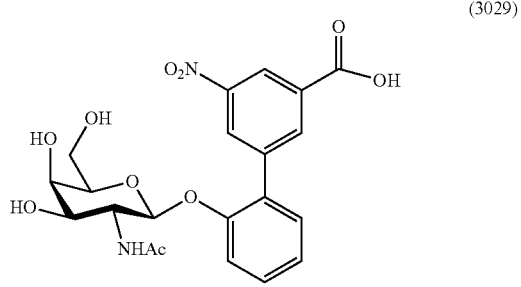

Compound was isolated as a white solid, 30 mg in 98% yield; NMR (400 MHz, CD$_3$OD) δ ppm 8.75 (s, 1H), 8.54 (d, J=1.6 Hz, 1H), 8.41 (d, J=1.6 Hz, 1H), 7.47-7.35 (m, 4H), 7.22-7.14 (m, 1H), 5.08 (d, J=8.2 Hz, 1H), 4.03 (t, J=9.6 Hz, 1H), 3.91-3.74 (m, 3H), 3.73-3.60 (m, 2H), 1.58 (s, 3H); $^{13}$C NMR (100 MHz, CD$_3$OD) δ ppm 173.67, 167.67, 156.07, 149.69, 141.81, 137.16, 133.74, 131.65, 131.54, 129.77, 124.17, 123.83, 117.13, 111.59, 101.67, 77.45, 73.24, 69.78, 62.63, 54.21, 22.69; LCMS (ESI): C$_{21}$H$_{22}$N$_2$O$_{10}$, found [M+Na]$^+$, 485.2.

Example 64: N-(2'-(((2S,3S,4R,5R)-3-acetamido-4,5-dihydroxy-6-(hydroxymethyl)tetrahydro-2H-pyran-2-yl)oxy)-[1,1'-biphenyl]-3-yl)-2,2,2-trifluoroacetamide (3044)

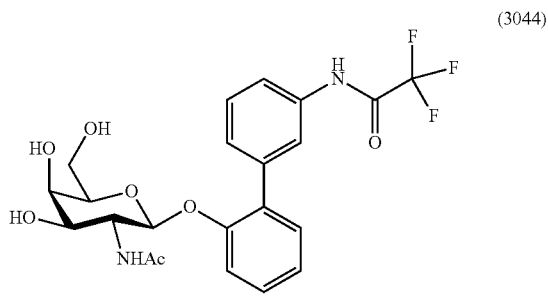

(3044)

Compound was isolated as a white solid, 20 mg in 63% yield; $^1$H NMR (400 MHz, CD$_3$OD) δ ppm 7.70-7.65 (m, 2H), 7.44-7.38 (m, 1H), 7.38-7.31 (m, 4H), 7.13-7.08 (m, 1H), 5.10 (d, J=8.2 Hz, 1H), 4.18 (dd, J=8.6, 10.6 Hz, 1H), 3.89 (d, J=3.1 Hz, 1H), 3.85-3.73 (m, 2H), 3.72-3.61 (m, 2H), 1.72 (s, 3H); $^{13}$C NMR (100 MHz, CD$_3$OD) δ ppm 174.09, 155.88, 140.47, 137.15, 131.80, 130.33, 129.85, 128.45, 124.18, 123.80, 121.26, 116.52, 100.88, 77.31, 73.38, 69.76, 62.59, 54.06, 22.94; LCMS (ESI): C$_{22}$H$_{23}$F$_3$N$_2$O$_7$, found [M+Na]$^+$, 507.4.

Example 65: N-((2S,3R,4R,5R,6R)-4,5-dihydroxy-6-(hydroxymethyl)-2-((3'-((trifluoromethyl) sulfonamido)-[1,1'-biphenyl]-2-yl)oxy)tetrahydro-2H-pyran-3-yl) acetamide (3049)

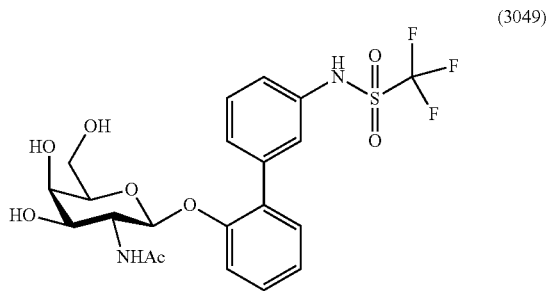

(3049)

Compound was isolated as a white solid, 25 mg in 63% yield; $^1$H NMR (400 MHz, CD$_3$OD) δ ppm 7.70-7.65 (m, 2H), 7.44-7.38 (m, 1H), 7.38-7.31 (m, 4H), 7.13-7.08 (m, 1H), 5.10 (d, J=8.2 Hz, 1H), 4.18 (dd, J=8.6, 10.6 Hz, 1H), 3.89 (d, J=3.1 Hz, 1H), 3.85-3.73 (m, 2H), 3.72-3.61 (m, 2H), 1.72 (s, 3H); $^{13}$C NMR (100 MHz, CD$_3$OD) δ ppm 174.09, 155.88, 140.47, 137.15, 131.80, 130.33, 129.85, 128.45, 124.18, 123.80, 121.26, 116.52, 100.88, 77.31, 73.38, 69.76, 62.59, 54.06, 22.94; LCMS (ESI): C$_{20}$H$_{23}$F$_3$N$_2$O$_8$S, found [M+Na]$^+$, 543.2.

Example 66. Biochemical Analysis of Ortho-Biphenyl Gal and GalNAc Compounds

The ability of the newly synthesized Gal and GalNAc analogs 3029, 3044, and 3049 and previously synthesized compounds 29β-NAc, 2050, 2051, 2021, 2078, 2073, 2077, 2028, 2029, 2030, 2035, 2037, 2059, 2064, 2062, 2065, 2032, 1189, 2033, 2038, and 2043 to inhibit FmlH activity was assessed using a previously described enzyme-linked immunosorbent assay (ELISA) (Example 18). Briefly, 1 μg bovine submaxillary mucin (Sigma) in 100 uL PBS were incubated with Immulon 4HBX 96-well plates overnight prior to treatment with 1 mU *Arthrobacter ureafaciens* sialidase for 1 hour at 37° C. to remove terminal sialic acid sugars. Wells were then blocked with 200 μL PBS+1% BSA for 2 hours at room temperature. Biotinylated FmlH$^{LD}$ was diluted to 20 μg/mL in blocking buffer and incubated in the presence or absence of compounds serially diluted 2× down eight rows for 1 hour at room temperature. Wells were washed three times with PBS 0.05% TWEEN-20 then incubated with 100 μL of streptavidin-HRP conjugate (BD Biosciences; 1:2,000 dilution in blocking buffer) for one hour. After three additional PBS+0.05% TWEEN washes, plates were developed with 100 μL of tetramethylbenzidine (BD Biosciences) substrate and quenched with 50 μL of 1 M H$_2$SO$_4$. Total bound portion concentration was measured by the absorbance at 450 nm. IC50s were determined using the Graphpad Prism software.

This competitive binding assay measures the concentration of compound required to inhibit 50% of binding (IC$_{50}$) to desialylated bovine submaxillary mucin, which contains high levels of Gal and GalNAc epitopes. The resultant IC$_{50}$ values for each compound are shown in Table 5. The majority of compounds (2021, 2078, 2073, 2077, 2028, 2029, 2030, 2035, 2037, 2059, 2064, 2065, 2032, 1189, and 2033) had equal or slightly reduced potency relative parent compound 29β-NAc. It is noteworthy that the ortho-methoxy biphenyl GalNAc carboxylic analog 2051 showed the weakest activity with a 6-fold drop in activity (IC$_{50}$, 3.87 μM) relative to 29β-NAc. This is most likely a result of forced ring twisting of the B-ring due to steric interference from the large ortho substituent. However, changing the carboxylic acid to a smaller phenol in compound 2073 increases the potency (IC$_{50}$, 0.51 μM) back to the level of compound 29β-NAc and is equivalent to the desmethoxy analog 2021. The potency was slightly enhanced when the acid is replaced with a reverse amide as in 2062 (IC$_{50}$, 0.31 μM), but decreases in the normal amide 1189 (IC$_{50}$, 3.36 μM). However, the addition of a reverse methyl sulfonamide 2038 resulted in a 3-fold greater potency than 29β-NAc (IC$_{50}$ 0.23 μM), but as in amide 1189, the methyl sulfonamide derivative 2043 showed a loss in activity relative to 29β-NAc. This SAR suggests that distal placement of an H-bond acceptor (i.e., a carbonyl of the reverse amide or S═O bond of the sulfonamide) provides a greater binding benefit than a H-bond donor, presumably due to improved interactions with the Arg142 and/or Lys132 of FmlH. In general, it was discovered that groups which can accept an H-bond in the meta position of the B-ring show the best activity.

Similarly to the FmlH ligands shown in Example 23 (Table 3) the lead biphenyl GalNAc sulfonamide 2038 is more potent than its matched pair Gal derivative 2043 by about 5-fold. This trend has been demonstrated in all paired analogs hitherto synthesized. However, surprisingly, a reversal of this trend was seen when the potency of compounds 3029 and 2050 were assessed, as the B-ring disubstituted 3-nitro 5-carboxy analog 2050 ($IC_{50}$, 0.28 µM) was 6-fold more active than the corresponding GalNAc version 3029 ($IC_{50}$, 2.20 µM).

TABLE 5

Gal and GalNAc inhibition of FmlH activity.

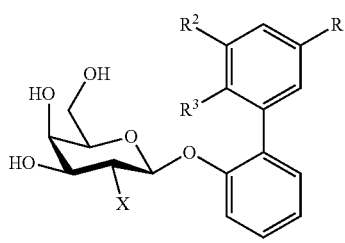

| Compound | $R^1$ | $R^2$ | $R^3$ | X | $IC_{50}$ (µM) |
|---|---|---|---|---|---|
| 29β-NAc | COOH | H | H | NAc | 0.64 |
| 3029 | COOH | $NO_2$ | H | NAc | 2.20 |
| 2050 | COOH | $NO_2$ | H | OH | 0.28 |
| 2051* | COOH | H | OMe | NAc | 3.87 |
| 2021 | OH | H | H | NAc | 0.70 |
| 2078 | $OSO_2Me$ | H | H | NAc | 0.89 |
| 2073* | OH | H | OMe | NAc | 0.51 |
| 2077 | $OSO_2Me$ | H | OMe | NAc | 3.72 |
| 2028 | F | H | H | NAc | 1.48 |
| 2029 | $NO_2$ | H | H | NAc | 2.00 |
| 2030 | $NO_2$ | H | H | NAc | 2.66 |
| 2035 | CN | H | H | NAc | 0.97 |
| 2037 | $CF_3$ | H | H | NAc | 1.51 |
| 2059 | $SO_2Me$ | H | H | NAc | 0.70 |
| 2064 | $CH_2OH$ | H | H | NAc | 0.63 |
| 2062 | NHCOMe | H | H | NAc | 0.31 |
| 3044 | $NHCOCF_3$ | H | H | NAc | 0.37 |
| 2065 | $NHCO_2Me$ | H | H | NAc | 0.63 |
| 2032 | $CON(Me)_2$ | H | H | NAc | 3.13 |
| 1189 | CONHMe | H | H | NAc | 3.36 |
| 2033 | $CONH_2$ | H | H | NAc | 1.65 |
| 3049 | $NHSO_2CF_3$ | H | H | NAc | 1.17 |
| 2038 | $NHSO_2Me$ | H | H | NAc | 0.23 |
| 2043 | $NHSO_2Me$ | H | H | OH | 1.11 |

Example 67. X-Ray Structure Determination of Di-Substituted Biphenyl Gal 2050 and GalNAc 3029 Matched Pairs Bound to the FmlH Lectin Domain To determine the structural basis for the divergent SAR of Gal (2050) versus GalNAc (3029) and attempt to explain the unfavorable effect on binding from the N-acetyl group on GalNAc 3029 potency relative to Gal 2050, co-crystals were obtained and the X-ray structures of both 2050 and 3029 in complex with $FimH^{LD}$ were solved to 1.39 Å and 1.31 Å resolution, respectively (FIG. 11).

FmlH Protein Expression and Purification

FmlH protein used in crystallographic studies was expressed and purified as previously described (Kalas V et al., Structure-based discovery of glycomimetic FmlH ligands as inhibitors of bacterial adhesion during urinary tract infection. PNAS 2018). Briefly, protein was expressed in the periplasm of E. coli C600 cells containing pTRC99a encoding the first 182 amino acids of the CFT073 FmlH protein (corresponding to the signal sequence and lectin domain) and a C-terminal 6x-his tag. Periplasmic isolates prepared as previously described were washed over a cobalt affinity column (GoldBio) and eluted in 20 mM Tris 8.0+250 mM Imidazole. Fractions containing protein of the expected molecular weight were then diluted 5-fold in 20 mM Tris 8.0 to a final concentration of 50 mM Imidazole, washed over an anion exchange column (GE Healthcare Mono Q) with 20 mM Tris 8.0, and eluted in 20 mM Tris 8.0+250 mM NaCl. Resulting fractions were pooled and dialyzed in 1 mM HEPES pH 7.5+50 mM NaCl and concentrated as needed for further study. Note that FmlH protein purified in this way was also used in the ELISA assays described in Example 66 above. Protein used in ELISA assays was biotinylated using anNHS-PEG4-Biotin and Biotinylation Kits (ThermoFisher).

Crystallography Studies

All protein solutions were generated by adding 10 µL 50 mM compound dissolved in 100% DMSO to FmlH in 10 mM HEPES pH 7.5+50 mM NaCl immediately before setting up drops for a final concentration of 9 mg/mL $FmlD^{LD}$, 5 mM compound, and 10% DMSO. Crystals of FmlH-3029 were grown by mixing 1 µL protein solution (9 mM $FmlH^{LD}$, 5 mM compound 3029, 9 mM HEPES pH 7.5, 45 mM NaCl) with 1 µL 0.1 M Tris 8.0+0.8 M $AmSO_4$ using the hanging drop vapor diffusion method. Square pyramidal crystals began appearing after approximately 24 hours and continued to grow for up to seven days. Crystals were harvested after 10 days, cryoprotected in a solution containing 0.1 M Tris 8.0, 0.8 M $AmSO_4$, and 30% glycerol for 10 seconds, and flash-frozen in liquid nitrogen. To generate crystals of FmlH-2050, drops containing 9 mg/mL FmlH, 2.5 mM 2050, 10% DSMO, 0.1 M Tris 8.0 and 0.8 M $AmSO_4$ were allowed to equilibrate over a 1M well solution of 0.1 M Tris 8.0+0.8 M $AmSO_4$ for two days FmlH-2050 co-crystals were then transferred the pre-equilibrated drops and allowed to soak for 48 hours before cryoprotection in 0.1 M Tris 8.0, 0.8 M $AmSO_4$, and 30% and flash-freezing in liquid nitrogen.

All data were collected on ALS Beamline 4.2.2 at an X-ray wavelength of 1.00 Å. Raw data were processed using XDS, Aimless, and Pointless (14, 15). The phase problem was solved using Phaser-MR in the Phenix suite using the apo $FmlH_{LD}$ structure (PDBID: 6AOW) as a search model (16). Iterative rounds of Phenix. Refine and Coot were used to refine the final model. Guided ligand replacement was performed using Phenix.

Surprisingly, it was found that the nitro group on the biphenyl B-ring, and not the carboxylic acid as previously observed, was bound in the pocket with R142. This contrasts with the FmlH co-crystal structure of 29β-NAc, in which the carboxylic acid occupies that pocket (FIGS. 7, 12 and 14). In both the 3029 and 2050 structures, the nitro oxygens on the second phenyl ring (B) form two interactions with R142, while the carboxyl oxygens of the carboxylic acid group interact with S2 on the N terminus and the backbone of I11 and G12 in loop 1. In compound 3029, one nitro oxygen resides within 3.2 Å of the acetamide carbonyl, causing the second phenyl ring to tilt 45° relative to the plane of the first phenyl ring. In contrast, the angular offset between the plane of the two rings is 32.5° in 2050 altering the position of the carboxylic acid oxygens and attenuating their interaction with loop 1 residues I11 and G12.

Example 68. Synthesis of Compounds with Additional Substitution of Reverse Methyl Sulfonamide Scaffold to Increase Galactoside Potency In an effort to further improve the potency of lead compound 2038, a series of additional rationally-directed modifications were explored. These include substitutions at the meta ($R^4$) and para ($R^5$)-positions of the biphenyl ring A while keeping the meta-substituted methyl sulfonamide B ring constant (3078-3085, 3090; Table 6). Also evaluated were different sulfonamides as in 3086-3087 and N-substitutions on the GalNAc ring including 3088 and 3089. This focused library of substituted biphenyl sulfonamide analogs (3086-3087) were synthesized as outlined in Scheme 2 and the N-substituted galactosamine derivatives 3088-3089 in Scheme 3. Compounds 3078-3085 and 3090 were synthesized following a similar reaction sequence as described in Scheme 1 (Examples 29 and 62). However, sulfonamide analogs 3086 and 3087 were prepared via sulfonylation of intermediate aniline 726. As shown in Scheme 3, GalNAc derivatives 3088 and 3089 were generated first by Koenig-Knorr type glycosylation reaction[28] between 3,4,6-tri-O-acetyl-2-amino-2-deoxy-α-D-galactopynosyl bromide·HBr[29] (52σ) and sodium 2-bromo-3-methylphenolate[30] (53σ) to give bromide intermediate 62σ. Derivatization with trifluoroacetic acid anhydride or methanesulfonyl chloride yielded N-substituted galactosamine intermediates 75σ and 76σ. Subsequent Suzuki cross-coupling reaction with (3-(methylsulfonamido)phenyl)boronic acid followed by treatment with 33% Methylamine in absolute ethanol provided the target compounds 3088 and 3089.

Reaction schemes 2 and 3 are illustrated here and specific details are described in the following Example 68.

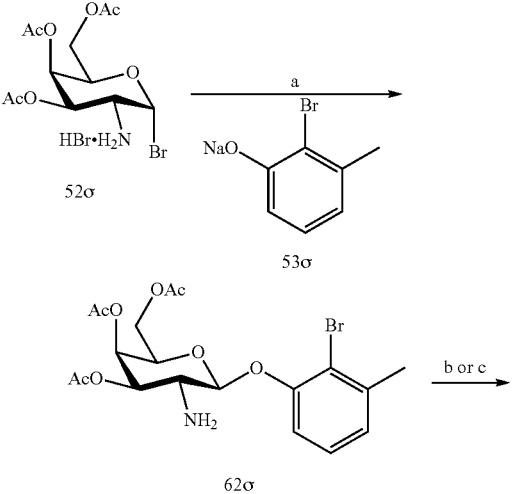

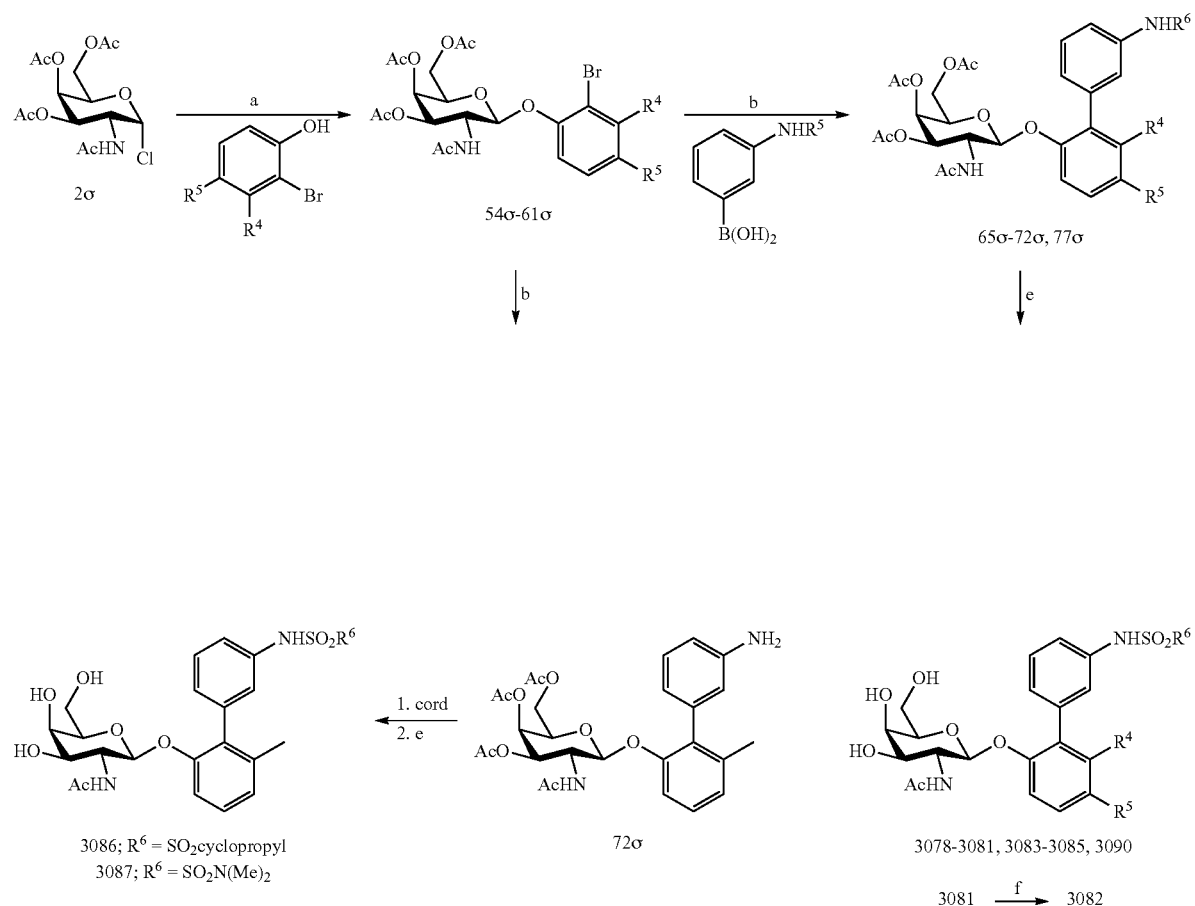

[a]Reagents and conditions: (a) DCM, 1N NaOH, TBAB, r.t., 1 h; (b) Pd(PPh3)4, CsCO3, 1,4-dioxane/water (5:1), 80° C., 1 h; (c) DCM, Cyclopropanesulfonyl chloride/TEA, r.t., 2 h, (d) DMF, N,N-Dimethylsulfonyl Chloride/Cs2CO3, MW, 80° C., 2 h (e) 33% Methylamine in absolute ethanol, r.t., 1 h; (f) NaOH, methanol/water (1:1), r.t., overnight.

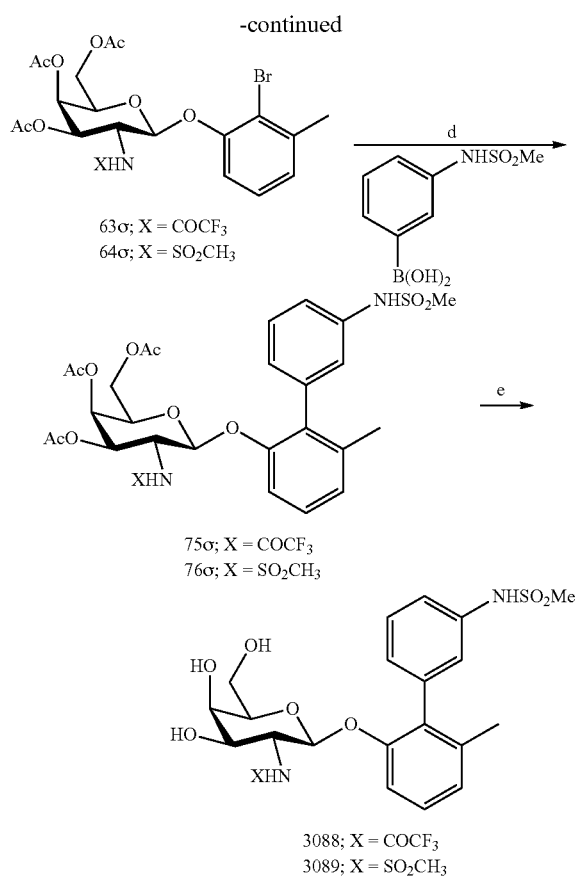

63σ; X = COCF₃
64σ; X = SO₂CH₃

75σ; X = COCF₃
76σ; X = SO₂CH₃

3088; X = COCF₃
3089; X = SO₂CH₃

ᵃReagents and conditions: (a) ACN, 80° C., 2 h; (b) DCM, (CF₃CO)₂/TEA, r.t., 1 h; (c) DCM, MsCl/TEA, r.t., 3 h; (d) Pd(PPh₃)₄, Cs₂CO₃, 1,4-dioxane/water (5:1), 80° C., 1 h,; (e) 33% Methylamine in absolute ethanol, r.t., 1 h.

Example 69. Synthesis of Biphenyl Glycosides Evaluating A-Ring Substitution, B-Ring Sulfonamides and N-Substitution of GalNAc Ring As described above in Example 68, new compounds 3078-3085 and 3090 were synthesized following a similar procedure to Example 29. Compounds 3086-3089 were each synthesized using newer protocols described in Schemes 2 and 3. However, for ease of reference, all synthesis procedures are described herein below (including those previously described in Example 29 which are represented in Scheme 1 and 2, steps (a), (b), and (e)). In general, the reactions performed were classified as "glycosylation", Suzuki, or deacetylation reactions.

General Materials and Methods

Starting materials, reagents, and solvents were purchased from commercial vendors unless otherwise noted. In general, anhydrous solvents are used for carrying out all reactions. ¹H and ¹³C NMR spectra were measured on a Varian 400 MHz and 100 MHz NMR spectrometers. The chemical shifts were reported as δ ppm relative to TMS using residual solvent peak as the reference unless otherwise noted. The following abbreviations were used to express the peak multiplicities: s=singlet; d=doublet; t=triplet; q=quartet; m=multiplet; br=broad. High-performance liquid chromatography (HPLC) was carried out on GILSON GX-281 using Waters C18 5 µM, 4.6*50 mm and Waters Prep C18 5 µM, 19*150 mm reverse phase columns, eluted with a gradient system of 5:95 to 95:5 acetonitrile:water with a buffer consisting of 0.05-0.1% TFA. Mass spectroscopy (MS) was performed on HPLC/MSD using a gradient system of 5:95 to 95:5 acetonitrile:water with a buffer consisting of 0.05-0.1% TFA on a C18 or C8 reversed phased column and electrospray ionization (ESI) for detection. All reactions were monitored by thin layer chromatography (TLC) carried out on either Merck silica gel plates (0.25 mm thick, 60F254) and visualized by using UV (254 nm) or dyes such as 5% H₂SO₄ in ethanol. Silica gel chromatography was carried out on a Teledyne ISCO CombiFlash purification system using pre-packed silica gel columns (4 g to 80 g sizes). All compounds used for biological assays are greater than 95% purity based on NMR and HPLC by absorbance at 220 nm and 254 nm wavelengths.

Glycosylation Reactions

Method A (corresponding to step "a" in Scheme 2). Synthesis of (2R,3R,4R,5R,6S)-5-acetamido-2-(acetoxymethyl)-6-(2-bromophenoxy)tetrahydro-2H-pyran-3,4-diyl diacetate (46). 1N aqueous NaOH solution (1 mL) was added into a solution of 2-Acetamido-3,4,6,-tri-O-acetyl-1-chloro-1,2-dideoxy-α-D-galactopyranose 2²⁶ (100 mg, 0.273 mmol), tetrabutylammonium bromide (88 mg, 0.273 mmol) and 2-bromo phenol (79 mg, 0.546 mmol) in dichloromethane (2 mL) at room temperature. Stir the reaction solution at the same temperature until the TLC indicates complete disappearance of chloride. Dilute the reaction mass with dichloromethane (10 mL) and washed with water followed by brine. The organic layer was collected, dried over Na₂SO₄ and concentrated undervacuo. The resulting residue was purified by silica gel chromatography with hexane/ethyl acetate (2:3) combinations as eluent, giving rise to the compound 4σ and followed the same procedure for compounds 54σ-61σ (Note: Analytical data in SI)

Method B (step "a" in Scheme 1 only; not used in Schemes 2 or 3). (2R,3S,4S,5R,6S)-2-(acetoxymethyl)-6-(2-bromophenoxy)tetrahydro-2H-pyran-3,4,5-triyl triacetate (5σ). 1N aqueous NaOH solution (1 mL) was added into a solution of (2R,3S,4S,5R,6R)-2-(acetoxymethyl)-6-bromotetrahydro-2H-pyran-3,4,5-triyl triacetate 36 (200 mg, 0.487 mmol), benzyltriethylammonium chloride (111 mg, 0.0.487 mmol) and 2-bromo phenol (79 mg, 0.975 mmol) in chloroform (2 mL) at room temperature. Stir the reaction solution at 60° C. temperature until the TLC indicates complete disappearance of starting material. Cool the reaction solution and dilute with the dichloromethane (10 mL) and washed with water followed by brine. The organic layer was collected, dried over Na₂SO₄ and concentrated under vacuo. The resulting residue was purified by silica gel chromatography with hexane/ethyl acetate combinations as eluent, giving rise to the desired compound 5σ (Note: Analytical data in SI)

Method C corresponds to Scheme 3 and is divided into three steps (procedures 1-3) to result in the production of compounds 63σ and 64σ which are used to generate 3088 and 3089 using the Suzuki reaction and deacetylation procedures described below.

Procedure 1. Synthesis of (2R,3R,4R,5R,6S)-2-(acetoxymethyl)-5-amino-6-(2-bromo-3-methylphenoxy)tetrahydro-2H-pyran-3,4-diyl diacetate (62σ). Stir the solution of 3,4,6-Tri-O-acetyl-2-amino-2-deoxy-α-D-galactopyranosyl bromide·HBr, 52σ (550 mg, 1.363 mmol) and sodium 2-bromo-3-methyl phenol 53σ (570 mg, 2.726 mmol) in acetonitrile (40 mL) at room temperature for 24 h. Evaporate the solvent under reduced pressure, residue was diluted with DCM (50 mL) and washed with Sat.NaHCO₃ and brine. The organic layer was collected, dried over Na₂SO₄ and concentrated under vacuo and the resulting residue was purified by silica gel chromatography with hexane/ethyl acetate (2:3) provides the compound 62σ (Note: Analytical data in SI)

Procedure 2. Synthesis of (2R,3R,4R,5R,6S)-2-(acetoxymethyl)-6-(2-bromo-3-methylphenoxy)-5-(methylsulfonamido)tetrahydro-2H-pyran-3,4-diyl diacetate (63a). Trifluoroacetic anhydride (0.22 mL, 1.581 mmol) was added into a solution of (2R,3R,4R,5R,6S)-2-(acetoxymethyl)-5-amino-6-(2-bromo-3-methylphenoxy)tetrahydro-2H-pyran-3,4-diyl diacetate 62σ (250 mg, 0.527 mmol) and triethylamine (0.22 mL, 1.581 mmol) in dichloromethane (1 mL), stirred the solution at room temperature for 15 h. Dilute the reaction mass with dichloromethane (10 mL) and washed with Sat. NaHCO₃ (5 mL) followed by brine (5 mL). The organic layer was collected, dried over Na₂SO₄ and concentrated under vacuo. The resulting residue was purified by silica gel chromatography with hexane/ethyl acetate (2:3) combinations as eluent, giving rise to the compound 63σ (Note: Analytical data in SI).

Procedure 3. Synthesis of (2R,3R,4R,5R,6S)-2-(acetoxymethyl)-6-(2-bromo-3-methylphenoxy)-5-(methylsulfonamido)tetrahydro-2H-pyran-3,4-diyl diacetate (64σ). Methane sulfonyl chloride (119 mg, 1.038 mmol) was added into a solution of (2R,3R,4R,5R,6S)-2-(acetoxymethyl)-5-amino-6-(2-bromo-3-methylphenoxy)tetrahydro-2H-pyran-3,4-diyl diacetate 62σ (246 mg, 0.519 mmol) and triethylamine (0.22 mL, 1.556 mmol) in dichloromethane (1 mL), stirred the solution at room temperature for 1 h. Dilute the reaction mass with dichloromethane (10 mL) and washed with Sat.NaHCO₃ (5 mL) followed by brine (5 mL). The organic layer was collected, dried over Na₂SO₄ and concentrated under vacuo. The resulting residue was purified by silica gel chromatography with hexane/ethyl acetate (2:3) combinations as eluent, giving rise to the compound 646 (Note: Analytical data in SI).

Suzuki Reactions

The synthesis of compounds 3078-3085 and 3088-3090 used a Suzuki reaction procedure described in Example 29 (and here referred to as Procedure 1). The Suzuki reactions used in the synthesis of intermediates of 3086 (73σ) and 3087 (74σ) are described in Procedures 2 and 3, respectively.

Procedure 1. Under nitrogen atmosphere charge (2R,3R,4R,5R,6S)-5-acetamido-2-(acetoxymethyl)-6-(2-bromophenoxy) tetrahydro-2H-pyran-3,4-diyl diacetate (100 mg, 0.199 mmol), 3 (N-methyl amino carbonyl) phenyl boronic acid (78 mg, 0.298 mmol), Pd(PPh₃)₄ (23 mg, 0.0199 mmol) and Cesium carbonate (211 mg, 0.597 mmol) in reaction vial and add nitrogen gas bobbled 1,4-dioxane/water mixture (5:1, 3.6 mL) was added, heated the reaction solution to 80° C. Stir the reaction mixture at 80° C. until TLC indicates complete disappearance of staring material (1 h). Cool the reaction solution to RT and dilute with the dichloromethane (10 mL) and washed with water followed by brine. The organic layer was collected, dried over Na₂SO₄ and concentrated undervacuo. The resulting residue was purified by column chromatography with hexane/ethyl acetate (1:3) combinations as eluent, giving rise to the desired products 66-28σ (Scheme 1), 656-72σ (Scheme 2) and 756-77σ (Scheme 3)(Note: Analytical data in SI)

Procedure 2. Synthesis of (2R,3R,4R,5R,6S)-5-acetamido-2-(acetoxymethyl)-6-((3'-(cyclopropanesulfonamido)-6-methyl-[1,1'-biphenyl]-2-yl)oxy)tetrahydro-2H-pyran-3,4-diyl diacetate (73σ, acetylated form of 3086)). Cyclopropanesulfonyl chloride (54 mg, 0.189 mmol) was added into a solution of amine 72σ (100 mg, 0.378 mmol) and triethyl amine (0.08 mL, 0.567 mmol) in DCM (2.5 mL) at room temperature, stirred solution for 2 h. Dilute with the dichloromethane (10 mL) and washed with water followed by brine. The organic layer was collected, dried over Na₂SO₄ and concentrated under vacuo. The resulting residue was purified by column chromatography with hexane/ethyl acetate (3:2) giving rise to the desired products 736, acetylated form of 3086. (Note: Analytical data in SI).

Procedure 3. Synthesis of (2R,3R,4R,5R,6S)-5-acetamido-2-(acetoxymethyl)-6-((3'-((N,N-dimethylsulfamoyl)amino)-6-methyl-[1,1'-biphenyl]-2-yl)oxy)tetrahydro-2H-pyran-3,4-diyl diacetate (74σ, acetylated form of 3087). N,N-Dimethylsulfonyl chloride (54 mg, 0.189 mmol) was added into a solution of amine 72σ (100 mg, 0.378 mmol) and triethylamine (0.08 mL, 0.567 mmol) in DMF (2.5 mL) mixed in, stirred under microwaves at 80° C. for 2 h. Cool the reaction solution to RT and dilute with the dichloromethane (10 mL) and washed with water followed by brine. The organic layer was collected, dried over Na₂SO₄ and concentrated under vacuo. The resulting residue was purified by column chromatography with hexane/ethyl acetate (4:1) combinations as eluent, giving rise to the desired products 74σ (acetylated form of 3087). (Note: Analytical data in SI).

Deacetylation Reactions

Procedure 1. Synthesis of Compounds (3029). NaOH (27 mg, 0.66 mmol) was added into a solution of compound 6σ (110 mg, 0.066 mmol) in methanol-water (1:1, 5 mL) at room temperature, stirred (15 h) until the TLC indicated complete disappearance of the staring material. The reaction solution was acidified pH~2 with 3N aqueous HCl and the product was extracted with ethyl acetate (3×10 mL). The organic layers were combined and washed with brine, dried over Na₂SO₄, and concentrated in vacuo. The resulting residue was subjected for HPLC purification provided compound 3029 and followed the same procedure for compounds 2050, 2051 and 3082.

Procedure 2. Excess amount of 33% Wt. methylamine in absolute ethanol solution (5 mL) was added into (2R,3R,4R,5R,6S)-5-acetamido-2-(acetoxymethyl)-6-((3'-hydroxy-[1,1'-biphenyl]-2-yl)oxy)tetrahydro-2H-pyran-3,4-diyl diacetate (50 mg, 0.097 mmol). Stir the reaction solution at the same temperature (0.5-1 h) until TLC indicates complete disappearance of staring material. Complete evaporation of the solvent provides the desired product compound 2021, which was subjected for HPLC purification and followed the same procedure for compounds 2078, 2073, 2077, 2028, 2029, 2030, 2035, 2037, 2059, 2064, 2062, 3044, 2065, 2032, 1189, 2033, 3049, 2038, and 2043 (described in Examples 30-60 and Example 62), 3078-3081 and 3083-3090.

Example 70. N-((2S,3R,4R,5R,6R)-4,5-dihydroxy-6-(hydroxymethyl)-2-((3'-(methylsulfonamido)-6-nitro-[1,1'-biphenyl]-2-yl)oxy)tetrahydro-2H-pyran-3-yl)acetamide (3078)

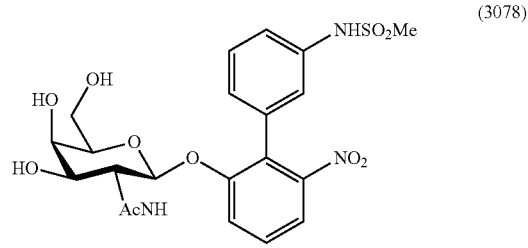

(3078)

Compound was isolated as a white solid, 30 mg in 94% yield; ¹H NMR (400 MHz, CD₃OD) δ ppm 7.63-7.58 (m, 1H), 7.57-7.49 (m, 3H), 7.39-7.33 (m, 1H), 7.23 (d, J=8.2 Hz, 1H), 7.16 (s, 1H), 6.98 (d, J=7.4 Hz, 1H), 5.11 (d, J=8.6 Hz, 1H), 3.97 (t, J=9.6 Hz, 1H), 3.87 (d, J=2.4 Hz, 1H), 3.85-3.73 (m, 2H), 3.73-3.67 (m, 1H), 3.63 (dd, J=2.4, 10.6 Hz, 1H), 3.00 (s, 3H), 1.78 (s, 3H); ¹³C NMR (100 MHz, CD₃OD) δ ppm 173.81, 156.82, 152.49, 139.54, 135.32, 130.82, 130.48, 126.29, 121.27, 120.33, 118.20, 101.19, 77.60, 73.35, 69.74, 62.63, 53.92, 39.34, 23.16; LCMS (ESI): $C_{21}H_{25}N_3O_{10}S$, found [M+H]⁺, 512.3.

Example 71. N-((2S,3S,4R,5R)-2-((6-cyano-3'-(methylsulfonamido)-[1,1'-biphenyl]-2-yl)oxy)-4,5-dihydroxy-6-(hydroxymethyl)tetrahydro-2H-pyran-3-yl)acetamide (3079)

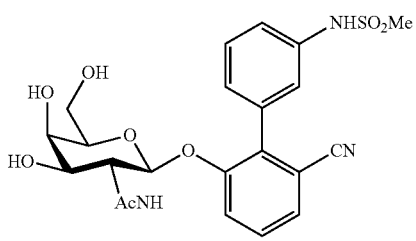

(3079)

Compound was isolated as a white solid, 25 mg in 88% yield; ¹H NMR (400 MHz, CD₃OD) δ ppm 7.64 (dd, J=2.9, 6.46 Hz, 1H), 7.53-7.47 (m, 2H), 7.45-7.39 (m, 1H), 7.34-7.26 (m, 2H), 7.14 (d, J=7.4 Hz, 1H), 5.09 (d, J=8.6 Hz, 1H), 4.03-3.96 (m, 1H), 3.87 (d, J=2.7 Hz, 1H), 3.83-3.73 (m, 2H), 3.72-3.66 (m, 1H), 3.65-3.60 (m, 1H), 3.05 (s, 3H), 1.78 (s, 3H); ¹³C NMR (100 MHz, CD₃OD) δ ppm 173.83, 156.43, 139.53, 136.87, 135.97, 131.11, 130.50, 128.08, 127.49, 121.62, 119.11, 114.82, 101.08, 77.57, 73.29, 69.74, 62.63, 53.95, 39.60, 23.11; LCMS (ESI): $C_{22}H_{25}N_3O_8S$, found [M+Na]⁺, 514.2.

Example 72. N-((2S,3R,4R,5R,6R)-2-((6-fluoro-3'-(methylsulfonamido)-[1,1'-biphenyl]-2-yl)oxy)-4,5-dihydroxy-6-(hydroxymethyl)tetrahydro-2H-pyran-3-yl)acetamide (3080)

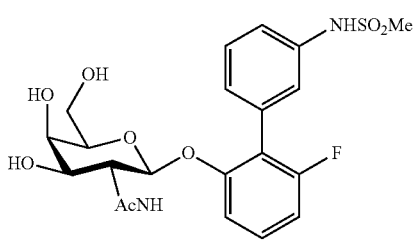

(3080)

Compound was isolated as a white solid, 7 mg in 59% yield; ¹H NMR (400 MHz, CD₃OD) δ ppm 7.40-7.28 (m, 2H), 7.25 (br. s., 2H), 7.14 (dd, J=8.0, 12.3 Hz, 2H), 6.88 (t, J=9.0 Hz, 1H), 5.10 (d, J=8.2 Hz, 1H), 4.00 (t, J=9.6 Hz, 1H), 3.87 (d, J=2.4 Hz, 1H), 3.84-3.73 (m, 2H), 3.71-3.60 (m, 2H), 3.03 (s, 3H), 1.77 (s, 3H); ¹³C NMR (100 MHz, CD₃OD) δ ppm 173.91, 139.12, 133.95, 130.61, 130.01, 128.28, 124.36, 121.10, 112.25, 110.79, 110.56, 101.05, 77.42, 73.40, 69.74, 62.59, 54.09, 39.50, 23.11; LCMS (ESI): $C_{21}H_{25}FN_2O_8S$, found [M+H]⁺, 485.3.

Example 73. Benzyl 6-(((2S,3S,4R,5R)-3-acetamido-4,5-dihydroxy-6-(hydroxymethyl)tetrahydro-2H-pyran-2-yl)oxy)-3'-(methylsulfonamido)-[1,1'-biphenyl]-2-carboxylate (3081)

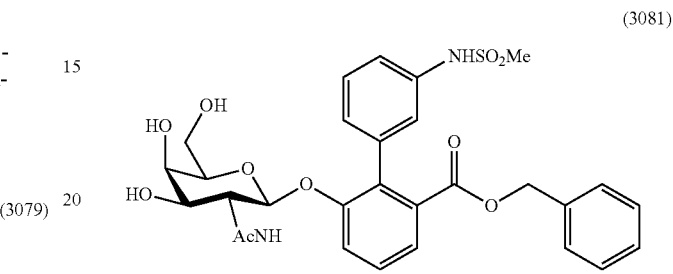

(3081)

Compound was isolated as a white solid, 37 mg in 90% yield; ¹H NMR (400 MHz, CD₃OD) δ ppm 7.52-7.45 (m, 1H), 7.45-7.40 (m, 2H), 7.30-7.23 (m, 3H), 7.18-7.10 (m, 2H), 7.06-7.00 (m, 2H), 6.94 (d, J=8.2 Hz, 1H), 5.06 (d, J=8.2 Hz, 1H), 5.00 (s, 2H), 4.01-3.93 (m, 1H), 3.85 (d, J=2.7 Hz, 1H), 3.84-3.71 (m, 2H), 3.70-3.64 (m, 1H), 3.60 (dd, J=3.1, 10.6 Hz, 1H), 2.90 (s, 3H), 1.76 (s, 3H); ¹³C NMR (100 MHz, CD₃OD) δ ppm 170.06, 156.30, 139.07, 138.98, 134.93, 131.98, 130.13, 129.62, 129.30, 124.27, 123.41, 120.80, 119.40, 101.05, 77.43, 73.54, 69.75, 68.27, 62.62, 54.02, 39.46, 23.15; LCMS (ESI): $C_{29}H_{32}N_2O_{10}S$, found [M+H]⁺, 601.3.

Example 74. 6-(((2S,3S,4R,5R)-3-acetamido-4,5-dihydroxy-6-(hydroxymethyl)tetrahydro-2H-pyran-2-yl)oxy)-3'-(methylsulfonamido)-[1,1'-biphenyl]-2-carboxylic acid (3082)

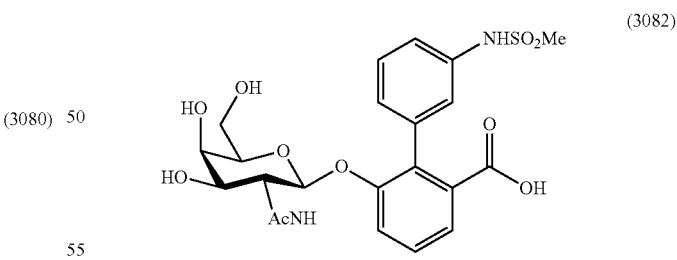

(3082)

Compound was isolated as a white solid, 22 mg in 92% yield; H NMR (400 MHz, CD₃OD) δ ppm 7.49-7.37 (m, 3H), 7.33-7.27 (m, 1H), 7.19-7.13 (m, 2H), 7.00 (d, J=7.4 Hz, 1H), 5.06 (d, J=8.6 Hz, 1H), 4.00-3.91 (m, 1H), 3.86 (d, J=2.7 Hz, 1H), 3.83-3.72 (m, 2H), 3.71-3.65 (m, 1H), 3.61 (dd, J=3.1, 10.6 Hz, 1H), 2.99 (s, 3H), 1.78 (s, 3H); ¹³C NMR (100 MHz, CD3OD) δ ppm 173.87, 171.76, 156.34, 139.18, 138.89, 135.62, 132.08, 129.79, 124.11, 120.69, 119.15, 101.09, 77.41, 73.55, 69.77, 62.63, 54.07, 39.29, 23.18; LCMS (ESI): $C_{22}H_{26}N_2O_{10}S$, found [M+H]⁺, 511.2

Example 75. N-((2S,3S,4R,5R)-4,5-dihydroxy-6-(hydroxymethyl)-2-((6-methoxy-3'-(methylsulfonamido)-[1,1'-biphenyl]-2-yl)oxy)tetrahydro-2H-pyran-3-yl)acetamide (3083)

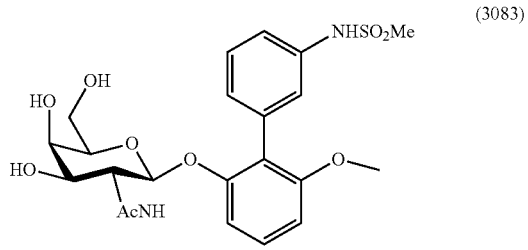

(3083)

Compound was isolated as a white solid, 13 mg in 93% yield; $^1$H NMR (400 MHz, CD$_3$OD) δ ppm 7.28 (q, J=8.4 Hz, 2H), 7.18-7.14 (m, 2H), 7.04 (d, J=7.8 Hz, 1H), 6.95 (d, J=8.6 Hz, 1H), 6.77 (d, J=8.2 Hz, 1H), 5.06 (d, J=8.6 Hz, 1H), 3.93 (dd, J=8.6, 10.6 Hz, 1H), 3.86 (d, J=3.1 Hz, 1H), 3.82-3.73 (m, 2H), 3.71 (s, 3H), 3.68-3.59 (m, 2H), 3.02 (s, 3H), 1.78 (s, 3H); $^{13}$C NMR (100 MHz, CD$_3$OD) δ ppm 173.90, 159.07, 156.88, 138.65, 136.71, 130.33, 129.54, 128.81, 124.94, 120.47, 109.18, 106.85, 100.95, 77.27, 73.56, 69.75, 62.58, 56.49, 54.21, 39.35, 23.16; LCMS (ESI): C$_{22}$H$_{28}$N$_2$O$_9$S, found [M+Na]$^+$, 519.3.

Example 76. N-((2S,3R,4R,5R,6R)-4,5-dihydroxy-6-(hydroxymethyl)-2-((6-methyl-3'-(methylsulfonamido)-[1,1'-biphenyl]-2-yl)oxy)tetrahydro-2H-pyran-3-yl)acetamide (3084)

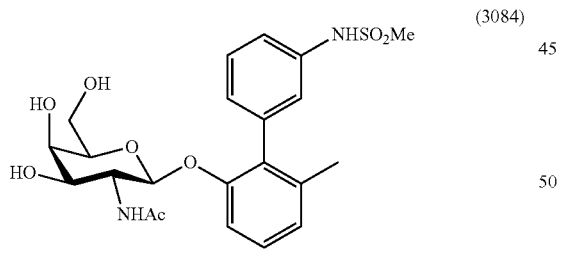

(3084)

Compound was isolated as a white solid, 31 mg in 97% yield; $^1$H NMR (400 MHz, CD$_3$OD) δ ppm 7.35 (t, J=7.0 Hz, 1H), 7.23-7.16 (m, 2H), 7.15-7.10 (m, 1H), 7.07 (s, 1H), 6.95 (d, J=7.4 Hz, 2H), 5.01 (d, J=8.6 Hz, 1H), 3.94-3.71 (m, 4H), 3.68-3.56 (m, 2H), 3.01 (s, 3H), 2.05 (s, 3H), 1.81 (s, 3H); $^{13}$C NMR (100 MHz, CD$_3$OD) δ ppm 171.92, 140.15, 138.68, 132.35, 130.18, 129.51, 125.15, 100.98, 77.21, 69.75, 62.58, 54.15, 39.46, 23.24, 20.79; LCMS (ESI): C$_{22}$H$_{28}$N$_2$O$_8$S, found [M+H]$^+$, 481.4.

Example 77. N-((2S,3R,4R,5R,6R)-4,5-dihydroxy-6-(hydroxymethyl)-2-((1-(3-(methylsulfonamido)phenyl)naphthalen-2-yl)oxy)tetrahydro-2H-pyran-3-yl)acetamide (3085)

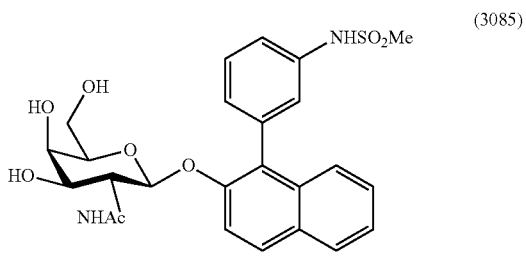

(3085)

Compound was isolated as a white solid, 54 mg in 97% yield; $^1$H NMR (400 MHz, CD3OD) δ ppm 7.92-7.82 (m, 2H), 7.65-7.59 (m, 1H), 7.47-7.41 (m, 2H), 7.39-7.26 (m, 3H), 7.21 (d, J=12.9 Hz, 1H), 7.03 (d, J=7.0 Hz, 1H), 5.15 (d, J=8.6 Hz, 1H), 4.02-3.94 (m, 1H), 3.87 (br. s., 1H), 3.86-3.76 (m, 2H), 3.73-3.58 (m, 2H), 3.07 (s, 3H), 1.80 (s, 3H); $^{13}$C NMR (100 MHz, CD$_3$OD) δ ppm 173.36, 129.10, 128.02, 127.62, 126.97, 126.39, 125.34, 124.61, 124.44, 120.75, 101.40, 39.59.23.25; LCMS (ESI): C$_{25}$H$_{28}$N$_2$O$_8$S, found [M+Na]$^+$, 517.3

Example 78. N-((2S,3R,4R,5R,6R)-2-((3'-(cyclopropanesulfonamido)-6-methyl-[1,1'-biphenyl]-2-yl)oxy)-4,5-dihydroxy-6-(hydroxymethyl)tetrahydro-2H-pyran-3-yl)acetamide (3086)

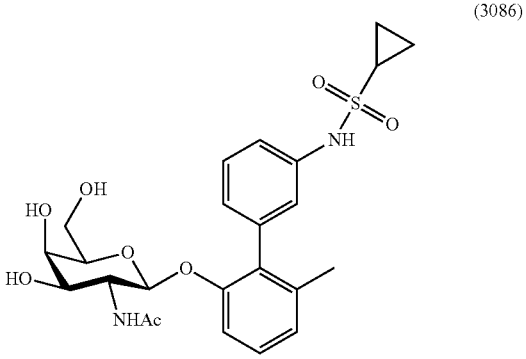

(3086)

Compound was isolated as a white solid, 22 mg in 93% yield; $^1$H NMR (400 MHz, CD$_3$OD) δ ppm 7.31-7.38 (m, 1H), 7.26-7.16 (m, 2H), 7.11 (d, J=9.8 Hz, 2H), 6.95 (d, J=7.4 Hz, 2H), 5.03 (d, J=8.2 Hz, 1H), 3.91-3.81 (m, 2H), 3.80-3.71 (m, 2H), 3.67-3.56 (m, 2H), 2.65-2.53 (m, 1H), 2.05 (s, 3H, 1.83 (s, 3H), 1.07-0.95 (m, 4H); $^{13}$C NMR (100 MHz, CD3OD) δ ppm 156.23, 139.99, 138.70, 132.40, 129.98, 125.10, 124.87, 100.85, 77.18, 69.73, 62.60, 54.22, 30.52, 23.24, 20.81, 6.06; LCMS (ESI): C$_{24}$H$_{30}$N$_2$O$_8$S, found [M+Na]$^+$, 529.3.

Example 79. N-((2S,3S,4R,5R)-2-((3'-((N,N-dimethylsulfamoyl)amino)-6-methyl-[1,1'-biphenyl]-2-yl)oxy)-4,5-dihydroxy-6-(hydroxymethyl)tetrahydro-2H-pyran-3-yl)acetamide (3087)

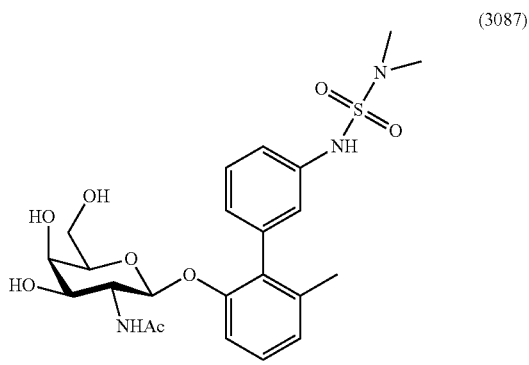

Compound was isolated as a white solid, 21 mg in 89% yield; $^1$H NMR (400 MHz, DMSO-d$_6$) δ ppm 9.77 (br. s., 1H), 7.56 (d, J=7.8 Hz, 1H), 7.28-7.17 (m, 2H), 7.14 (d, J=7.8 Hz, 1H), 7.02 (d, J=8.2 Hz, 1H), 6.82 (d, J=7.4 Hz, 1H), 4.93 (d, J=8.6 Hz, 1H), 3.79-3.69 (m, 1H), 3.66 (br. s., 1H), 3.57-3.47 (m, 3H), 3.47-3.40 (m, 1H), 2.70 (s, 6H), 1.99 (s, 3H), 1.74 (s, 3H); $^{13}$C NMR (100 MHz, DMSO-d$_6$) δ ppm 171.99, 155.37, 135.52, 128.92, 128.12, 126.42, 125.47, 118.37, 99.26, 99.08, 75.89, 72.05, 71.74, 68.16, 61.03, 52.29, 37.60, 21.68; LCMS (ESI): C$_{23}$H$_{31}$N$_3$O$_8$S, found [M+Na]$^+$, 532.3.

Example 80. N-((2S,3S,4R,5R)-4,5-dihydroxy-6-(hydroxymethyl)-2-((6-methyl-3'-(methylsulfonamido)-[1,1'-biphenyl]-2-yl)oxy)tetrahydro-2H-pyran-3-yl)-2,2,2-trifluoroacetimidic acid (3088)

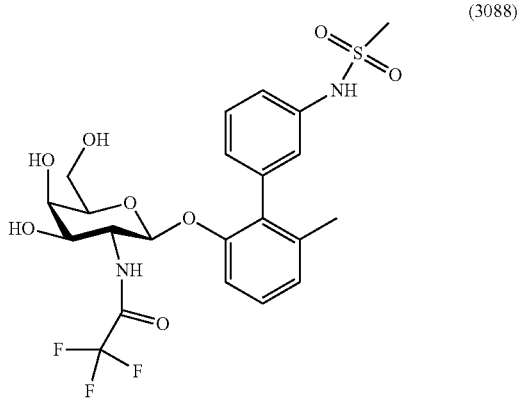

Compound was isolated as a white solid, 6 mg in 23% yield; $^1$H NMR (400 MHz, CD$_3$OD) δ ppm 8.93 (d, J=9.4 Hz, 1H), 7.29 (t, J=6.5 Hz, 1H), 7.22 (br. s., 2H), 7.08-6.98 (m, 2H), 6.95 (d, J=7.4 Hz, 1H), 6.83 (br. s., 1H), 5.11 (d, J=8.6 Hz, 1H), 4.05-3.95 (m, 1H), 3.87 (d, J=2.4 Hz, 1H), 3.83-3.72 (m, 2H), 3.66 (d, J=9.4 Hz, 2H), 3.02 (br. s., 3H), 2.04 (s, 3H) (Note: $^{13}$C NMR not provide due to due to insufficient quantity); LCMS (ESI): C$_{22}$H$_{25}$F$_3$N$_2$O$_8$S, found [M+Na]$^+$, 557.3.

Example 81. N-((2S,3R,4R,5R,6R)-4,5-dihydroxy-6-(hydroxymethyl)-2-((6-methyl-3'-(methylsulfonamido)-[1,1'-biphenyl]-2-yl)oxy)tetrahydro-2H-pyran-3-yl)methanesulfonamide (3089)

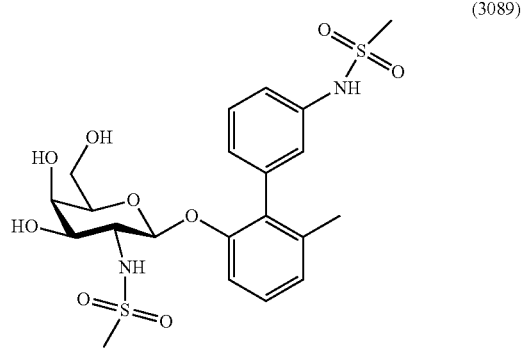

Compound was isolated as a white solid, 39 mg in 97% yield; $^1$H NMR (400 MHz, CD$_3$OD) δ ppm 7.40-7.35 (m, 1H), 7.28-7.19 (m, 2H), 7.14 (d, J=9.8 Hz, 1H), 7.09-6.94 (m, 3H), 5.08 (d, J=16.8 Hz, 1H), 3.89 (br. s., 1H), 3.73 (d, J=5.9 Hz, 2H), 3.64-3.60 (m, 1H), 3.55-3.50 (m, 1H), 3.48-3.37 (m, 1H), 2.59-2.39 (m, 3H), 2.08 (br. s., 3H); $^{13}$C NMR (100 MHz, CD$_3$OD) δ ppm 149.33, 130.37, 129.45, 125.22, 77.05, 69.81, 62.34, 57.85, 41.92, 39.63, 20.94; LCMS (ESI): C$_{20}$H$_{28}$N$_2$O$_9$S$_2$, found [M+Na]$^+$, 539.3

Example 82. N-((2S,3S,4R,5R)-4,5-dihydroxy-6-(hydroxymethyl)-2-((3'-(methylsulfonamido)-6-(trifluoromethyl)-[1,1'-biphenyl]-2-yl)oxy)tetrahydro-2H-pyran-3-yl)acetamide (3090)

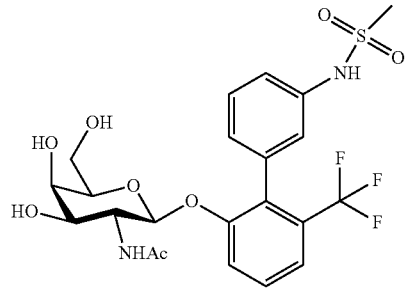

Compound was isolated as a white solid, 20 mg in 84% yield; $^1$H NMR (400 MHz, CD$_3$OD) δ ppm 7.57-7.48 (m, 2H), 7.46-7.41 (m, 1H), 7.37-7.30 (m, 1H), 7.27-7.21 (m, 1H), 7.21-7.14 (m, 1H), 7.10 (s, 3H), 6.98-6.89 (m, 1H), 5.06 (d, J=8.0, 1H), 3.91-3.83 (m, 2H), 3.83-3.72 (m, 2H), 3.68 (t, J=6.1 Hz, 1H), 3.65-3.55 (m, 1H), 2.99 (s, 3H), 1.83 (s, 3H); $^{13}$C NMR (100 MHz, CD$_3$OD) δ ppm 173.60, 157.18, 139.04, 137.11, 130.51, 129.72, 120.90, 120.39, 120.30, 119.97, 100.84, 77.48, 73.64, 73.34, 69.76, 62.63, 53.89, 39.20, 39.13, 23.28; LCMS (ESI): C$_{22}$H$_{25}$F$_3$N$_2$O$_8$S, found [M+H]$^+$, 535.3.

Example 83. Potency of Sulfonamides 3078-3090

The potency of all compounds 3078-3090 were assessed using the ELISA assay described above to measure the IC$_{50}$.

These values are shown in Table 2. All N-acetyl compounds had excellent activity with an $IC_{50}$ of 180 nM or better. We found that all analogs substituted with any of the various functional groups installed at the ortho position ($R^4$) of the biphenyl A-ring (relative to the B-ring) further improved $IC_{50}$s relative to lead compound 50 ($R^4$=H). It is noteworthy that the cyclopropyl sulfonamide 3086 and the dimethyl sulfonyl urea derivative 3087 retain the same activity as the methyl sulfonamides. Compound 3090, containing the methyl sulfonamide in the meta position of the biphenyl B-ring and a trifluoromethyl group in the ortho $R^4$ position on the B-ring exhibited the highest potency of the compounds tested, with an $IC_{50}$ of 85 nM. Even the fused naphthyl A-ring 3085 has excellent potency with an $IC_{50}$ of 0.18 μM. When the acetyl group of compound 3084 is replaced, the trifluoroacetamide retains potent activity ($IC_{50}$ 0.11 μM) while the methyl sulfonamide loses significant activity with an $IC_{50}$ of only 3.5 μM. Table 6 summarizes the results.

TABLE 6

| Compound | Y | $R^4$ | $R^6$ | $IC_{50}$ (μM) |
|---|---|---|---|---|
| 3078 | Ac | $NO_2$ | Me | 0.11 |
| 3079 | Ac | CN | Me | 0.11 |
| 3080 | Ac | F | Me | 0.15 |
| 3081 | Ac | $CO_2Bn$ | Me | 0.18 |
| 3082 | Ac | COOH | Me | 0.13 |
| 3083 | Ac | OMe | Me | 0.15 |
| 3084 | Ac | Me | Me | 0.12 |
| 3085 | NA | NA | NA | 0.18 |
| 3086 | Ac | Me | Cyclopropyl | 0.12 |
| 3087 | Ac | Me | $N(Me)_2$ | 0.13 |
| 3088 | $COCF_3$ | Me | Me | 0.11 |
| 3089 | $SO_2Me$ | Me | Me | 3.50 |
| 3090 | Ac | $CF_3$ | Me | 0.085 |

Example 84. X-Ray Structure Determination of Biphenyl Sulfonamide GalNAc 3090 Bound to the FmlH Lectin Domain To determine the molecular basis for the high potency exhibited by the biphenyl sulfonamides and the corresponding SAR, we solved an X-ray crystal structure of compound 3090 bound to $FmlH^{LD}$. The co-crystal structure was solved to 1.75 Å resolution (FIG. 13, PDB ID 6MAW).

As previously described, all protein solutions were generated by adding 10 μL 50 mM compound dissolved in 100% DMSO to FmlH in 10 mM HEPES pH 7.5+50 mM NaCl immediately before setting up drops for a final concentration of 9 mg/mL $FmlD^{LD}$, 5 mM compound, and 10% DMSO. Co-crystals of FmlH-3090 (AM2134) were grown by mixing 14 protein solution with 14 mother liquor containing 0.7 M $LiSO_4$+20% PEG 8000 on a glass coverslip over 1 mL mother liquor. Thin, needle-like crystals appeared after approximately 72 hours. Crystals were cryoprotected in 1 M LiSO4+20% PEG 8000+25% glycerol for 10 seconds before and flash-freezing in liquid nitrogen. All data were collected on ALS Beamline 4.2.2 at an X-ray wavelength of 1.00 Å. Raw data were processed using XDS, Aimless, and Pointless (14, 15). The phase problem was solved using Phaser-MR in the Phenix suite using the apo $FmlH_{LD}$ structure (PDBID: 6AOW) as a search model (16). Iterative rounds of Phenix. Refine and Coot were used to refine the final model. Guided ligand replacement was performed using Phenix.

As previously observed in the 29β-NAc-$FmlH^{LD}$ co-crystal structure (FIGS. 7, 12 and 14), the terminal N-acetyl galactosamine ring forms key H-bonds with the amide backbone of F1, as well as the side chains of D45, Y46, and D53 in loop 2, and the side chains of K132 and N140 in loop 3 (see Example 18). The nitrogen of the N-acetylgalactosamine group forms multiple H-bonds with K132 and a water molecule present in the binding pocket. In addition, FIG. 12 shows an additional water-mediated H-bond between the N-acetylglucosamine carbonyl and R142 that had not been previously observed (e.g., in FIG. 7). In contrast to the structure of compound 29β-NAc bound to FmlH, in which the carboxylate group of the biphenyl B-ring faces the N-acetyl group of the sugar and interacts with the pocket formed by R142 and K132, the sulfonamide is interacting in a pocket just opposite from this (FIG. 14). This happens to be the same pocket the carboxylate of GalNAc 3029 occupies (FIG. 11, panel A). The sulfonamide nitrogen atom of 3090 forms an H-bond with the backbone hydroxyl group of F1. Additionally, one of the sulfonamide oxygens interacts with the side chain of S2, the side chain of S10 side chain and backbone of I11 in loop 1. The addition of the ortho-trifluoromethyl group to the biphenyl A-ring likely locks the position of the second phenyl ring at a preferred 80 degree offset relative to the first ring, providing a favorable entropic contribution to FmlH lectin domain binding. Additionally, it is speculated that one of the fluorine atoms interacts directly with D45 and indirectly with S2 through a water molecule.

Example 85. In Vitro Metabolic Stability Studies of Lead FmlH Antagonists

Due to the labile nature of the 0-glycosidic linkage of the biphenyl Gal and GalNAc FmlH antagonists, studies were pursued to evaluate their stability. To evaluate their therapeutic potential for advancing into planned animal studies, the in vitro stability was assessed of six leading compounds 3079, 3080, 3084, 3086, 3088, and 3090 based on their potency and structural diversity (Table 6). These compounds were assessed for their stability in simulated gastric fluid (SGF), simulated intestinal fluid (SIF), mouse liver microsomes, and blood plasma (Table 7). All compounds tested exhibited a high degree of stability, with some variation seen in the plasma stability. These findings are consistent with our earlier characterization of FimH antagonists (mannosides). In these studies, it was demonstrated that the lability of the O-glycosidic linkage both in vitro and in vivo resulted in the appearance and detection of the phenol product of metabolism in mouse plasma and urine. The two most stable analogs, 3086 and 3090, were subjected to further testing for their pharmacokinetics (PK) in rats.

TABLE 7

In vitro metabolic stability studies.

| Compound | SGF % remaining 6 h | SIF % remaining 2 h | Mouse liver microsomes ($t_{1/2}$ min) | Mouse plasma % remaining 2 h | Kinetic Solubility (µM) |
|---|---|---|---|---|---|
| 3079 | 86.77 | 100.00 | >145 | 89.1 | 196 |
| 3080 | 91.95 | 93.79 | >145 | 89.1 | 197 |
| 3084 | 100.00 | 100.00 | >145 | 100.00 | 195 |
| 3086 | 100.00 | 100.00 | >145 | 84.1 | 196 |
| 3088 | 90.95 | 89.15 | >145 | 88.9 | 164 |
| 3090 | 89.25 | 91.9 | >145 | 92.2 | 197 |

Example 86. In Vivo Pharmacokinetic Studies

In this example, the concentration of compounds 3086 and 3090 in rat plasma and urine following either a 10 mg/kg oral dose (PO; circular dots) or a 3 mg/kg intravenous dose (IV; square dots) was determined (FIG. 16, panel A (3086) and panel B (3090)). Analysis of the rat PK data revealed that compound 3086 has a longer long life ($t_{1/2}$=1.46 h) and lower clearance (Cl=43.8 mL/min/kg) in plasma than compound 3090 ($t_{1/2}$=1.16 h and Cl=57.0 mL/min/kg). However, both compounds displayed low renal clearance to the urine (FIG. 15) and an oral bioavailability (F) of less than 1%. Thus, the metabolic stability of these compounds and clearance of these compounds has no relation to the permeability (oral or otherwise) of compounds. The highly polar nature of these molecules containing the sugar GalNAc and multiple polar functionalities precludes their permeability in the gut.

In order to determine if the improved PK properties of 3086 relative to 3090 are a consequence of the $CH_3$ versus $CF_3$ group on the biphenyl A-ring or the cyclopropyl sulfonamide versus methyl sulfonamide of the B-ring, an additional study was performed in mice with compound 3084, the methyl sulfonamide derivative of 3086 or the $CH_3$ derivative of 3090. This enabled the determination of the isolated effects of a single substitution. These studies were conducted via 20 mg/kg intraperitoneal (IP) injection to inform planned future IP studies in murine studies of chronic UTI, which require a single IP dose of galactoside to persist in the plasma for 6 hours prior to measurement of bladder bacterial burdens (FIG. 17)[22].

While not a perfect comparison to 3086 and 3090, the half-life, $t_{1/2}$ in the mouse is calculated to be 1.13 h and the clearance rate appears to be slower than either that of 3086 or 3090. The compound 3084 shows moderate compound exposure at 8 h with a $C_{max}$ of 7897 ng/mL and a calculated AUC of 6300 ng·h/mL. This compound has an $IC_{50}$ of 120 nM, which equates to a concentration of 57.7 ng/mL. At the 4 h timepoint the average concentration of 3084 was 79.5 ng/mL. By extrapolating these kinetics we can infer that the plasma concentration of this compound would likely remain well above the $IC_{50}$ for the 6 h, the exact timeframe required for our murine model of chronic UTI.

Example 86. Summary of Biochemical Results of Substituted Galactoside Compounds

The compounds synthesized herein were tested in the ELISA-based competition assay for their ability to inhibit binding of $FmlH_{LD}$ to ds-BSM. The ELISA assay was performed using the protocol described in Example 18. Compounds were tested at 10004, 1004, 1 µM, and 100 nM. as indicated on the table. In addition, the Kd and $IC_{50}$ values for some of the compounds are noted. Results are summarized in Table 8. ND means the corresponding value was not determined for this summary (but may be available elsewhere in the Examples).

TABLE 8

| Name | Structure | % Inhibition at [µM] [100] | [10] | [1] | [0.1] | Kd (µM) | $IC_{50}$ (nM) |
|---|---|---|---|---|---|---|---|
| 200b-GalNAc | | 99.54 | 93.00 | 35.07 | ND | 0.089 | ND |
| ONPG-NAc | | 99.36 | 87.17 | 22.41 | ND | 2.3 | ND |

TABLE 8-continued

| Name | Structure | % Inhibition at [µM] [100] | [10] | [1] | [0.1] | Kd (µM) | IC$_{50}$ (nM) |
|---|---|---|---|---|---|---|---|
| 200b | 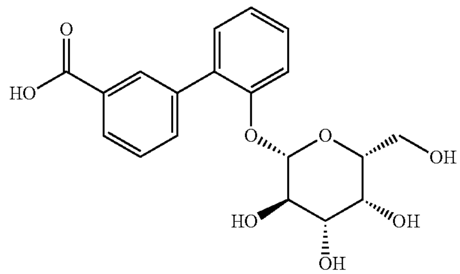 [SMILES: O=C(O)c1cccc(-c2ccccc2O[C@@H]2O[C@H](CO)[C@H](O)[C@H](O)[C@H]2O)c1] | 99.00 | 75.13 | 12.29 | ND | 2.1 | ND |
| 149e | 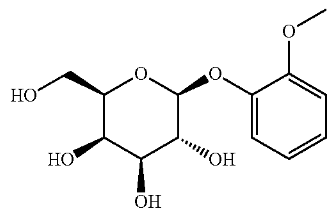 [SMILES: COc1ccccc1O[C@@H]1O[C@H](CO)[C@H](O)[C@H](O)[C@H]1O] | 97.16 | 55.74 | 9.99 | ND | 6.5 | ND |
| 8HQG | 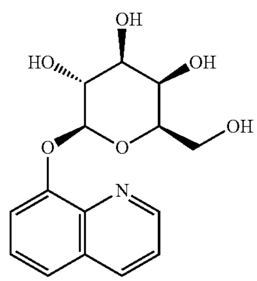 [SMILES: OC[C@H]1O[C@@H](Oc2cccc3cccnc23)[C@H](O)[C@@H](O)[C@H]1O] | 95.10 | 48.08 | 19.21 | ND | 7.1 | ND |
| 137b | 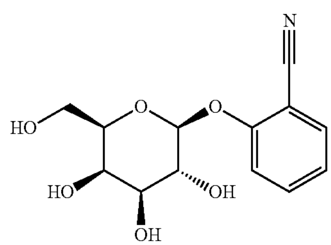 [SMILES: N#Cc1ccccc1O[C@@H]1O[C@H](CO)[C@H](O)[C@H](O)[C@H]1O] | 94.54 | 30.40 | 12.11 | ND | ND | ND |
| ONPG | 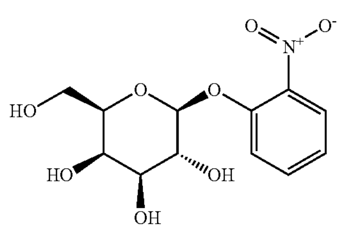 [SMILES: O=[N+]([O-])c1ccccc1O[C@@H]1O[C@H](CO)[C@H](O)[C@H](O)[C@H]1O] | 93.03 | 31.08 | 14.21 | ND | 10.6 | ND |
| 113f2 | 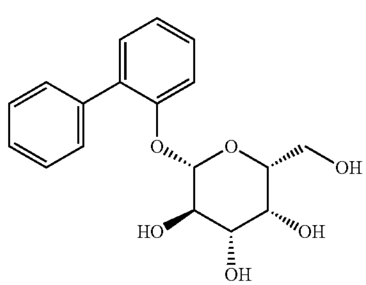 [SMILES: OC[C@H]1O[C@@H](Oc2ccccc2-c2ccccc2)[C@H](O)[C@@H](O)[C@H]1O] | 91.08 | 31.01 | 8.10 | ND | ND | ND |

TABLE 8-continued

| Name | Structure | % Inhibition at [μM] [100] | [10] | [1] | [0.1] | Kd (μM) | IC$_{50}$ (nM) |
|---|---|---|---|---|---|---|---|
| 154c | 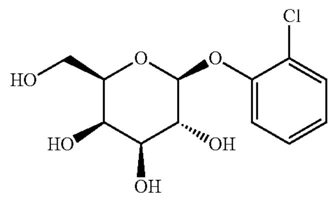 [SMILES: OC[C@H]1O[C@@H](Oc2ccccc2Cl)[C@H](O)[C@@H](O)[C@H]1O] | 90.49 | 20.70 | 7.95 | ND | ND | ND |
| D715-0293 | 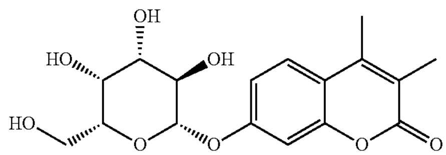 [SMILES: Cc1c(C)c2ccc(O[C@@H]3O[C@H](CO)[C@H](O)[C@H](O)[C@H]3O)cc2oc1=O] | 89.20 | 19.75 | 10.22 | ND | ND | ND |
| 135b | 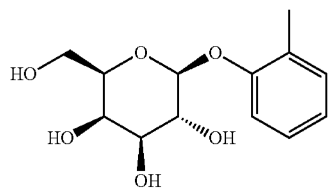 [SMILES: Cc1ccccc1O[C@@H]1O[C@H](CO)[C@H](O)[C@H](O)[C@H]1O] | 87.31 | 28.16 | 1.81 | ND | ND | ND |
| 116f | 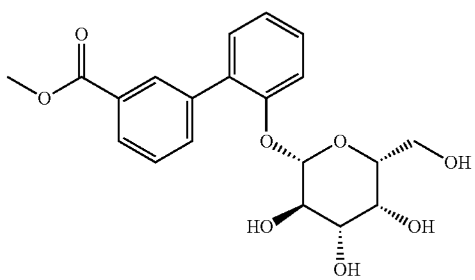 [SMILES: COC(=O)c1cccc(-c2ccccc2O[C@@H]2O[C@H](CO)[C@H](O)[C@H](O)[C@H]2O)c1] | 86.57 | 22.38 | 3.70 | ND | ND | ND |
| 114bf1 | 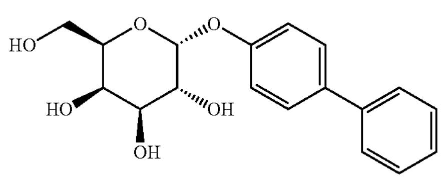 [SMILES: OC[C@H]1O[C@H](Oc2ccc(-c3ccccc3)cc2)[C@H](O)[C@@H](O)[C@H]1O] | 86.45 | 22.61 | ND | ND | ND | ND |
| 153a | 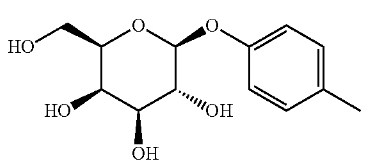 [SMILES: Cc1ccc(O[C@@H]2O[C@H](CO)[C@H](O)[C@H](O)[C@H]2O)cc1] | 85.80 | 16.46 | 4.59 | ND | ND | ND |
| 152b | 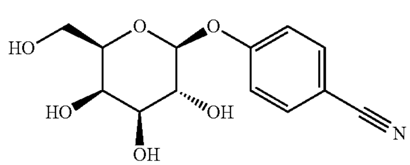 [SMILES: N#Cc1ccc(O[C@@H]2O[C@H](CO)[C@H](O)[C@H](O)[C@H]2O)cc1] | 85.66 | 19.17 | 9.47 | ND | ND | ND |
| MUG | 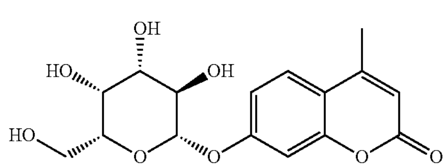 [SMILES: Cc1cc(=O)oc2cc(O[C@@H]3O[C@H](CO)[C@H](O)[C@H](O)[C@H]3O)ccc12] | 85.25 | 19.71 | 8.73 | ND | ND | ND |

TABLE 8-continued

| Name | Structure | % Inhibition at [µM] | | | | Kd (µM) | IC₅₀ (nM) |
|---|---|---|---|---|---|---|---|
| | | [100] | [10] | [1] | [0.1] | | |
| PNP-aGalNAc | 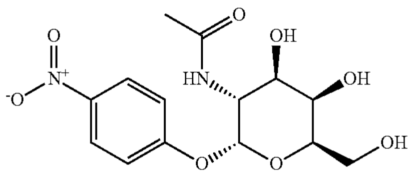 | 82.04 | 6.29 | ND | ND | ND | ND |
| Resorufin Gal | 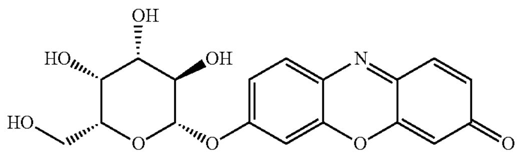 [SMILES: O=c1ccc2nc3ccc(O[C@@H]4O[C@H](CO)[C@H](O)[C@H](O)[C@H]4O)cc3oc-2c1] | 80.38 | 23.96 | ND | ND | ND | ND |
| 2-napthyl Gal | 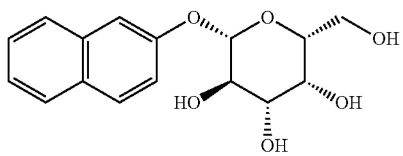 [SMILES: OC[C@H]1O[C@@H](Oc2ccc3ccccc3c2)[C@H](O)[C@@H](O)[C@H]1O] | 78.79 | 14.62 | ND | ND | ND | ND |
| p-Nitrophenyl Gal | 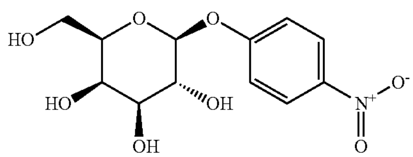 [SMILES: O=[N+]([O-])c1ccc(O[C@@H]2O[C@H](CO)[C@H](O)[C@H](O)[C@H]2O)cc1] | 78.13 | 13.73 | ND | ND | ND | ND |
| Phenyl Gal | 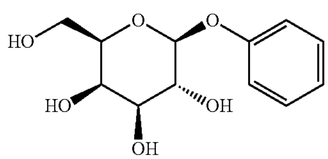 [SMILES: OC[C@H]1O[C@@H](Oc2ccccc2)[C@H](O)[C@@H](O)[C@H]1O] | 76.88 | 15.50 | ND | ND | ND | ND |
| 151d | 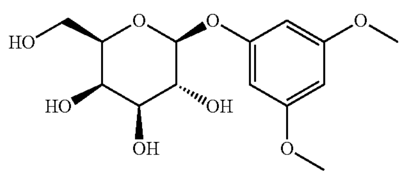 [SMILES: COc1cc(OC)cc(O[C@@H]2O[C@H](CO)[C@H](O)[C@H](O)[C@H]2O)c1] | 76.36 | 11.74 | ND | ND | ND | ND |
| PNPTG | 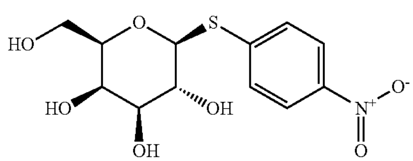 [SMILES: O=[N+]([O-])c1ccc(S[C@@H]2O[C@H](CO)[C@H](O)[C@H](O)[C@H]2O)cc1] | 72.48 | 17.02 | ND | ND | ND | ND |
| 4-amino-phenyl Gal | 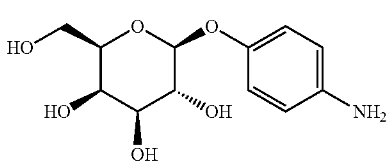 [SMILES: Nc1ccc(O[C@@H]2O[C@H](CO)[C@H](O)[C@H](O)[C@H]2O)cc1] | 65.07 | 9.80 | ND | ND | ND | ND |
| 114af2 | 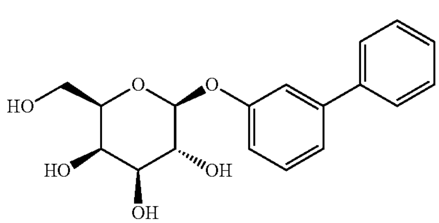 [SMILES: OC[C@H]1O[C@@H](Oc2cccc(-c3ccccc3)c2)[C@H](O)[C@@H](O)[C@H]1O] | 56.92 | 7.80 | ND | ND | ND | ND |

TABLE 8-continued
| Name | Structure | % Inhibition at [μM] | | | | Kd (μM) | IC$_{50}$ (nM) |
|---|---|---|---|---|---|---|---|
| | | [100] | [10] | [1] | [0.1] | | |
| 2-phenylethyl-thio-galactoside | 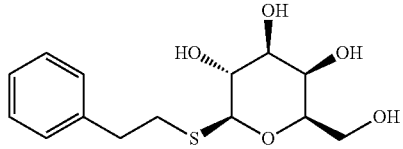 | 49.85 | 2.31 | ND | ND | ND | ND |
| DiF-MUG | 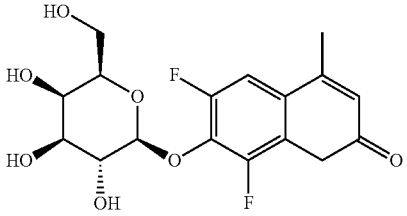 [SMILES: CC1=CC(=O)Cc2c1cc(F)c(O[C@@H]1O[C@H](CO)[C@H](O)[C@H](O)[C@H]1O)c2F] | 49.69 | 0.85 | ND | ND | ND | ND |
| 115af2 | 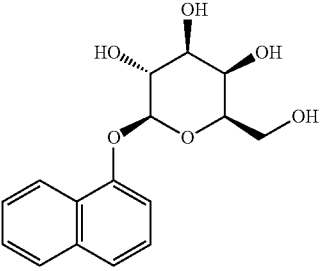 [SMILES: OC[C@H]1O[C@@H](Oc2cccc3ccccc23)[C@H](O)[C@@H](O)[C@H]1O] | 45.91 | ND | ND | ND | ND | ND |
| 114af1 | 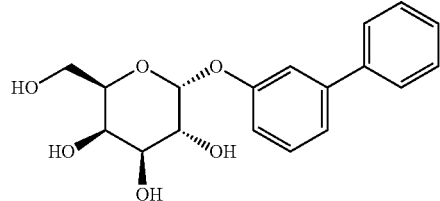 [SMILES: OC[C@H]1O[C@H](Oc2cccc(-c3ccccc3)c2)[C@H](O)[C@@H](O)[C@H]1O] | 45.62 | ND | ND | ND | ND | ND |
| Salmon Gal | 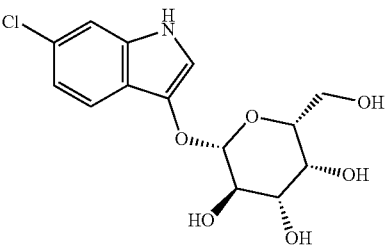 [SMILES: OC[C@H]1O[C@@H](Oc2c[nH]c3cc(Cl)ccc23)[C@H](O)[C@@H](O)[C@H]1O] | 41.21 | ND | ND | ND | ND | ND |
| 135a | 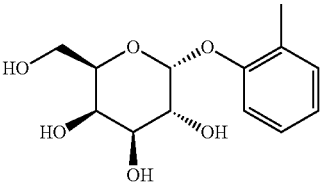 | 29.99 | ND | ND | ND | ND | ND |
| 114bf2 | 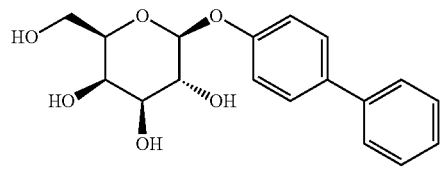 [SMILES: OC[C@H]1O[C@@H](Oc2ccc(-c3ccccc3)cc2)[C@H](O)[C@@H](O)[C@H]1O] | 29.96 | ND | ND | ND | ND | ND |

TABLE 8-continued

| Name | Structure | % Inhibition at [μM] | | | | Kd (μM) | IC$_{50}$ (nM) |
|---|---|---|---|---|---|---|---|
| | | [100] | [10] | [1] | [0.1] | | |
| CG | | 28.78 | ND | ND | ND | 212 | ND |
| GalNAc | | 28.45 | ND | ND | ND | ND | ND |
| 115af1 | | 28.07 | ND | ND | ND | ND | ND |
| 200a | | 26.23 | ND | ND | ND | ND | ND |
| IPTG | | 23.70 | ND | ND | ND | ND | ND |
| 3-indoxyl Gal | | 21.72 | ND | ND | ND | ND | ND |

TABLE 8-continued

| Name | Structure | % Inhibition at [μM] | | | | Kd (μM) | IC$_{50}$ (nM) |
|---|---|---|---|---|---|---|---|
| | | [100] | [10] | [1] | [0.1] | | |
| Gal-b1-6-PNPG | | 19.41 | ND | ND | ND | ND | ND |
| 113f1 | | 19.21 | ND | ND | ND | ND | ND |
| 137a | | 17.81 | ND | ND | ND | ND | ND |
| TF | | 15.46 | ND | ND | ND | 248 | ND |
| Gal-b1-3-PNPGalNAc | | 15.28 | ND | ND | ND | ND | ND |

TABLE 8-continued
| Name | Structure | % Inhibition at [µM] [100] | [10] | [1] | [0.1] | Kd (µM) | IC$_{50}$ (nM) |
|---|---|---|---|---|---|---|---|
| EXW020a | 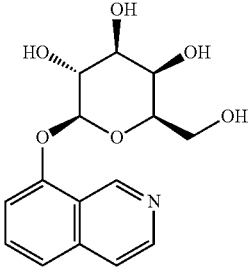 | 15.16 | ND | ND | ND | ND | ND |
| QG | 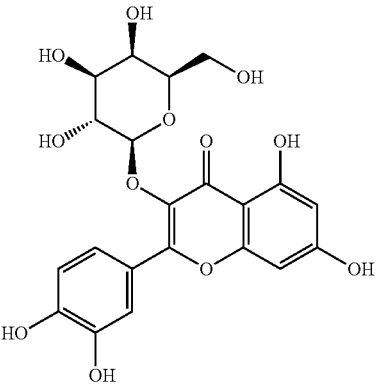 [SMILES: O=c1c(O[C@@H]2O[C@H](CO)[C@H](O)[C@H](O)[C@H]2O)c(-c2ccc(O)c(O)c2)oc2cc(O)cc(O)c12] | 14.44 | ND | ND | ND | 391 | ND |
| 116e | 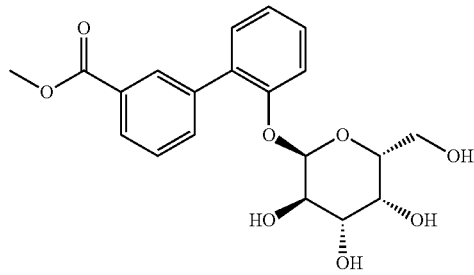 [SMILES: COC(=O)c1cccc(-c2ccccc2O[C@H]2O[C@H](CO)[C@H](O)[C@H](O)[C@H]2O)c1] | 13.10 | ND | ND | ND | ND | ND |
| MyrG | 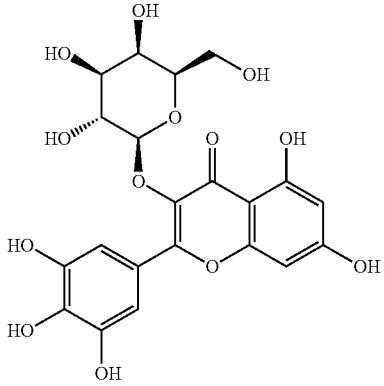 [SMILES: O=c1c(O[C@@H]2O[C@H](CO)[C@H](O)[C@H](O)[C@H]2O)c(-c2cc(O)c(O)c(O)c2)oc2cc(O)cc(O)c12] | 10.75 | ND | ND | ND | ND | ND |
| Gal | 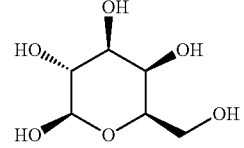 [SMILES: OC[C@H]1O[C@@H](O)[C@H](O)[C@@H](O)[C@H]1O] | 8.15 | ND | ND | ND | 694 | ND |

TABLE 8-continued
| Name | Structure | % Inhibition at [µM] | | | | Kd (µM) | IC₅₀ (nM) |
|---|---|---|---|---|---|---|---|
| | | [100] | [10] | [1] | [0.1] | | |
| PeoG | 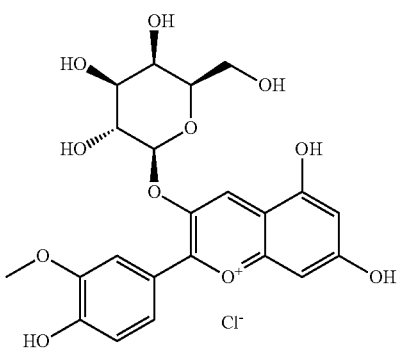 [SMILES: COc1cc(-c2[o+]c3cc(O)cc(O)c3cc2O[C@@H]2O[C@H](CO)[C@H](O)[C@H](O)[C@H]2O)ccc1O ; [Cl-]] | 3.64 | ND | ND | ND | ND | ND |
| ONPG-6P | 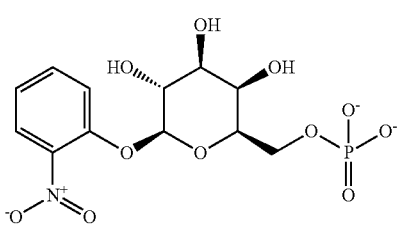 | 1.31 | ND | ND | ND | ND | ND |
| PelG | 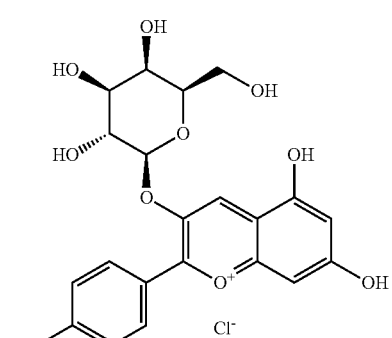 | 0.74 | ND | ND | ND | ND | ND |
| PNP Galacturonide | 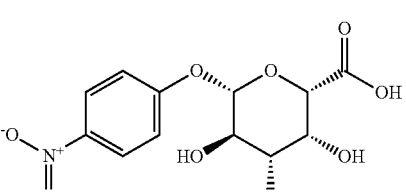 | −2.40 | ND | ND | ND | ND | ND |
| Gal-b1-3-PNPGlcNAc | 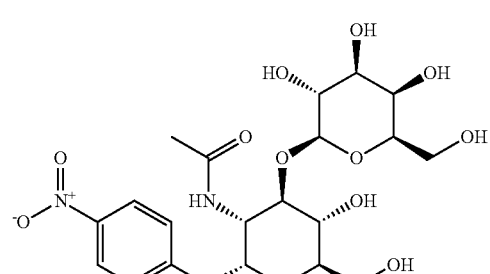 | −3.60 | ND | ND | ND | ND | ND |

TABLE 8-continued

| Name | Structure | % Inhibition at [μM] | | | | Kd (μM) | IC$_{50}$ (nM) |
|---|---|---|---|---|---|---|---|
| | | [100] | [10] | [1] | [0.1] | | |
| AM2003 | 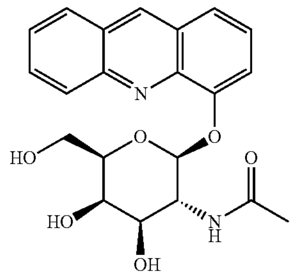 [SMILES: CC(=O)N[C@H]1[C@H](Oc2cccc3cc4ccccc4nc23)O[C@H](CO)[C@H](O)[C@@H]1O] | ND | ND | 15.44 | ND | ND | ND |
| AM1179 | 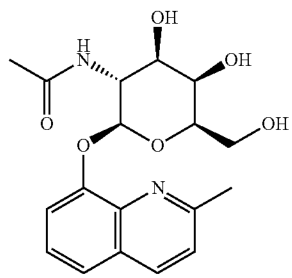 [SMILES: CC(=O)N[C@H]1[C@H](Oc2cccc3ccc(C)nc23)O[C@H](CO)[C@H](O)[C@@H]1O] | ND | ND | 25.22 | ND | ND | ND |
| AM1192 | 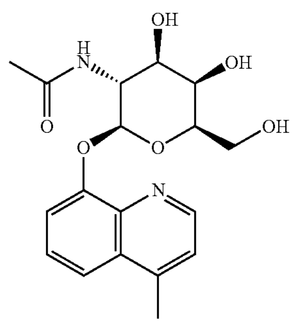 [SMILES: CC(=O)N[C@H]1[C@H](Oc2cccc3c(C)ccnc23)O[C@H](CO)[C@H](O)[C@@H]1O] | ND | ND | 16.83 | ND | ND | ND |
| AM1176 | 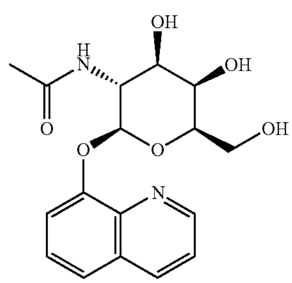 [SMILES: CC(=O)N[C@H]1[C@H](Oc2cccc3cccnc23)O[C@H](CO)[C@H](O)[C@@H]1O] | ND | ND | 20.96 | ND | ND | ND |
| AM1180 | 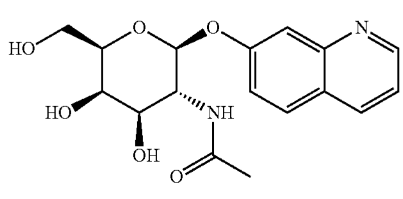 [SMILES: CC(=O)N[C@H]1[C@H](Oc2ccc3cccnc3c2)O[C@H](CO)[C@H](O)[C@@H]1O] | ND | ND | 15.39 | ND | ND | ND |
| AM1184 | 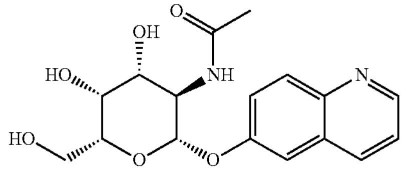 [SMILES: CC(=O)N[C@H]1[C@H](Oc2ccc3ncccc3c2)O[C@H](CO)[C@H](O)[C@@H]1O] | ND | ND | 7.56 | ND | ND | ND |

TABLE 8-continued

| Name | Structure | % Inhibition at [μM] | | | | Kd (μM) | IC$_{50}$ (nM) |
|---|---|---|---|---|---|---|---|
| | | [100] | [10] | [1] | [0.1] | | |
| AM2007 | 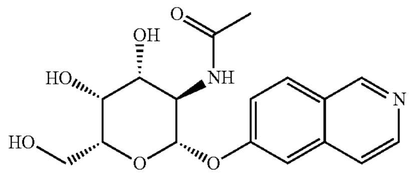 [SMILES: CC(=O)N[C@H]1[C@H](Oc2ccc3cnccc3c2)O[C@H](CO)[C@H](O)[C@@H]1O] | ND | ND | 12.59 | ND | ND | ND |
| AM1186 | 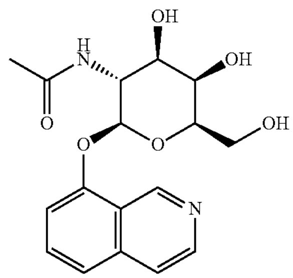 [SMILES: CC(=O)N[C@H]1[C@H](Oc2cccc3ccncc23)O[C@H](CO)[C@H](O)[C@@H]1O] | ND | ND | 23.51 | ND | ND | ND |
| AM2002 | 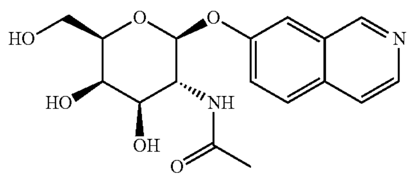 [SMILES: CC(=O)N[C@H]1[C@H](Oc2ccc3ccncc3c2)O[C@H](CO)[C@H](O)[C@@H]1O] | ND | ND | 20.24 | ND | ND | ND |
| AM1189 | 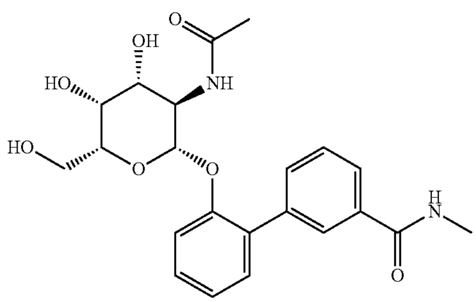 [SMILES: CNC(=O)c1cccc(-c2ccccc2O[C@@H]2O[C@H](CO)[C@H](O)[C@H](O)[C@H]2NC(C)=O)c1] | ND | ND | 12.32 | ND | ND | ND |
| AM2035 | 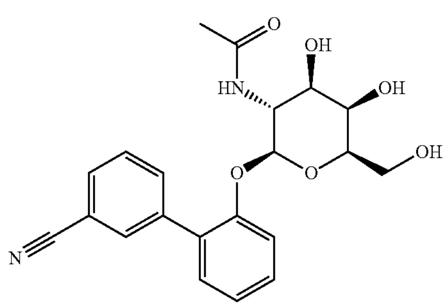 [SMILES: CC(=O)N[C@H]1[C@H](Oc2ccccc2-c2cccc(C#N)c2)O[C@H](CO)[C@H](O)[C@@H]1O] | ND | ND | 20.93 | ND | ND | ND |
| AM2029 | 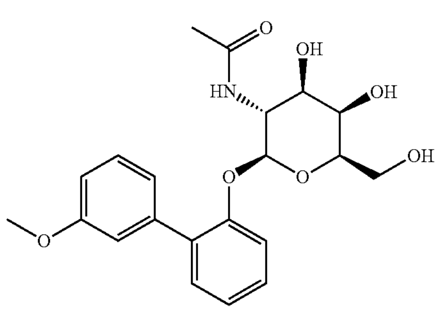 [SMILES: COc1cccc(-c2ccccc2O[C@@H]2O[C@H](CO)[C@H](O)[C@H](O)[C@H]2NC(C)=O)c1] | ND | ND | 15.54 | ND | ND | ND |

TABLE 8-continued

| Name | Structure | % Inhibition at [μM] [100] | [10] | [1] | [0.1] | Kd (μM) | IC$_{50}$ (nM) |
|---|---|---|---|---|---|---|---|
| AM2028 | 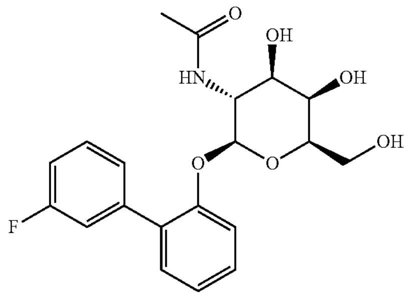 [SMILES: CC(=O)N[C@H]1[C@H](Oc2ccccc2-c2cccc(F)c2)O[C@H](CO)[C@H](O)[C@@H]1O] | ND | ND | 11.76 | ND | ND | ND |
| AM2037 | 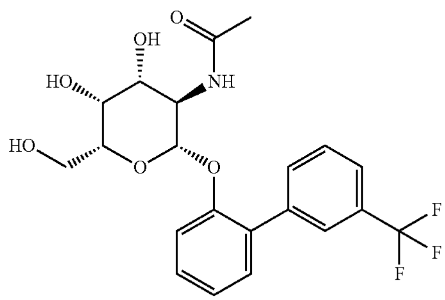 [SMILES: CC(=O)N[C@H]1[C@H](Oc2ccccc2-c2cccc(C(F)(F)F)c2)O[C@H](CO)[C@H](O)[C@@H]1O] | ND | ND | 15.72 | ND | ND | ND |
| AM2038 | 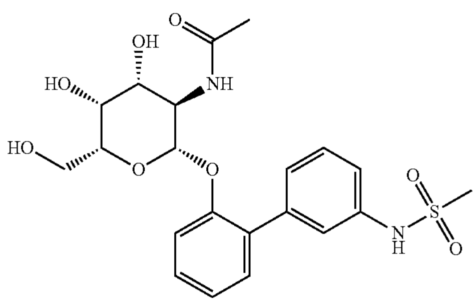 | ND | ND | 81.40 | 16.50 | ND | 271 |
| AM2030 | 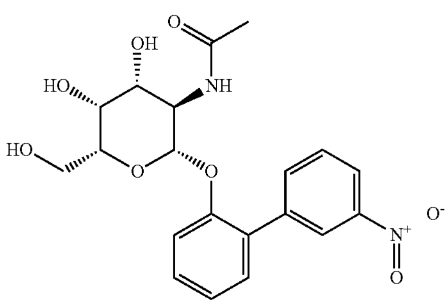 | ND | ND | 9.25 | ND | ND | ND |
| AM2033 | 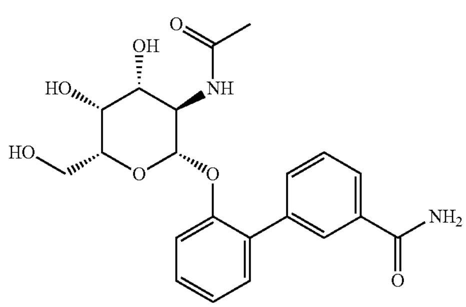 [SMILES: CC(=O)N[C@H]1[C@H](Oc2ccccc2-c2cccc(C(N)=O)c2)O[C@H](CO)[C@H](O)[C@@H]1O] | ND | ND | 3.52 | ND | ND | ND |

TABLE 8-continued

| Name | Structure | % Inhibition at [µM] | | | | Kd (µM) | IC$_{50}$ (nM) |
|---|---|---|---|---|---|---|---|
| | | [100] | [10] | [1] | [0.1] | | |
| AM2032 | 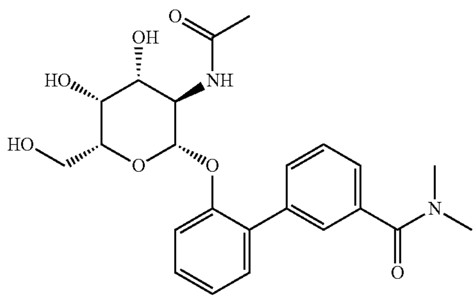 [SMILES: CC(=O)N[C@H]1[C@H](Oc2ccccc2-c2cccc(C(=O)N(C)C)c2)O[C@H](CO)[C@H](O)[C@@H]1O] | ND | ND | −3.61 | ND | ND | ND |
| AM2021 | 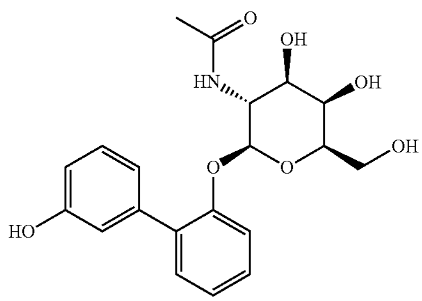 [SMILES: CC(=O)N[C@H]1[C@H](Oc2ccccc2-c2cccc(O)c2)O[C@H](CO)[C@H](O)[C@@H]1O] | ND | ND | 17.71 | ND | ND | ND |
| AM1181 | 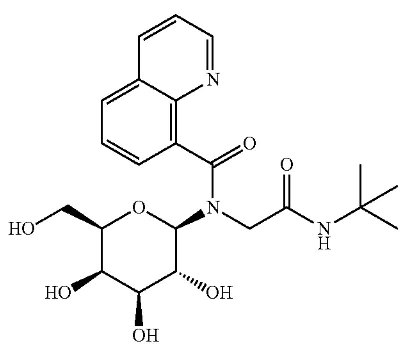 [SMILES: CC(C)(C)NC(=O)CN(C(=O)c1cccc2cccnc12)[C@@H]1O[C@H](CO)[C@H](O)[C@H](O)[C@H]1O] | ND | ND | 10.78 | ND | ND | ND |
| AM1165 | 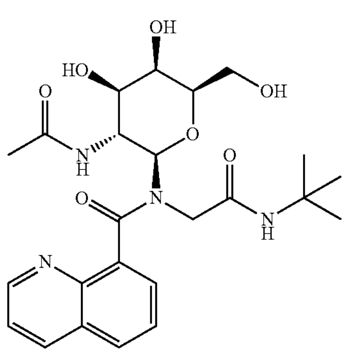 [SMILES: CC(=O)N[C@@H]1[C@@H](O)[C@@H](O)[C@@H](CO)O[C@H]1N(CC(=O)NC(C)(C)C)C(=O)c1cccc2cccnc12] | ND | ND | 5.57 | ND | ND | ND |

TABLE 8-continued
| Name | Structure | % Inhibition at [μM] | | | | Kd (μM) | IC₅₀ (nM) |
|---|---|---|---|---|---|---|---|
| | | [100] | [10] | [1] | [0.1] | | |
| AM2051 | 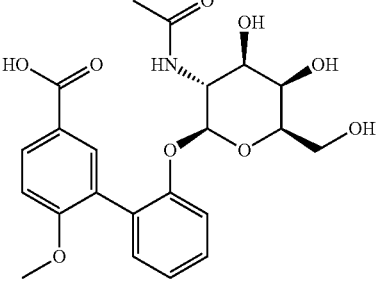 | ND | ND | 15.90 | 0.00 | ND | ND |
| AM2053 | 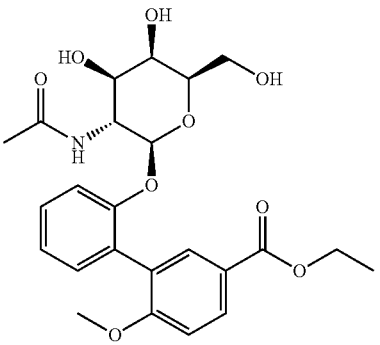 [SMILES: CCOC(=O)c1ccc(OC)c(-c2ccccc2O[C@@H]2O[C@H](CO)[C@H](O)[C@H](O)[C@H]2NC(C)=O)c1] | ND | ND | 13.70 | 0.00 | ND | ND |
| AM2059 | 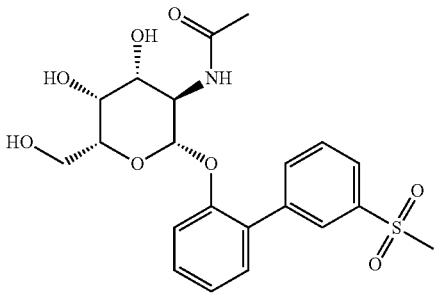 [SMILES: CC(=O)N[C@H]1[C@H](Oc2ccccc2-c2cccc(S(C)(=O)=O)c2)O[C@H](CO)[C@H](O)[C@@H]1O] | ND | ND | 23.30 | 0.10 | ND | ND |
| AM2062 | 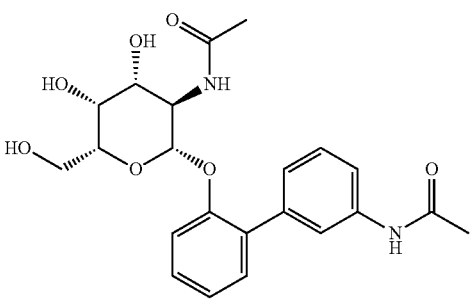 [SMILES: CC(=O)Nc1cccc(-c2ccccc2O[C@@H]2O[C@H](CO)[C@H](O)[C@H](O)[C@H]2NC(C)=O)c1] | ND | ND | 67.90 | 14.80 | ND | 623 |

TABLE 8-continued

| Name | Structure | % Inhibition at [µM] [100] | [10] | [1] | [0.1] | Kd (µM) | IC₅₀ (nM) |
|---|---|---|---|---|---|---|---|
| AM2065 | 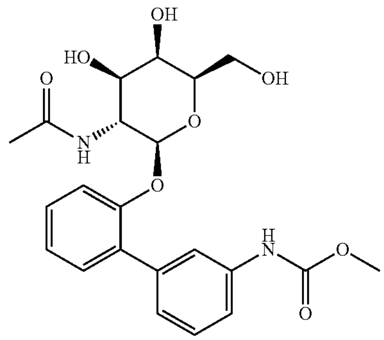 [SMILES: COC(=O)Nc1cccc(-c2ccccc2O[C@@H]2O[C@H](CO)[C@H](O)[C@H](O)[C@H]2NC(C)=O)c1] | ND | ND | 45.30 | 0.00 | ND | 1050 |
| AM2064 | 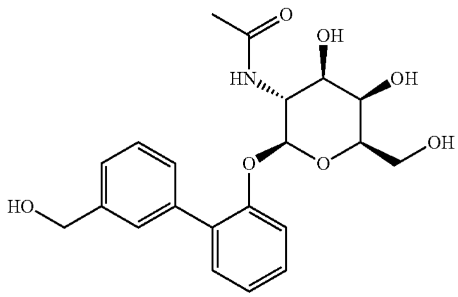 [SMILES: CC(=O)N[C@H]1[C@H](Oc2ccccc2-c2cccc(CO)c2)O[C@H](CO)[C@H](O)[C@@H]1O] | ND | ND | 38.90 | 2.00 | ND | ND |
| AM2078 | 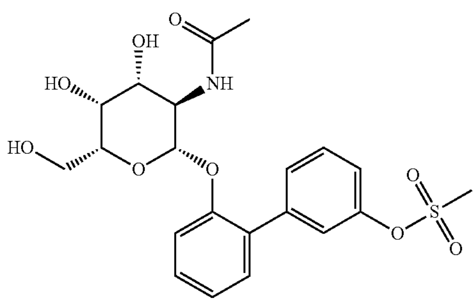 [SMILES: CC(=O)N[C@H]1[C@H](Oc2ccccc2-c2cccc(OS(C)(=O)=O)c2)O[C@H](CO)[C@H](O)[C@@H]1O] | ND | ND | 32.50 | 2.00 | ND | ND |
| AM2073 | 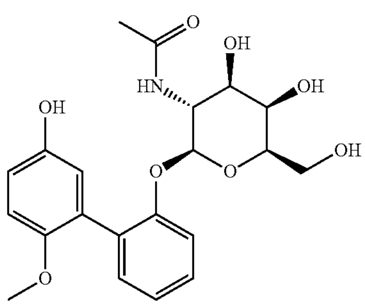 [SMILES: COc1ccc(O)cc1-c1ccccc1O[C@@H]1O[C@H](CO)[C@H](O)[C@H](O)[C@H]1NC(C)=O] | ND | ND | 34.20 | 7.10 | ND | ND |
| AM2077 | 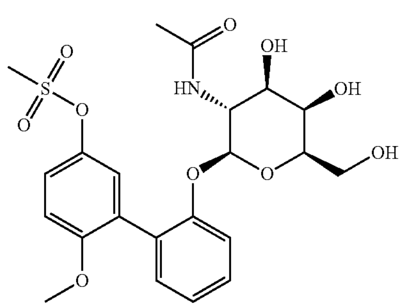 [SMILES: COc1ccc(OS(C)(=O)=O)cc1-c1ccccc1O[C@@H]1O[C@H](CO)[C@H](O)[C@H](O)[C@H]1NC(C)=O] | ND | ND | 0.00 | 2.50 | ND | ND |

TABLE 8-continued

| Name | Structure | % Inhibition at [μM] [100] | [10] | [1] | [0.1] | Kd (μM) | IC$_{50}$ (nM) |
|---|---|---|---|---|---|---|---|
| AM2042 | 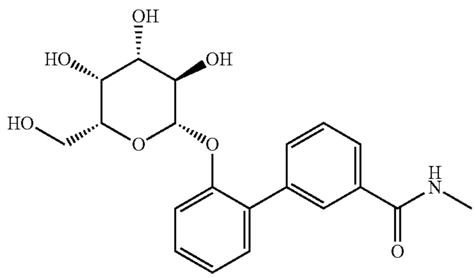 [SMILES: CNC(=O)c1cccc(-c2ccccc2O[C@@H]2O[C@H](CO)[C@H](O)[C@H](O)[C@H]2O)c1] | ND | ND | 16.60 | 0.00 | ND | ND |
| AM2043 | 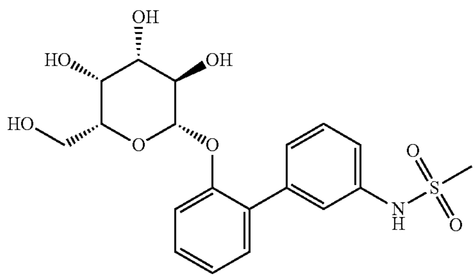 [SMILES: CS(=O)(=O)Nc1cccc(-c2ccccc2O[C@@H]2O[C@H](CO)[C@H](O)[C@H](O)[C@H]2O)c1] | ND | ND | 49.80 | 1.60 | ND | 1113 |
| AM2049 | 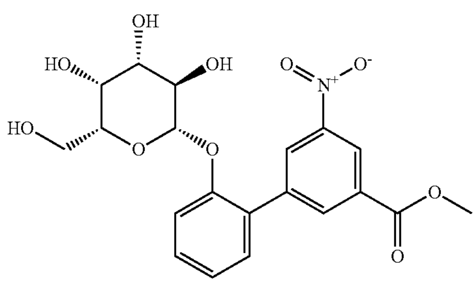 | ND | ND | 0.00 | 0.00 | ND | ND |
| AM2050 | 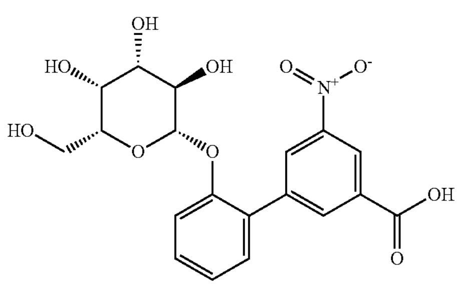 | ND | ND | 68.00 | 7.6 | ND | 418 |
| AM2082 | 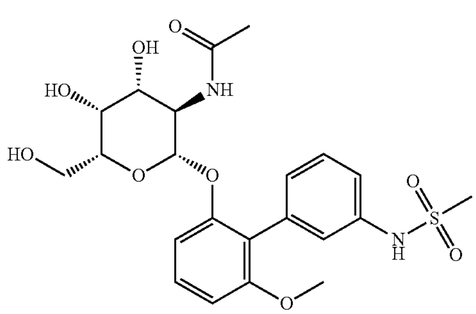 [SMILES: COc1cccc(O[C@@H]2O[C@H](CO)[C@H](O)[C@H](O)[C@H]2NC(C)=O)c1-c1cccc(NS(C)(=O)=O)c1] | ND | ND | ND | ND | ND | 151 |

TABLE 8-continued

| Name | Structure | % Inhibition at [µM] [100] | [10] | [1] | [0.1] | Kd (µM) | IC$_{50}$ (nM) |
|---|---|---|---|---|---|---|---|
| AM2098 | 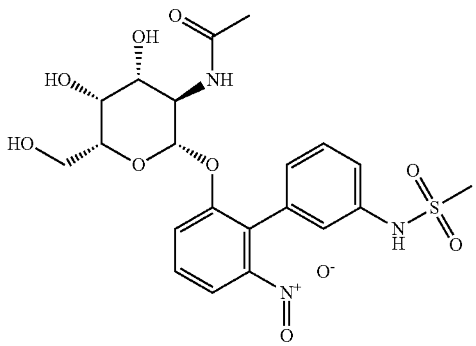 | ND | ND | ND | ND | ND | 110 |
| AM2101 | 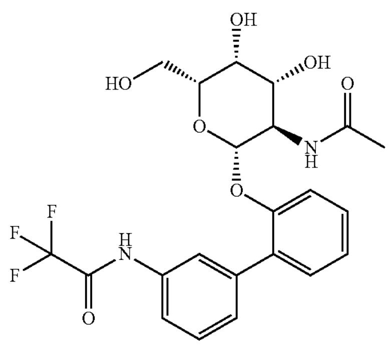 [SMILES: CC(=O)N[C@H]1[C@H](Oc2ccccc2-c2cccc(NC(=O)C(F)(F)F)c2)O[C@H](CO)[C@H](O)[C@@H]1O] | ND | ND | ND | ND | ND | 1025 |
| AM2107 | 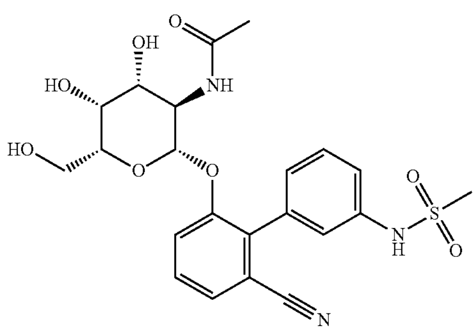 [SMILES: CC(=O)N[C@H]1[C@H](Oc2cccc(C#N)c2-c2cccc(NS(C)(=O)=O)c2)O[C@H](CO)[C@H](O)[C@@H]1O] | ND | ND | ND | ND | ND | 109 |
| AM2109 | 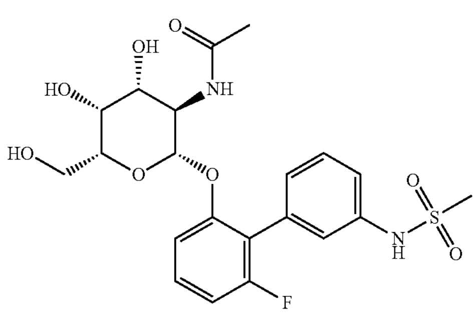 [SMILES: CC(=O)N[C@H]1[C@H](Oc2cccc(F)c2-c2cccc(NS(C)(=O)=O)c2)O[C@H](CO)[C@H](O)[C@@H]1O] | ND | ND | ND | ND | ND | 151 |

TABLE 8-continued

| Name | Structure | % Inhibition at [μM] | | | | Kd (μM) | IC$_{50}$ (nM) |
|---|---|---|---|---|---|---|---|
| | | [100] | [10] | [1] | [0.1] | | |
| AM2110 | 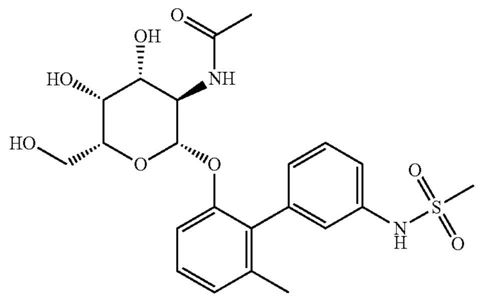 [SMILES: CC(=O)N[C@H]1[C@H](Oc2cccc(C)c2-c2cccc(NS(C)(=O)=O)c2)O[C@H](CO)[C@H](O)[C@@H]1O] | ND | ND | ND | ND | ND | 122 |
| AM2112 | 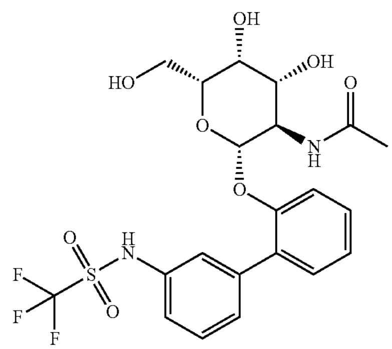 [SMILES: CC(=O)N[C@H]1[C@H](Oc2ccccc2-c2cccc(NS(=O)(=O)C(F)(F)F)c2)O[C@H](CO)[C@H](O)[C@@H]1O] | ND | ND | ND | ND | ND | 2433 |
| AM2116 | 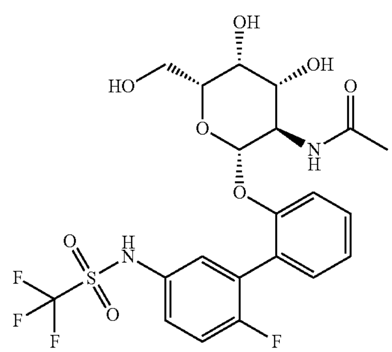 [SMILES: CC(=O)N[C@H]1[C@H](Oc2ccccc2-c2cc(NS(=O)(=O)C(F)(F)F)ccc2F)O[C@H](CO)[C@H](O)[C@@H]1O] | ND | ND | ND | ND | ND | 3067 |
| AM2119 | 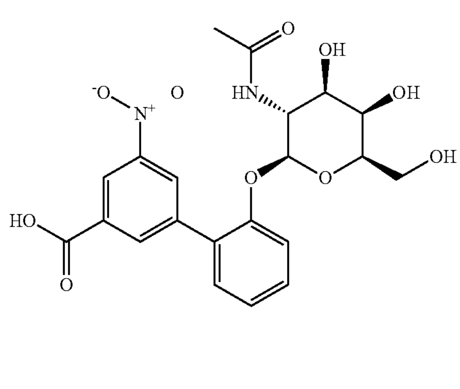 | ND | ND | ND | ND | ND | 1717 |

TABLE 8-continued

| Name | Structure | % Inhibition at [μM] | | | | Kd (μM) | IC₅₀ (nM) |
|---|---|---|---|---|---|---|---|
| | | [100] | [10] | [1] | [0.1] | | |
| AM2129 | 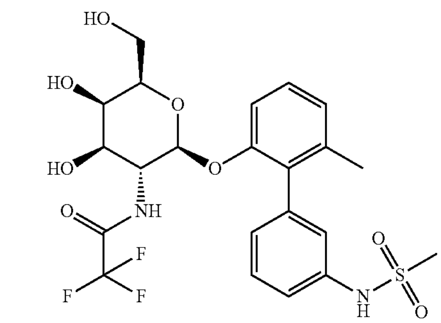 [SMILES: Cc1cccc(O[C@@H]2O[C@H](CO)[C@H](O)[C@H](O)[C@H]2NC(=O)C(F)(F)F)c1-c1cccc(NS(C)(=O)=O)c1] | ND | ND | ND | ND | ND | 105 |
| AM2134 | 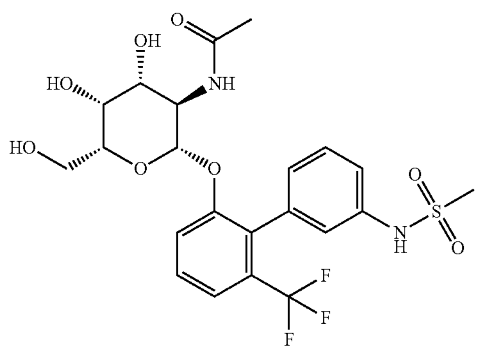 [SMILES: CC(=O)N[C@H]1[C@H](Oc2cccc(C(F)(F)F)c2-c2cccc(NS(C)(=O)=O)c2)O[C@H](CO)[C@H](O)[C@@H]1O] | ND | ND | ND | ND | ND | 85 |
| AM2141 | 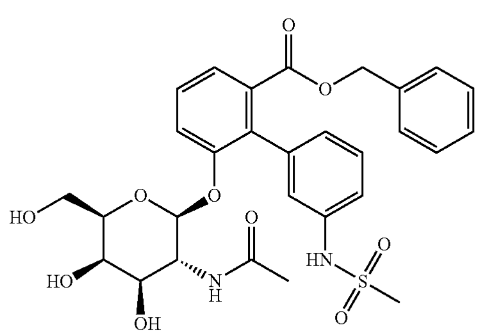 [SMILES: CC(=O)N[C@H]1[C@H](Oc2cccc(C(=O)OCc3ccccc3)c2-c2cccc(NS(C)(=O)=O)c2)O[C@H](CO)[C@H](O)[C@@H]1O] | ND | ND | ND | ND | ND | 180 |
| AM2144 | 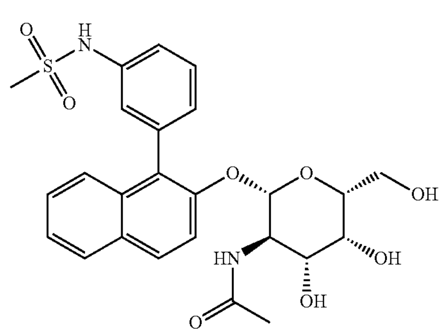 [SMILES: CC(=O)N[C@H]1[C@H](Oc2ccc3ccccc3c2-c2cccc(NS(C)(=O)=O)c2)O[C@H](CO)[C@H](O)[C@@H]1O] | ND | ND | ND | ND | ND | 180 |

TABLE 8-continued

| Name | Structure | % Inhibition at [μM] | | | | Kd (μM) | IC$_{50}$ (nM) |
|---|---|---|---|---|---|---|---|
| | | [100] | [10] | [1] | [0.1] | | |
| AM2148 | 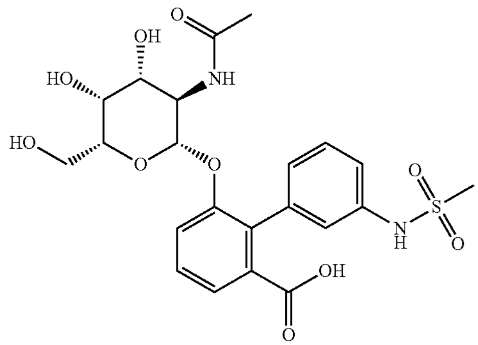 [SMILES: CC(=O)N[C@H]1[C@H](Oc2cccc(C(=O)O)c2-c2cccc(NS(C)(=O)=O)c2)O[C@H](CO)[C@H](O)[C@@H]1O] | ND | ND | ND | ND | ND | 130 |
| AM2151 | 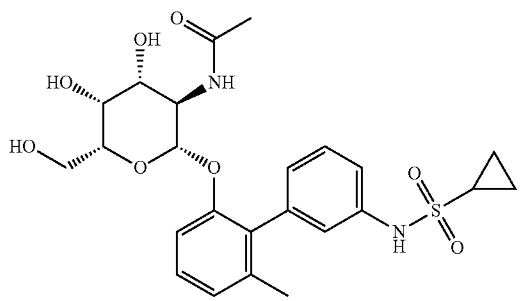 [SMILES: CC(=O)N[C@H]1[C@H](Oc2cccc(C)c2-c2cccc(NS(=O)(=O)C3CC3)c2)O[C@H](CO)[C@H](O)[C@@H]1O] | ND | ND | ND | ND | ND | 120 |
| AM2152 | 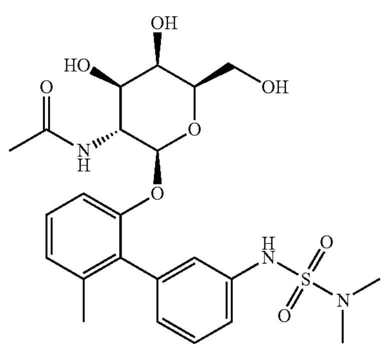 [SMILES: CC(=O)N[C@H]1[C@H](Oc2cccc(C)c2-c2cccc(NS(=O)(=O)N(C)C)c2)O[C@H](CO)[C@H](O)[C@@H]1O] | ND | ND | ND | ND | ND | 130 |
| AM2186 | 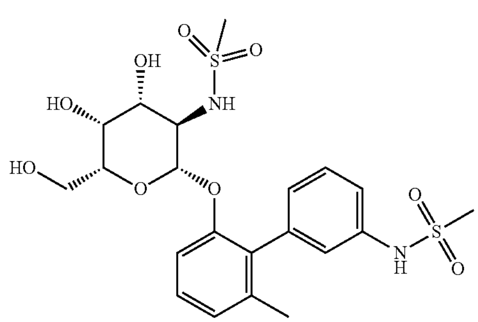 [SMILES: Cc1cccc(O[C@@H]2O[C@H](CO)[C@H](O)[C@H](O)[C@H]2NS(C)(=O)=O)c1-c1cccc(NS(C)(=O)=O)c1] | ND | ND | ND | ND | ND | 3500 |

TABLE 8-continued

| Name | Structure | % Inhibition at [μM] [100] | [10] | [1] | [0.1] | Kd (μM) | IC$_{50}$ (nM) |
|---|---|---|---|---|---|---|---|
| AM3049 | 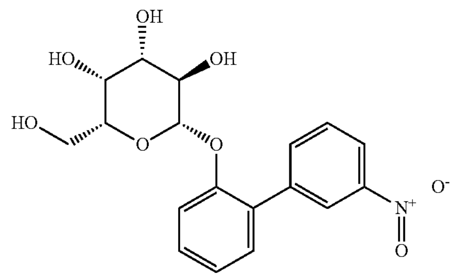 | ND | ND | ND | ND | ND | 15000 |
| AM3082 | 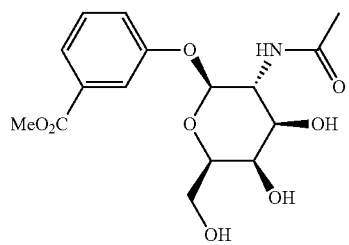 [SMILES: COC(=O)c1cccc(O[C@@H]2O[C@H](CO)[C@H](O)[C@H](O)[C@H]2NC(C)=O)c1] | ND | ND | ND | ND | ND | ND |
| AM3088 | 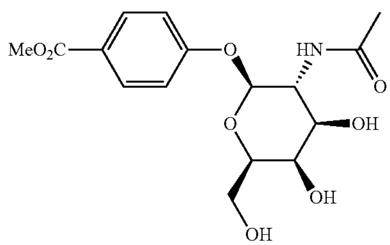 [SMILES: COC(=O)c1ccc(O[C@@H]2O[C@H](CO)[C@H](O)[C@H](O)[C@H]2NC(C)=O)cc1] | ND | ND | ND | ND | ND | ND |
| AM3104 | 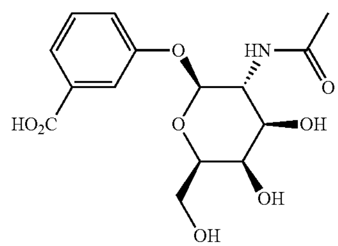 [SMILES: CC(=O)N[C@H]1[C@H](Oc2cccc(C(=O)O)c2)O[C@H](CO)[C@H](O)[C@@H]1O] | ND | ND | ND | ND | ND | ND |
| AM3105 | 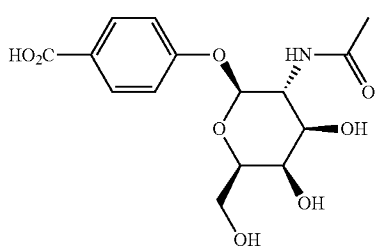 [SMILES: CC(=O)N[C@H]1[C@H](Oc2ccc(C(=O)O)cc2)O[C@H](CO)[C@H](O)[C@@H]1O] | ND | ND | ND | ND | ND | ND |
| VD3007 | 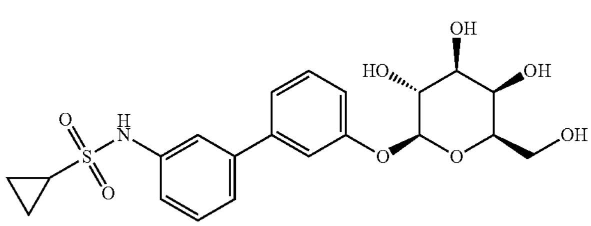 [SMILES: O=S(=O)(Nc1cccc(-c2cccc(O[C@@H]3O[C@H](CO)[C@H](O)[C@H](O)[C@H]3O)c2)c1)C1CC1] | ND | ND | ND | ND | ND | ND |

TABLE 8-continued

| Name | Structure | % Inhibition at [μM] [100] | [10] | [1] | [0.1] | Kd (μM) | IC$_{50}$ (nM) |
|---|---|---|---|---|---|---|---|
| VD3026 | 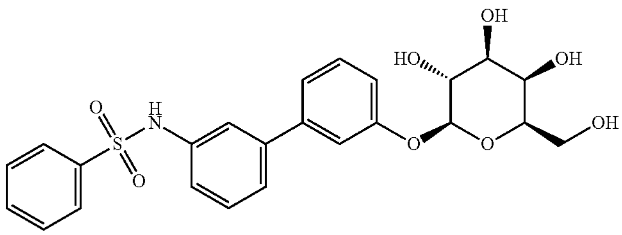 [SMILES: O=S(=O)(Nc1cccc(-c2cccc(O[C@@H]3O[C@H](CO)[C@H](O)[C@H](O)[C@H]3O)c2)c1)c1ccccc1] | ND | ND | ND | ND | ND | ND |
| VD3026 (disub) | 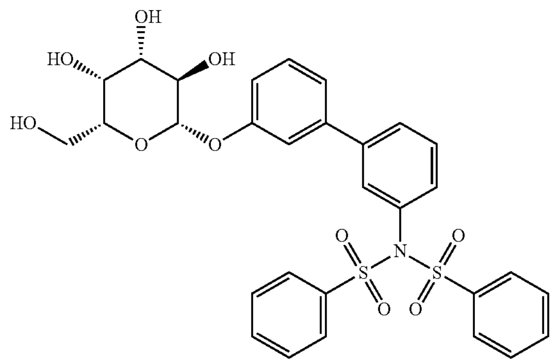 [SMILES: O=S(=O)(c1ccccc1)N(c1cccc(-c2cccc(O[C@@H]3O[C@H](CO)[C@H](O)[C@H](O)[C@H]3O)c2)c1)S(=O)(=O)c1ccccc1] | ND | ND | ND | ND | ND | ND |
| VD3028 | 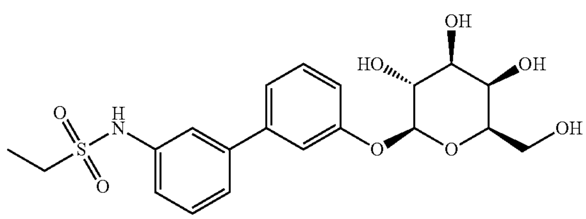 [SMILES: CCS(=O)(=O)Nc1cccc(-c2cccc(O[C@@H]3O[C@H](CO)[C@H](O)[C@H](O)[C@H]3O)c2)c1] | ND | ND | ND | ND | ND | ND |
| VD3061 | 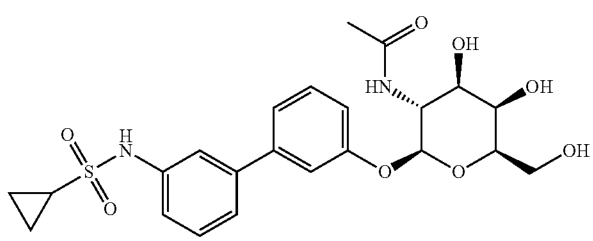 [SMILES: CC(=O)N[C@H]1[C@H](Oc2cccc(-c3cccc(NS(=O)(=O)C4CC4)c3)c2)O[C@H](CO)[C@H](O)[C@@H]1O] | ND | ND | ND | ND | ND | ND |
| VD3078 | 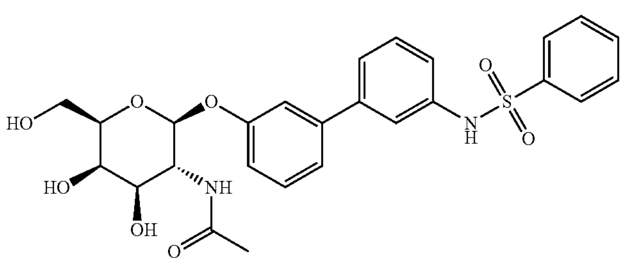 [SMILES: CC(=O)N[C@H]1[C@H](Oc2cccc(-c3cccc(NS(=O)(=O)c4ccccc4)c3)c2)O[C@H](CO)[C@H](O)[C@@H]1O] | ND | ND | ND | ND | ND | ND |
| VD3079 | 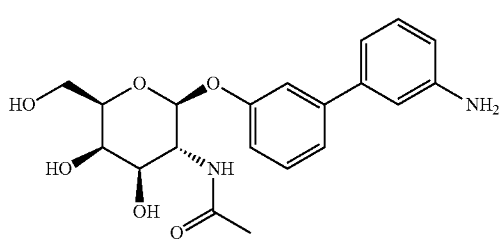 [SMILES: CC(=O)N[C@H]1[C@H](Oc2cccc(-c3cccc(N)c3)c2)O[C@H](CO)[C@H](O)[C@@H]1O] | ND | ND | ND | ND | ND | ND |

TABLE 8-continued

| Name | Structure | % Inhibition at [µM] [100] | [10] | [1] | [0.1] | Kd (µM) | IC50 (nM) |
|---|---|---|---|---|---|---|---|
| VD3081 | 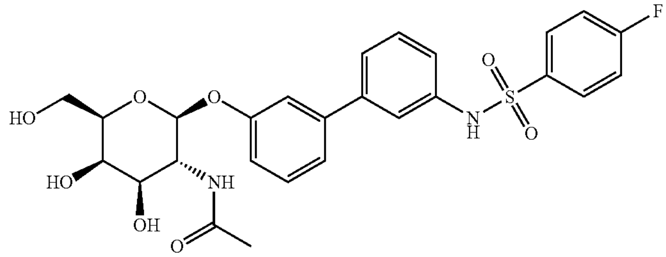 [SMILES: CC(=O)N[C@H]1[C@H](Oc2cccc(-c3cccc(NS(=O)(=O)c4ccc(F)cc4)c3)c2)O[C@H](CO)[C@H](O)[C@@H]1O] | ND | ND | ND | ND | ND | ND |
| VD3086 | 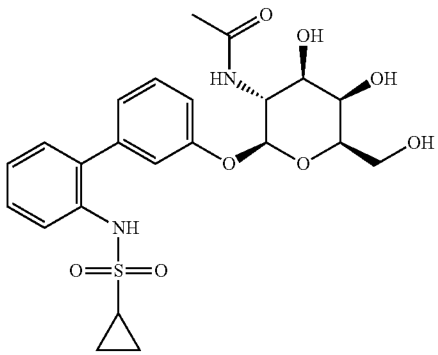 [SMILES: CC(=O)N[C@H]1[C@H](Oc2cccc(-c3ccccc3NS(=O)(=O)C3CC3)c2)O[C@H](CO)[C@H](O)[C@@H]1O] | ND | ND | ND | ND | ND | ND |

ABBREVIATIONS

The following abbreviations used herein are defined as follows:
Ac=acetyl; Ac$_2$O=aceic anhydride; Bn=benzyl; BnBr=benzyl bromide; OSO$_4$=osmium tetraoxide; BCl$_3$=boron trichloride; NaIO$_4$=sodium periodate; CuSO$_4$=copper sulfate; n-BuiLi=n-butyl lithium; Cy=cyclohexyl; dba=dibenzylideneacetone; DCI=4,5-dicyanoimidazole; DDTT=3-((dimethylaminomethylidene)amino)-3H-1,2,4-dithiazole-5-thione; DMA=N,N-dimethylacetamide; DMAP=4-Dimethylaminopyridine; DMOCP=2-chloro-5,5-dimethyl-2-oxo-1,3,2-dioxaphosphorinane; DMP=Dess-Martin periodinane; DMTr=dimethoxytrityl= (4-methoxyphenyl)$_2$ (phenyl)methyl; Piv=pivaloyl=(CH$_3$)$_3$C—C(=O)—; NaOH=sodium hydroxide; NaH=sodium hydride; M=molar; nM=nanomolar; µM=micromolar mL=milliliter; h=hour; min.=minute; HCl=hydrogen chloride; H$_2$O=water; MS=mass spectrometry; LCMS=Liquid chromatography/mass spectrometry; ES+=electrospray positive ionization; $^1$H-NMR=proton nuclear magnetic resonance; $^{13}$C-NMR=carbon-13 nuclear magnetic resonance; $^{31}$P-NMR=phosphorous-31 nuclear magnetic resonance; MHz=megahertz; H=hydrogen; RT=rt=room temperature; ° C.=Celsius; Br$_2$=bromine; NaHSO$_3$=sodium bisulfite; NMP=N-Methyl-2-pyrrolidone; NMM=N-methyl morpholine; NMO=N-methyl morpholine N-oxide; MW=microwave; KF=potassium fluoride; Pd (dppf)Cl$_2$=[1,1'-bis (diphenylphosphino)ferrocene]palladium (II) dichloride; PE=petroleum ether; EtOAc=EA=EtOAc; CDCl$_3$=deuterated chloroform; DMSO-d$_6$=dimethyl sulfoxide deuterated-6; CD$_3$CN=deuterated acetonitrile; LTBA=lithium tri (tert-butoxy)aluminium hydride=LiAlH (Ot-Bu)$_3$; MeOH=methanol; NaOMe=sodium methoxide; D$_2$O=deuterated water; prep-HPLC=preparative high pressure liquid chromatography, also known as preparative high performance liquid chromatography; DMSO=dimethyl sulfoxide; MeCN=CH$_3$CN=acetonitrile; CH$_3$I=methyl iodide; NH$_3$=ammonia; NH$_4$OH=ammonium hydroxide; NIS=N-iodosuccinimide; DMF=N,N-dimethylformamide; K$_3$PO$_4$=potassium phosphate, tribasic; N$_2$=nitrogen; Py=pyridine; THF=tetrahydrofuran; Cs$_2$CO$_3$=cesium carbonate; Na$_2$CO$_3$=sodium carbonate; NaHCO$_3$=sodium bicarbonate; Na$_2$SO$_4$=sodium sulfate; TEA=triethylamine; TBSCl=tert-butyldimethylsilyl chloride; TMSCl=trimethylsilyl chloride; TMS=trimethylsilyl; TMSOTf=trimethylsilyl triflate; TFA=trifluoroacetic acid; DCM=CH$_2$Cl$_2$=dichloromethane; Hunig's base=DIPEA=iPr$_2$NEt=N,N-diisopropylethylamine; K$_2$CO$_3$=potassium carbonate; KOAc=potassium acetate; µl=microliter; g=gram; mg=milligram.

REFERENCES

1. Foxman, B., *Epidemiology of urinary tract infections: incidence, morbidity, and economic costs.* Dis Mon, 2003. 49(2): p. 53-70.
2. Griebling, T. L., *Urologic diseases in America project: trends in resource use for urinary tract infections in women.* J Urol, 2005. 173(4): p. 1281-7.
3. Gupta, K., et al., *Patient-initiated treatment of uncomplicated recurrent urinary tract infections in young women.* Ann Intern Med, 2001. 135(1): p. 9-16.
4. Foxman, B., *The epidemiology of urinary tract infection.* Nat Rev Urol, 2010. 7(12): p. 653-60.
5. Ramakrishnan, K. and D. C. Scheid, *Diagnosis and management of acute pyelonephritis in adults.* Am Fam Physician, 2005. 71(5): p. 933-42.
6. Pertel, P. E. and D. Haverstock, *Risk factors for a poor outcome after therapy for acute pyelonephritis.* BJU Int, 2006. 98(1): p. 141-7.

7. Efstathiou, S. P., et al., *Acute pyelonephritis in adults: prediction of mortality and failure of treatment*. Arch Intern Med, 2003. 163(10): p. 1206-12.
8. Roberts, F. J., I. W. Geere, and A. Coldman, *A three-year study of positive blood cultures, with emphasis on prognosis*. Rev Infect Dis, 1991. 13(1): p. 34-46.
9. WHO, *Antimicrobial Resistance: global report on surveillance*. 2014: Online. p. 257.
10. Guneysel, O., et al., *Trimethoprim/sulfamethoxazole resistance in urinary tract infections*. J Emerg Med, 2009. 36(4): p. 338-41.
11. Raz, R., et al., *Empiric use of trimethoprim-sulfamethoxazole (T P-SMX) in the treatment of women with uncomplicated urinary tract infections, in a geographical area with a high prevalence of TMP-SMX-resistant uropathogens*. Clin Infect Dis, 2002. 34(9): p. 1165-9.
12. Aypak, C., A. Altunsoy, and N. Duzgun, *Empiric antibiotic therapy in acute uncomplicated urinary tract infections and fluoroquinolone resistance: a prospective observational study*. Ann Clin Microbiol Antimicrob, 2009. 8: p. 27.
13. Kallen, A. J., H. G. Welch, and B. E. Sirovich, *Current antibiotic therapy for isolated urinary tract infections in women*. Arch Intern Med, 2006. 166(6): p. 635-9.
14. Karlowsky, J. A., et al., *Fluoroquinolone-resistant urinary isolates of Escherichia coli from outpatients are frequently multidrug resistant: results from the North American Urinary Tract Infection Collaborative Alliance-Quinolone Resistance study*. Antimicrob Agents Chemother, 2006. 50(6): p. 2251-4.
15. McGann, P., et al., *Escherichia coli Harboring mcr-1 and blaCTX-M on a Novel IncF Plasmid: First Report of mcr-1 in the United States*. Antimicrob Agents Chemother, 2016. 60(7): p. 4420-1.
16. Rasko, D. A. and V. Sperandio, *Anti-virulence strategies to combat bacteria-mediated disease*. Nat Rev Drug Discov, 2010. 9(2): p. 117-28.
17. Ronald, A., *The etiology of urinary tract infection: traditional and emerging pathogens*. Dis Mon, 2003. 49(2): p. 71-82.
18. Ronald, A. R., et al., *Urinary tract infection in adults: research priorities and strategies*. Int J Antimicrob Agents, 2001. 17(4): p. 343-8.
19. Waksman, G. and S. J. Hultgren, *Structural biology of the chaperone-usher pathway of pilus biogenesis*. Nat Rev Microbiol, 2009. 7(11): p. 765-74.
20. Wurpel, D. J., et al., *Chaperone-usher fimbriae of Escherichia coli*. PLoS One, 2013. 8(1): p. e52835.
21. Jones, C. H., et al., *FimH adhesin of type 1 pili is assembled into a fibrillar tip structure in the Enterobacteriaceae*. Proc Natl Acad Sci USA, 1995. 92(6): p. 2081-5.
22. Mulvey, M. A., et al., *Induction and evasion of host defenses by type 1-piliated uropathogenic Escherichia coli*. Science, 1998. 282(5393): p. 1494-7.
23. Han, Z., et al., *Structure-based drug design and optimization of mannoside bacterial FimH antagonists*. J Med Chem, 2010. 53(12): p. 4779-92.
24. Jarvis, C., et al., *Antivirulence Isoquinolone Mannosides: Optimization of the Biaryl Aglycone for FimH Lectin Binding Affinity and Efficacy in the Treatment of Chronic UTI*. ChemMedChem, 2016. 11(4): p. 367-73.
25. Mydock-McGrane, L., et al., *Antivirulence C-Mannosides as Antibiotic-Sparing, Oral Therapeutics for Urinary Tract Infections*. J Med Chem, 2016. 59(20): p. 9390-9408.
26. Cusumano, C. K., et al., *Treatment and prevention of urinary tract infection with orally active FimH inhibitors*. Sci Transl Med, 2011. 3(109): p. 109ra115.
27. Conover, M. S., et al., *Inflammation-Induced Adhesin-Receptor Interaction Provides a Fitness Advantage to Uropathogenic E. coli during Chronic Infection*. Cell Host Microbe, 2016. 20(4): p. 482-492.
28. Kalas, V., et al., *Evolutionary fine-tuning of conformational ensembles in FimH during host-pathogen interactions*. Sci Adv, 2017. 3(2): p. e1601944.
29. Irwin, J. J., et al., *ZINC: a free tool to discover chemistry for biology*. J Chem Inf Model, 2012. 52(7): p. 1757-68.
30. Hannan, T J, et al., *Early severe inflammatory responses to uropathogenic E. coli predispose to chronic and recurrent urinary tract infection*. PLoS Pathog, 2010. 6(8): p. e1001042.
31. Subashchandrabose, S., et al., *t-specific induction of Escherichia coli fitness genes during human urinary tract infection*. Proc Natl Acad Sci USA, 2014. 111(51): p. 18327-32.
32. Bouckaert, J., et al., *The affinity of the FimH fimbrial adhesin is receptor-driven and quasi-independent of Escherichia coli pathotypes*. Mol Microbiol, 2006. 61(6): p. 1556-68.
33. Hung, C. S., et al., *Structural basis of tropism of Escherichia coli to the bladder during urinary tract infection*. Mol Microbiol, 2002. 44(4): p. 903-15.
34. Ernst, B. and J. L. Magnani, *From carbohydrate leads to glycomimetic drugs*. Nat Rev Drug Discov, 2009. 8(8): p. 661-77.
35. Hsu, C. H., et al., *The Dependence of Carbohydrate-Aromatic Interaction Strengths on the Structure of the Carbohydrate*. J Am Chem Soc, 2016. 138(24): p. 7636-48.
36. Hudson, K. L., et al., *Carbohydrate-Aromatic Interactions in Proteins*. J Am Chem Soc, 2015. 137(48): p. 15152-60.
37. Ter Kuile, B. H., N. Kraupner, and S. Brul, *The risk of low concentrations of antibiotics in agriculture for resistance in human health care*. FEMS Microbiol Lett, 2016. 363(19).
38. Llor, C. and L. Bjerrum, *Antimicrobial resistance: risk associated with antibiotic overuse and initiatives to reduce the problem*. Ther Adv Drug Saf, 2014. 5(6): p. 229-41.
39. Kardas, P., et al., *A systematic review and meta-analysis of misuse of antibiotic therapies in the community*. Int J Antimicrob Agents, 2005. 26(2): p. 106-13.
40. Chang, Q., et al., *Antibiotics in agriculture and the risk to human health: how worried should we be?* Evol Appl, 2015. 8(3): p. 240-7.
41. Trott, O. and A. J. Olson, *AutoDock Vina: improving the speed and accuracy of docking with a new scoring function, efficient optimization, and multithreading*. J Comput Chem, 2010. 31(2): p. 455-61.
42. O'Boyle, N. M., et al., *Open Babel: An open chemical toolbox*. J Cheminform, 2011. 3: p. 33.
43. Battye, T. G., et al., *iMOSFLM: a new graphical interface for diffraction-image processing with MOSFLM*. Acta Crystallogr D Biol Crystallogr, 2011. 67(Pt 4): p. 271-81.
44. Kabsch, W., *Xds*. Acta Crystallogr D Biol Crystallogr, 2010. 66(Pt 2): p. 125-32.
45. Winn, M. D., et al., *Overview of the CCP4 suite and current developments*. Acta Crystallogr D Biol Crystallogr, 2011. 67(Pt 4): p. 235-42.

46. Adams, P. D., et al., *PHENIX: a comprehensive Python-based system for macromolecular structure solution.* Acta Crystallogr D Biol Crystallogr, 2010. 66(Pt 2): p. 213-21.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compounds, compositions and methods without departing from the scope of the invention, it is intended that all matter contained in the above description and shown in the accompanying figures shall be interpreted as illustrative and not in a limiting sense.

Having described the invention in detail, it will be apparent that modifications and variations are possible without departing from the scope of the invention defined in the appended claims.

What is claimed is:

1. A compound of Formula (I) or salt or prodrug thereof:

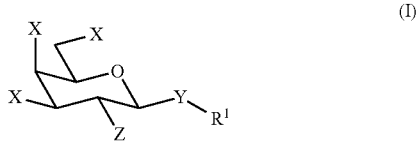

(I)

wherein:
each X is independently hydrogen, fluoro, or $OR^2$;
each $R^2$ is independently hydrogen or substituted or unsubstituted hydrocarbyl;
Y is O, S, substituted or unsubstituted hydrocarbylene, substituted or unsubstituted amino, substituted or unsubstituted amido, substituted or unsubstituted thio, $C(R^3)_2$, $(CH_2)_m$, $N(R^3)$, $N(H)R^3$, $CO_2$, $COOR^3$, $SO_2$, $SO_2R^3$, $(CH_2)_mO$, $O(CH_2)_m$, $(CH_2)_mS$, $S(CH_2)_m$, $C(O)$, $C(O)N(R^3)$, $N(R^3)C(O)$, $R^3N(R^3)C(O)$, $C(O)N(R^3)R^3$, $SO_2N(R^3)$, or $N(R^3)SO_2$;
each $R^3$ is independently hydrogen or substituted or unsubstituted hydrocarbyl;
Z is $OR^4$ or $NHR^4$;
each $R^4$ is independently hydrogen or substituted or unsubstituted hydrocarbyl;
each m is independently an integer from 0 to 10; and
$R^1$ is

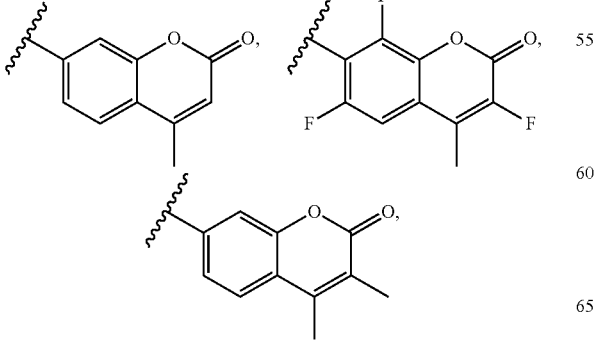

-continued

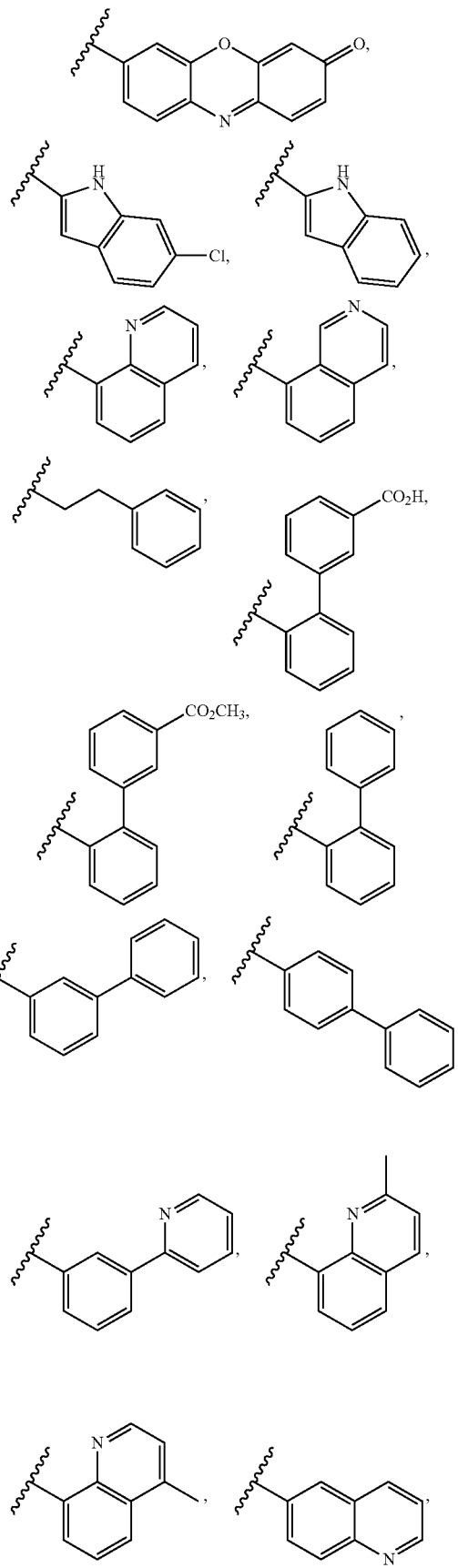

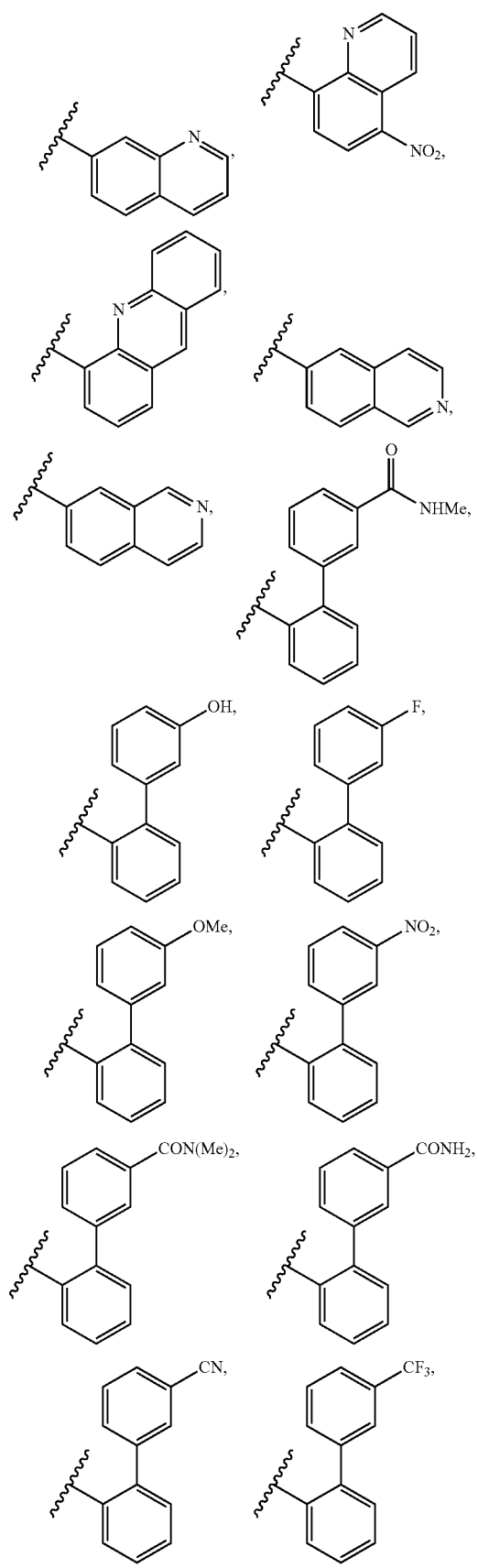
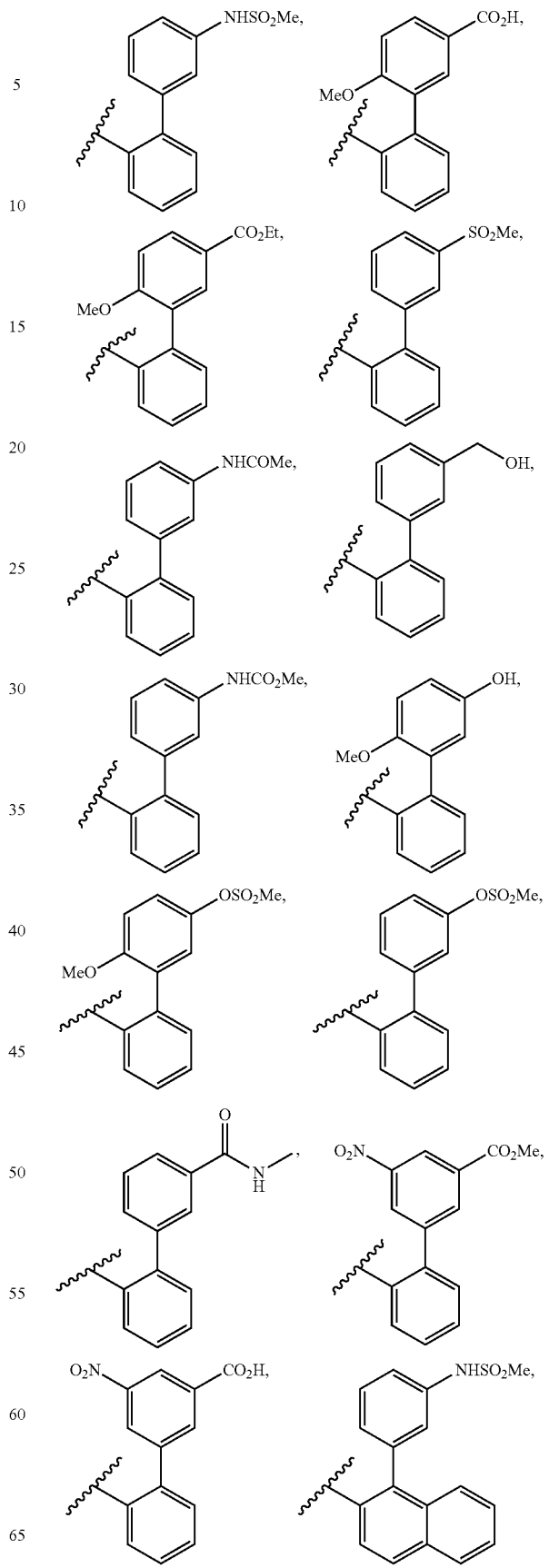

-continued

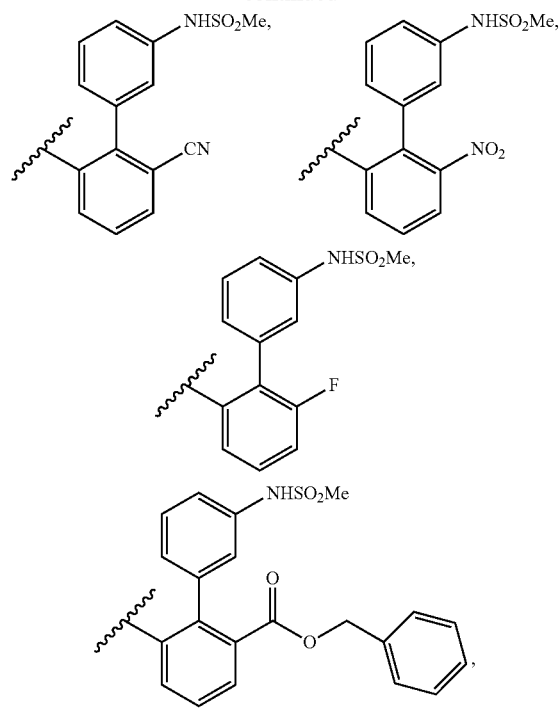

-continued

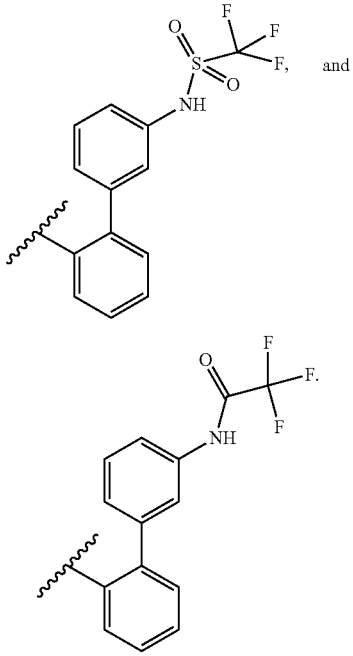

2. The compound of claim 1 wherein each X is independently OH.

3. The compound of claim 1 wherein each $R^2$ is independently hydrogen or substituted or unsubstituted $C_1$-$C_{30}$ alkyl.

4. The compound of claim 1 wherein Y is O, S, $C(R^3)_2$, $(CH_2)_n$, $N(R^3)$, $N(H)R^3$, $CO_2$, $COOR^3$, $SO_2$, $SO_2R^3$, $(CH_2)_n$O, $O(CH_2)_n$, $(CH_2)_nS$, $S(CH_2)_n$, $C(O)$, $C(O)N(R^3)$, $N(R^3)C(O)$, $R^3N(R^3)C(O)$, $C(O)N(R^3)R^3$, $SO_2N(R^3)$, or $N(R^3)SO_2$.

5. The compound of claim 1 wherein each $R^3$ is independently hydrogen, substituted or unsubstituted $C_1$-$C_{30}$ alkyl, or $C(R^8)_2C(O)N(R^9)_2$, and each $R^8$ and $R^9$ are independently hydrogen, $C_1$-$C_{30}$ alkyl, or aryl.

6. The compound of claim 1 wherein Z is OH, $NHSO_2CF_3$, $NHC(O)CF_3$, $NHC(O)CH_3$, $OR^4$, or $NHR^4$.

7. The compound of claim 1 wherein each $R^4$ is independently hydrogen, substituted or unsubstituted $C_1$-$C_{30}$ alkyl, $SO_2R^{10}$, or $C(O)R^{10}$ and $R^{10}$ is a $C_1$-$C_{10}$ alkyl or haloalkyl.

8. The compound of claim 1 wherein each B is independently O, S, C(O), or $NR^6$.

9. The compound of claim 1 selected from the group consisting of:

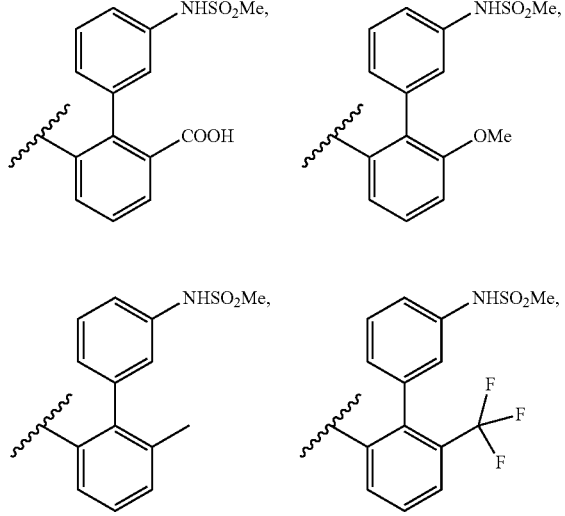

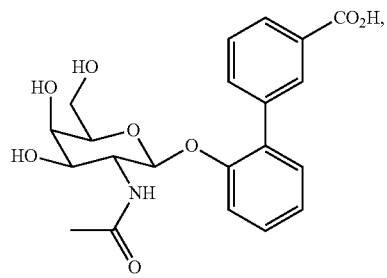

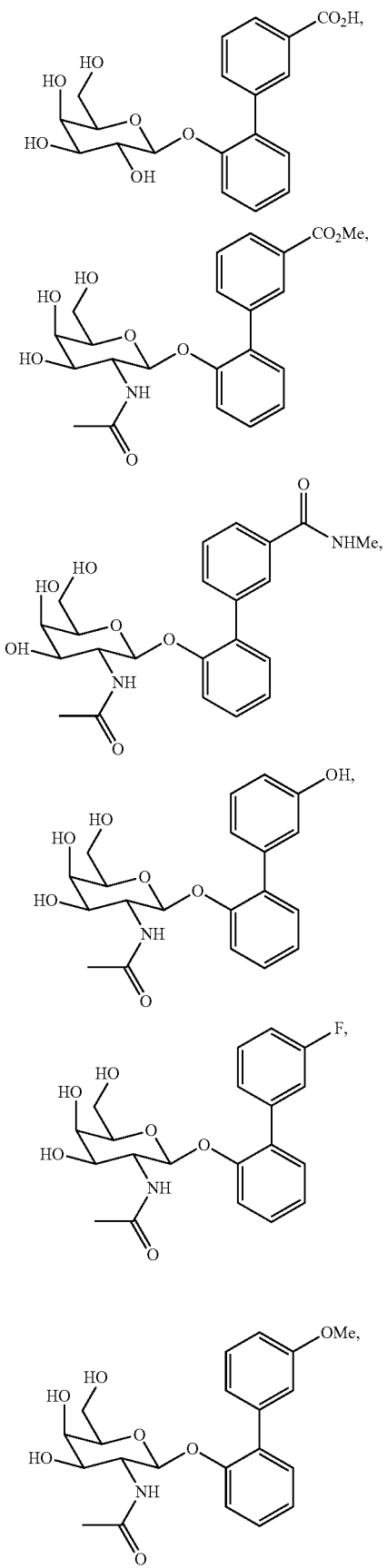
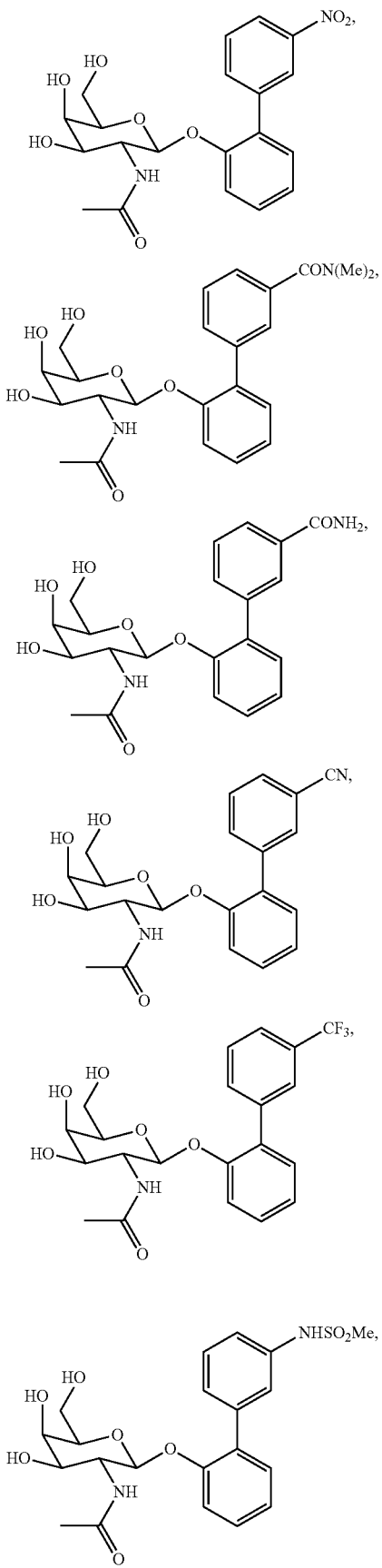

237
-continued
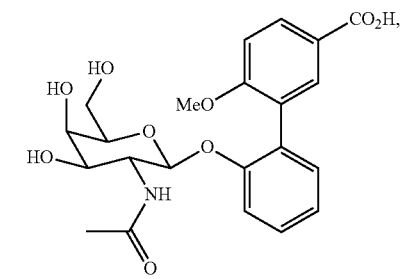
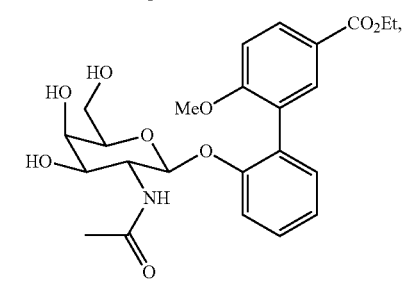
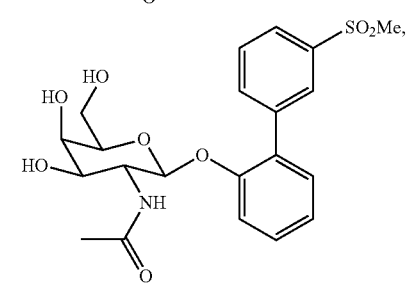
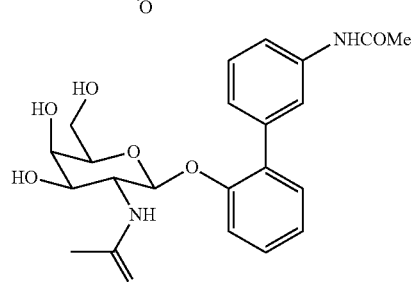
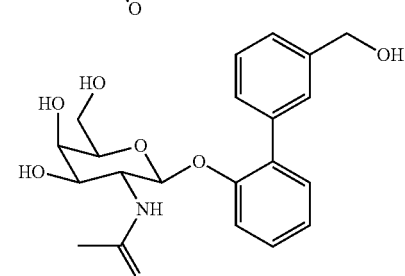
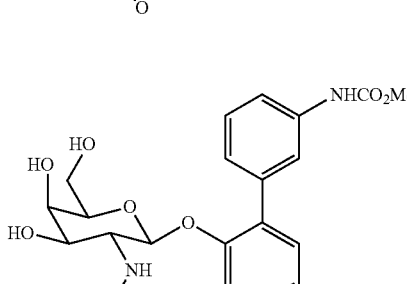
238
-continued
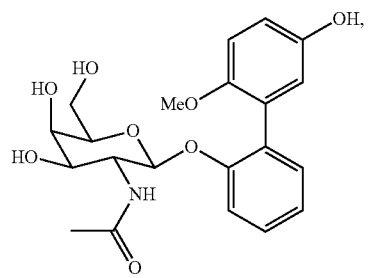
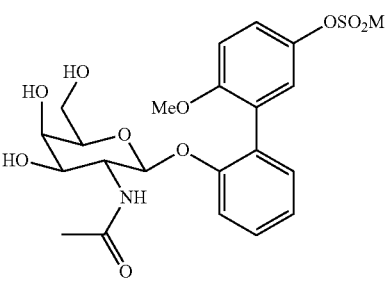
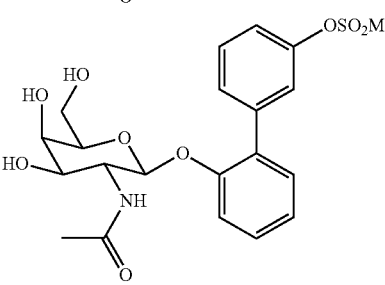
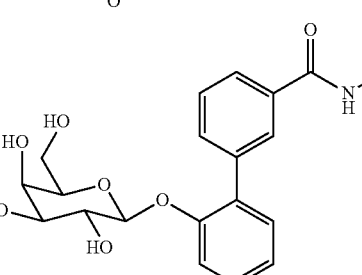
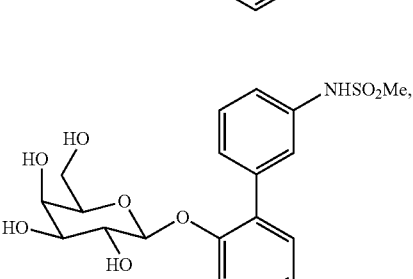
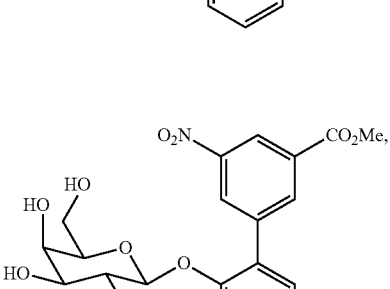

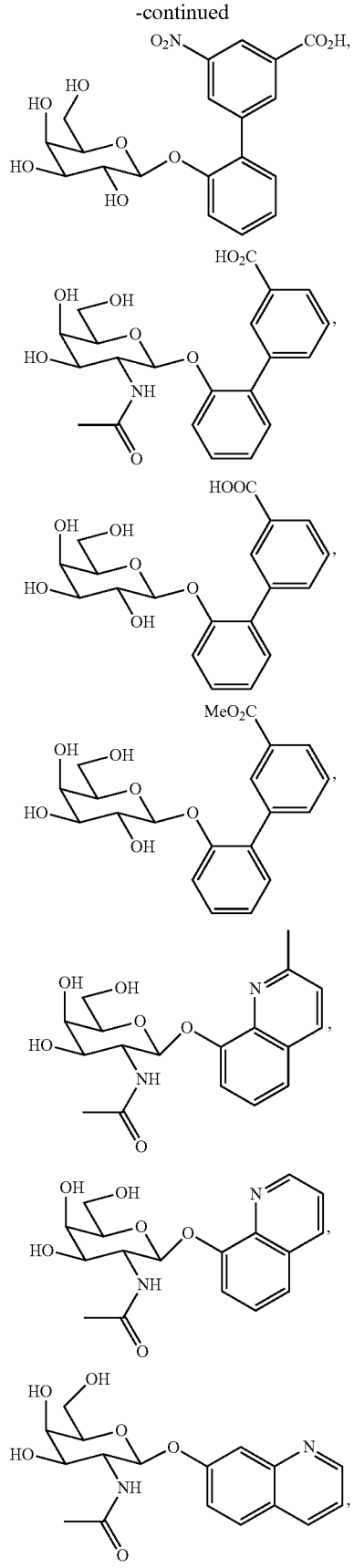
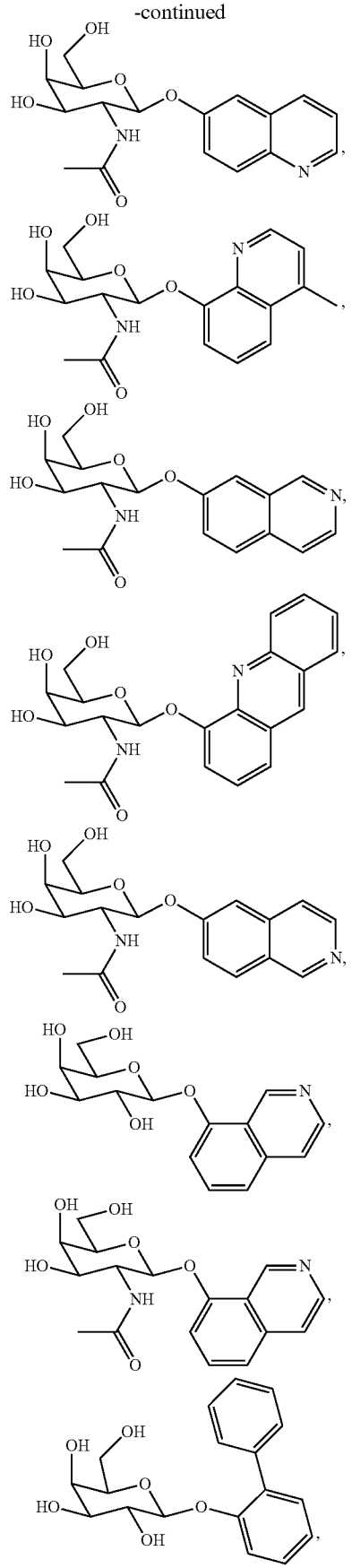

-continued
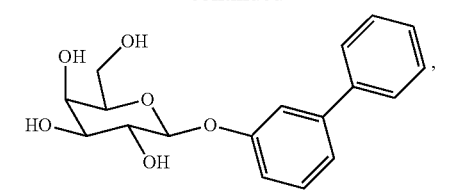
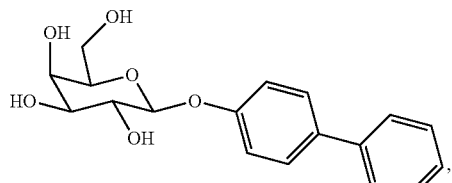
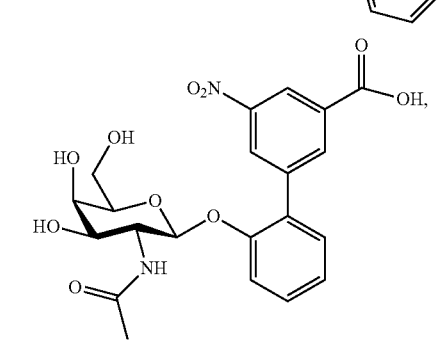
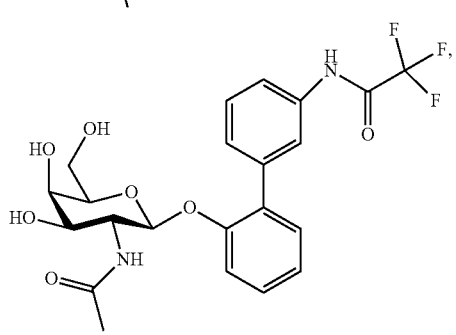
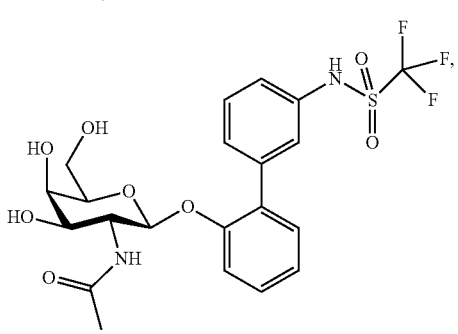
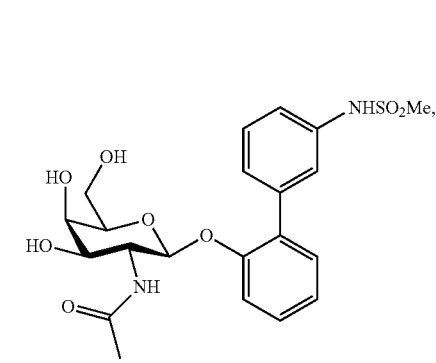
-continued
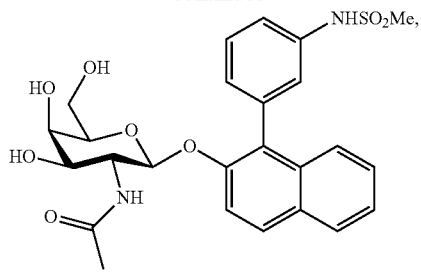
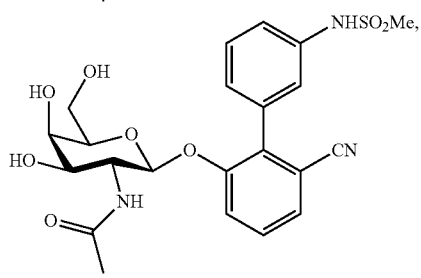
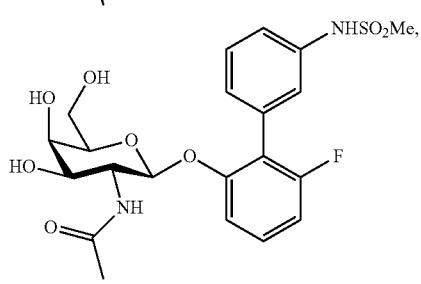
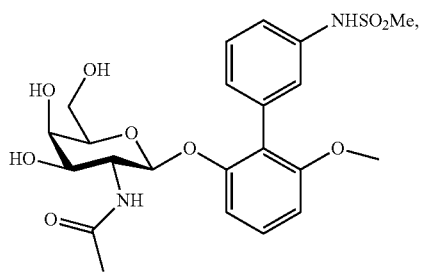
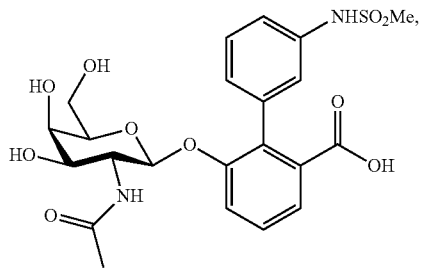
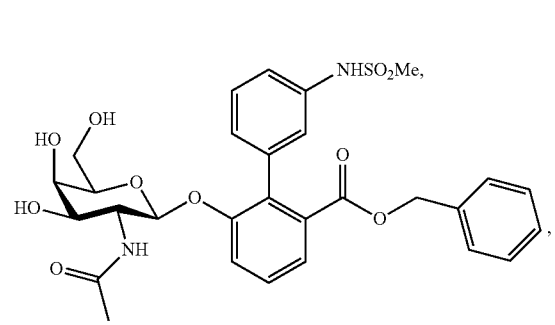

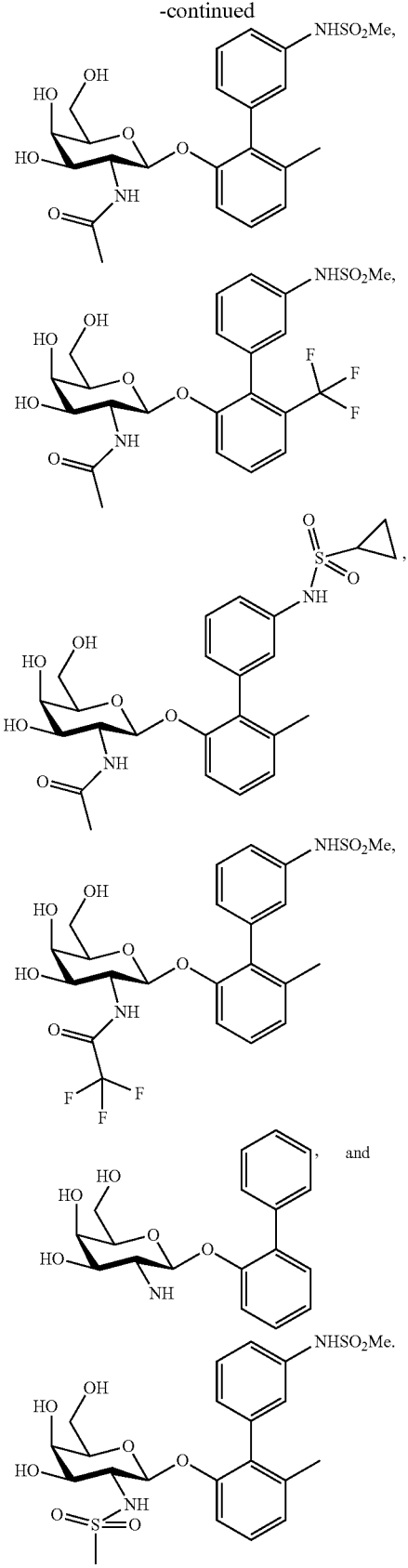

10. A pharmaceutical composition comprising a therapeutically effective amount of at least one compound of Formula (I) or salt or prodrug thereof according to claim 1.

11. A method of treating a bacterial infection in a subject in need thereof comprising administering a pharmaceutical composition comprising a compound of claim 1 to the subject.

12. A method of treating a bacterial infection in a subject in need thereof comprising administering the pharmaceutical composition of claim 10 to the subject.

13. The method of claim 12 wherein the bacterial infection is a urinary tract infection or a kidney infection.

14. The method of claim 12, further comprising administering one or more additional active ingredients comprising an antibacterial.

15. A compound of Formula (I) or salt or prodrug thereof:

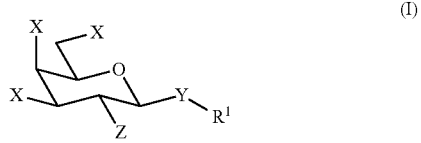

(I)

wherein:
each X is independently hydrogen, fluoro, or OR$^2$;
each R$^2$ is independently hydrogen or substituted or unsubstituted hydrocarbyl;
Y is O;
Z is OR$^4$ or NHR$^4$;
each R$^4$ is independently hydrogen or substituted or unsubstituted hydrocarbyl; and
R$^1$ is a substituent of Formula (VI)

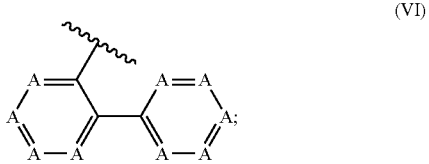

(VI)

wherein:
A is CR$^5$;
each R$^5$ is independently hydrogen, oxygen, halo, haloalkyl, $(CH_2)_pNO_2$, $(CH_2)_pCN$, $(CH_2)_pOR^7$, $(CH_2)_pC(R^7)_2OR^7$, $(CH_2)_pCO_2R^7$, $(CH_2)_pSO_2R^7$, $(CH_2)_pNR^7C(O)R^7$, $(CH_2)_pNR^7CO_2R^7$, $(CH_2)_pNR^7SO_2R^7$, $(CH_2)_pCON(R^7)_2$, $(CH_2)_pN(R^7)SO_2N(R^7)_2$, or $(CH_2)_pOSO_2R^7$;
each R$^7$ is independently hydrogen or substituted or unsubstituted hydrocarbyl; and
p is 0.

* * * * *